US011986535B2

(12) United States Patent
Grawunder et al.

(10) Patent No.: US 11,986,535 B2

(45) Date of Patent: *May 21, 2024

(54) METHOD OF PRODUCING AN IMMUNOLIGAND/PAYLOAD CONJUGATE

(71) Applicant: NBE Therapeutics AG, Basel (CH)

(72) Inventors: Ulf Grawunder, Basel (CH); Roger Renzo Beerli, Basel (CH)

(73) Assignee: NBE THERAPEUTICS AG, Basel (CH)

(*) Notice: Subject to any disclaimer, the term of this patent is extended or adjusted under 35 U.S.C. 154(b) by 0 days.

This patent is subject to a terminal disclaimer.

(21) Appl. No.: 17/839,395

(22) Filed: Jun. 13, 2022

(65) Prior Publication Data

US 2022/0378927 A1 Dec. 1, 2022

Related U.S. Application Data

(60) Continuation of application No. 16/915,343, filed on Jun. 29, 2020, now Pat. No. 11,364,301, which is a continuation of application No. 15/819,116, filed on Nov. 21, 2017, now Pat. No. 10,864,277, which is a division of application No. 14/775,374, filed as application No. PCT/EP2014/055173 on Mar. 14, 2014, now Pat. No. 9,872,923.

(60) Provisional application No. 61/939,754, filed on Feb. 14, 2014, provisional application No. 61/787,371, filed on Mar. 15, 2013.

(30) Foreign Application Priority Data

Mar. 15, 2013 (EP) .................................... 13159484

(51) Int. Cl.

| | |
|---|---|
| ***A61K 39/00*** | (2006.01) |
| ***A61K 47/65*** | (2017.01) |
| ***A61K 47/68*** | (2017.01) |
| ***C07K 1/107*** | (2006.01) |
| ***C07K 16/40*** | (2006.01) |
| ***C12P 21/00*** | (2006.01) |

(52) U.S. Cl.

CPC .......... *A61K 47/65* (2017.08); *A61K 47/6803* (2017.08); *A61K 47/6851* (2017.08); *A61K 47/6889* (2017.08); *C07K 1/1075* (2013.01); *C07K 16/40* (2013.01); *C12P 21/00* (2013.01); *A61K 2039/505* (2013.01); *C07K 2317/24* (2013.01); *C12Q 2521/537* (2013.01)

(58) Field of Classification Search

CPC ...................................................... A61K 47/65

See application file for complete search history.

(56) References Cited

U.S. PATENT DOCUMENTS

| | | | | |
|---|---|---|---|---|
| 8,389,697 | B2 | 3/2013 | Beria et al. | |
| 8,470,984 | B2 | 6/2013 | Caruso et al. | |
| 8,742,076 | B2 | 6/2014 | Cohen et al. | |
| 8,900,589 | B2 | 12/2014 | Beria et al. | |
| 9,492,553 | B2 | 11/2016 | Cohen et al. | |
| 9,695,240 | B2 | 7/2017 | Beria et al. | |
| 9,872,923 | B2 | 1/2018 | Grawunder et al. | |
| 10,864,277 | B2 * | 12/2020 | Grawunder | A61P 37/02 |
| 11,364,301 | B2 * | 6/2022 | Grawunder | C12P 21/00 |
| 2004/0077842 | A1 | 4/2004 | Himawan | |
| 2010/0055761 | A1 | 3/2010 | Seed et al. | |
| 2010/0111851 | A1 | 5/2010 | Aburatani et al. | |
| 2011/0321183 | A1 | 12/2011 | Ploegh et al. | |
| 2014/0065171 | A1 | 3/2014 | Geierstanger et al. | |
| 2016/0136298 | A1 | 5/2016 | Grawunder et al. | |
| 2016/0193355 | A1 | 7/2016 | Qin et al. | |
| 2019/0262461 | A1 | 8/2019 | Grawunder et al. | |
| 2021/0015936 | A1 | 1/2021 | Grawunder et al. | |

FOREIGN PATENT DOCUMENTS

| | | | |
|---|---|---|---|
| EP | 2968583 | A2 | 1/2016 |
| EP | 2990423 | A1 | 3/2016 |
| JP | H08-501059 | A | 2/1996 |
| JP | H11-506915 | A | 6/1999 |
| JP | 2008-138004 | A | 6/2008 |
| JP | 2008-523062 | A | 7/2008 |
| JP | 2008523062 | A | 7/2008 |
| JP | 2010500967 | A | 1/2010 |
| JP | 2012-050441 | A | 3/2012 |
| JP | 2012-519711 | A | 8/2012 |
| JP | 2012519711 | A | 8/2012 |
| JP | 2012-523383 | A | 10/2012 |
| JP | 2012523383 | A | 10/2012 |
| KR | 1020130046322 | | 4/2014 |
| NO | 2013177231 | A1 | 11/2013 |
| WO | 2006062779 | A2 | 6/2006 |
| WO | 2007/076974 | A2 | 7/2007 |
| WO | 2007/108013 | A2 | 9/2007 |
| WO | 2009099741 | A1 | 8/2009 |
| WO | 2009/132455 | A1 | 11/2009 |
| WO | 2010009124 | A2 | 1/2010 |
| WO | 2010111018 | A1 | 9/2010 |
| WO | 2010115630 | A1 | 10/2010 |
| WO | 2011/133704 | A2 | 10/2011 |
| WO | 2012073217 | A1 | 6/2012 |
| WO | 2012/142659 | A1 | 10/2012 |
| WO | 2013/022808 | A2 | 2/2013 |

(Continued)

OTHER PUBLICATIONS

Office Action for Brazilian Patent Application No. 112015023589-1, dated Mar. 23, 2023 (6 pages).

(Continued)

*Primary Examiner* — Albert M Navarro

(74) *Attorney, Agent, or Firm* — Morgan, Lewis & Bockius LLP

(57) ABSTRACT

The present invention relates to a method of producing an immunoligand/payload conjugate, which method encompasses conjugating a payload to an immunoligand by means of a sequence-specific transpeptidase, or a catalytic domain thereof (Fig. 6b).

23 Claims, 21 Drawing Sheets

Figure 1A:
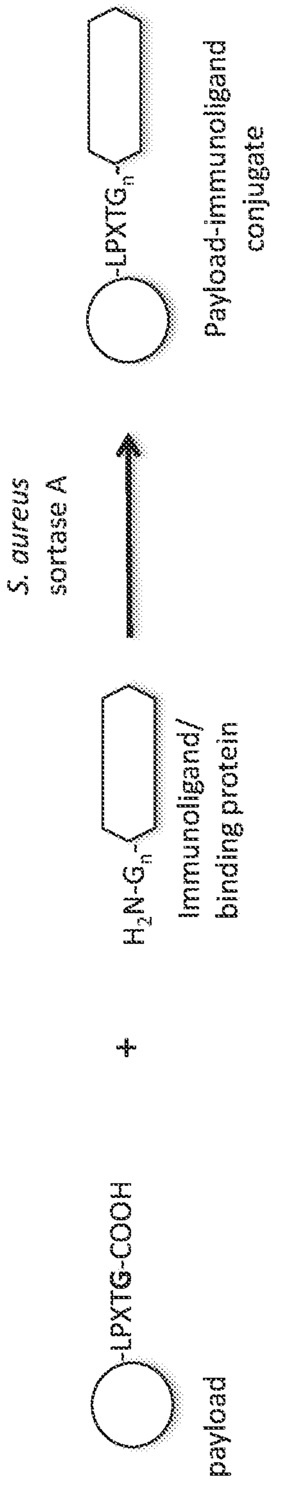

Specification includes a Sequence Listing.

(56) References Cited

FOREIGN PATENT DOCUMENTS

| | | | |
|---|---|---|---|
| WO | 2013177055 | A2 | 11/2013 |
| WO | 2014088928 | A1 | 6/2014 |
| WO | 2014140317 | A2 | 9/2014 |
| WO | 2014177042 | A1 | 11/2014 |

OTHER PUBLICATIONS

Office Action for Canadian Patent Application No. 2,903,581, dated Sep. 12, 2022 (3 pages).
Lee Kim Swee et al., Sortase-mediated modification of alpha DEC205 affords optimization of antigen presentation and immunization against a set of viral epitopes, Proceedings of the National Academy of Sciences of the United States of America, Jan. 7, 2013 (Jan. 7, 2013), vol. 110, No. 4, pp. 1428-1433, https://doi.org/10.1073/pnas.1214994110 (6 pages).
Shinya Tsukiji et al., Sortase-Mediated Ligation: A Gift from Gram-Positive Bacteria to Protein Engineering, ChemBioChem—An Official Journal of the EFMC, Mar. 23, 2009 (Mar. 23, 2009), vol. 10, Issue 5, pp. 787-798, DOI: 10.1002/CBIC.200800724 (12 pages).
H.T. Ta et al., Enzymatic Single-Chain Antibody Tagging—A Universal Approach to Targeted Molecular Imaging and Cell Homing in Cardiovascular Disease, Circulation Research, Aug. 2011, vol. 109, No. 4, pp. 365-373, https://doi.org/10.1161/CIRCRESAHA.111.249375 (28 pages).
Mariusz P. Madej et al., Engineering of an anti-epidermal growth factor receptor antibody to single chain format and labeling by sortase A-mediated protein ligation, Biotechnology and Bioengineering, Jun. 2012, vol. 109, Issue 6, pp. 1461-1470, https://doi.org/10.1002/bit.24407 (10 pages).
Samuel Baer et al., Comparison of alternative nucleophiles for Sortase A-mediated bioconjugation and application in neuronal cell labelling, Organic & Biomolecular Chemisry, May 7, 2014 (May 7, 2014), vol. 12, Issue 17, pp. 2675-2685, DOI: 10.1039/c3ob42325e (12 pages).
Anadrew J. McCluskey et al., Receptor-Directed Chimeric Toxins Created by Sortase-Mediated Protein Fusion, Molecular Cancer Therapeutics, Oct. 1, 2013 (Oct. 1, 2013), American Association for Cancer Research Inc., USA, vol. 12, Issue 10, pp. 2273-2281, https://doi.org/10.1158/1535-7163.MCT-13-0358 (10 pages).
Gerrit Volkmann et al., Protein C-Terminal Labeling and Biotinylation Using Synthetic Peptide and Split-Intein, PLOS One, Dec. 21, 2009 (Dec. 21, 2009), vol. 4, No. 12, pp. 1-12, https://doi.org/10.1371/journal.pone.0008381 (12 pages).
Huiling Song et al., Protein Trans-Splicing of an Atypical Split Intein Showing Structural Flexibility and Cross-Reactivity, PLOS One Sep. 14, 2012 Public Library of Science U.S.A., vol. 7, No. 9, Sep. 14, 2012 (Sep. 14, 2012), XP002730634, ISSN: 1932-6203, https://doi.org/10.1371/journal.pone.0045355 (6 pages).
Office Action for Canadian Patent Application No. 2,903,581, dated Aug. 31, 2021 (4 pages).
Stephen C. Alley et al., Contribution of linker stability to the activities of anticancer immunoconjugates, (2008), Bioconjug Chem. Epub, vol. 19, No. 3, pp. 759-765, https://doi.org/10.1021/bc7004329 (7 pages).
W. Ardelt et al., Onconase and amphinase, the antitumor ribonucleases from Rana pipiens oocytes, Current Pharmaceutical Biotechnology, Jun. 2008, vol. 9, No. 3, pp. 215-225, 10.2174/138920108784567245 (18 pages).
Alain Beck et al., Introduction/Background: Conjugating Cytotoxic Drugs to Antibodies, Pierre Fabre Research Institute, Discovery Medicine, Oct. 2010, vol. 10, No. 53, pp. 329-339 (8 pages).
Roger R. Beerli et al., Sortase Enzyme-Mediated Generation of Site-Specifically Conjugated Antibody Drug Conjugates with High In Vitro Potency, PLoS One, 2015, vol. 10, No. 7. e0131177, https://doi.org/10.1371/journal.pone.0131177 (17 pages).
Stanley T. Crooke et al. (1981), The anthracyclines, Cancer and Chemotherapy, vol. III, Antineoplastic Agents, Academic Press, Inc, Chapter 8, pp. 111-132 (13 pages).
Wim Dokter et al. (2014), Preclinical Profile of the HER2-Targeting ADC SYD983/SYD985: Introduction of a New Duocarmycin-Based Linker-Drug Platform, Molecular Cancer Therapeutics, vol. 13, No. 11, pp. 2618-2629 DOI: 10.1158/1535-7163.MCT-14-0040-T (13 pages).
Brent M. Dorr et al., Reprogramming the specificity of sortase enzymes, PNAS, 2014, vol. 111, No. 37, pp. 13343-13348, https://doi.org/10.1073/pnas.1411179111 (30 pages).
Laurent Ducry et al., Antibody-Drug Conjugates: Linking Cytotoxic Payloads to Monoclonal Antibodies, Bioconjugate Chem., 2010, vol. 21, No. 1, pp. 5-13, https://doi.org/10.1021/bc9002019 (9 pages).
European Office Action for Application No. 14710285.9, dated Nov. 8, 2017 (9 pages).
Extended European Search Report, dated Nov. 21, 2013, for Application No. 13159484.8. (11 pages).
John A. Hartley et al. (2012), Small molecule drugs—optimizing DNA damaging agent-based therapeutics, Curr. Opin. Pharmacol., vol. 12, No. 4, pp. 398-402 (5 pages).
International Search Report and Written Opinion for Application No. PCT/EP2014/055173, dated Oct. 24, 2014 (23 pages).
Jain Nareshkumar et al., Current ADC Linker Chemistry, Pharm Res., Nov. 2015, vol. 32, No. 11, pp. 3526-3540, doi: 10.1007/s11095-015-1657-7 (15 pages).
Japanese Office Action for Application No. 2015-562218, dated Nov. 7, 2017 (12 pages).
Patricia M. Lorusso et al., Trastuzumab Emtansine: A Unique Antibody-Drug Conjugate in Development for Human Epidermal Growth Factor Receptor 2-Positive Cancer, Clinical Cancer Research, 2011, vol. 17, No. 20, pp. 6437-6447 (12 pages).
A. Younes et al., Brentuximab Vedotin (SGN-35) for Relapsed CD30-Positive Lymphomas, New England Journal of Medicine, 2010, vol. 363, pp. 1812-1821 (10 pages).
Jessica R. Mccombs et al., Antibody Drug Conjugates: Design and Selection of Linker, Payload and Conjugation Chemistry, AAPS Journal, 2015, vol. 17, No. 2, pp. 339-351 (13 pages).
Asher Mullard et al., Maturing antibody-drug conjugates pipeline hits 30, Nature Rev. Drug Disc., 2013, vol. 12, pp. 329-332 (5 pages).
Siler Panowski et al., Site-specific antibody drug conjugates for cancer therapy, mAbs, (2014) vol. 6, No. 1, pp. 34-45 12 pages.
Heidi L. Perez et al., Antibody-drug conjugates: current status and future directions, Drug Discovery Today, vol. 19, No. 9, pp. 869-881, epub Dec. 2013 (13 pages).
Pfizer Oncology Press Release, "Pfizer Prepares for Voluntary Withdrawal of U.S. new Drug Application and for Discontinuation of Commercial Availability of Mylotarg®", Jun. 21, 2010 (6 pages).
Luigi Quintieri et al., Formation and Antitumor Activity of PNU-159682, A Major Metabolite of Nemorubicin in Human Liver Microsomes, Clinical Cancer Research, Feb. 15, 2005, vol. 11, No. 4, pp. 1608-1617 (11 pages).
Michael Roguska et al., Humanization of murine monoclonal antibodies through variable domain resurfacing, PNAS, Feb. 1994, vol. 91, No. 3, pp. 969-973 (5 pages).
Thomas Spirig et al., Sortase enzymes in Gram-positive bacteria, Mol. Microbial., 2011, vol. 82, No. 5, pp. 1044-1059 (16 pages).
Written Opinion for Singaporean Application No. 11201507385Y, dated Sep. 18, 2017 (12 pages).
Hang T. Ta et al., Enzymatic Antibody Tagging: Toward a Universal Biocompatible Targeting Tool, Trends in Cardiovascular Medicine, 2012, vol. 22, No. 4, pp. 105-111 (7 pages).
Antonio C. Wolff et al., Recommendations for Human Epidermal Growth Factor Receptor 2 Testing in Breast Cancer: American Society of Clinical Oncology/College of American Pathologists Clinical Practice Guideline Update, Journal of Clinjical Oncology, Nov. 1, 2013, vol. 31, No. 31, pp. 3997-4013 (18 pages).
Office Action issued in counterpart Japanese Patent Application No. 2015-562218 dated Jun. 7, 2022.
David A. Levary et al., Protein-Protein Fusion Catalyzed by Sortase A, PLOS One, Apr. 2011, vol. 6, No. 4 (6 pages).

(56) References Cited

OTHER PUBLICATIONS

Office Action for Brazilian Patent Application No. 122021025118-5, dated Mar. 25, 2023 (6 pages).
Office Action issued in counterpart Chinese Patent Application No. 202110883878.4 dated Apr. 17, 2023.
Office Action issued in counterpart Japanese Patent Application No. 2022-105670 dated Jun. 6, 2023.
Office Action issued in counterpart Chinese Patent Application No. 202110883878.4 dated Nov. 17, 2023.
Office Action issued in counterpart European Patent Application No. 14 710 285.9 dated Jan. 30, 2024.
Office Action issued in counterpart Japanese Patent Application No. 2020-15265 dated Oct. 3, 2023.
Levary, D. et al. "Protein-Protein Fusion Catalyzed by Sortase A," PLoS One, vol. 6, pp. 1-6 (Apr. 6, 2011).
Hang, T. et al. "Enzymatic Antibody Tagging: Toward a Universal Biocompatible Targeting Tool," TCM, vol. 22, pp. 105-111 (2012).
Chopra, A. "Radioiodinated humanized monoclonal antibody A33," Molecular Imaging and Contrast Agent Database (MICAD), pp. 1-6 (Sep. 16, 2007).
Sakamoto et al., Journal of the Society of Japan Surgical Engineers, vol. 22, pp. 555-561 (1997).

* cited by examiner $Gly_5$ - modified alpha-amanitin

Mass Spectral Analysis of $Gly_5$ - modified alpha-amanitin:

RP-HPLC Analysis of $Gly_5$ - modified alpha-amanitin:

Gly$_5$ - modified maytansine

Mass Spectral Analysis of Gly$_5$ - modified maytansine:

RP-HPLC Analysis of Gly$_5$ - modified maytansine:

structure 1:

Gly5-vc-PAB-MMAE structure 2:

Gly5-DM1 structure 3:

Gly5-DM4 structure 4:

Gly5-MMAE structure 5:

Gly5-MMAF structure 6:

Gly5-Maytansine structure 7:

Gly5 structure 8:

Gly5

Gly5-alpha-amanitin (II)

structure 9:

Gly5

Gly5-alpha-amanitin (III)

SEQUENCE LISTING

```
<160> NUMBER OF SEQ ID NOS: 58

<210> SEQ ID NO 1
<211> LENGTH: 417
<212> TYPE: DNA
<213> ORGANISM: Artificial Sequence
```

-continued

<220> FEATURE:
<223> OTHER INFORMATION: VH coding region of humanized anti-human CD19
      antibody hBU12

<400> SEQUENCE: 1
atgggatgga gctggatctt tcttttcctc ctgtcaggaa ctgcaggtgt ccattgtcag     60
gttcagctgc aagagtctgg ccctgggttg gttaagccct cccagaccct cagtctgact    120
tgtactgtgt ctggggggttc aatcagcact tctggtatgg gtgtaggctg gattaggcag    180
cacccaggga agggtctgga gtggattgga cacatttggt gggatgatga caagagatat    240
aacccagccc tgaagagcag agtgacaatc tctgtggata cctccaagaa ccagtttagc    300
ctcaagctgt ccagtgtgac agctgcagat actgctgtct actactgtgc tagaatggaa    360
ctttggtcct actattttga ctactggggc caaggcaccc ttgtcacagt ctcctca       417

<210> SEQ ID NO 2
<211> LENGTH: 139
<212> TYPE: PRT
<213> ORGANISM: Artificial Sequence
<220> FEATURE:
<223> OTHER INFORMATION: amino acid sequence of VH region of humanized
      anti-human CD19 antibody hBU12

<400> SEQUENCE: 2

Met Gly Trp Ser Trp Ile Phe Leu Phe Leu Leu Ser Gly Thr Ala Gly
1               5                   10                  15

Val His Cys Gln Val Gln Leu Gln Glu Ser Gly Pro Gly Leu Val Lys
            20                  25                  30

Pro Ser Gln Thr Leu Ser Leu Thr Cys Thr Val Ser Gly Gly Ser Ile
        35                  40                  45

Ser Thr Ser Gly Met Gly Val Gly Trp Ile Arg Gln His Pro Gly Lys
    50                  55                  60

Gly Leu Glu Trp Ile Gly His Ile Trp Trp Asp Asp Asp Lys Arg Tyr
65                  70                  75                  80

Asn Pro Ala Leu Lys Ser Arg Val Thr Ile Ser Val Asp Thr Ser Lys
                85                  90                  95

Asn Gln Phe Ser Leu Lys Leu Ser Ser Val Thr Ala Ala Asp Thr Ala
            100                 105                 110

Val Tyr Tyr Cys Ala Arg Met Glu Leu Trp Ser Tyr Tyr Phe Asp Tyr
        115                 120                 125

Trp Gly Gln Gly Thr Leu Val Thr Val Ser Ser
    130                 135

<210> SEQ ID NO 3
<211> LENGTH: 375
<212> TYPE: DNA
<213> ORGANISM: Artificial Sequence
<220> FEATURE:
<223> OTHER INFORMATION: VL coding region of humanized anti-human CD19
      antibody hBU12

<400> SEQUENCE: 3
atgaagttgc ctgttaggct gttggtgctg atgttctgga ttcctgcttc cagcagtgaa     60
attgttctca cccagtctcc agcaaccctg tctctctctc caggggaaag ggctaccctg    120
agctgcagtg ccagctcaag tgtaagttac atgcactggt accagcagaa gccagggcag    180
gctcccagac tcctgattta tgacacatcc aaactggctt ctggtattcc agcaaggttc    240
agtggcagtg ggtctggaac agattttaca ctcacaatca gcagcctgga gccagaggat    300

-continued gttgctgtct attactgttt tcaggggagt gtatacccat tcacttttgg ccaagggaca 360
aagttggaaa tcaaa 375

<210> SEQ ID NO 4
<211> LENGTH: 125
<212> TYPE: PRT
<213> ORGANISM: Artificial Sequence
<220> FEATURE:
<223> OTHER INFORMATION: amino acid sequence of VL region of humanized anti-human CD19 antibody hBU12

<400> SEQUENCE: 4

Met Lys Leu Pro Val Arg Leu Leu Val Leu Met Phe Trp Ile Pro Ala
1 5 10 15

Ser Ser Ser Glu Ile Val Leu Thr Gln Ser Pro Ala Thr Leu Ser Leu
20 25 30

Ser Pro Gly Glu Arg Ala Thr Leu Ser Cys Ser Ala Ser Ser Ser Val
35 40 45

Ser Tyr Met His Trp Tyr Gln Gln Lys Pro Gly Gln Ala Pro Arg Leu
50 55 60

Leu Ile Tyr Asp Thr Ser Lys Leu Ala Ser Gly Ile Pro Ala Arg Phe
65 70 75 80

Ser Gly Ser Gly Ser Gly Thr Asp Phe Thr Leu Thr Ile Ser Ser Leu
85 90 95

Glu Pro Glu Asp Val Ala Val Tyr Tyr Cys Phe Gln Gly Ser Val Tyr
100 105 110

Pro Phe Thr Phe Gly Gln Gly Thr Lys Leu Glu Ile Lys
115 120 125

<210> SEQ ID NO 5
<211> LENGTH: 1083
<212> TYPE: DNA
<213> ORGANISM: Artificial Sequence
<220> FEATURE:
<223> OTHER INFORMATION: human IgG1 heavy chain constant coding region with in-frame 3' extension encoding an LPETG sortase tag, an 6xHis tag and a strepII tag

<400> SEQUENCE: 5
agcaccaagg gcccatctgt cttccccctg gcaccctcct ccaagagcac ctctgggggc 60
acagctgccc tgggctgcct ggtcaaggac tacttccctg aacctgtgac agtgtcctgg 120
aactcaggcg ccctgaccag cggcgtgcac accttcccgg ctgtcctaca gtcctcagga 180
ctctactccc tcagcagcgt ggtgaccgtg ccctccagca gcttgggcac ccagacctac 240
atctgcaacg tgaatcacaa gcccagcaac accaaggtgg acaagaaagt tgagcccaaa 300
tcttgtgaca aaactcacac atgcccaccg tgcccagcac ctgaactcct ggggggaccg 360
tcagtcttcc tcttcccccc aaaacccaag gacaccctca tgatctcccg gacccctgag 420
gtcacatgcg tggtggtgga cgtgagccac gaagaccctg aggtcaagtt caactggtac 480
gtggacggcg tggaggtgca taatgccaag acaaagccgc gggaggagca gtacaacagc 540
acgtaccgtg tggtcagcgt cctcaccgtc ctgcaccagg actggctgaa tggcaaggag 600
tacaagtgca aggtctccaa caaagccctc ccagccccca tcgagaaaac catctccaaa 660
gccaaagggc agccccgaga accacaggtg tacaccctgc ccccatcccg ggatgagctg 720
accaagaacc aggtcagcct gacctgcctg gtcaaaggct tctatcccag cgacatcgcc 780
gtggagtggg agagcaatgg gcagccggag aacaactaca agaccacgcc tcccgtgctg 840

-continued

```
gactccgacg gctccttctt cctctacagc aagctcaccg tggacaagag caggtggcag    900

caggggaacg tcttctcatg ctccgtgatg catgaggctc tgcacaacca ctacacacag    960

aagagcctct ccctgtctcc gggtaaactg cccgagaccg gccaccacca ccaccaccac   1020

ggcgagcaga agctgatcag cgaggaggac ctgggctgga gccacccca gttcgagaag    1080

tag                                                                 1083


<210> SEQ ID NO 6
<211> LENGTH: 360
<212> TYPE: PRT
<213> ORGANISM: Artificial Sequence
<220> FEATURE:
<223> OTHER INFORMATION: amino acid sequence of human IgG1 heavy chain
      constant region with LPETG sortase tag, an 6xHis tag and a strepII
      tag

<400> SEQUENCE: 6

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Lys
                85                  90                  95

Val Glu Pro Lys Ser Cys Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300
```

-continued

```
Phe Ser Cys Ser Val Met His Glu Ala Leu His Asn His Tyr Thr Gln
305                 310                 315                 320

Lys Ser Leu Ser Leu Ser Pro Gly Lys Leu Pro Glu Thr Gly His His
                325                 330                 335

His His His His Gly Glu Gln Lys Leu Ile Ser Glu Glu Asp Leu Gly
            340                 345                 350

Trp Ser His Pro Gln Phe Glu Lys
        355                 360


<210> SEQ ID NO 7
<211> LENGTH: 414
<212> TYPE: DNA
<213> ORGANISM: Artificial Sequence
<220> FEATURE:
<223> OTHER INFORMATION: human IgG1 kappa light chain constant coding
      region with in-frame 3' extension encoding an LPETG sortase tag,
      an 6xHis tag and a strepII tag.

<400> SEQUENCE: 7

acggtggctg caccatctgt cttcatcttc ccgccatctg atgagcagtt gaaatctgga      60

actgcctctg ttgtgtgcct gctgaataac ttctatccca gagaggccaa agtacagtgg     120

aaggtggata acgccctcca atcgggtaac tcccaggaga gtgtcacaga gcaggacagc     180

aaggacagca cctacagcct cagcagcacc ctgacgctga gcaaagcaga ctacgagaaa     240

cacaaagtct acgcctgcga agtcacccat cagggcctga gctcgcccgt cacaaagagc     300

ttcaacaggg gagagtgtct gcccgagacc ggccaccacc accaccacca cggcgagcag     360

aagctgatca gcgaggagga cctgggctgg agccaccccc agttcgagaa gtag           414


<210> SEQ ID NO 8
<211> LENGTH: 137
<212> TYPE: PRT
<213> ORGANISM: Artificial Sequence
<220> FEATURE:
<223> OTHER INFORMATION: amino acid sequence of human IgG1 kappa light
      chain constant region with LPETG sortase tag, an 6xHis tag and a
      strepII tag.

<400> SEQUENCE: 8

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys Leu Pro Glu Thr Gly His
            100                 105                 110

His His His His His Gly Glu Gln Lys Leu Ile Ser Glu Glu Asp Leu
        115                 120                 125

Gly Trp Ser His Pro Gln Phe Glu Lys
    130                 135


<210> SEQ ID NO 9
```

-continued

<211> LENGTH: 1503
<212> TYPE: DNA
<213> ORGANISM: Artificial Sequence
<220> FEATURE:
<223> OTHER INFORMATION: Complete human IgG1 VH-CH heavy chain coding region for hBU12 with C-terminal LPETG sortase tag, 6xHis tag and a strepII tag

<400> SEQUENCE: 9

```
atgggatgga gctggatctt tcttttcctc ctgtcaggaa ctgcaggtgt ccattgtcag     60

gttcagctgc aagagtctgg ccctgggttg gttaagccct cccagaccct cagtctgact    120

tgtactgtgt ctggggggttc aatcagcact tctggtatgg gtgtaggctg gattaggcag    180

cacccaggga agggtctgga gtggattgga cacatttggt gggatgatga caagagatat    240

aacccagccc tgaagagcag agtgacaatc tctgtggata cctccaagaa ccagtttagc    300

ctcaagctgt ccagtgtgac agctgcagat actgctgtct actactgtgc tagaatggaa    360

ctttggtcct actattttga ctactggggc caaggcaccc ttgtcacagt ctcctcagct    420

agcaccaagg gcccatctgt cttccccctg gcaccctcct ccaagagcac ctctgggggc    480

acagctgccc tgggctgcct ggtcaaggac tacttccctg aacctgtgac agtgtcctgg    540

aactcaggcg ccctgaccag cggcgtgcac accttcccgg ctgtcctaca gtcctcagga    600

ctctactccc tcagcagcgt ggtgaccgtg ccctccagca gcttgggcac ccagacctac    660

atctgcaacg tgaatcacaa gcccagcaac accaaggtgg acaagaaagt tgagcccaaa    720

tcttgtgaca aaactcacac atgcccaccg tgcccagcac ctgaactcct ggggggaccg    780

tcagtcttcc tcttcccccc aaaacccaag gacaccctca tgatctcccg gacccctgag    840

gtcacatgcg tggtggtgga cgtgagccac gaagaccctg aggtcaagtt caactggtac    900

gtggacggcg tggaggtgca taatgccaag acaaagccgc gggaggagca gtacaacagc    960

acgtaccgtg tggtcagcgt cctcaccgtc ctgcaccagg actggctgaa tggcaaggag   1020

tacaagtgca aggtctccaa caaagccctc ccagccccca tcgagaaaac catctccaaa   1080

gccaaagggc agccccgaga accacaggtg tacaccctgc ccccatcccg ggatgagctg   1140

accaagaacc aggtcagcct gacctgcctg gtcaaaggct tctatcccag cgacatcgcc   1200

gtggagtggg agagcaatgg gcagccggag aacaactaca agaccacgcc tcccgtgctg   1260

gactccgacg gctccttctt cctctacagc aagctcaccg tggacaagag caggtggcag   1320

caggggaacg tcttctcatg ctccgtgatg catgaggctc tgcacaacca ctacacacag   1380

aagagcctct ccctgtctcc gggtaaactg cccgagaccg gccaccacca ccaccaccac   1440

ggcgagcaga agctgatcag cgaggaggac ctgggctgga gccacccccca gttcgagaag   1500

tag                                                                 1503
```

<210> SEQ ID NO 10
<211> LENGTH: 500
<212> TYPE: PRT
<213> ORGANISM: Artificial Sequence
<220> FEATURE:
<223> OTHER INFORMATION: amino acid sequence of complete human IgG1 VH-CH heavy chain region of hBU12 with C-terminal LPETG sortase tag, 6xHis tag and a strepII tag

<400> SEQUENCE: 10

```
Met Gly Trp Ser Trp Ile Phe Leu Phe Leu Leu Ser Gly Thr Ala Gly
1               5                   10                  15

Val His Cys Gln Val Gln Leu Gln Glu Ser Gly Pro Gly Leu Val Lys
            20                  25                  30
```

-continued

```
Pro Ser Gln Thr Leu Ser Leu Thr Cys Thr Val Ser Gly Gly Ser Ile
        35                  40                  45

Ser Thr Ser Gly Met Gly Val Gly Trp Ile Arg Gln His Pro Gly Lys
    50                  55                  60

Gly Leu Glu Trp Ile Gly His Ile Trp Trp Asp Asp Asp Lys Arg Tyr
65                  70                  75                  80

Asn Pro Ala Leu Lys Ser Arg Val Thr Ile Ser Val Asp Thr Ser Lys
                85                  90                  95

Asn Gln Phe Ser Leu Lys Leu Ser Ser Val Thr Ala Ala Asp Thr Ala
            100                 105                 110

Val Tyr Tyr Cys Ala Arg Met Glu Leu Trp Ser Tyr Tyr Phe Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445
```

```
Val Met His Glu Ala Leu His Asn His Tyr Thr Gln Lys Ser Leu Ser
    450                 455                 460

Leu Ser Pro Gly Lys Leu Pro Glu Thr Gly His His His His His His
465                 470                 475                 480

Gly Glu Gln Lys Leu Ile Ser Glu Glu Asp Leu Gly Trp Ser His Pro
                485                 490                 495

Gln Phe Glu Lys
            500
```

<210> SEQ ID NO 11
<211> LENGTH: 792
<212> TYPE: DNA
<213> ORGANISM: Artificial Sequence
<220> FEATURE:
<223> OTHER INFORMATION: Complete human IgG1 VL-CL kappa chain coding region for hBU12 with C-terminal LPETG sortase tag, 6xHis tag and a strepII tag

<400> SEQUENCE: 11

```
atgaagttgc ctgttaggct gttggtgctg atgttctgga ttcctgcttc cagcagtgaa     60

attgttctca cccagtctcc agcaaccctg tctctctctc caggggaaag ggctaccctg    120

agctgcagtg ccagctcaag tgtaagttac atgcactggt accagcagaa gccagggcag    180

gctcccagac tcctgattta tgacacatcc aaactggctt ctggtattcc agcaaggttc    240

agtggcagtg ggtctggaac agattttaca ctcacaatca gcagcctgga gccagaggat    300

gttgctgtct attactgttt tcaggggagt gtatacccat tcacttttgg ccaagggaca    360

aagttggaaa tcaaaagaac tgtggctgca ccatctgtct tcatcttccc gccatctgat    420

gagcagttga aatctggaac tgcctctgtt gtgtgcctgc tgaataactt ctatcccaga    480

gaggccaaag tacagtggaa ggtggataac gccctccaat cgggtaactc ccaggagagt    540

gtcacagagc aggacagcaa ggacagcacc tacagcctca gcagcaccct gacgctgagc    600

aaagcagact acgagaaaca caaagtctac gcctgcgaag tcacccatca gggcctgagc    660

tcgcccgtca caaagagctt caacagggga gagtgtctgc ccgagaccgg ccaccaccac    720

caccaccacg gcgagcagaa gctgatcagc gaggaggacc tgggctggag ccacccccag    780

ttcgagaagt ag                                                        792
```

<210> SEQ ID NO 12
<211> LENGTH: 263
<212> TYPE: PRT
<213> ORGANISM: Artificial Sequence
<220> FEATURE:
<223> OTHER INFORMATION: amino acid sequence of complete human IgG1 VL-CL kappa chain region of hBU12 with C-terminal LPETG sortase tag, 6xHis tag and a strepII tag

<400> SEQUENCE: 12

```
Met Lys Leu Pro Val Arg Leu Leu Val Leu Met Phe Trp Ile Pro Ala
1               5                   10                  15

Ser Ser Ser Glu Ile Val Leu Thr Gln Ser Pro Ala Thr Leu Ser Leu
            20                  25                  30

Ser Pro Gly Glu Arg Ala Thr Leu Ser Cys Ser Ala Ser Ser Ser Val
        35                  40                  45

Ser Tyr Met His Trp Tyr Gln Gln Lys Pro Gly Gln Ala Pro Arg Leu
    50                  55                  60

Leu Ile Tyr Asp Thr Ser Lys Leu Ala Ser Gly Ile Pro Ala Arg Phe
65                  70                  75                  80
```

-continued

```
Ser Gly Ser Gly Ser Gly Thr Asp Phe Thr Leu Thr Ile Ser Ser Leu
                85                  90                  95

Glu Pro Glu Asp Val Ala Val Tyr Tyr Cys Phe Gln Gly Ser Val Tyr
            100                 105                 110

Pro Phe Thr Phe Gly Gln Gly Thr Lys Leu Glu Ile Lys Arg Thr Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys Leu Pro Glu Thr Gly His His His
225                 230                 235                 240

His His His Gly Glu Gln Lys Leu Ile Ser Glu Glu Asp Leu Gly Trp
                245                 250                 255

Ser His Pro Gln Phe Glu Lys
            260
```

<210> SEQ ID NO 13
<211> LENGTH: 7045
<212> TYPE: DNA
<213> ORGANISM: Artificial Sequence
<220> FEATURE:
<223> OTHER INFORMATION: coding region of human IgG1 VH-CH heavy chain for hBU12 with C-terminal LPETG sortase tag, 6xHis tag and a strepII tag and HindIII and NotI cloning sites

<400> SEQUENCE: 13

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctagc    900

gtttaaactt aagcttccat gggatggagc tggatctttc ttttcctcct gtcaggaact    960
```

-continued

```
gcaggtgtcc attgtcaggt tcagctgcaa gagtctggcc ctgggttggt taagccctcc   1020

cagaccctca gtctgacttg tactgtgtct gggggttcaa tcagcacttc tggtatgggt   1080

gtaggctgga ttaggcagca cccagggaag ggtctggagt ggattggaca catttggtgg   1140

gatgatgaca agagatataa cccagccctg aagagcagag tgacaatctc tgtggatacc   1200

tccaagaacc agtttagcct caagctgtcc agtgtgacag ctgcagatac tgctgtctac   1260

tactgtgcta gaatggaact ttggtcctac tattttgact actggggcca aggcaccctt   1320

gtcacagtct cctcagctag caccaagggc ccatctgtct tccccctggc accctcctcc   1380

aagagcacct ctgggggcac agctgccctg ggctgcctgg tcaaggacta cttccctgaa   1440

cctgtgacag tgtcctggaa ctcaggcgcc ctgaccagcg gcgtgcacac cttcccggct   1500

gtcctacagt cctcaggact ctactccctc agcagcgtgg tgaccgtgcc ctccagcagc   1560

ttgggcaccc agacctacat ctgcaacgtg aatcacaagc ccagcaacac caaggtggac   1620

aagaaagttg agcccaaatc ttgtgacaaa actcacacat gcccaccgtg cccagcacct   1680

gaactcctgg ggggaccgtc agtcttcctc ttccccccaa aacccaagga caccctcatg   1740

atctcccgga cccctgaggt cacatgcgtg gtggtggacg tgagccacga agaccctgag   1800

gtcaagttca actggtacgt ggacggcgtg gaggtgcata atgccaagac aaagccgcgg   1860

gaggagcagt acaacagcac gtaccgtgtg gtcagcgtcc tcaccgtcct gcaccaggac   1920

tggctgaatg gcaaggagta caagtgcaag gtctccaaca aagccctccc agcccccatc   1980

gagaaaacca tctccaaagc caaagggcag ccccgagaac cacaggtgta caccctgccc   2040

ccatcccggg atgagctgac caagaaccag gtcagcctga cctgcctggt caaaggcttc   2100

tatcccagcg acatcgccgt ggagtgggag agcaatgggc agccggagaa caactacaag   2160

accacgcctc ccgtgctgga ctccgacggc tccttcttcc tctacagcaa gctcaccgtg   2220

gacaagagca ggtggcagca ggggaacgtc ttctcatgct ccgtgatgca tgaggctctg   2280

cacaaccact acacacagaa gagcctctcc ctgtctccgg gtaaactgcc cgagaccggc   2340

caccaccacc accaccacgg cgagcagaag ctgatcagcg aggaggacct gggctggagc   2400

cacccccagt tcgagaagta ggcggccgct cgagtctaga gggcccgttt aaacccgctg   2460

atcagcctcg actgtgcctt ctagttgcca gccatctgtt gtttgcccct cccccgtgcc   2520

ttccttgacc ctggaaggtg ccactcccac tgtcctttcc taataaaatg aggaaattgc   2580

atcgcattgt ctgagtaggt gtcattctat tctggggggt ggggtggggc aggacagcaa   2640

gggggaggat tgggaagaca atagcaggca tgctggggat gcggtgggct ctatggcttc   2700

tgaggcggaa agaaccagct ggggctctag ggggtatccc cacgcgccct gtagcggcgc   2760

attaagcgcg gcgggtgtgg tggttacgcg cagcgtgacc gctacacttg ccagcgccct   2820

agcgcccgct cctttcgctt tcttcccttc ctttctcgcc acgttcgccg gctttccccg   2880

tcaagctcta aatcgggggc tccctttagg gttccgattt agtgctttac ggcacctcga   2940

ccccaaaaaa cttgattagg gtgatggttc acgtagtggg ccatcgccct gatagacggt   3000

ttttcgccct ttgacgttgg agtccacgtt ctttaatagt ggactcttgt tccaaactgg   3060

aacaacactc aaccctatct cggtctattc ttttgattta taagggattt tggggatttc   3120

ggcctattgg ttaaaaaatg agctgattta acaaaaattt aacgcgaatt aattctgtgg   3180

aatgtgtgtc agttagggtg tggaaagtcc ccaggctccc caggcaggca gaagtatgca   3240

aagcatgcat ctcaattagt cagcaaccag gtgtggaaag tccccaggct ccccagcagg   3300
```

-continued

```
cagaagtatg caaagcatgc atctcaatta gtcagcaacc atagtcccgc ccctaactcc   3360
gcccatcccg cccctaactc cgcccagttc cgcccattct ccgccccatg gctgactaat   3420
ttttttattt tatgcagagg ccgaggccgc ctctgcctct gagctattcc agaagtagtg   3480
aggaggcttt tttggaggcc taggcttttg caaaaagctc ccgggagctt gtatatccat   3540
tttcggatct gatcagcacg tgatgaaaaa gcctgaactc accgcgacgt ctgtcgagaa   3600
gtttctgatc gaaaagttcg acagcgtctc cgacctgatg cagctctcgg agggcgaaga   3660
atctcgtgct ttcagcttcg atgtaggagg gcgtggatat gtcctgcggg taaatagctg   3720
cgccgatggt ttctacaaag atcgttatgt ttatcggcac tttgcatcgg ccgcgctccc   3780
gattccggaa gtgcttgaca ttggggaatt cagcgagagc ctgacctatt gcatctcccg   3840
ccgtgcacag ggtgtcacgt tgcaagacct gcctgaaacc gaactgcccg ctgttctgca   3900
gccggtcgcg gaggccatgg atgcgatcgc tgcggccgat cttagccaga cgagcgggtt   3960
cggcccattc ggaccgcaag gaatcggtca atacactaca tggcgtgatt tcatatgcgc   4020
gattgctgat ccccatgtgt atcactggca aactgtgatg gacgacaccg tcagtgcgtc   4080
cgtcgcgcag gctctcgatg agctgatgct ttgggccgag gactgccccg aagtccggca   4140
cctcgtgcac gcggatttcg gctccaacaa tgtcctgacg gacaatggcc gcataacagc   4200
ggtcattgac tggagcgagg cgatgttcgg ggattcccaa tacgaggtcg ccaacatctt   4260
cttctggagg ccgtggttgg cttgtatgga gcagcagacg cgctacttcg agcggaggca   4320
tccggagctt gcaggatcgc cgcggctccg ggcgtatatg ctccgcattg gtcttgacca   4380
actctatcag agcttggttg acggcaattt cgatgatgca gcttgggcgc agggtcgatg   4440
cgacgcaatc gtccgatccg gagccgggac tgtcgggcgt acacaaatcg cccgcagaag   4500
cgcggccgtc tggaccgatg gctgtgtaga agtactcgcc gatagtggaa accgacgccc   4560
cagcactcgt ccgagggcaa aggaatagca cgtgctacga gatttcgatt ccaccgccgc   4620
cttctatgaa aggttgggct tcggaatcgt tttccgggac gccggctgga tgatcctcca   4680
gcgcggggat ctcatgctgg agttcttcgc ccaccccaac ttgtttattg cagcttataa   4740
tggttacaaa taaagcaata gcatcacaaa tttcacaaat aaagcatttt tttcactgca   4800
ttctagttgt ggtttgtcca aactcatcaa tgtatcttat catgtctgta taccgtcgac   4860
ctctagctag agcttggcgt aatcatggtc atagctgttt cctgtgtgaa attgttatcc   4920
gctcacaatt ccacacaaca tacgagccgg aagcataaag tgtaaagcct ggggtgccta   4980
atgagtgagc taactcacat taattgcgtt gcgctcactg cccgctttcc agtcgggaaa   5040
cctgtcgtgc cagctgcatt aatgaatcgg ccaacgcgcg gggagaggcg gtttgcgtat   5100
tgggcgctct tccgcttcct cgctcactga ctcgctgcgc tcggtcgttc ggctgcggcg   5160
agcggtatca gctcactcaa aggcggtaat acggttatcc acagaatcag gggataacgc   5220
aggaaagaac atgtgagcaa aaggccagca aaaggccagg aaccgtaaaa aggccgcgtt   5280
gctggcgttt ttccataggc tccgcccccc tgacgagcat cacaaaaatc gacgctcaag   5340
tcagaggtgg cgaaacccga caggactata aagataccag gcgtttcccc ctggaagctc   5400
cctcgtgcgc tctcctgttc cgaccctgcc gcttaccgga tacctgtccg cctttctccc   5460
ttcgggaagc gtggcgcttt ctcaatgctc acgctgtagg tatctcagtt cggtgtaggt   5520
cgttcgctcc aagctgggct gtgtgcacga accccccgtt cagcccgacc gctgcgcctt   5580
atccggtaac tatcgtcttg agtccaaccc ggtaagacac gacttatcgc cactggcagc   5640
agccactggt aacaggatta gcagagcgag gtatgtaggc ggtgctacag agttcttgaa   5700
```

```
gtggtggcct aactacggct acactagaag gacagtattt ggtatctgcg ctctgctgaa   5760

gccagttacc ttcggaaaaa gagttggtag ctcttgatcc ggcaaacaaa ccaccgctgg   5820

tagcggtggt ttttttgttt gcaagcagca gattacgcgc agaaaaaaag gatctcaaga   5880

agatcctttg atcttttcta cggggtctga cgctcagtgg aacgaaaact cacgttaagg   5940

gattttggtc atgagattat caaaaaggat cttcacctag atccttttaa attaaaaatg   6000

aagttttaaa tcaatctaaa gtatatatga gtaaacttgg tctgacagtt accaatgctt   6060

aatcagtgag gcacctatct cagcgatctg tctatttcgt tcatccatag ttgcctgact   6120

ccccgtcgtg tagataacta cgatacggga gggcttacca tctggcccca gtgctgcaat   6180

gataccgcga gacccacgct caccggctcc agatttatca gcaataaacc agccagccgg   6240

aagggccgag cgcagaagtg gtcctgcaac tttatccgcc tccatccagt ctattaattg   6300

ttgccgggaa gctagagtaa gtagttcgcc agttaatagt ttgcgcaacg ttgttgccat   6360

tgctacaggc atcgtggtgt cacgctcgtc gtttggtatg gcttcattca gctccggttc   6420

ccaacgatca aggcgagtta catgatcccc catgttgtgc aaaaaagcgg ttagctcctt   6480

cggtcctccg atcgttgtca gaagtaagtt ggccgcagtg ttatcactca tggttatggc   6540

agcactgcat aattctctta ctgtcatgcc atccgtaaga tgcttttctg tgactggtga   6600

gtactcaacc aagtcattct gagaatagtg tatgcggcga ccgagttgct cttgcccggc   6660

gtcaatacgg gataataccg cgccacatag cagaacttta aaagtgctca tcattggaaa   6720

acgttcttcg gggcgaaaac tctcaaggat cttaccgctg ttgagatcca gttcgatgta   6780

acccactcgt gcacccaact gatcttcagc atcttttact ttcaccagcg tttctgggtg   6840

agcaaaaaca ggaaggcaaa atgccgcaaa aaagggaata agggcgacac ggaaatgttg   6900

aatactcata ctcttccttt ttcaatatta ttgaagcatt tatcagggtt attgtctcat   6960

gagcggatac atatttgaat gtatttagaa aaataaacaa ataggggttc cgcgcacatt   7020

tccccgaaaa gtgccacctg acgtc                                          7045
```

<210> SEQ ID NO 14
<211> LENGTH: 6334
<212> TYPE: DNA
<213> ORGANISM: Artificial Sequence
<220> FEATURE:
<223> OTHER INFORMATION: coding region of human IgG1 VL-CL kappa light chain for hBU12 with C-terminal LPETG sortase tag, 6xHis tag and a strepII tag and HindIII and NotI cloning sites

<400> SEQUENCE: 14

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600
```

```
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttccat gaagttgcct gttaggctgt tggtgctgat gttctggatt    960
cctgcttcca gcagtgaaat tgttctcacc cagtctccag caaccctgtc tctctctcca   1020
ggggaaaggg ctaccctgag ctgcagtgcc agctcaagtg taagttacat gcactggtac   1080
cagcagaagc cagggcaggc tcccagactc ctgatttatg acacatccaa actggcttct   1140
ggtattccag caaggttcag tggcagtggg tctggaacag attttacact cacaatcagc   1200
agcctggagc cagaggatgt tgctgtctat tactgttttc aggggagtgt atacccattc   1260
acttttggcc aagggacaaa gttggaaatc aaaagaactg tggctgcacc atctgtcttc   1320
atcttcccgc catctgatga gcagttgaaa tctggaactg cctctgttgt gtgcctgctg   1380
aataacttct atcccagaga ggccaaagta cagtggaagg tggataacgc cctccaatcg   1440
ggtaactccc aggagagtgt cacagagcag gacagcaagg acagcaccta cagcctcagc   1500
agcaccctga cgctgagcaa agcagactac gagaaacaca aagtctacgc ctgcgaagtc   1560
acccatcagg gcctgagctc gcccgtcaca aagagcttca acaggggaga gtgtctgccc   1620
gagaccggcc accaccacca ccaccacggc gagcagaagc tgatcagcga ggaggacctg   1680
ggctggagcc acccccagtt cgagaagtag gcggccgctc gagtctagag ggcccgttta   1740
aacccgctga tcagcctcga ctgtgccttc tagttgccag ccatctgttg tttgcccctc   1800
ccccgtgcct tccttgaccc tggaaggtgc cactcccact gtcctttcct aataaaatga   1860
ggaaattgca tcgcattgtc tgagtaggtg tcattctatt ctggggggtg gggtggggca   1920
ggacagcaag ggggaggatt gggaagacaa tagcaggcat gctggggatg cggtgggctc   1980
tatggcttct gaggcggaaa gaaccagctg gggctctagg gggtatcccc acgcgccctg   2040
tagcggcgca ttaagcgcgg cgggtgtggt ggttacgcgc agcgtgaccg ctacacttgc   2100
cagcgcccta gcgcccgctc ctttcgcttt cttcccttcc tttctcgcca cgttcgccgg   2160
ctttccccgt caagctctaa atcggggcat ccctttaggg ttccgattta gtgctttacg   2220
gcacctcgac cccaaaaaac ttgattaggg tgatggttca cgtagtgggc catcgccctg   2280
atagacggtt tttcgccctt tgacgttgga gtccacgttc tttaatagtg gactcttgtt   2340
ccaaactgga acaacactca accctatctc ggtctattct tttgatttat aagggatttt   2400
ggggatttcg gcctattggt taaaaaatga gctgatttaa caaaaattta acgcgaatta   2460
attctgtgga atgtgtgtca gttagggtgt ggaaagtccc caggctcccc aggcaggcag   2520
aagtatgcaa agcatgcatc tcaattagtc agcaaccagg tgtggaaagt ccccaggctc   2580
cccagcaggc agaagtatgc aaagcatgca tctcaattag tcagcaacca tagtcccgcc   2640
cctaactccg cccatcccgc ccctaactcc gcccagttcc gcccattctc cgccccatgg   2700
ctgactaatt ttttttattt atgcagaggc cgaggccgcc tctgcctctg agctattcca   2760
gaagtagtga ggaggctttt ttggaggcct aggcttttgc aaaaagctcc cgggagcttg   2820
tatatccatt ttcggatctg atcagcacgt gatgaaaaag cctgaactca ccgcgacgtc   2880
tgtcgagaag tttctgatcg aaaagttcga cagcgtctcc gacctgatgc agctctcgga   2940
gggcgaagaa tctcgtgctt tcagcttcga tgtaggaggg cgtggatatg tcctgcgggt   3000
```

-continued

```
aaatagctgc gccgatggtt tctacaaaga tcgttatgtt tatcggcact ttgcatcggc   3060
cgcgctcccg attccggaag tgcttgacat tggggaattc agcgagagcc tgacctattg   3120
catctcccgc cgtgcacagg gtgtcacgtt gcaagacctg cctgaaaccg aactgcccgc   3180
tgttctgcag ccggtcgcgg aggccatgga tgcgatcgct gcggccgatc ttagccagac   3240
gagcgggttc ggcccattcg gaccgcaagg aatcggtcaa tacactacat ggcgtgattt   3300
catatgcgcg attgctgatc cccatgtgta tcactggcaa actgtgatgg acgacaccgt   3360
cagtgcgtcc gtcgcgcagg ctctcgatga gctgatgctt tgggccgagg actgccccga   3420
agtccggcac ctcgtgcacg cggatttcgg ctccaacaat gtcctgacgg acaatggccg   3480
cataacagcg gtcattgact ggagcgaggc gatgttcggg gattcccaat acgaggtcgc   3540
caacatcttc ttctggaggc cgtggttggc ttgtatggag cagcagacgc gctacttcga   3600
gcggaggcat ccggagcttg caggatcgcc gcggctccgg gcgtatatgc tccgcattgg   3660
tcttgaccaa ctctatcaga gcttggttga cggcaatttc gatgatgcag cttgggcgca   3720
gggtcgatgc gacgcaatcg tccgatccgg agccgggact gtcgggcgta cacaaatcgc   3780
ccgcagaagc gcggccgtct ggaccgatgg ctgtgtagaa gtactcgccg atagtggaaa   3840
ccgacgcccc agcactcgtc cgagggcaaa ggaatagcac gtgctacgag atttcgattc   3900
caccgccgcc ttctatgaaa ggttgggctt cggaatcgtt ttccgggacg ccggctggat   3960
gatcctccag cgcggggatc tcatgctgga gttcttcgcc caccccaact tgtttattgc   4020
agcttataat ggttacaaat aaagcaatag catcacaaat ttcacaaata aagcattttt   4080
ttcactgcat tctagttgtg gtttgtccaa actcatcaat gtatcttatc atgtctgtat   4140
accgtcgacc tctagctaga gcttggcgta atcatggtca tagctgtttc ctgtgtgaaa   4200
ttgttatccg ctcacaattc cacacaacat acgagccgga agcataaagt gtaaagcctg   4260
gggtgcctaa tgagtgagct aactcacatt aattgcgttg cgctcactgc ccgctttcca   4320
gtcgggaaac ctgtcgtgcc agctgcatta atgaatcggc caacgcgcgg ggagaggcgg   4380
tttgcgtatt gggcgctctt ccgcttcctc gctcactgac tcgctgcgct cggtcgttcg   4440
gctgcggcga gcggtatcag ctcactcaaa ggcggtaata cggttatcca cagaatcagg   4500
ggataacgca ggaaagaaca tgtgagcaaa aggccagcaa aaggccagga accgtaaaaa   4560
ggccgcgttg ctggcgtttt tccataggct ccgcccccct gacgagcatc acaaaaatcg   4620
acgctcaagt cagaggtggc gaaacccgac aggactataa agataccagg cgtttccccc   4680
tggaagctcc ctcgtgcgct ctcctgttcc gaccctgccg cttaccggat acctgtccgc   4740
ctttctccct tcgggaagcg tggcgctttc tcaatgctca cgctgtaggt atctcagttc   4800
ggtgtaggtc gttcgctcca agctgggctg tgtgcacgaa ccccccgttc agcccgaccg   4860
ctgcgcctta tccggtaact atcgtcttga gtccaacccg gtaagacacg acttatcgcc   4920
actggcagca gccactggta acaggattag cagagcgagg tatgtaggcg gtgctacaga   4980
gttcttgaag tggtggccta actacggcta cactagaagg acagtatttg gtatctgcgc   5040
tctgctgaag ccagttacct tcggaaaaag agttggtagc tcttgatccg gcaaacaaac   5100
caccgctggt agcggtggtt tttttgtttg caagcagcag attacgcgca gaaaaaaagg   5160
atctcaagaa gatcctttga tcttttctac ggggtctgac gctcagtgga acgaaaactc   5220
acgttaaggg attttggtca tgagattatc aaaaaggatc ttcacctaga tccttttaaa   5280
ttaaaaatga agttttaaat caatctaaag tatatatgag taaacttggt ctgacagtta   5340
```

-continued

```
ccaatgctta atcagtgagg cacctatctc agcgatctgt ctatttcgtt catccatagt   5400

tgcctgactc cccgtcgtgt agataactac gatacgggag ggcttaccat ctggccccag   5460

tgctgcaatg ataccgcgag acccacgctc accggctcca gatttatcag caataaacca   5520

gccagccgga agggccgagc gcagaagtgg tcctgcaact ttatccgcct ccatccagtc   5580

tattaattgt tgccgggaag ctagagtaag tagttcgcca gttaatagtt tgcgcaacgt   5640

tgttgccatt gctacaggca tcgtggtgtc acgctcgtcg tttggtatgg cttcattcag   5700

ctccggttcc caacgatcaa ggcgagttac atgatccccc atgttgtgca aaaaagcggt   5760

tagctccttc ggtcctccga tcgttgtcag aagtaagttg gccgcagtgt tatcactcat   5820

ggttatggca gcactgcata attctcttac tgtcatgcca tccgtaagat gcttttctgt   5880

gactggtgag tactcaacca agtcattctg agaatagtgt atgcggcgac cgagttgctc   5940

ttgcccggcg tcaatacggg ataataccgc gccacatagc agaactttaa aagtgctcat   6000

cattggaaaa cgttcttcgg ggcgaaaact ctcaaggatc ttaccgctgt tgagatccag   6060

ttcgatgtaa cccactcgtg cacccaactg atcttcagca tcttttactt tcaccagcgt   6120

ttctgggtga gcaaaaacag gaaggcaaaa tgccgcaaaa aagggaataa gggcgacacg   6180

gaaatgttga atactcatac tcttcctttt tcaatattat tgaagcattt atcagggtta   6240

ttgtctcatg agcggataca tatttgaatg tatttagaaa aataaacaaa taggggttcc   6300

gcgcacattt ccccgaaaag tgccacctga cgtc                               6334
```

<210> SEQ ID NO 15
<211> LENGTH: 150
<212> TYPE: PRT
<213> ORGANISM: Artificial Sequence
<220> FEATURE:
<223> OTHER INFORMATION: amino acid sequence of the N-intein domain of Ssp GyrB 11 split-intein

<400> SEQUENCE: 15

```
Cys Phe Ser Gly Asp Thr Leu Val Ala Leu Thr Asp Gly Arg Ser Val
1               5                   10                  15

Ser Phe Glu Gln Leu Val Glu Glu Glu Lys Gln Gly Lys Gln Asn Phe
            20                  25                  30

Cys Tyr Thr Ile Arg His Asp Gly Ser Ile Gly Val Glu Lys Ile Ile
        35                  40                  45

Asn Ala Arg Lys Thr Lys Thr Asn Ala Lys Val Ile Lys Val Thr Leu
    50                  55                  60

Asp Asn Gly Glu Ser Ile Ile Cys Thr Pro Asp His Lys Phe Met Leu
65                  70                  75                  80

Arg Asp Gly Ser Tyr Lys Cys Ala Met Asp Leu Thr Leu Asp Asp Ser
                85                  90                  95

Leu Met Pro Leu His Arg Lys Ile Ser Thr Thr Glu Asp Ser Gly His
            100                 105                 110

Met Glu Ala Val Leu Asn Tyr Asn His Arg Ile Val Asn Ile Glu Ala
        115                 120                 125

Val Ser Glu Thr Ile Asp Val Tyr Asp Ile Glu Val Pro His Thr His
    130                 135                 140

Asn Phe Ala Leu Ala Ser
145                 150
```

<210> SEQ ID NO 16
<211> LENGTH: 450
<212> TYPE: DNA

<213> ORGANISM: Artificial Sequence
<220> FEATURE:
<223> OTHER INFORMATION: Reverse translation of SEQ ID NO 15 with mammalian codon usage results in the coding sequence for the N-intein domain of Ssp GyrB 11 split-intein

<400> SEQUENCE: 16

```
tgcttcagcg gcgacaccct ggtggccctg accgacggca gaagcgtgag cttcgagcag     60

ctggtggagg aggagaagca gggcaagcag aacttctgct acaccatcag acacgacggc    120

agcatcggcg tggagaagat catcaacgcc agaaagacca agaccaacgc caaggtgatc    180

aaggtgaccc tggacaacgg cgagagcatc atctgcaccc ccgaccacaa gttcatgctg    240

agagacggca gctacaagtg cgccatggac ctgaccctgg acgacagcct gatgcccctg    300

cacagaaaga tcagcaccac cgaggacagc ggccacatgg aggccgtgct gaactacaac    360

cacagaatcg tgaacatcga ggccgtgagc gagaccatcg acgtgtacga catcgaggtg    420

ccccacaccc acaacttcgc cctggccagc                                     450
```

<210> SEQ ID NO 17
<211> LENGTH: 1905
<212> TYPE: DNA
<213> ORGANISM: Artificial Sequence
<220> FEATURE:
<223> OTHER INFORMATION: complete IgG1 heavy chain coding region for anti-human CD19 antibody hBU12 with C-terminal extension, comprising the N-intein domain of Ssp GyrB 11 split-intein, followed by a 6xHis-tag and a strepII tag

<400> SEQUENCE: 17

```
atgaattttg gactgaggct gattttcctg gtgctgaccc tgaaaggcgt ccagtgtcag     60

gttcagctgc aagagtctgg ccctgggttg gttaagccct cccagaccct cagtctgact    120

tgtactgtgt ctggggggttc aatcagcact tctggtatgg gtgtaggctg gattaggcag    180

cacccaggga agggtctgga gtggattgga cacatttggt gggatgatga caagagatat    240

aacccagccc tgaagagcag agtgacaatc tctgtggata cctccaagaa ccagtttagc    300

ctcaagctgt ccagtgtgac agctgcagat actgctgtct actactgtgc tagaatggaa    360

ctttggtcct actattttga ctactggggc caaggcaccc ttgtcacagt ctcctcagct    420

agcaccaagg gcccatctgt cttccccctg gcaccctcct ccaagagcac ctctgggggc    480

acagctgccc tgggctgcct ggtcaaggac tacttccctg aacctgtgac agtgtcctgg    540

aactcaggcg ccctgaccag cggcgtgcac accttcccgg ctgtcctaca gtcctcagga    600

ctctactccc tcagcagcgt ggtgaccgtg ccctccagca gcttgggcac ccagacctac    660

atctgcaacg tgaatcacaa gcccagcaac accaaggtgg acaagaaagt tgagcccaaa    720

tcttgtgaca aaactcacac atgcccaccg tgcccagcac ctgaactcct ggggggaccg    780

tcagtcttcc tcttcccccc aaaacccaag gacaccctca tgatctcccg gacccctgag    840

gtcacatgcg tggtggtgga cgtgagccac gaagaccctg aggtcaagtt caactggtac    900

gtggacggcg tggaggtgca taatgccaag acaaagccgc gggaggagca gtacaacagc    960

acgtaccgtg tggtcagcgt cctcaccgtc ctgcaccagg actggctgaa tggcaaggag   1020

tacaagtgca aggtctccaa caaagccctc ccagccccca tcgagaaaac catctccaaa   1080

gccaaagggc agccccgaga accacaggtg tacaccctgc ccccatcccg ggatgagctg   1140

accaagaacc aggtcagcct gacctgcctg gtcaaaggct tctatcccag cgacatcgcc   1200

gtggagtggg agagcaatgg gcagccggag aacaactaca agaccacgcc tcccgtgctg   1260
```

```
gactccgacg gctccttctt cctctacagc aagctcaccg tggacaagag caggtggcag   1320

caggggaacg tcttctcatg ctccgtgatg catgaggctc tgcacaacca ctacacacag   1380

aagagcctct ccctgtctcc gggtaaatgc ttcagcggcg acaccctggt ggccctgacc   1440

gacggcagaa gcgtgagctt cgagcagctg gtggaggagg agaagcaggg caagcagaac   1500

ttctgctaca ccatcagaca cgacggcagc atcggcgtgg agaagatcat caacgccaga   1560

aagaccaaga ccaacgccaa ggtgatcaag gtgaccctgg acaacggcga gagcatcatc   1620

tgcacccccg accacaagtt catgctgaga gacggcagct acaagtgcgc catggacctg   1680

accctggacg acagcctgat gcccctgcac agaaagatca gcaccaccga ggacagcggc   1740

cacatggagg ccgtgctgaa ctacaaccac agaatcgtga acatcgaggc cgtgagcgag   1800

accatcgacg tgtacgacat cgaggtgccc cacacccaca acttcgccct ggccagccac   1860

catcaccatc accatggctg gagccacccc cagttcgaga agtag                   1905
```

```
<210> SEQ ID NO 18
<211> LENGTH: 634
<212> TYPE: PRT
<213> ORGANISM: Artificial Sequence
<220> FEATURE:
<223> OTHER INFORMATION: Amino acid sequence translated from SEQ ID NO
      17

<400> SEQUENCE: 18

Met Asn Phe Gly Leu Arg Leu Ile Phe Leu Val Leu Thr Leu Lys Gly
1               5                   10                  15

Val Gln Cys Gln Val Gln Leu Gln Glu Ser Gly Pro Gly Leu Val Lys
            20                  25                  30

Pro Ser Gln Thr Leu Ser Leu Thr Cys Thr Val Ser Gly Gly Ser Ile
        35                  40                  45

Ser Thr Ser Gly Met Gly Val Gly Trp Ile Arg Gln His Pro Gly Lys
    50                  55                  60

Gly Leu Glu Trp Ile Gly His Ile Trp Trp Asp Asp Asp Lys Arg Tyr
65                  70                  75                  80

Asn Pro Ala Leu Lys Ser Arg Val Thr Ile Ser Val Asp Thr Ser Lys
                85                  90                  95

Asn Gln Phe Ser Leu Lys Leu Ser Ser Val Thr Ala Ala Asp Thr Ala
            100                 105                 110

Val Tyr Tyr Cys Ala Arg Met Glu Leu Trp Ser Tyr Tyr Phe Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
```

-continued

```
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys Cys Phe Ser Gly Asp Thr Leu Val Ala Leu Thr
465                 470                 475                 480

Asp Gly Arg Ser Val Ser Phe Glu Gln Leu Val Glu Glu Glu Lys Gln
                485                 490                 495

Gly Lys Gln Asn Phe Cys Tyr Thr Ile Arg His Asp Gly Ser Ile Gly
            500                 505                 510

Val Glu Lys Ile Ile Asn Ala Arg Lys Thr Lys Thr Asn Ala Lys Val
        515                 520                 525

Ile Lys Val Thr Leu Asp Asn Gly Glu Ser Ile Ile Cys Thr Pro Asp
    530                 535                 540

His Lys Phe Met Leu Arg Asp Gly Ser Tyr Lys Cys Ala Met Asp Leu
545                 550                 555                 560

Thr Leu Asp Asp Ser Leu Met Pro Leu His Arg Lys Ile Ser Thr Thr
                565                 570                 575

Glu Asp Ser Gly His Met Glu Ala Val Leu Asn Tyr Asn His Arg Ile
            580                 585                 590

Val Asn Ile Glu Ala Val Ser Glu Thr Ile Asp Val Tyr Asp Ile Glu
        595                 600                 605

Val Pro His Thr His Asn Phe Ala Leu Ala Ser His His His His His
    610                 615                 620

His Gly Trp Ser His Pro Gln Phe Glu Lys
625                 630
```

<210> SEQ ID NO 19
<211> LENGTH: 1206
<212> TYPE: DNA
<213> ORGANISM: Artificial Sequence
<220> FEATURE:
<223> OTHER INFORMATION: complete IgG1 kappa light chain coding region for anti-human CD19 antibody hBU12 with C-terminal extension, comprising the N-intein domain of Ssp GyrB 11 split-intein, followed by a 6xHis-tag and a strepII tag

<400> SEQUENCE: 19

```
atgaattttg gactgaggct gattttcctg gtgctgaccc tgaaaggcgt ccagtgtgac     60
attgtgctga cccaatctcc agcttctttg gctgtgtctc tagggcagag ggccaccatc    120
tcctgcaagg ccagccaaag tgttgatttt gatggtgata gttatatgaa ctggtaccaa    180
cagaaaccag gacagccacc caaagtcctc atctatgctg catccaatct agaatctggg    240
atcccagcca ggtttagtgg cagtgggtct gggacagact tcaccctcaa catccatcct    300
gtggaggagg aggatgctgc aacctattac tgtcagcaaa gtaatgagga tccgtggacg    360
ttcggtggag gcaccaagct ggaaatcaaa cgtacggtgg ctgcaccatc tgtcttcatc    420
ttcccgccat ctgatgagca gttgaaatct ggaactgcct ctgttgtgtg cctgctgaat    480
aacttctatc ccagagaggc caaagtacag tggaaggtgg ataacgccct ccaatcgggt    540
aactcccagg agagtgtcac agagcaggac agcaaggaca gcacctacag cctcagcagc    600
accctgacgc tgagcaaagc agactacgag aaacacaaag tctacgcctg cgaagtcacc    660
catcagggcc tgagctcgcc cgtcacaaag agcttcaaca ggggagagtg cttcagcggc    720
gacaccctgg tggccctgac cgacggcaga agcgtgagct tcgagcagct ggtggaggag    780
gagaagcagg gcaagcagaa cttctgctac accatcagac acgacggcag catcggcgtg    840
gagaagatca tcaacgccag aaagaccaag accaacgcca aggtgatcaa ggtgaccctg    900
gacaacggcg agagcatcat ctgcaccccc gaccacaagt tcatgctgag agacggcagc    960
tacaagtgcg ccatggacct gaccctggac gacagcctga tgcccctgca cagaaagatc   1020
agcaccaccg aggacagcgg ccacatggag gccgtgctga actacaacca cagaatcgtg   1080
aacatcgagg ccgtgagcga gaccatcgac gtgtacgaca tcgaggtgcc ccacacccac   1140
aacttcgccc tggccagcca ccatcaccat caccatggct ggagccaccc ccagttcgag   1200
aagtag                                                              1206
```

<210> SEQ ID NO 20
<211> LENGTH: 401
<212> TYPE: PRT
<213> ORGANISM: Artificial Sequence
<220> FEATURE:
<223> OTHER INFORMATION: Amino acid sequence translated from SEQ ID NO 19

<400> SEQUENCE: 20

```
Met Asn Phe Gly Leu Arg Leu Ile Phe Leu Val Leu Thr Leu Lys Gly
1               5                   10                  15

Val Gln Cys Asp Ile Val Leu Thr Gln Ser Pro Ala Ser Leu Ala Val
            20                  25                  30

Ser Leu Gly Gln Arg Ala Thr Ile Ser Cys Lys Ala Ser Gln Ser Val
        35                  40                  45

Asp Phe Asp Gly Asp Ser Tyr Met Asn Trp Tyr Gln Gln Lys Pro Gly
    50                  55                  60

Gln Pro Pro Lys Val Leu Ile Tyr Ala Ala Ser Asn Leu Glu Ser Gly
65                  70                  75                  80

Ile Pro Ala Arg Phe Ser Gly Ser Gly Ser Gly Thr Asp Phe Thr Leu
                85                  90                  95
```

```
Asn Ile His Pro Val Glu Glu Glu Asp Ala Ala Thr Tyr Tyr Cys Gln
            100                 105                 110

Gln Ser Asn Glu Asp Pro Trp Thr Phe Gly Gly Gly Thr Lys Leu Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys Phe Ser Gly
225                 230                 235                 240

Asp Thr Leu Val Ala Leu Thr Asp Gly Arg Ser Val Ser Phe Glu Gln
                245                 250                 255

Leu Val Glu Glu Glu Lys Gln Gly Lys Gln Asn Phe Cys Tyr Thr Ile
            260                 265                 270

Arg His Asp Gly Ser Ile Gly Val Glu Lys Ile Ile Asn Ala Arg Lys
        275                 280                 285

Thr Lys Thr Asn Ala Lys Val Ile Lys Val Thr Leu Asp Asn Gly Glu
    290                 295                 300

Ser Ile Ile Cys Thr Pro Asp His Lys Phe Met Leu Arg Asp Gly Ser
305                 310                 315                 320

Tyr Lys Cys Ala Met Asp Leu Thr Leu Asp Asp Ser Leu Met Pro Leu
                325                 330                 335

His Arg Lys Ile Ser Thr Thr Glu Asp Ser Gly His Met Glu Ala Val
            340                 345                 350

Leu Asn Tyr Asn His Arg Ile Val Asn Ile Glu Ala Val Ser Glu Thr
        355                 360                 365

Ile Asp Val Tyr Asp Ile Glu Val Pro His Thr His Asn Phe Ala Leu
    370                 375                 380

Ala Ser His His His His His His Gly Trp Ser His Pro Gln Phe Glu
385                 390                 395                 400

Lys
```

<210> SEQ ID NO 21
<211> LENGTH: 7447
<212> TYPE: DNA
<213> ORGANISM: Artificial Sequence
<220> FEATURE:
<223> OTHER INFORMATION: coding region of human IgG1 VH-CH heavy chain for hBU12 with C-terminal N-intein domain of Ssp GyrB S11 split intein, followed by 6xHis tag strepII tag and HindIII and NotI cloning sites

<400> SEQUENCE: 21

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240
```

```
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttccat gaattttgga ctgaggctga ttttcctggt gctgaccctg    960
aaaggcgtcc agtgtcaggt tcagctgcaa gagtctggcc ctgggttggt taagccctcc   1020
cagaccctca gtctgacttg tactgtgtct gggggttcaa tcagcacttc tggtatgggt   1080
gtaggctgga ttaggcagca cccagggaag ggtctggagt ggattggaca catttggtgg   1140
gatgatgaca agagatataa cccagccctg aagagcagag tgacaatctc tgtggatacc   1200
tccaagaacc agtttagcct caagctgtcc agtgtgacag ctgcagatac tgctgtctac   1260
tactgtgcta gaatggaact ttggtcctac tattttgact actggggcca aggcaccctt   1320
gtcacagtct cctcagctag caccaagggc ccatctgtct tccccctggc accctcctcc   1380
aagagcacct ctgggggcac agctgccctg ggctgcctgg tcaaggacta cttccctgaa   1440
cctgtgacag tgtcctggaa ctcaggcgcc ctgaccagcg gcgtgcacac cttcccggct   1500
gtcctacagt cctcaggact ctactccctc agcagcgtgg tgaccgtgcc ctccagcagc   1560
ttgggcaccc agacctacat ctgcaacgtg aatcacaagc ccagcaacac caaggtggac   1620
aagaaagttg agcccaaatc ttgtgacaaa actcacacat gcccaccgtg cccagcacct   1680
gaactcctgg ggggaccgtc agtcttcctc ttccccccaa aacccaagga caccctcatg   1740
atctcccgga cccctgaggt cacatgcgtg gtggtggacg tgagccacga agaccctgag   1800
gtcaagttca actggtacgt ggacggcgtg gaggtgcata atgccaagac aaagccgcgg   1860
gaggagcagt acaacagcac gtaccgtgtg gtcagcgtcc tcaccgtcct gcaccaggac   1920
tggctgaatg gcaaggagta caagtgcaag gtctccaaca aagccctccc agcccccatc   1980
gagaaaacca tctccaaagc caaagggcag ccccgagaac cacaggtgta caccctgccc   2040
ccatcccggg atgagctgac caagaaccag gtcagcctga cctgcctggt caaaggcttc   2100
tatcccagcg acatcgccgt ggagtgggag agcaatgggc agccggagaa caactacaag   2160
accacgcctc ccgtgctgga ctccgacggc tccttcttcc tctacagcaa gctcaccgtg   2220
gacaagagca ggtggcagca ggggaacgtc ttctcatgct ccgtgatgca tgaggctctg   2280
cacaaccact acacacagaa gagcctctcc ctgtctccgg gtaaatgctt cagcggcgac   2340
accctggtgg ccctgaccga cggcagaagc gtgagcttcg agcagctggt ggaggaggag   2400
aagcagggca agcagaactt ctgctacacc atcagacacg acggcagcat cggcgtggag   2460
aagatcatca acgccagaaa gaccaagacc aacgccaagg tgatcaaggt gaccctggac   2520
aacggcgaga gcatcatctg cacccccgac cacaagttca tgctgagaga cggcagctac   2580
```

-continued

```
aagtgcgcca tggacctgac cctggacgac agcctgatgc ccctgcacag aaagatcagc   2640
accaccgagg acagcggcca catggaggcc gtgctgaact acaaccacag aatcgtgaac   2700
atcgaggccg tgagcgagac catcgacgtg tacgacatcg aggtgcccca cacccacaac   2760
ttcgccctgg ccagccacca tcaccatcac catggctgga gccacccccca gttcgagaag   2820
taggcggccg ctcgagtcta gagggcccgt ttaaacccgc tgatcagcct cgactgtgcc   2880
ttctagttgc cagccatctg ttgtttgccc ctcccccgtg ccttccttga ccctggaagg   2940
tgccactccc actgtccttt cctaataaaa tgaggaaatt gcatcgcatt gtctgagtag   3000
gtgtcattct attctggggg gtggggtggg gcaggacagc aagggggagg attgggaaga   3060
caatagcagg catgctgggg atgcggtggg ctctatggct tctgaggcgg aaagaaccag   3120
ctggggctct agggggtatc cccacgcgcc ctgtagcggc gcattaagcg cggcgggtgt   3180
ggtggttacg cgcagcgtga ccgctacact tgccagcgcc ctagcgcccg ctcctttcgc   3240
tttcttccct tcctttctcg ccacgttcgc cggctttccc cgtcaagctc taaatcgggg   3300
catcccttta gggttccgat ttagtgcttt acggcacctc gaccccaaaa aacttgatta   3360
gggtgatggt tcacgtagtg ggccatcgcc ctgatagacg gtttttcgcc ctttgacgtt   3420
ggagtccacg ttctttaata gtggactctt gttccaaact ggaacaacac tcaaccctat   3480
ctcggtctat tcttttgatt tataagggat tttggggatt tcggcctatt ggttaaaaaa   3540
tgagctgatt taacaaaaat ttaacgcgaa ttaattctgt ggaatgtgtg tcagttaggg   3600
tgtggaaagt ccccaggctc cccaggcagg cagaagtatg caaagcatgc atctcaatta   3660
gtcagcaacc aggtgtggaa agtccccagg ctccccagca ggcagaagta tgcaaagcat   3720
gcatctcaat tagtcagcaa ccatagtccc gcccctaact ccgcccatcc cgcccctaac   3780
tccgcccagt tccgcccatt ctccgcccca tggctgacta attttttta tttatgcaga   3840
ggccgaggcc gcctctgcct ctgagctatt ccagaagtag tgaggaggct tttttggagg   3900
cctaggcttt tgcaaaaagc tcccgggagc ttgtatatcc attttcggat ctgatcagca   3960
cgtgatgaaa aagcctgaac tcaccgcgac gtctgtcgag aagtttctga tcgaaaagtt   4020
cgacagcgtc tccgacctga tgcagctctc ggagggcgaa gaatctcgtg ctttcagctt   4080
cgatgtagga gggcgtggat atgtcctgcg ggtaaatagc tgcgccgatg gtttctacaa   4140
agatcgttat gtttatcggc actttgcatc ggccgcgctc ccgattccgg aagtgcttga   4200
cattggggaa ttcagcgaga gcctgaccta ttgcatctcc cgccgtgcac agggtgtcac   4260
gttgcaagac ctgcctgaaa ccgaactgcc cgctgttctg cagccggtcg cggaggccat   4320
ggatgcgatc gctgcggccg atcttagcca gacgagcggg ttcggcccat tcggaccgca   4380
aggaatcggt caatacacta catggcgtga tttcatatgc gcgattgctg atccccatgt   4440
gtatcactgg caaactgtga tggacgacac cgtcagtgcg tccgtcgcgc aggctctcga   4500
tgagctgatg ctttgggccg aggactgccc cgaagtccgg cacctcgtgc acgcggattt   4560
cggctccaac aatgtcctga cggacaatgg ccgcataaca gcggtcattg actggagcga   4620
ggcgatgttc ggggattccc aatacgaggt cgccaacatc ttcttctgga ggccgtggtt   4680
ggcttgtatg gagcagcaga cgcgctactt cgagcggagg catccggagc ttgcaggatc   4740
gccgcggctc cgggcgtata tgctccgcat tggtcttgac caactctatc agagcttggt   4800
tgacggcaat ttcgatgatg cagcttgggc gcagggtcga tgcgacgcaa tcgtccgatc   4860
cggagccggg actgtcgggc gtacacaaat cgcccgcaga agcgcggccg tctggaccga   4920
tggctgtgta gaagtactcg ccgatagtgg aaaccgacgc cccagcactc gtccgagggc   4980
```

```
aaaggaatag cacgtgctac gagatttcga ttccaccgcc gccttctatg aaaggttggg   5040
cttcggaatc gttttccggg acgccggctg gatgatcctc cagcgcgggg atctcatgct   5100
ggagttcttc gcccacccca acttgtttat tgcagcttat aatggttaca aataaagcaa   5160
tagcatcaca aatttcacaa ataaagcatt tttttcactg cattctagtt gtggtttgtc   5220
caaactcatc aatgtatctt atcatgtctg tataccgtcg acctctagct agagcttggc   5280
gtaatcatgg tcatagctgt ttcctgtgtg aaattgttat ccgctcacaa ttccacacaa   5340
catacgagcc ggaagcataa agtgtaaagc ctggggtgcc taatgagtga gctaactcac   5400
attaattgcg ttgcgctcac tgcccgcttt ccagtcggga aacctgtcgt gccagctgca   5460
ttaatgaatc ggccaacgcg cggggagagg cggtttgcgt attgggcgct cttccgcttc   5520
ctcgctcact gactcgctgc gctcggtcgt tcggctgcgg cgagcggtat cagctcactc   5580
aaaggcggta atacggttat ccacagaatc aggggataac gcaggaaaga acatgtgagc   5640
aaaaggccag caaaaggcca ggaaccgtaa aaaggccgcg ttgctggcgt ttttccatag   5700
gctccgcccc cctgacgagc atcacaaaaa tcgacgctca agtcagaggt ggcgaaaccc   5760
gacaggacta taaagatacc aggcgtttcc ccctggaagc tccctcgtgc gctctcctgt   5820
tccgaccctg ccgcttaccg gatacctgtc cgcctttctc ccttcgggaa gcgtggcgct   5880
ttctcaatgc tcacgctgta ggtatctcag ttcggtgtag gtcgttcgct ccaagctggg   5940
ctgtgtgcac gaaccccccg ttcagcccga ccgctgcgcc ttatccggta actatcgtct   6000
tgagtccaac ccggtaagac acgacttatc gccactggca gcagccactg gtaacaggat   6060
tagcagagcg aggtatgtag gcggtgctac agagttcttg aagtggtggc ctaactacgg   6120
ctacactaga aggacagtat ttggtatctg cgctctgctg aagccagtta ccttcggaaa   6180
aagagttggt agctcttgat ccggcaaaca aaccaccgct ggtagcggtg gtttttttgt   6240
ttgcaagcag cagattacgc gcagaaaaaa aggatctcaa gaagatcctt tgatcttttc   6300
tacggggtct gacgctcagt ggaacgaaaa ctcacgttaa gggattttgg tcatgagatt   6360
atcaaaaagg atcttcacct agatcctttt aaattaaaaa tgaagtttta aatcaatcta   6420
aagtatatat gagtaaactt ggtctgacag ttaccaatgc ttaatcagtg aggcacctat   6480
ctcagcgatc tgtctatttc gttcatccat agttgcctga ctccccgtcg tgtagataac   6540
tacgatacgg gagggcttac catctggccc cagtgctgca atgataccgc gagacccacg   6600
ctcaccggct ccagatttat cagcaataaa ccagccagcc ggaagggccg agcgcagaag   6660
tggtcctgca actttatccg cctccatcca gtctattaat tgttgccggg aagctagagt   6720
aagtagttcg ccagttaata gtttgcgcaa cgttgttgcc attgctacag gcatcgtggt   6780
gtcacgctcg tcgtttggta tggcttcatt cagctccggt tcccaacgat caaggcgagt   6840
tacatgatcc cccatgttgt gcaaaaaagc ggttagctcc ttcggtcctc cgatcgttgt   6900
cagaagtaag ttggccgcag tgttatcact catggttatg gcagcactgc ataattctct   6960
tactgtcatg ccatccgtaa gatgcttttc tgtgactggt gagtactcaa ccaagtcatt   7020
ctgagaatag tgtatgcggc gaccgagttg ctcttgcccg gcgtcaatac gggataatac   7080
cgcgccacat agcagaactt taaaagtgct catcattgga aaacgttctt cggggcgaaa   7140
actctcaagg atcttaccgc tgttgagatc cagttcgatg taacccactc gtgcacccaa   7200
ctgatcttca gcatctttta ctttcaccag cgtttctggg tgagcaaaaa caggaaggca   7260
aaatgccgca aaaaagggaa taagggcgac acggaaatgt tgaatactca tactcttcct   7320
```

ttttcaatat tattgaagca tttatcaggg ttattgtctc atgagcggat acatatttga 7380
atgtatttag aaaaataaac aaataggggt tccgcgcaca tttccccgaa aagtgccacc 7440
tgacgtc 7447

<210> SEQ ID NO 22
<211> LENGTH: 6748
<212> TYPE: DNA
<213> ORGANISM: Artificial Sequence
<220> FEATURE:
<223> OTHER INFORMATION: coding region of human IgG1 VL-CL kappa light chain for hBU12 with C-terminal Ssp GyrB S11 N-intein domain, 6xHis tag and a strepII tag, and HindIII and NotI cloning sites

<400> SEQUENCE: 22
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gctggctagc 900
gtttaaactt aagcttccat gaattttgga ctgaggctga ttttcctggt gctgaccctg 960
aaaggcgtcc agtgtgacat tgtgctgacc caatctccag cttctttggc tgtgtctcta 1020
gggcagaggg ccaccatctc ctgcaaggcc agccaaagtg ttgattttga tggtgatagt 1080
tatatgaact ggtaccaaca gaaaccagga cagccaccca aagtcctcat ctatgctgca 1140
tccaatctag aatctgggat cccagccagg tttagtggca gtgggtctgg gacagacttc 1200
accctcaaca tccatcctgt ggaggaggag gatgctgcaa cctattactg tcagcaaagt 1260
aatgaggatc cgtggacgtt cggtggaggc accaagctgg aaatcaaacg tacggtggct 1320
gcaccatctg tcttcatctt cccgccatct gatgagcagt tgaaatctgg aactgcctct 1380
gttgtgtgcc tgctgaataa cttctatccc agagaggcca aagtacagtg gaaggtggat 1440
aacgccctcc aatcgggtaa ctcccaggag agtgtcacag agcaggacag caaggacagc 1500
acctacagcc tcagcagcac cctgacgctg agcaaagcag actacgagaa acacaaagtc 1560
tacgcctgcg aagtcaccca tcagggcctg agctcgcccg tcacaaagag cttcaacagg 1620
ggagagtgct tcagcggcga caccctggtg gccctgaccg acggcagaag cgtgagcttc 1680
gagcagctgg tggaggagga gaagcagggc aagcagaact tctgctacac catcagacac 1740
gacggcagca tcggcgtgga gaagatcatc aacgccagaa agaccaagac caacgccaag 1800
gtgatcaagg tgaccctgga caacggcgag agcatcatct gcacccccga ccacaagttc 1860

-continued

```
atgctgagag acggcagcta caagtgcgcc atggacctga ccctggacga cagcctgatg   1920
cccctgcaca gaaagatcag caccaccgag gacagcggcc acatggaggc cgtgctgaac   1980
tacaaccaca gaatcgtgaa catcgaggcc gtgagcgaga ccatcgacgt gtacgacatc   2040
gaggtgcccc acacccacaa cttcgccctg gccagccacc atcaccatca ccatggctgg   2100
agccaccccc agttcgagaa gtaggcggcc gctcgagtct agagggcccg tttaaacccg   2160
ctgatcagcc tcgactgtgc cttctagttg ccagccatct gttgtttgcc cctcccccgt   2220
gccttccttg accctggaag gtgccactcc cactgtcctt tcctaataaa atgaggaaat   2280
tgcatcgcat tgtctgagta ggtgtcattc tattctgggg ggtggggtgg ggcaggacag   2340
caagggggag gattgggaag acaatagcag gcatgctggg gatgcggtgg gctctatggc   2400
ttctgaggcg gaaagaacca gctggggctc taggggggtat ccccacgcgc cctgtagcgg   2460
cgcattaagc gcggcgggtg tggtggttac gcgcagcgtg accgctacac ttgccagcgc   2520
cctagcgccc gctcctttcg ctttcttccc ttcctttctc gccacgttcg ccggctttcc   2580
ccgtcaagct ctaaatcggg gcatcccttt agggttccga tttagtgctt tacggcacct   2640
cgaccccaaa aaacttgatt agggtgatgg ttcacgtagt gggccatcgc cctgatagac   2700
ggtttttcgc cctttgacgt tggagtccac gttctttaat agtggactct tgttccaaac   2760
tggaacaaca ctcaacccta tctcggtcta ttcttttgat ttataaggga ttttggggat   2820
ttcggcctat tggttaaaaa atgagctgat ttaacaaaaa tttaacgcga attaattctg   2880
tggaatgtgt gtcagttagg gtgtggaaag tccccaggct ccccaggcag gcagaagtat   2940
gcaaagcatg catctcaatt agtcagcaac caggtgtgga aagtccccag gctccccagc   3000
aggcagaagt atgcaaagca tgcatctcaa ttagtcagca accatagtcc cgcccctaac   3060
tccgcccatc ccgcccctaa ctccgcccag ttccgcccat tctccgcccc atggctgact   3120
aattttttt atttatgcag aggccgaggc cgcctctgcc tctgagctat tccagaagta   3180
gtgaggaggc ttttttggag gcctaggctt ttgcaaaaag ctcccgggag cttgtatatc   3240
cattttcgga tctgatcagc acgtgatgaa aaagcctgaa ctcaccgcga cgtctgtcga   3300
gaagtttctg atcgaaaagt tcgacagcgt ctccgacctg atgcagctct cggagggcga   3360
agaatctcgt gctttcagct tcgatgtagg agggcgtgga tatgtcctgc gggtaaatag   3420
ctgcgccgat ggtttctaca aagatcgtta tgtttatcgg cactttgcat cggccgcgct   3480
cccgattccg gaagtgcttg acattgggga attcagcgag agcctgacct attgcatctc   3540
ccgccgtgca cagggtgtca cgttgcaaga cctgcctgaa accgaactgc ccgctgttct   3600
gcagccggtc gcggaggcca tggatgcgat cgctgcggcc gatcttagcc agacgagcgg   3660
gttcggccca ttcggaccgc aaggaatcgg tcaatacact acatggcgtg atttcatatg   3720
cgcgattgct gatccccatg tgtatcactg gcaaactgtg atggacgaca ccgtcagtgc   3780
gtccgtcgcg caggctctcg atgagctgat gctttgggcc gaggactgcc ccgaagtccg   3840
gcacctcgtg cacgcggatt tcggctccaa caatgtcctg acggacaatg gccgcataac   3900
agcggtcatt gactggagcg aggcgatgtt cggggattcc caatacgagg tcgccaacat   3960
cttcttctgg aggccgtggt tggcttgtat ggagcagcag acgcgctact tcgagcggag   4020
gcatccggag cttgcaggat cgccgcggct ccgggcgtat atgctccgca ttggtcttga   4080
ccaactctat cagagcttgg ttgacggcaa tttcgatgat gcagcttggg cgcagggtcg   4140
atgcgacgca atcgtccgat ccggagccgg gactgtcggg cgtacacaaa tcgcccgcag   4200
```

-continued

```
aagcgcggcc gtctggaccg atggctgtgt agaagtactc gccgatagtg gaaaccgacg   4260
ccccagcact cgtccgaggg caaaggaata gcacgtgcta cgagatttcg attccaccgc   4320
cgccttctat gaaaggttgg gcttcggaat cgttttccgg gacgccggct ggatgatcct   4380
ccagcgcggg gatctcatgc tggagttctt cgcccacccc aacttgttta ttgcagctta   4440
taatggttac aaataaagca atagcatcac aaatttcaca aataaagcat ttttttcact   4500
gcattctagt tgtggtttgt ccaaactcat caatgtatct tatcatgtct gtataccgtc   4560
gacctctagc tagagcttgg cgtaatcatg gtcatagctg tttcctgtgt gaaattgtta   4620
tccgctcaca attccacaca acatacgagc cggaagcata aagtgtaaag cctggggtgc   4680
ctaatgagtg agctaactca cattaattgc gttgcgctca ctgcccgctt tccagtcggg   4740
aaacctgtcg tgccagctgc attaatgaat cggccaacgc gcggggagag gcggtttgcg   4800
tattgggcgc tcttccgctt cctcgctcac tgactcgctg cgctcggtcg ttcggctgcg   4860
gcgagcggta tcagctcact caaaggcggt aatacggtta tccacagaat caggggataa   4920
cgcaggaaag aacatgtgag caaaaggcca gcaaaaggcc aggaaccgta aaaaggccgc   4980
gttgctggcg tttttccata ggctccgccc ccctgacgag catcacaaaa atcgacgctc   5040
aagtcagagg tggcgaaacc cgacaggact ataaagatac caggcgtttc cccctggaag   5100
ctccctcgtg cgctctcctg ttccgaccct gccgcttacc ggatacctgt ccgcctttct   5160
cccttcggga agcgtggcgc tttctcaatg ctcacgctgt aggtatctca gttcggtgta   5220
ggtcgttcgc tccaagctgg gctgtgtgca cgaacccccc gttcagcccg accgctgcgc   5280
cttatccggt aactatcgtc ttgagtccaa cccggtaaga cacgacttat cgccactggc   5340
agcagccact ggtaacagga ttagcagagc gaggtatgta ggcggtgcta cagagttctt   5400
gaagtggtgg cctaactacg gctacactag aaggacagta tttggtatct gcgctctgct   5460
gaagccagtt accttcggaa aaagagttgg tagctcttga tccggcaaac aaaccaccgc   5520
tggtagcggt ggtttttttg tttgcaagca gcagattacg cgcagaaaaa aaggatctca   5580
agaagatcct ttgatctttt ctacggggtc tgacgctcag tggaacgaaa actcacgtta   5640
agggattttg gtcatgagat tatcaaaaag gatcttcacc tagatccttt taaattaaaa   5700
atgaagtttt aaatcaatct aaagtatata tgagtaaact tggtctgaca gttaccaatg   5760
cttaatcagt gaggcaccta tctcagcgat ctgtctattt cgttcatcca tagttgcctg   5820
actccccgtc gtgtagataa ctacgatacg ggagggctta ccatctggcc ccagtgctgc   5880
aatgataccg cgagacccac gctcaccggc tccagattta tcagcaataa accagccagc   5940
cggaagggcc gagcgcagaa gtggtcctgc aactttatcc gcctccatcc agtctattaa   6000
ttgttgccgg gaagctagag taagtagttc gccagttaat agtttgcgca acgttgttgc   6060
cattgctaca ggcatcgtgg tgtcacgctc gtcgtttggt atggcttcat tcagctccgg   6120
ttcccaacga tcaaggcgag ttacatgatc ccccatgttg tgcaaaaaag cggttagctc   6180
cttcggtcct ccgatcgttg tcagaagtaa gttggccgca gtgttatcac tcatggttat   6240
ggcagcactg cataattctc ttactgtcat gccatccgta agatgctttt ctgtgactgg   6300
tgagtactca accaagtcat tctgagaata gtgtatgcgg cgaccgagtt gctcttgccc   6360
ggcgtcaata cgggataata ccgcgccaca tagcagaact ttaaaagtgc tcatcattgg   6420
aaaacgttct tcggggcgaa aactctcaag gatcttaccg ctgttgagat ccagttcgat   6480
gtaacccact cgtgcaccca actgatcttc agcatctttt actttcacca gcgtttctgg   6540
gtgagcaaaa acaggaaggc aaaatgccgc aaaaaaggga ataagggcga cacggaaatg   6600
```

ttgaatactc atactcttcc tttttcaata ttattgaagc atttatcagg gttattgtct 6660
catgagcgga tacatatttg aatgtattta gaaaaataaa caaatagggg ttccgcgcac 6720
atttccccga aaagtgccac ctgacgtc 6748

<210> SEQ ID NO 23
<211> LENGTH: 206
<212> TYPE: PRT
<213> ORGANISM: Artificial Sequence
<220> FEATURE:
<223> OTHER INFORMATION: amino acid sequence of sortase A from Staphylococcus aureus

<400> SEQUENCE: 23

```
Met Lys Lys Trp Thr Asn Arg Leu Met Thr Ile Ala Gly Val Val Leu
1               5                   10                  15

Ile Leu Val Ala Ala Tyr Leu Phe Ala Lys Pro His Ile Asp Asn Tyr
            20                  25                  30

Leu His Asp Lys Asp Lys Asp Glu Lys Ile Glu Gln Tyr Asp Lys Asn
        35                  40                  45

Val Lys Glu Gln Ala Ser Lys Asp Lys Lys Gln Gln Ala Lys Pro Gln
    50                  55                  60

Ile Pro Lys Asp Lys Ser Lys Val Ala Gly Tyr Ile Glu Ile Pro Asp
65                  70                  75                  80

Ala Asp Ile Lys Glu Pro Val Tyr Pro Gly Pro Ala Thr Pro Glu Gln
                85                  90                  95

Leu Asn Arg Gly Val Ser Phe Ala Glu Glu Asn Glu Ser Leu Asp Asp
            100                 105                 110

Gln Asn Ile Ser Ile Ala Gly His Thr Phe Ile Asp Arg Pro Asn Tyr
        115                 120                 125

Gln Phe Thr Asn Leu Lys Ala Ala Lys Lys Gly Ser Met Val Tyr Phe
    130                 135                 140

Lys Val Gly Asn Glu Thr Arg Lys Tyr Lys Met Thr Ser Ile Arg Asp
145                 150                 155                 160

Val Lys Pro Thr Asp Val Gly Val Leu Asp Glu Gln Lys Gly Lys Asp
                165                 170                 175

Lys Gln Leu Thr Leu Ile Thr Cys Asp Asp Tyr Asn Glu Lys Thr Gly
            180                 185                 190

Val Trp Glu Lys Arg Lys Ile Phe Val Ala Thr Glu Val Lys
        195                 200                 205
```

<210> SEQ ID NO 24
<211> LENGTH: 621
<212> TYPE: DNA
<213> ORGANISM: Artificial Sequence
<220> FEATURE:
<223> OTHER INFORMATION: Nucleotide sequence encoding for SEQ ID NO 23

<400> SEQUENCE: 24
atgaaaaaat ggacaaatcg attaatgaca atcgctggtg tggtacttat cctagtggca 60
gcatatttgt ttgctaaacc acatatcgat aattatcttc acgataaaga taaagatgaa 120
aagattgaac aatatgataa aaatgtaaaa gaacaggcga gtaaagataa aaagcagcaa 180
gctaaacctc aaattccgaa agataaatcg aaagtggcag gctatattga aattccagat 240
gctgatatta aagaaccagt atatccagga ccagcaacac ctgaacaatt aaatagaggt 300
gtaagctttg cagaagaaaa tgaatcacta gatgatcaaa atatttcaat tgcaggacac 360

```
actttcattg accgtccgaa ctatcaattt acaaatctta aagcagccaa aaaaggtagt    420

atggtgtact ttaaagttgg taatgaaaca cgtaagtata aaatgacaag tataagagat    480

gttaagccta cagatgtagg agttctagat gaacaaaaag gtaaagataa acaattaaca    540

ttaattactt gtgatgatta caatgaaaag acaggcgttt gggaaaaacg taaaatcttt    600

gtagctacag aagtcaaata a                                              621
```

```
<210> SEQ ID NO 25
<211> LENGTH: 465
<212> TYPE: DNA
<213> ORGANISM: Artificial Sequence
<220> FEATURE:
<223> OTHER INFORMATION: coding region for a 6xHis tagged version of
      Staphylococcus aureus sortase A (aa60-205)

<400> SEQUENCE: 25

atgcaagcta aacctcaaat tccgaaagat aaatcgaaag tggcaggcta tattgaaatt     60

ccagatgctg atattaaaga accagtatat ccaggaccag caacacctga acaattaaat    120

agaggtgtaa gctttgcaga agaaaatgaa tcactagatg atcaaaatat ttcaattgca    180

ggacacactt tcattgaccg tccgaactat caatttacaa atcttaaagc agccaaaaaa    240

ggtagtatgg tgtactttaa agttggtaat gaaacacgta agtataaaat gacaagtata    300

agagatgtta agcctacaga tgtaggagtt ctagatgaac aaaaaggtaa agataaacaa    360

ttaacattaa ttacttgtga tgattacaat gaaaagacag gcgtttggga aaaacgtaaa    420

atctttgtag ctacagaagt caaacaccat caccatcacc attaa                    465
```

```
<210> SEQ ID NO 26
<211> LENGTH: 154
<212> TYPE: PRT
<213> ORGANISM: Artificial Sequence
<220> FEATURE:
<223> OTHER INFORMATION: Amino acid sequence translated from SEQ ID NO
      25

<400> SEQUENCE: 26

Met Gln Ala Lys Pro Gln Ile Pro Lys Asp Lys Ser Lys Val Ala Gly
1               5                   10                  15

Tyr Ile Glu Ile Pro Asp Ala Asp Ile Lys Glu Pro Val Tyr Pro Gly
            20                  25                  30

Pro Ala Thr Pro Glu Gln Leu Asn Arg Gly Val Ser Phe Ala Glu Glu
        35                  40                  45

Asn Glu Ser Leu Asp Asp Gln Asn Ile Ser Ile Ala Gly His Thr Phe
    50                  55                  60

Ile Asp Arg Pro Asn Tyr Gln Phe Thr Asn Leu Lys Ala Ala Lys Lys
65                  70                  75                  80

Gly Ser Met Val Tyr Phe Lys Val Gly Asn Glu Thr Arg Lys Tyr Lys
                85                  90                  95

Met Thr Ser Ile Arg Asp Val Lys Pro Thr Asp Val Gly Val Leu Asp
            100                 105                 110

Glu Gln Lys Gly Lys Asp Lys Gln Leu Thr Leu Ile Thr Cys Asp Asp
        115                 120                 125

Tyr Asn Glu Lys Thr Gly Val Trp Glu Lys Arg Lys Ile Phe Val Ala
    130                 135                 140

Thr Glu Val Lys His His His His His His
145                 150
```

<210> SEQ ID NO 27
<211> LENGTH: 1401
<212> TYPE: DNA
<213> ORGANISM: Artificial Sequence
<220> FEATURE:
<223> OTHER INFORMATION: Nucleotide sequence of mAb Ac10 Heavy Chain

<400> SEQUENCE: 27 atgaatttg gactgaggct gattttcctg gtgctgaccc tgaaaggcgt ccagtgtcag 60
atccagctgc agcagtctgg ccccgaggtc gtgaaacctg gcgcctccgt gaagatctcc 120
tgcaaggcct ccggctacac cttcaccgac tactacatca cctgggtcaa gcagaagccc 180
ggccagggcc tggaatggat cggctggatc tatcccggct ccggcaacac caagtacaac 240
gagaagttca agggcaaggc caccctgacc gtggacacct cctcttccac cgccttcatg 300
cagctgtcct ccctgacctc cgaggatacc gccgtgtact tctgcgccaa ctacggcaac 360
tattggttcg cctactgggg ccagggcaca caagtgaccg tgtctgctgc tagcaccaag 420
ggcccatcgg tcttcccct ggcaccctcc tccaagagca cctctggggg cacagcagcc 480
ctgggctgcc tggtcaagga ctacttcccc gaaccggtga cggtgtcgtg gaactcaggc 540
gccctgacca gcggcgtgca caccttcccg gctgtcctac agtcctcagg actctactcc 600
ctcagcagcg tggtgaccgt gccctccagc agcttgggca cccagaccta catctgcaac 660
gtgaatcaca agcccagcaa caccaaggtg gacaagaaag ttgagcccaa atcttgtgac 720
aaaactcaca catgcccacc gtgcccagca cctgaactcc tggggggacc gtcagtcttc 780
ctcttccccc caaaacccaa ggacaccctc atgatctccc ggacccctga ggtcacatgc 840
gtggtggtgg acgtgagcca cgaagaccct gaggtcaagt tcaactggta cgtggacggc 900
gtggaggtgc ataatgccaa gacaaagccg cgggaggagc agtacaacag cacgtaccgt 960
gtggtcagcg tcctcaccgt cctgcaccag gactggctga atggcaagga gtacaagtgc 1020
aaggtctcca acaaagccct cccagccccc atcgagaaaa ccatctccaa agccaaaggg 1080
cagccccgag aaccacaggt gtacaccctg cccccatccc gggatgagct gaccaagaac 1140
caggtcagcc tgacctgcct ggtcaaaggc ttctatccca gcgacatcgc cgtggagtgg 1200
gagagcaatg ggcagccgga gaacaactac aagaccacgc ctcccgtgct ggactccgac 1260
ggctccttct tcctctacag caagctcacc gtggacaaga gcaggtggca gcaggggaac 1320
gtcttctcat gctccgtgat gcatgaggct ctgcacaacc actacacaca gaagagcctc 1380
tccctgtctc cgggtaaata g 1401

<210> SEQ ID NO 28
<211> LENGTH: 466
<212> TYPE: PRT
<213> ORGANISM: Artificial Sequence
<220> FEATURE:
<223> OTHER INFORMATION: AMINO ACID SEQUENCE OF MAB AC10 HEAVY CHAIN

<400> SEQUENCE: 28

Met Asn Phe Gly Leu Arg Leu Ile Phe Leu Val Leu Thr Leu Lys Gly
1 5 10 15

Val Gln Cys Gln Ile Gln Leu Gln Gln Ser Gly Pro Glu Val Val Lys
20 25 30

Pro Gly Ala Ser Val Lys Ile Ser Cys Lys Ala Ser Gly Tyr Thr Phe
35 40 45

Thr Asp Tyr Tyr Ile Thr Trp Val Lys Gln Lys Pro Gly Gln Gly Leu
50 55 60

-continued

```
Glu Trp Ile Gly Trp Ile Tyr Pro Gly Ser Gly Asn Thr Lys Tyr Asn
65                  70                  75                  80

Glu Lys Phe Lys Gly Lys Ala Thr Leu Thr Val Asp Thr Ser Ser Ser
                85                  90                  95

Thr Ala Phe Met Gln Leu Ser Ser Leu Thr Ser Glu Asp Thr Ala Val
            100                 105                 110

Tyr Phe Cys Ala Asn Tyr Gly Asn Tyr Trp Phe Ala Tyr Trp Gly Gln
        115                 120                 125

Gly Thr Gln Val Thr Val Ser Ala Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465
```

<210> SEQ ID NO 29
<211> LENGTH: 714
<212> TYPE: DNA
<213> ORGANISM: Artificial Sequence
<220> FEATURE:
<223> OTHER INFORMATION: Nucleotide sequence of mAb Ac10 Light Chain

<400> SEQUENCE: 29

```
atgaattttg gactgaggct gattttcctg gtgctgaccc tgaaaggcgt ccagtgtgac      60

attgtgctga cccaatctcc agcttctttg gctgtgtctc tagggcagag ggccaccatc     120

tcctgcaagg ccagccaaag tgttgatttt gatggtgata gttatatgaa ctggtaccaa     180

cagaaaccag gacagccacc caaagtcctc atctatgctg catccaatct agaatctggg     240

atcccagcca ggtttagtgg cagtgggtct gggacagact tcaccctcaa catccatcct     300

gtggaggagg aggatgctgc aacctattac tgtcagcaaa gtaatgagga tccgtggacg     360

ttcggtggag gcaccaagct ggaaatcaaa cgtacggtgg ctgcaccatc tgtcttcatc     420

ttcccgccat ctgatgagca gttgaaatct ggaactgcct ctgttgtgtg cctgctgaat     480

aacttctatc ccagagaggc caaagtacag tggaaggtgg ataacgccct ccaatcgggt     540

aactcccagg agagtgtcac agagcaggac agcaaggaca gcacctacag cctcagcagc     600

accctgacgc tgagcaaagc agactacgag aaacacaaag tctacgcctg cgaagtcacc     660

catcagggcc tgagctcgcc cgtcacaaag agcttcaaca ggggagagtg ttag           714
```

<210> SEQ ID NO 30
<211> LENGTH: 237
<212> TYPE: PRT
<213> ORGANISM: Artificial Sequence
<220> FEATURE:
<223> OTHER INFORMATION: Amino acid sequence of mAb Ac10 Light Chain

<400> SEQUENCE: 30

```
Met Asn Phe Gly Leu Arg Leu Ile Phe Leu Val Leu Thr Leu Lys Gly
1               5                   10                  15

Val Gln Cys Asp Ile Val Leu Thr Gln Ser Pro Ala Ser Leu Ala Val
            20                  25                  30

Ser Leu Gly Gln Arg Ala Thr Ile Ser Cys Lys Ala Ser Gln Ser Val
        35                  40                  45

Asp Phe Asp Gly Asp Ser Tyr Met Asn Trp Tyr Gln Gln Lys Pro Gly
    50                  55                  60

Gln Pro Pro Lys Val Leu Ile Tyr Ala Ala Ser Asn Leu Glu Ser Gly
65                  70                  75                  80

Ile Pro Ala Arg Phe Ser Gly Ser Gly Ser Gly Thr Asp Phe Thr Leu
                85                  90                  95

Asn Ile His Pro Val Glu Glu Glu Asp Ala Ala Thr Tyr Tyr Cys Gln
            100                 105                 110

Gln Ser Asn Glu Asp Pro Trp Thr Phe Gly Gly Gly Thr Lys Leu Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190
```

```
Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235


<210> SEQ ID NO 31
<211> LENGTH: 1422
<212> TYPE: DNA
<213> ORGANISM: Artificial Sequence
<220> FEATURE:
<223> OTHER INFORMATION: Nucleotide sequence of Trastuzumab Heavy Chain

<400> SEQUENCE: 31

atgaaaaaaa acattgcctt tctgctggcc tccatgttcg tgttctctat cgccacaaac      60

gcttacgctg aagtccagct ggtcgaatct ggtggtggcc tggtccagcc tggtggatca     120

ctgagactgt cctgtgctgc ttctggtttc aacatcaagg acacctacat ccattgggtc     180

agacaggcac ctggcaaggg actggaatgg gtcgcccgaa tctaccctac aaacggctac     240

actcgctacg ccgactccgt caagggacgc tttaccatct ccgccgacac ctctaaaaac     300

accgcctacc tgcagatgaa tagtctgagg gccgaggata ctgctgtgta ctactgctca     360

cgatggggag gcgacggctt ttacgctatg gattactggg gacagggaac tctggtcact     420

gtgtctagcg ctagcaccaa gggcccatcg gtcttccccc tggcaccctc ctccaagagc     480

acctctgggg gcacagcagc cctgggctgc ctggtcaagg actacttccc cgaaccggtg     540

acggtgtcgt ggaactcagg cgccctgacc agcggcgtgc acaccttccc ggctgtccta     600

cagtcctcag gactctactc cctcagcagc gtggtgaccg tgccctccag cagcttgggc     660

acccagacct acatctgcaa cgtgaatcac aagcccagca acaccaaggt ggacaagaaa     720

gttgagccca aatcttgtga caaaactcac acatgcccac cgtgcccagc acctgaactc     780

ctggggggac cgtcagtctt cctcttcccc ccaaaaccca aggacaccct catgatctcc     840

cggacccctg aggtcacatg cgtggtggtg gacgtgagcc acgaagaccc tgaggtcaag     900

ttcaactggt acgtggacgg cgtggaggtg cataatgcca agacaaagcc gcgggaggag     960

cagtacaaca gcacgtaccg tgtggtcagc gtcctcaccg tcctgcacca ggactggctg    1020

aatggcaagg agtacaagtg caaggtctcc aacaaagccc tcccagcccc catcgagaaa    1080

accatctcca aagccaaagg gcagccccga gaaccacagg tgtacaccct gcccccatcc    1140

cgggatgagc tgaccaagaa ccaggtcagc ctgacctgcc tggtcaaagg cttctatccc    1200

agcgacatcg ccgtggagtg ggagagcaat gggcagccgg agaacaacta caagaccacg    1260

cctcccgtgc tggactccga cggctccttc ttcctctaca gcaagctcac cgtggacaag    1320

agcaggtggc agcaggggaa cgtcttctca tgctccgtga tgcatgaggc tctgcacaac    1380

cactacacac agaagagcct ctccctgtct ccgggtaaat ag                       1422


<210> SEQ ID NO 32
<211> LENGTH: 473
<212> TYPE: PRT
<213> ORGANISM: Artificial Sequence
<220> FEATURE:
<223> OTHER INFORMATION: Amino acid sequence of Trastuzumab Heavy Chain

<400> SEQUENCE: 32

Met Lys Lys Asn Ile Ala Phe Leu Leu Ala Ser Met Phe Val Phe Ser
1               5                   10                  15
```

-continued

```
Ile Ala Thr Asn Ala Tyr Ala Glu Val Gln Leu Val Glu Ser Gly Gly
            20                  25                  30

Gly Leu Val Gln Pro Gly Gly Ser Leu Arg Leu Ser Cys Ala Ala Ser
        35                  40                  45

Gly Phe Asn Ile Lys Asp Thr Tyr Ile His Trp Val Arg Gln Ala Pro
    50                  55                  60

Gly Lys Gly Leu Glu Trp Val Ala Arg Ile Tyr Pro Thr Asn Gly Tyr
65                  70                  75                  80

Thr Arg Tyr Ala Asp Ser Val Lys Gly Arg Phe Thr Ile Ser Ala Asp
                85                  90                  95

Thr Ser Lys Asn Thr Ala Tyr Leu Gln Met Asn Ser Leu Arg Ala Glu
            100                 105                 110

Asp Thr Ala Val Tyr Tyr Cys Ser Arg Trp Gly Gly Asp Gly Phe Tyr
        115                 120                 125

Ala Met Asp Tyr Trp Gly Gln Gly Thr Leu Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430
```

-continued

```
Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470


<210> SEQ ID NO 33
<211> LENGTH: 1491
<212> TYPE: DNA
<213> ORGANISM: Artificial Sequence
<220> FEATURE:
<223> OTHER INFORMATION: Nucleotide sequence of Trastuzumab Heavy Chain
      with C-terminal GS peptide spacer, LPETG sortase A recognition
      motif and additional 6x-His and strep-II affinity purification
      tags

<400> SEQUENCE: 33

atgaaaaaaa acattgcctt tctgctggcc tccatgttcg tgttctctat cgccacaaac     60

gcttacgctg aagtccagct ggtcgaatct ggtggtggcc tggtccagcc tggtggatca    120

ctgagactgt cctgtgctgc ttctggtttc aacatcaagg acacctacat ccattgggtc    180

agacaggcac ctggcaaggg actggaatgg gtcgcccgaa tctaccctac aaacggctac    240

actcgctacg ccgactccgt caagggacgc tttaccatct ccgccgacac ctctaaaaac    300

accgcctacc tgcagatgaa tagtctgagg gccgaggata ctgctgtgta ctactgctca    360

cgatggggag gcgacggctt ttacgctatg gattactggg gacagggaac tctggtcact    420

gtgtctagcg ctagcaccaa gggcccatcg gtcttccccc tggcaccctc ctccaagagc    480

acctctgggg gcacagcagc cctgggctgc ctggtcaagg actacttccc cgaaccggtg    540

acggtgtcgt ggaactcagg cgccctgacc agcggcgtgc acaccttccc ggctgtccta    600

cagtcctcag gactctactc cctcagcagc gtggtgaccg tgccctccag cagcttgggc    660

acccagacct acatctgcaa cgtgaatcac aagcccagca acaccaaggt ggacaagaaa    720

gttgagccca aatcttgtga caaaactcac acatgcccac cgtgcccagc acctgaactc    780

ctggggggac cgtcagtctt cctcttcccc ccaaaaccca aggacaccct catgatctcc    840

cggacccctg aggtcacatg cgtggtggtg gacgtgagcc acgaagaccc tgaggtcaag    900

ttcaactggt acgtggacgg cgtggaggtg cataatgcca agacaaagcc gcgggaggag    960

cagtacaaca gcacgtaccg tgtggtcagc gtcctcaccg tcctgcacca ggactggctg   1020

aatggcaagg agtacaagtg caaggtctcc aacaaagccc tcccagcccc catcgagaaa   1080

accatctcca aagccaaagg gcagccccga gaaccacagg tgtacaccct gcccccatcc   1140

cgggatgagc tgaccaagaa ccaggtcagc ctgacctgcc tggtcaaagg cttctatccc   1200

agcgacatcg ccgtggagtg ggagagcaat gggcagccgg agaacaacta caagaccacg   1260

cctcccgtgc tggactccga cggctccttc ttcctctaca gcaagctcac cgtggacaag   1320

agcaggtggc agcaggggaa cgtcttctca tgctccgtga tgcatgaggc tctgcacaac   1380

cactacacac agaagagcct ctccctgtct ccgggtaaag gatccctgcc cgagaccggc   1440

ggacaccatc accatcacca tggctggagc cacccccagt tcgagaagta g            1491


<210> SEQ ID NO 34
<211> LENGTH: 496
<212> TYPE: PRT
<213> ORGANISM: Artificial Sequence
<220> FEATURE:
<223> OTHER INFORMATION: Amino acid sequence of Trastuzumab Heavy Chain
```

-continued with C-terminal GS peptide spacer, LPETG sortase A recognition
motif and additional 6x-His and strep-II affinity purification
tags

<400> SEQUENCE: 34

```
Met Lys Lys Asn Ile Ala Phe Leu Leu Ala Ser Met Phe Val Phe Ser
1               5                   10                  15

Ile Ala Thr Asn Ala Tyr Ala Glu Val Gln Leu Val Glu Ser Gly Gly
            20                  25                  30

Gly Leu Val Gln Pro Gly Gly Ser Leu Arg Leu Ser Cys Ala Ala Ser
        35                  40                  45

Gly Phe Asn Ile Lys Asp Thr Tyr Ile His Trp Val Arg Gln Ala Pro
    50                  55                  60

Gly Lys Gly Leu Glu Trp Val Ala Arg Ile Tyr Pro Thr Asn Gly Tyr
65                  70                  75                  80

Thr Arg Tyr Ala Asp Ser Val Lys Gly Arg Phe Thr Ile Ser Ala Asp
                85                  90                  95

Thr Ser Lys Asn Thr Ala Tyr Leu Gln Met Asn Ser Leu Arg Ala Glu
            100                 105                 110

Asp Thr Ala Val Tyr Tyr Cys Ser Arg Trp Gly Gly Asp Gly Phe Tyr
        115                 120                 125

Ala Met Asp Tyr Trp Gly Gln Gly Thr Leu Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
```

385 390 395 400

Ser Asp Ile Ala Val Glu Trp Glu Ser Asn Gly Gln Pro Glu Asn Asn
405 410 415

Tyr Lys Thr Thr Pro Pro Val Leu Asp Ser Asp Gly Ser Phe Phe Leu
420 425 430

Tyr Ser Lys Leu Thr Val Asp Lys Ser Arg Trp Gln Gln Gly Asn Val
435 440 445

Phe Ser Cys Ser Val Met His Glu Ala Leu His Asn His Tyr Thr Gln
450 455 460

Lys Ser Leu Ser Leu Ser Pro Gly Lys Gly Ser Leu Pro Glu Thr Gly
465 470 475 480

Gly His His His His His His Gly Trp Ser His Pro Gln Phe Glu Lys
485 490 495

<210> SEQ ID NO 35
<211> LENGTH: 714
<212> TYPE: DNA
<213> ORGANISM: Artificial Sequence
<220> FEATURE:
<223> OTHER INFORMATION: Nucleotide sequence of Trastuzumab Light Chain

<400> SEQUENCE: 35
atgaaaaaaa acattgcctt tctgctggcc tccatgttcg tgttctctat cgccacaaat 60
gcttatgccg acatccagat gacacagtct ccctcttccc tgtccgcttc tgtgggcgat 120
cgagtgacaa tcacctgtag ggctagtcag gatgtgaata ctgctgttgc ttggtaccag 180
cagaaaccag gaaaagcccc taaactgctg atctactctg cctcattcct gtactctggg 240
gtgccttctc gattcagtgg ttctagatct ggcaccgatt tcacactgac catttcttca 300
ctgcaacctg aggattttgc cacctactac tgtcagcagc actacacaac acctcccaca 360
tttggccagg gcacaaaagt ggagatcaaa cgtacggtgg ctgcaccatc tgtcttcatc 420
ttcccgccat ctgatgagca gttgaaatct ggaactgcct ctgttgtgtg cctgctgaat 480
aacttctatc ccagagaggc caaagtacag tggaaggtgg ataacgccct ccaatcgggt 540
aactcccagg agagtgtcac agagcaggac agcaaggaca gcacctacag cctcagcagc 600
accctgacgc tgagcaaagc agactacgag aaacacaaag tctacgcctg cgaagtcacc 660
catcagggcc tgagctcgcc cgtcacaaag agcttcaaca ggggagagtg ttag 714

<210> SEQ ID NO 36
<211> LENGTH: 237
<212> TYPE: PRT
<213> ORGANISM: Artificial Sequence
<220> FEATURE:
<223> OTHER INFORMATION: Amino acid sequence of Trastuzumab Light Chain

<400> SEQUENCE: 36

Met Lys Lys Asn Ile Ala Phe Leu Leu Ala Ser Met Phe Val Phe Ser
1 5 10 15

Ile Ala Thr Asn Ala Tyr Ala Asp Ile Gln Met Thr Gln Ser Pro Ser
20 25 30

Ser Leu Ser Ala Ser Val Gly Asp Arg Val Thr Ile Thr Cys Arg Ala
35 40 45

Ser Gln Asp Val Asn Thr Ala Val Ala Trp Tyr Gln Gln Lys Pro Gly
50 55 60

Lys Ala Pro Lys Leu Leu Ile Tyr Ser Ala Ser Phe Leu Tyr Ser Gly
65 70 75 80

```
Val Pro Ser Arg Phe Ser Gly Ser Arg Ser Gly Thr Asp Phe Thr Leu
                85                  90                  95

Thr Ile Ser Ser Leu Gln Pro Glu Asp Phe Ala Thr Tyr Tyr Cys Gln
            100                 105                 110

Gln His Tyr Thr Thr Pro Pro Thr Phe Gly Gln Gly Thr Lys Val Glu
        115                 120                 125

Ile Lys Arg Thr Val Ala Ala Pro Ser Val Phe Ile Phe Pro Pro Ser
130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
210                 215                 220

Ser Ser Pro Val Thr Lys Ser Phe Asn Arg Gly Glu Cys
225                 230                 235
```

<210> SEQ ID NO 37
<211> LENGTH: 783
<212> TYPE: DNA
<213> ORGANISM: Artificial Sequence
<220> FEATURE:
<223> OTHER INFORMATION: Nucleotide sequence of Trastuzumab Light Chain
      with C-terminal GS peptide spacer, LPETG sortase A recognition
      motif and additional 6x-His and strep-II affinity purification
      tags

<400> SEQUENCE: 37

```
atgaaaaaaa acattgcctt tctgctggcc tccatgttcg tgttctctat cgccacaaat     60

gcttatgccg acatccagat gacacagtct ccctcttccc tgtccgcttc tgtgggcgat    120

cgagtgacaa tcacctgtag ggctagtcag gatgtgaata ctgctgttgc ttggtaccag    180

cagaaaccag gaaaagcccc taaactgctg atctactctg cctcattcct gtactctggg    240

gtgccttctc gattcagtgg ttctagatct ggcaccgatt tcacactgac catttcttca    300

ctgcaacctg aggattttgc cacctactac tgtcagcagc actacacaac acctcccaca    360

tttggccagg gcacaaaagt ggagatcaaa cgtacggtgg ctgcaccatc tgtcttcatc    420

ttcccgccat ctgatgagca gttgaaatct ggaactgcct ctgttgtgtg cctgctgaat    480

aacttctatc ccagagaggc caaagtacag tggaaggtgg ataacgccct ccaatcgggt    540

aactcccagg agagtgtcac agagcaggac agcaaggaca gcacctacag cctcagcagc    600

accctgacgc tgagcaaagc agactacgag aaacacaaag tctacgcctg cgaagtcacc    660

catcagggcc tgagctcgcc cgtcacaaag agcttcaaca ggggagagtg tggatccctg    720

cccgagaccg gcggacacca tcaccatcac catggctgga gccaccccca gttcgagaag    780

tag                                                                  783
```

<210> SEQ ID NO 38
<211> LENGTH: 260
<212> TYPE: PRT
<213> ORGANISM: Artificial Sequence
<220> FEATURE:
<223> OTHER INFORMATION: Amino acid sequence of Trastuzumab Light Chain
      with C-terminal GS peptide-spacer, LPETG sortase A recognition motif and additional 6x-His and strep-II affinity purification
tags

<400> SEQUENCE: 38

Met Lys Lys Asn Ile Ala Phe Leu Leu Ala Ser Met Phe Val Phe Ser
1 5 10 15

Ile Ala Thr Asn Ala Tyr Ala Asp Ile Gln Met Thr Gln Ser Pro Ser
20 25 30

Ser Leu Ser Ala Ser Val Gly Asp Arg Val Thr Ile Thr Cys Arg Ala
35 40 45

Ser Gln Asp Val Asn Thr Ala Val Ala Trp Tyr Gln Gln Lys Pro Gly
50 55 60

Lys Ala Pro Lys Leu Leu Ile Tyr Ser Ala Ser Phe Leu Tyr Ser Gly
65 70 75 80

Val Pro Ser Arg Phe Ser Gly Ser Arg Ser Gly Thr Asp Phe Thr Leu
85 90 95

Thr Ile Ser Ser Leu Gln Pro Glu Asp Phe Ala Thr Tyr Tyr Cys Gln
100 105 110

Gln His Tyr Thr Thr Pro Pro Thr Phe Gly Gln Gly Thr Lys Val Glu
115 120 125

Ile Lys Arg Thr Val Ala Ala Pro Ser Val Phe Ile Phe Pro Pro Ser
130 135 140

Asp Glu Gln Leu Lys Ser Gly Thr Ala Ser Val Val Cys Leu Leu Asn
145 150 155 160

Asn Phe Tyr Pro Arg Glu Ala Lys Val Gln Trp Lys Val Asp Asn Ala
165 170 175

Leu Gln Ser Gly Asn Ser Gln Glu Ser Val Thr Glu Gln Asp Ser Lys
180 185 190

Asp Ser Thr Tyr Ser Leu Ser Ser Thr Leu Thr Leu Ser Lys Ala Asp
195 200 205

Tyr Glu Lys His Lys Val Tyr Ala Cys Glu Val Thr His Gln Gly Leu
210 215 220

Ser Ser Pro Val Thr Lys Ser Phe Asn Arg Gly Glu Cys Gly Ser Leu
225 230 235 240

Pro Glu Thr Gly Gly His His His His His His Gly Trp Ser His Pro
245 250 255

Gln Phe Glu Lys
260

<210> SEQ ID NO 39
<211> LENGTH: 1470
<212> TYPE: DNA
<213> ORGANISM: Artificial Sequence
<220> FEATURE:
<223> OTHER INFORMATION: Nucleotide sequence of mAb Ac10 Heavy Chain
with C-terminal GS peptide-spacer, LPETG sortase A recognition
motif and additional 6x-His and strep-II affinity purification
tags

<400> SEQUENCE: 39
atgaattttg gactgaggct gattttcctg gtgctgaccc tgaaaggcgt ccagtgtcag 60
atccagctgc agcagtctgg ccccgaggtc gtgaaacctg gcgcctccgt gaagatctcc 120
tgcaaggcct ccggctacac cttcaccgac tactacatca cctgggtcaa gcagaagccc 180
ggccagggcc tggaatggat cggctggatc tatcccggct ccggcaacac caagtacaac 240
gagaagttca agggcaaggc caccctgacc gtggacacct cctcttccac cgccttcatg 300

```
cagctgtcct ccctgacctc cgaggatacc gccgtgtact tctgcgccaa ctacggcaac    360

tattggttcg cctactgggg ccagggcaca caagtgaccg tgtctgctgc tagcaccaag    420

ggcccatcgg tcttcccct ggcaccctcc tccaagagca cctctggggg cacagcagcc    480

ctgggctgcc tggtcaagga ctacttcccc gaaccggtga cggtgtcgtg gaactcaggc    540

gccctgacca gcggcgtgca caccttcccg gctgtcctac agtcctcagg actctactcc    600

ctcagcagcg tggtgaccgt gccctccagc agcttgggca cccagaccta catctgcaac    660

gtgaatcaca agcccagcaa caccaaggtg gacaagaaag ttgagcccaa atcttgtgac    720

aaaactcaca catgcccacc gtgcccagca cctgaactcc tggggggacc gtcagtcttc    780

ctcttccccc caaaacccaa ggacaccctc atgatctccc ggacccctga ggtcacatgc    840

gtggtggtgg acgtgagcca cgaagaccct gaggtcaagt tcaactggta cgtggacggc    900

gtggaggtgc ataatgccaa gacaaagccg cgggaggagc agtacaacag cacgtaccgt    960

gtggtcagcg tcctcaccgt cctgcaccag gactggctga atggcaagga gtacaagtgc   1020

aaggtctcca acaaagccct cccagccccc atcgagaaaa ccatctccaa agccaaaggg   1080

cagccccgag aaccacaggt gtacaccctg cccccatccc gggatgagct gaccaagaac   1140

caggtcagcc tgacctgcct ggtcaaaggc ttctatccca gcgacatcgc cgtggagtgg   1200

gagagcaatg ggcagccgga gaacaactac aagaccacgc ctcccgtgct ggactccgac   1260

ggctccttct tcctctacag caagctcacc gtggacaaga gcaggtggca gcaggggaac   1320

gtcttctcat gctccgtgat gcatgaggct ctgcacaacc actacacaca gaagagcctc   1380

tccctgtctc cgggtaaagg atccctgccc gagaccggcg gacaccatca ccatcaccat   1440

ggctggagcc acccccagtt cgagaagtag                                    1470
```

<210> SEQ ID NO 40
<211> LENGTH: 489
<212> TYPE: PRT
<213> ORGANISM: Artificial Sequence
<220> FEATURE:
<223> OTHER INFORMATION: Amino acid sequence of mAb Ac10 Heavy Chain with C-terminal GS peptide-spacer, LPETG sortase A recognition motif and additional 6x-His and strep II affinity purification tags

<400> SEQUENCE: 40

```
Met Asn Phe Gly Leu Arg Leu Ile Phe Leu Val Leu Thr Leu Lys Gly
1               5                   10                  15

Val Gln Cys Gln Ile Gln Leu Gln Gln Ser Gly Pro Glu Val Val Lys
            20                  25                  30

Pro Gly Ala Ser Val Lys Ile Ser Cys Lys Ala Ser Gly Tyr Thr Phe
        35                  40                  45

Thr Asp Tyr Tyr Ile Thr Trp Val Lys Gln Lys Pro Gly Gln Gly Leu
    50                  55                  60

Glu Trp Ile Gly Trp Ile Tyr Pro Gly Ser Gly Asn Thr Lys Tyr Asn
65                  70                  75                  80

Glu Lys Phe Lys Gly Lys Ala Thr Leu Thr Val Asp Thr Ser Ser Ser
                85                  90                  95

Thr Ala Phe Met Gln Leu Ser Ser Leu Thr Ser Glu Asp Thr Ala Val
            100                 105                 110

Tyr Phe Cys Ala Asn Tyr Gly Asn Tyr Trp Phe Ala Tyr Trp Gly Gln
        115                 120                 125

Gly Thr Gln Val Thr Val Ser Ala Ala Ser Thr Lys Gly Pro Ser Val
    130                 135                 140
```

```
Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys Gly Ser Leu Pro Glu Thr Gly Gly His His His His His His
465                 470                 475                 480

Gly Trp Ser His Pro Gln Phe Glu Lys
                485
```

<210> SEQ ID NO 41
<211> LENGTH: 783
<212> TYPE: DNA
<213> ORGANISM: Artificial Sequence
<220> FEATURE:
<223> OTHER INFORMATION: Nucleotide sequence of mAb Ac10 Light Chain with C-terminal GS peptide-spacer, LPETG sortase A recognition motif and additional 6x-His and strep II affinity purification tags

<400> SEQUENCE: 41

```
atgaatttg gactgaggct gattttcctg gtgctgaccc tgaaaggcgt ccagtgtgac     60

attgtgctga cccaatctcc agcttctttg gctgtgtctc tagggcagag ggccaccatc    120

tcctgcaagg ccagccaaag tgttgatttt gatggtgata gttatatgaa ctggtaccaa    180

cagaaaccag gacagccacc caaagtcctc atctatgctg catccaatct agaatctggg    240

atcccagcca ggtttagtgg cagtgggtct gggacagact tcaccctcaa catccatcct    300

gtggaggagg aggatgctgc aacctattac tgtcagcaaa gtaatgagga tccgtggacg    360

ttcggtggag gcaccaagct ggaaatcaaa cgtacggtgg ctgcaccatc tgtcttcatc    420

ttcccgccat ctgatgagca gttgaaatct ggaactgcct ctgttgtgtg cctgctgaat    480

aacttctatc ccagagaggc caaagtacag tggaaggtgg ataacgccct ccaatcgggt    540

aactcccagg agagtgtcac agagcaggac agcaaggaca gcacctacag cctcagcagc    600

accctgacgc tgagcaaagc agactacgag aaacacaaag tctacgcctg cgaagtcacc    660

catcagggcc tgagctcgcc cgtcacaaag agcttcaaca ggggagagtg tggatccctg    720

cccgagaccg gcggacacca tcaccatcac catggctgga gccaccccca gttcgagaag    780

tag                                                                  783
```

<210> SEQ ID NO 42
<211> LENGTH: 260
<212> TYPE: PRT
<213> ORGANISM: Artificial Sequence
<220> FEATURE:
<223> OTHER INFORMATION: Amino acid sequence of mAb Ac10 Light Chain with C-terminal GS peptide-spacer, LPETG sortase A recognition motif and additional 6x-His and strep II affinity purification tags

<400> SEQUENCE: 42

```
Met Asn Phe Gly Leu Arg Leu Ile Phe Leu Val Leu Thr Leu Lys Gly
1               5                   10                  15

Val Gln Cys Asp Ile Val Leu Thr Gln Ser Pro Ala Ser Leu Ala Val
            20                  25                  30

Ser Leu Gly Gln Arg Ala Thr Ile Ser Cys Lys Ala Ser Gln Ser Val
        35                  40                  45

Asp Phe Asp Gly Asp Ser Tyr Met Asn Trp Tyr Gln Gln Lys Pro Gly
    50                  55                  60

Gln Pro Pro Lys Val Leu Ile Tyr Ala Ala Ser Asn Leu Glu Ser Gly
65                  70                  75                  80

Ile Pro Ala Arg Phe Ser Gly Ser Gly Ser Gly Thr Asp Phe Thr Leu
                85                  90                  95

Asn Ile His Pro Val Glu Glu Glu Asp Ala Ala Thr Tyr Tyr Cys Gln
            100                 105                 110

Gln Ser Asn Glu Asp Pro Trp Thr Phe Gly Gly Gly Thr Lys Leu Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
```

```
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys Gly Ser Leu
225                 230                 235                 240

Pro Glu Thr Gly Gly His His His His His His Gly Trp Ser His Pro
                245                 250                 255

Gln Phe Glu Lys
            260


<210> SEQ ID NO 43
<211> LENGTH: 1443
<212> TYPE: DNA
<213> ORGANISM: Artificial Sequence
<220> FEATURE:
<223> OTHER INFORMATION: Nucleotide sequence of mAb Ac10 Heavy Chain
      with C-terminal LPETG sortase A recognition motif and strep II
      affinity purification tag

<400> SEQUENCE: 43

atgaattttg gactgaggct gattttcctg gtgctgaccc tgaaaggcgt ccagtgtcag     60

atccagctgc agcagtctgg ccccgaggtc gtgaaacctg gcgcctccgt gaagatctcc    120

tgcaaggcct ccggctacac cttcaccgac tactacatca cctgggtcaa gcagaagccc    180

ggccagggcc tggaatggat cggctggatc tatcccggct ccggcaacac caagtacaac    240

gagaagttca agggcaaggc caccctgacc gtggacacct cctcttccac cgccttcatg    300

cagctgtcct ccctgacctc cgaggatacc gccgtgtact tctgcgccaa ctacggcaac    360

tattggttcg cctactgggg ccagggcaca caagtgaccg tgtctgctgc tagcaccaag    420

ggcccatcgg tcttccccct ggcaccctcc tccaagagca cctctggggg cacagcagcc    480

ctgggctgcc tggtcaagga ctacttcccc gaaccggtga cggtgtcgtg gaactcaggc    540

gccctgacca gcggcgtgca caccttcccg gctgtcctac agtcctcagg actctactcc    600

ctcagcagcg tggtgaccgt gccctccagc agcttgggca cccagaccta catctgcaac    660

gtgaatcaca agcccagcaa caccaaggtg gacaagaaag ttgagcccaa atcttgtgac    720

aaaactcaca catgcccacc gtgcccagca cctgaactcc tggggggacc gtcagtcttc    780

ctcttccccc caaaacccaa ggacaccctc atgatctccc ggacccctga ggtcacatgc    840

gtggtggtgg acgtgagcca cgaagaccct gaggtcaagt tcaactggta cgtggacggc    900

gtggaggtgc ataatgccaa gacaaagccg cgggaggagc agtacaacag cacgtaccgt    960

gtggtcagcg tcctcaccgt cctgcaccag gactggctga atggcaagga gtacaagtgc   1020

aaggtctcca acaaagccct cccagccccc atcgagaaaa ccatctccaa agccaaaggg   1080

cagccccgag aaccacaggt gtacaccctg cccccatccc gggatgagct gaccaagaac   1140

caggtcagcc tgacctgcct ggtcaaaggc ttctatccca gcgacatcgc cgtggagtgg   1200

gagagcaatg ggcagccgga gaacaactac aagaccacgc ctcccgtgct ggactccgac   1260

ggctccttct tcctctacag caagctcacc gtggacaaga gcaggtggca gcaggggaac   1320

gtcttctcat gctccgtgat gcatgaggct ctgcacaacc actacacaca gaagagcctc   1380

tccctgtctc cgggtaaact gcccgagacc ggcggatgga gccaccccca gttcgagaag   1440

tag                                                                 1443


<210> SEQ ID NO 44
<211> LENGTH: 480
```

```
<212> TYPE: PRT
<213> ORGANISM: Artificial Sequence
<220> FEATURE:
<223> OTHER INFORMATION: Amino acid sequence of mAb Ac10 Heavy Chain
      with C-terminal LPETG sortase A recognition motif and strep-II
      affinity purification tag

<400> SEQUENCE: 44

Met Asn Phe Gly Leu Arg Leu Ile Phe Leu Val Leu Thr Leu Lys Gly
1               5                   10                  15

Val Gln Cys Gln Ile Gln Leu Gln Gln Ser Gly Pro Glu Val Val Lys
            20                  25                  30

Pro Gly Ala Ser Val Lys Ile Ser Cys Lys Ala Ser Gly Tyr Thr Phe
        35                  40                  45

Thr Asp Tyr Tyr Ile Thr Trp Val Lys Gln Lys Pro Gly Gln Gly Leu
    50                  55                  60

Glu Trp Ile Gly Trp Ile Tyr Pro Gly Ser Gly Asn Thr Lys Tyr Asn
65                  70                  75                  80

Glu Lys Phe Lys Gly Lys Ala Thr Leu Thr Val Asp Thr Ser Ser Ser
                85                  90                  95

Thr Ala Phe Met Gln Leu Ser Ser Leu Thr Ser Glu Asp Thr Ala Val
            100                 105                 110

Tyr Phe Cys Ala Asn Tyr Gly Asn Tyr Trp Phe Ala Tyr Trp Gly Gln
        115                 120                 125

Gly Thr Gln Val Thr Val Ser Ala Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
```

-continued

```
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys Leu Pro Glu Thr Gly Gly Trp Ser His Pro Gln Phe Glu Lys
465                 470                 475                 480


<210> SEQ ID NO 45
<211> LENGTH: 756
<212> TYPE: DNA
<213> ORGANISM: Artificial Sequence
<220> FEATURE:
<223> OTHER INFORMATION: Nucleotide sequence of mAb Ac10 Light Chain
      with C-terminal LPETG sortase A recognition motif and strep-II
      affinity purification tag

<400> SEQUENCE: 45

atgaattttg gactgaggct gattttcctg gtgctgaccc tgaaaggcgt ccagtgtgac     60

attgtgctga cccaatctcc agcttctttg gctgtgtctc tagggcagag ggccaccatc    120

tcctgcaagg ccagccaaag tgttgatttt gatggtgata gttatatgaa ctggtaccaa    180

cagaaaccag gacagccacc caaagtcctc atctatgctg catccaatct agaatctggg    240

atcccagcca ggtttagtgg cagtgggtct gggacagact tcaccctcaa catccatcct    300

gtggaggagg aggatgctgc aacctattac tgtcagcaaa gtaatgagga tccgtggacg    360

ttcggtggag gcaccaagct ggaaatcaaa cgtacggtgg ctgcaccatc tgtcttcatc    420

ttcccgccat ctgatgagca gttgaaatct ggaactgcct ctgttgtgtg cctgctgaat    480

aacttctatc ccagagaggc caaagtacag tggaaggtgg ataacgccct ccaatcgggt    540

aactcccagg agagtgtcac agagcaggac agcaaggaca gcacctacag cctcagcagc    600

accctgacgc tgagcaaagc agactacgag aaacacaaag tctacgcctg cgaagtcacc    660

catcagggcc tgagctcgcc cgtcacaaag agcttcaaca ggggagagtg tctgcccgag    720

accggcggat ggagccaccc ccagttcgag aagtag                              756


<210> SEQ ID NO 46
<211> LENGTH: 251
<212> TYPE: PRT
<213> ORGANISM: Artificial Sequence
<220> FEATURE:
<223> OTHER INFORMATION: Amino acid sequence of mAb Ac10 Light Chain
      with C-terminal LPETG sortase A recognition motif and strep-II
      affinity purification tag

<400> SEQUENCE: 46

Met Asn Phe Gly Leu Arg Leu Ile Phe Leu Val Leu Thr Leu Lys Gly
1               5                   10                  15

Val Gln Cys Asp Ile Val Leu Thr Gln Ser Pro Ala Ser Leu Ala Val
            20                  25                  30

Ser Leu Gly Gln Arg Ala Thr Ile Ser Cys Lys Ala Ser Gln Ser Val
        35                  40                  45
```

-continued

```
Asp Phe Asp Gly Asp Ser Tyr Met Asn Trp Tyr Gln Gln Lys Pro Gly
    50                  55                  60

Gln Pro Pro Lys Val Leu Ile Tyr Ala Ala Ser Asn Leu Glu Ser Gly
65                  70                  75                  80

Ile Pro Ala Arg Phe Ser Gly Ser Gly Ser Gly Thr Asp Phe Thr Leu
                85                  90                  95

Asn Ile His Pro Val Glu Glu Glu Asp Ala Ala Thr Tyr Tyr Cys Gln
            100                 105                 110

Gln Ser Asn Glu Asp Pro Trp Thr Phe Gly Gly Gly Thr Lys Leu Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys Leu Pro Glu
225                 230                 235                 240

Thr Gly Gly Trp Ser His Pro Gln Phe Glu Lys
                245                 250


<210> SEQ ID NO 47
<211> LENGTH: 762
<212> TYPE: DNA
<213> ORGANISM: Artificial Sequence
<220> FEATURE:
<223> OTHER INFORMATION: Nucleotide sequence of mAb Ac10 Light Chain
      with C-terminal GS peptide-spacer, LPETG sortase A recognition
      motif and strep II affinity purification tag

<400> SEQUENCE: 47

atgaattttg gactgaggct gattttcctg gtgctgaccc tgaaaggcgt ccagtgtgac      60

attgtgctga cccaatctcc agcttctttg gctgtgtctc tagggcagag ggccaccatc     120

tcctgcaagg ccagccaaag tgttgatttt gatggtgata gttatatgaa ctggtaccaa     180

cagaaaccag gacagccacc caaagtcctc atctatgctg catccaatct agaatctggg     240

atcccagcca ggtttagtgg cagtgggtct gggacagact tcaccctcaa catccatcct     300

gtggaggagg aggatgctgc aacctattac tgtcagcaaa gtaatgagga tccgtggacg     360

ttcggtggag gcaccaagct ggaaatcaaa cgtacggtgg ctgcaccatc tgtcttcatc     420

ttcccgccat ctgatgagca gttgaaatct ggaactgcct ctgttgtgtg cctgctgaat     480

aacttctatc ccagagaggc caaagtacag tggaaggtgg ataacgccct ccaatcgggt     540

aactcccagg agagtgtcac agagcaggac agcaaggaca gcacctacag cctcagcagc     600

accctgacgc tgagcaaagc agactacgag aaacacaaag tctacgcctg cgaagtcacc     660

catcagggcc tgagctcgcc cgtcacaaag agcttcaaca ggggagagtg tggatccctg     720

cccgagaccg gcggatggag ccacccccag ttcgagaagt ag                        762


<210> SEQ ID NO 48
```

<211> LENGTH: 253
<212> TYPE: PRT
<213> ORGANISM: Artificial Sequence
<220> FEATURE:
<223> OTHER INFORMATION: Amino acid sequence of mAb Ac10 Light Chain with C-terminal GS peptide-spacer, LPETG sortase A recognition motif and strep II affinity purification tag

<400> SEQUENCE: 48

```
Met Asn Phe Gly Leu Arg Leu Ile Phe Leu Val Leu Thr Leu Lys Gly
1               5                   10                  15

Val Gln Cys Asp Ile Val Leu Thr Gln Ser Pro Ala Ser Leu Ala Val
            20                  25                  30

Ser Leu Gly Gln Arg Ala Thr Ile Ser Cys Lys Ala Ser Gln Ser Val
        35                  40                  45

Asp Phe Asp Gly Asp Ser Tyr Met Asn Trp Tyr Gln Gln Lys Pro Gly
    50                  55                  60

Gln Pro Pro Lys Val Leu Ile Tyr Ala Ala Ser Asn Leu Glu Ser Gly
65                  70                  75                  80

Ile Pro Ala Arg Phe Ser Gly Ser Gly Ser Gly Thr Asp Phe Thr Leu
                85                  90                  95

Asn Ile His Pro Val Glu Glu Glu Asp Ala Ala Thr Tyr Tyr Cys Gln
            100                 105                 110

Gln Ser Asn Glu Asp Pro Trp Thr Phe Gly Gly Gly Thr Lys Leu Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys Gly Ser Leu
225                 230                 235                 240

Pro Glu Thr Gly Gly Trp Ser His Pro Gln Phe Glu Lys
                245                 250
```

<210> SEQ ID NO 49
<211> LENGTH: 765
<212> TYPE: DNA
<213> ORGANISM: Artificial Sequence
<220> FEATURE:
<223> OTHER INFORMATION: Nucleotide sequence of mAb Ac10 Light Chain with C-terminal GGS peptide-spacer, LPETG sortase A recognition motif and strep II affinity purification tag

<400> SEQUENCE: 49

```
atgaattttg gactgaggct gattttcctg gtgctgaccc tgaaaggcgt ccagtgtgac     60

attgtgctga cccaatctcc agcttctttg gctgtgtctc tagggcagag ggccaccatc    120

tcctgcaagg ccagccaaag tgttgatttt gatggtgata gttatatgaa ctggtaccaa    180

cagaaaccag gacagccacc caaagtcctc atctatgctg catccaatct agaatctggg    240

atcccagcca ggtttagtgg cagtgggtct gggacagact tcaccctcaa catccatcct    300
```

```
gtggaggagg aggatgctgc aacctattac tgtcagcaaa gtaatgagga tccgtggacg    360

ttcggtggag gcaccaagct ggaaatcaaa cgtacggtgg ctgcaccatc tgtcttcatc    420

ttcccgccat ctgatgagca gttgaaatct ggaactgcct ctgttgtgtg cctgctgaat    480

aacttctatc ccagagaggc caaagtacag tggaaggtgg ataacgccct ccaatcgggt    540

aactcccagg agagtgtcac agagcaggac agcaaggaca gcacctacag cctcagcagc    600

accctgacgc tgagcaaagc agactacgag aaacacaaag tctacgcctg cgaagtcacc    660

catcagggcc tgagctcgcc cgtcacaaag agcttcaaca ggggagagtg tggtggatcc    720

ctgcccgaga ccggcggatg gagccacccc cagttcgaga agtag                    765
```

<210> SEQ ID NO 50
<211> LENGTH: 254
<212> TYPE: PRT
<213> ORGANISM: Artificial Sequence
<220> FEATURE:
<223> OTHER INFORMATION: Amino acid sequence of mAb Ac10 Light Chain with C-terminal GGS peptide-spacer, LPETG sortase A recognition motif and strep II affinity purification tag

<400> SEQUENCE: 50

```
Met Asn Phe Gly Leu Arg Leu Ile Phe Leu Val Leu Thr Leu Lys Gly
1               5                   10                  15

Val Gln Cys Asp Ile Val Leu Thr Gln Ser Pro Ala Ser Leu Ala Val
            20                  25                  30

Ser Leu Gly Gln Arg Ala Thr Ile Ser Cys Lys Ala Ser Gln Ser Val
        35                  40                  45

Asp Phe Asp Gly Asp Ser Tyr Met Asn Trp Tyr Gln Gln Lys Pro Gly
    50                  55                  60

Gln Pro Pro Lys Val Leu Ile Tyr Ala Ala Ser Asn Leu Glu Ser Gly
65                  70                  75                  80

Ile Pro Ala Arg Phe Ser Gly Ser Gly Ser Gly Thr Asp Phe Thr Leu
                85                  90                  95

Asn Ile His Pro Val Glu Glu Glu Asp Ala Ala Thr Tyr Tyr Cys Gln
            100                 105                 110

Gln Ser Asn Glu Asp Pro Trp Thr Phe Gly Gly Gly Thr Lys Leu Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys Gly Gly Ser
225                 230                 235                 240

Leu Pro Glu Thr Gly Gly Trp Ser His Pro Gln Phe Glu Lys
                245                 250
```

<210> SEQ ID NO 51

<211> LENGTH: 768
<212> TYPE: DNA
<213> ORGANISM: Artificial Sequence
<220> FEATURE:
<223> OTHER INFORMATION: Nucleotide sequence of mAb Ac10 Light Chain with C-terminal GGGS peptide-spacer, LPETG sortase A recognition motif and strep II affinity purification tag

<400> SEQUENCE: 51 atgaatttg gactgaggct gattttcctg gtgctgaccc tgaaaggcgt ccagtgtgac 60
attgtgctga cccaatctcc agcttctttg gctgtgtctc tagggcagag ggccaccatc 120
tcctgcaagg ccagccaaag tgttgatttt gatggtgata gttatatgaa ctggtaccaa 180
cagaaaccag gacagccacc caaagtcctc atctatgctg catccaatct agaatctggg 240
atcccagcca ggtttagtgg cagtgggtct gggacagact tcaccctcaa catccatcct 300
gtggaggagg aggatgctgc aacctattac tgtcagcaaa gtaatgagga tccgtggacg 360
ttcggtggag gcaccaagct ggaaatcaaa cgtacggtgg ctgcaccatc tgtcttcatc 420
ttcccgccat ctgatgagca gttgaaatct ggaactgcct ctgttgtgtg cctgctgaat 480
aacttctatc ccagagaggc caaagtacag tggaaggtgg ataacgccct ccaatcgggt 540
aactcccagg agagtgtcac agagcaggac agcaaggaca gcacctacag cctcagcagc 600
accctgacgc tgagcaaagc agactacgag aaacacaaag tctacgcctg cgaagtcacc 660
catcagggcc tgagctcgcc cgtcacaaag agcttcaaca ggggagagtg tgggggtgga 720
tccctgcccg agaccggcgg atggagccac ccccagttcg agaagtag 768

<210> SEQ ID NO 52
<211> LENGTH: 255
<212> TYPE: PRT
<213> ORGANISM: Artificial Sequence
<220> FEATURE:
<223> OTHER INFORMATION: Amino acid sequence of mAb Ac10 Light Chain with C-terminal GGGS peptide-spacer, LPETG sortase A recognition motif and strep II affinity purification tag

<400> SEQUENCE: 52

Met Asn Phe Gly Leu Arg Leu Ile Phe Leu Val Leu Thr Leu Lys Gly
1 5 10 15

Val Gln Cys Asp Ile Val Leu Thr Gln Ser Pro Ala Ser Leu Ala Val
20 25 30

Ser Leu Gly Gln Arg Ala Thr Ile Ser Cys Lys Ala Ser Gln Ser Val
35 40 45

Asp Phe Asp Gly Asp Ser Tyr Met Asn Trp Tyr Gln Gln Lys Pro Gly
50 55 60

Gln Pro Pro Lys Val Leu Ile Tyr Ala Ala Ser Asn Leu Glu Ser Gly
65 70 75 80

Ile Pro Ala Arg Phe Ser Gly Ser Gly Ser Gly Thr Asp Phe Thr Leu
85 90 95

Asn Ile His Pro Val Glu Glu Glu Asp Ala Ala Thr Tyr Tyr Cys Gln
100 105 110

Gln Ser Asn Glu Asp Pro Trp Thr Phe Gly Gly Gly Thr Lys Leu Glu
115 120 125

Ile Lys Arg Thr Val Ala Ala Pro Ser Val Phe Ile Phe Pro Pro Ser
130 135 140

Asp Glu Gln Leu Lys Ser Gly Thr Ala Ser Val Val Cys Leu Leu Asn
145 150 155 160

Asn Phe Tyr Pro Arg Glu Ala Lys Val Gln Trp Lys Val Asp Asn Ala

```
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys Gly Gly Gly
225                 230                 235                 240

Ser Leu Pro Glu Thr Gly Gly Trp Ser His Pro Gln Phe Glu Lys
                245                 250                 255
```

```
<210> SEQ ID NO 53
<211> LENGTH: 771
<212> TYPE: DNA
<213> ORGANISM: Artificial Sequence
<220> FEATURE:
<223> OTHER INFORMATION: Nucleotide sequence of mAb Ac10 Light Chain
      with C-terminal GGGGS peptide-spacer, LPETG sortase A recognition
      motif and strep II affinity purification tag

<400> SEQUENCE: 53

atgaattttg gactgaggct gattttcctg gtgctgaccc tgaaaggcgt ccagtgtgac      60

attgtgctga cccaatctcc agcttctttg gctgtgtctc tagggcagag ggccaccatc     120

tcctgcaagg ccagccaaag tgttgatttt gatggtgata gttatatgaa ctggtaccaa     180

cagaaaccag gacagccacc caaagtcctc atctatgctg catccaatct agaatctggg     240

atcccagcca ggtttagtgg cagtgggtct gggacagact tcaccctcaa catccatcct     300

gtggaggagg aggatgctgc aacctattac tgtcagcaaa gtaatgagga tccgtggacg     360

ttcggtggag gcaccaagct ggaaatcaaa cgtacggtgg ctgcaccatc tgtcttcatc     420

ttcccgccat ctgatgagca gttgaaatct ggaactgcct ctgttgtgtg cctgctgaat     480

aacttctatc ccagagaggc caaagtacag tggaaggtgg ataacgccct ccaatcgggt     540

aactcccagg agagtgtcac agagcaggac agcaaggaca gcacctacag cctcagcagc     600

accctgacgc tgagcaaagc agactacgag aaacacaaag tctacgcctg cgaagtcacc     660

catcagggcc tgagctcgcc cgtcacaaag agcttcaaca ggggagagtg tggagggggt     720

ggatccctgc ccgagaccgg cggatggagc caccccagt tcgagaagta g              771

<210> SEQ ID NO 54
<211> LENGTH: 256
<212> TYPE: PRT
<213> ORGANISM: Artificial Sequence
<220> FEATURE:
<223> OTHER INFORMATION: Amino acid sequence of mAb Ac10 Light Chain
      with C-terminal GGGGS peptide-spacer, LPETG sortase A recognition
      motif and strep II affinity purification tag

<400> SEQUENCE: 54

Met Asn Phe Gly Leu Arg Leu Ile Phe Leu Val Leu Thr Leu Lys Gly
1               5                   10                  15

Val Gln Cys Asp Ile Val Leu Thr Gln Ser Pro Ala Ser Leu Ala Val
            20                  25                  30

Ser Leu Gly Gln Arg Ala Thr Ile Ser Cys Lys Ala Ser Gln Ser Val
        35                  40                  45

Asp Phe Asp Gly Asp Ser Tyr Met Asn Trp Tyr Gln Gln Lys Pro Gly
    50                  55                  60
```

-continued

```
Gln Pro Pro Lys Val Leu Ile Tyr Ala Ala Ser Asn Leu Glu Ser Gly
65                  70                  75                  80

Ile Pro Ala Arg Phe Ser Gly Ser Gly Ser Gly Thr Asp Phe Thr Leu
                85                  90                  95

Asn Ile His Pro Val Glu Glu Glu Asp Ala Ala Thr Tyr Tyr Cys Gln
            100                 105                 110

Gln Ser Asn Glu Asp Pro Trp Thr Phe Gly Gly Gly Thr Lys Leu Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys Gly Gly Gly
225                 230                 235                 240

Gly Ser Leu Pro Glu Thr Gly Gly Trp Ser His Pro Gln Phe Glu Lys
                245                 250                 255
```

```
<210> SEQ ID NO 55
<211> LENGTH: 1464
<212> TYPE: DNA
<213> ORGANISM: Artificial Sequence
<220> FEATURE:
<223> OTHER INFORMATION: Nucleotide sequence of Trastuzumab Heavy Chain
      with C-terminal LPETG Sortase tag and strep II affinity
      purification tag

<400> SEQUENCE: 55

atgaaaaaaa acattgcctt tctgctggcc tccatgttcg tgttctctat cgccacaaac     60

gcttacgctg aagtccagct ggtcgaatct ggtggtggcc tggtccagcc tggtggatca    120

ctgagactgt cctgtgctgc ttctggtttc aacatcaagg acacctacat ccattgggtc    180

agacaggcac ctggcaaggg actggaatgg gtcgcccgaa tctaccctac aaacggctac    240

actcgctacg ccgactccgt caagggacgc tttaccatct ccgccgacac ctctaaaaac    300

accgcctacc tgcagatgaa tagtctgagg gccgaggata ctgctgtgta ctactgctca    360

cgatggggag gcgacggctt ttacgctatg gattactggg gacagggaac tctggtcact    420

gtgtctagcg ctagcaccaa gggcccatcg gtcttccccc tggcaccctc ctccaagagc    480

acctctgggg gcacagcagc cctgggctgc ctggtcaagg actacttccc cgaaccggtg    540

acggtgtcgt ggaactcagg cgccctgacc agcggcgtgc acaccttccc ggctgtccta    600

cagtcctcag gactctactc cctcagcagc gtggtgaccg tgccctccag cagcttgggc    660

acccagacct acatctgcaa cgtgaatcac aagcccagca acaccaaggt ggacaagaaa    720

gttgagccca aatcttgtga caaaactcac acatgcccac cgtgcccagc acctgaactc    780

ctggggggac cgtcagtctt cctcttcccc ccaaaaccca aggacaccct catgatctcc    840

cggacccctg aggtcacatg cgtggtggtg gacgtgagcc acgaagaccc tgaggtcaag    900

ttcaactggt acgtggacgg cgtggaggtg cataatgcca agacaaagcc gcgggaggag    960
```

```
cagtacaaca gcacgtaccg tgtggtcagc gtcctcaccg tcctgcacca ggactggctg   1020

aatggcaagg agtacaagtg caaggtctcc aacaaagccc tcccagcccc catcgagaaa   1080

accatctcca aagccaaagg gcagccccga gaaccacagg tgtacaccct gcccccatcc   1140

cgggatgagc tgaccaagaa ccaggtcagc ctgacctgcc tggtcaaagg cttctatccc   1200

agcgacatcg ccgtggagtg ggagagcaat gggcagccgg agaacaacta caagaccacg   1260

cctcccgtgc tggactccga cggctccttc ttcctctaca gcaagctcac cgtggacaag   1320

agcaggtggc agcaggggaa cgtcttctca tgctccgtga tgcatgaggc tctgcacaac   1380

cactacacac agaagagcct ctccctgtct ccgggtaaac tgcccgagac cggcggatgg   1440

agccaccccc agttcgagaa gtag                                          1464
```

```
<210> SEQ ID NO 56
<211> LENGTH: 487
<212> TYPE: PRT
<213> ORGANISM: Artificial Sequence
<220> FEATURE:
<223> OTHER INFORMATION: Amino acid sequence of mAb Ac10 Heavy Chain
      with C-terminal LPETG Sortase tag and strep II affinity
      purification tag

<400> SEQUENCE: 56

Met Lys Lys Asn Ile Ala Phe Leu Leu Ala Ser Met Phe Val Phe Ser
1               5                   10                  15

Ile Ala Thr Asn Ala Tyr Ala Glu Val Gln Leu Val Glu Ser Gly Gly
            20                  25                  30

Gly Leu Val Gln Pro Gly Gly Ser Leu Arg Leu Ser Cys Ala Ala Ser
        35                  40                  45

Gly Phe Asn Ile Lys Asp Thr Tyr Ile His Trp Val Arg Gln Ala Pro
    50                  55                  60

Gly Lys Gly Leu Glu Trp Val Ala Arg Ile Tyr Pro Thr Asn Gly Tyr
65                  70                  75                  80

Thr Arg Tyr Ala Asp Ser Val Lys Gly Arg Phe Thr Ile Ser Ala Asp
                85                  90                  95

Thr Ser Lys Asn Thr Ala Tyr Leu Gln Met Asn Ser Leu Arg Ala Glu
            100                 105                 110

Asp Thr Ala Val Tyr Tyr Cys Ser Arg Trp Gly Gly Asp Gly Phe Tyr
        115                 120                 125

Ala Met Asp Tyr Trp Gly Gln Gly Thr Leu Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255
```

-continued

```
Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys Leu Pro Glu Thr Gly Gly Trp
465                 470                 475                 480

Ser His Pro Gln Phe Glu Lys
                485
```

<210> SEQ ID NO 57
<211> LENGTH: 771
<212> TYPE: DNA
<213> ORGANISM: Artificial Sequence
<220> FEATURE:
<223> OTHER INFORMATION: Nucleotide sequence of Trastuzumab Light Chain with C-terminal GGGGS linker, LPETG Sortase tag and strep II affinity purification tag

<400> SEQUENCE: 57

```
atgaaaaaaa acattgcctt tctgctggcc tccatgttcg tgttctctat cgccacaaat      60

gcttatgccg acatccagat gacacagtct ccctcttccc tgtccgcttc tgtgggcgat     120

cgagtgacaa tcacctgtag ggctagtcag gatgtgaata ctgctgttgc ttggtaccag     180

cagaaaccag gaaaagcccc taaactgctg atctactctg cctcattcct gtactctggg     240

gtgccttctc gattcagtgg ttctagatct ggcaccgatt tcacactgac catttcttca     300

ctgcaacctg aggattttgc cacctactac tgtcagcagc actacacaac acctcccaca     360

tttggccagg gcacaaaagt ggagatcaaa cgtacggtgg ctgcaccatc tgtcttcatc     420

ttcccgccat ctgatgagca gttgaaatct ggaactgcct ctgttgtgtg cctgctgaat     480

aacttctatc ccagagaggc caaagtacag tggaaggtgg ataacgccct ccaatcgggt     540

aactcccagg agagtgtcac agagcaggac agcaaggaca gcacctacag cctcagcagc     600

accctgacgc tgagcaaagc agactacgag aaacacaaag tctacgcctg cgaagtcacc     660
```

-continued

```
catcagggcc tgagctcgcc cgtcacaaag agcttcaaca ggggagagtg tggagggggt    720

ggatccctgc ccgagaccgg cggatggagc cacccccagt tcgagaagta g             771


<210> SEQ ID NO 58
<211> LENGTH: 256
<212> TYPE: PRT
<213> ORGANISM: Artificial Sequence
<220> FEATURE:
<223> OTHER INFORMATION: Amino acid sequence of mAb Ac10 Light Chain
      with C-terminal GGGGS linker, LPETG Sortase tag and strep II
      affinity purification tag

<400> SEQUENCE: 58

Met Lys Lys Asn Ile Ala Phe Leu Leu Ala Ser Met Phe Val Phe Ser
1               5                   10                  15

Ile Ala Thr Asn Ala Tyr Ala Asp Ile Gln Met Thr Gln Ser Pro Ser
            20                  25                  30

Ser Leu Ser Ala Ser Val Gly Asp Arg Val Thr Ile Thr Cys Arg Ala
        35                  40                  45

Ser Gln Asp Val Asn Thr Ala Val Ala Trp Tyr Gln Gln Lys Pro Gly
    50                  55                  60

Lys Ala Pro Lys Leu Leu Ile Tyr Ser Ala Ser Phe Leu Tyr Ser Gly
65                  70                  75                  80

Val Pro Ser Arg Phe Ser Gly Ser Arg Ser Gly Thr Asp Phe Thr Leu
                85                  90                  95

Thr Ile Ser Ser Leu Gln Pro Glu Asp Phe Ala Thr Tyr Tyr Cys Gln
            100                 105                 110

Gln His Tyr Thr Thr Pro Pro Thr Phe Gly Gln Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys Gly Gly Gly
225                 230                 235                 240

Gly Ser Leu Pro Glu Thr Gly Gly Trp Ser His Pro Gln Phe Glu Lys
                245                 250                 255
```

METHOD OF PRODUCING AN IMMUNOLIGAND/PAYLOAD CONJUGATE

RELATED APPLICATIONS

This application is a continuation of U.S. patent application Ser. No. 16/915,343, filed Jun. 29, 2020, which is a continuation of U.S. patent application Ser. No. 15/819,116, filed Nov. 21, 2017, now U.S. Pat. No. 10,864,277, which is a division of U.S. patent application Ser. No. 14/775,374, filed Sep. 11, 2015, now U.S. Pat. No. 9,872,923, which is a 35 U.S.C. § 371 filing of International Patent Application No. PCT/EP2014/055173, filed Mar. 14, 2014, which claims priority to U.S. Provisional Patent Application Serial Nos. 61/939,754, filed Feb. 14, 2014; and 61/787,371, filed Mar. 15, 2013, and European Patent Application No. 13159484.8, filed Mar. 15, 2013, the entire disclosures of which are hereby incorporated herein by reference.

SEQUENCE LISTING

The Sequence Listing associated with this application is provided in text format in lieu of a paper copy, and is hereby incorporated by reference into the specification. The name of the text file containing the Sequence Listing is 127755-5002-US03_Sequence_Listing. The text file is about 153 KB, was created on Jun. 13, 2022, and is being submitted electronically via EFS-Web.

INTRODUCTION

Currently, the predominant methods to label and/or to conjugate molecules to proteins, especially, when small-molecule payloads or labels are concerned, involve the chemical conjugation with specific linker molecules that covalently attach the payload to free lysine and/or cysteine amino acids of the proteins.

However, many proteins, like e.g. antibodies that are of particular interest for immunotargeting strategies, are fairly large proteins, that may contain several lysine and cysteine residues. Because linker-mediated, chemical conjugation is a stochastic process, linker-mediated chemical ligation of payloads leads to heterogeneous mixtures of conjugated proteins that may differ in their therapeutic efficacy and/or diagnostic utility. Obviously, mixtures of protein-payload conjugates also represent a significant challenge in the regulatory approval process for therapeutic conjugates, as batch-to-batch variation and/or variations in the active pharmaceutical ingredient (API) are negatively viewed by regulatory authorities due to potential safety concerns In addition, if a defined ratio of payload to protein is desired, it is often necessary to purify the conjugate with the desired conjugation stoichiometry. This is not only tedious, but can significantly add to the cost-of-goods in the manufacturing process, as often only a fraction of the linker-mediated conjugated protein represents the desired ratio of payload conjugation. This is particularly true for therapeutically relevant antibody/drug conjugates (ADCs), where depending on the toxin employed, 3 to 4 toxin molecules appear to be advantageous, but antibodies with no toxin coupled to up to 8 toxins per antibody coupled are found in typical linker-mediated chemical conjugation reactions (Panowski et al. (2014)).

Despite of the limitations described above, all antibody/drug conjugates currently in clinical trials, or approved by the health authorities for the therapy of disease, have been generated by linker-mediated chemical conjugation of toxic small-molecule drugs to antibodies (Lambert (2012) or Mullard (2013)).

It is widely acknowledged in the industry and by scientific experts in the field, that site-specific and stoichiometric conjugation of molecular payloads, including toxin or label molecules to immunoligands would have significant advantages in comparison to chemical, linker-mediated conjugation. This is evidenced by attempts to target the chemical conjugation to specific amino acids in the protein structure (Panowski et al. (2014)).

On one hand, this is attempted by mutating certain positions in the protein structure to delete unwanted and/or to provide desired conjugation sites (i.e. lysine and/or cysteine residues) to which the linker-ligation can be targeted (McDonagh et al. (2006) or Junutula et al. (2008)).

On the other hand, control of chemical conjugation to proteins is attempted by incorporation of unnatural amino acids at certain positions, like selenocysteine, p-azidophenylalanine, or acetylphenylalanine (Hofer et al. (2009), Axup et al. (2012), or Lemke (2011)).

However, all of these approaches change the primary amino acid sequence of the protein to be conjugated, and may result in undesired functional properties. Furthermore, the incorporation of unnatural amino acids, as described above, is often low efficient, and does not allow for a quantitative incorporation of specific labeling sites to proteins.

SUMMARY OF THE INVENTION

Therefore, there is an urgent need in the industry to overcome the known issues of stochastic conjugation methods in particular for the generation of therapeutically relevant immunoconjugates, including, but not limited to ADCs.

It is thus one object of the present invention to provide an efficient method for conjugating immunoligands and payloads, e.g., drugs, toxins, cytokines, markers, or the like, preferably full-length monoclonal antibodies to small-molecular weight toxins, for the generation of site-specifically conjugated antibody drug conjugates (ADCs).

It is another object of the present invention to create immunoligand/payload conjugates, which have better efficacy and/or can be produced with higher reproducibility.

It is another object of the present invention to allow the conjugation of payloads to immunoligands in a site-specific and/or sequence specific manner.

It is another object of the present invention to create immunoligand/payload conjugates which preserve the characteristic features of its components, e.g., target affinity, target specificity, target sensitivity, solubility, pharmacological function and the like These objects are achieved by the subject matter of the independent claims, while the dependent claims as well as the specification disclose further preferred embodiments.

DEFINITIONS

As used herein, the term "immunoligand" is meant to define an entity, an agent or a molecule that has affinity to a given target, e.g., a receptor, a cell surface protein, a cytokine or the like. Such immunoligand may optionally block or dampen agonist-mediated responses, or inhibit receptor-agonist interaction. Most importantly, however, the immonoligand may serve as a shuttle to deliver a payload to a specific site, which is defined by the target recognized by said immunoligand. Thus, an immunoligand targeting, for instance, but not limited to a receptor, delivers its payload to a site which is characterized by abundance of said receptor. Immunoligands include, but are not limited to, antibodies, antibody fragments, antibody-based binding proteins, antibody mimetics, receptors, soluble decoy receptors, scaffold proteins with affinity for a given target and ligands of receptors.

"Antibodies", also synonymously called "immunoglobulins" (Ig), are generally comprising four polypeptide chains, two heavy (H) chains and two light (L) chains, and are therefore multimeric proteins, or an equivalent Ig homologue thereof (e.g., a camelid nanobody, which comprises only a heavy chain, single domain antibodies (dAbs) which can be either be derived from a heavy or light chain); including full length functional mutants, variants, or derivatives thereof (including, but not limited to, murine, chimeric, humanized and fully human antibodies, which retain the essential epitope binding features of an Ig molecule, and including dual specific, bispecific, multispecific, and dual variable domain immunoglobulins; Immunoglobulin molecules can be of any class (e.g., IgG, IgE, IgM, IgD, IgA, and IgY), or subclass (e.g., IgG1, IgG2, IgG3, IgG4, IgA1, and IgA2) and allotype.

An "antibody-based binding protein", as used herein, may represent any protein that contains at least one antibody-derived $V_H$, $V_L$, or $C_H$ immunoglobulin domain in the context of other non-immunoglobulin, or non-antibody derived components. Such antibody-based proteins include, but are not limited to (i) $F_c$-fusion proteins of binding proteins, including receptors or receptor components with all or parts of the immunoglobulin $C_H$ domains, (ii) binding proteins, in which $V_H$ and or $V_L$ domains are coupled to alternative molecular scaffolds, or (iii) molecules, in which immunoglobulin $V_H$, and/or $V_L$, and/or $C_H$ domains are combined and/or assembled in a fashion not normally found in naturally occurring antibodies or antibody fragments.

An "antibody drug conjugate" (ADC), as used herein, relates to either an antibody, or an antibody fragment, or and antibody-based binding protein, coupled to a small molecular weight active pharmaceutical ingredient (API), including, but not limited to a toxin (including e.g., but not limited to, tubulin inhibitors, actin binders, RNA polymerase inhibitors, DNA-intercalating and modifying/damaging drugs), a kinase inhibitor, or any API that interferes with a particular cellular pathway that is essential for the survival of a cell and/or essential for a particular physiologic cellular pathway.

An "antibody derivative or fragment", as used herein, relates to a molecule comprising at least one polypeptide chain derived from an antibody that is not full length, including, but not limited to (i) a Fab fragment, which is a monovalent fragment consisting of the variable light ($V_L$), variable heavy ($V_H$), constant light ($C_L$) and constant heavy 1 ($C_H1$) domains; (ii) a F(ab')2 fragment, which is a bivalent fragment comprising two Fab fragments linked by a disulfide bridge at the hinge region; (iii) a heavy chain portion of a $F_{ab}$ ($F_d$) fragment, which consists of the $V_H$ and $C_H1$ domains; (iv) a variable fragment ($F_v$) fragment, which consists of the $V_L$ and $V_H$ domains of a single arm of an antibody, (v) a domain antibody (dAb) fragment, which comprises a single variable domain; (vi) an isolated complementarity determining region (CDR); (vii) a single chain $F_v$ Fragment ($scF_v$); (viii) a diabody, which is a bivalent, bispecific antibody in which $V_H$ and $V_L$ domains are expressed on a single polypeptide chain, but using a linker that is too short to allow for pairing between the two domains on the same chain, thereby forcing the domains to pair with the complementarity domains of another chain and creating two antigen binding sites; and (ix) a linear antibody, which comprises a pair of tandem $F_v$ segments ($V_H$-$C_H1$-$V_H$-$C_H1$) which, together with complementarity light chain polypeptides, form a pair of antigen binding regions; and (x) other non-full length portions of immunoglobulin heavy and/or light chains, or mutants, variants, or derivatives thereof, alone or in any combination.

The term "modified antibody format", as used herein, encompasses antibody-drug-conjugates, Polyalkylene oxide-modified scFv, Monobodies, Diabodies, Camelid Antibodies, Domain Antibodies, bi- or trispecific antibodies, IgA, or two IgG structures joined by a J chain and a secretory component, shark antibodies, new world primate framework+non-new world primate CDR, IgG4 antibodies with hinge region removed, IgG with two additional binding sites engineered into the CH3 domains, antibodies with altered Fc region to enhance affinity for Fc gamma receptors, dimerised constructs comprising CH3+VL+VH, and the like.

The term "antibody mimetic", as used herein, refers to proteins not belonging to the immunoglobulin family, and even non-proteins such as aptamers, or synthetic polymers. Some types have an antibody-like beta-sheet structure. Potential advantages of "antibody mimetics" or "alternative scaffolds" over antibodies are better solubility, higher tissue penetration, higher stability towards heat and enzymes, and comparatively low production costs.

Some antibody mimetics can be provided in large libraries, which offer specific binding candidates against every conceivable target. Just like with antibodies, target specific antibody mimetics can be developed by use of High Throughput Screening (HTS) technologies as well as with established display technologies, just like phage display, bacterial display, yeast or mammalian display. Currently developed antibody mimetics encompass, for example, ankyrin repeat proteins (called DARPins), C-type lectins, A-domain proteins of *S. aureus*, transferrins, lipocalins, 10th type III domains of fibronectin, Kunitz domain protease inhibitors, ubiquitin derived binders (called affilins), gamma crystallin derived binders, cysteine knots or knottins, thioredoxin A scaffold based binders, nucleic acid aptamers, artificial antibodies produced by molecular imprinting of polymers, peptide libraries from bacterial genomes, SH-3 domains, stradobodies, "A domains" of membrane receptors stabilised by disulfide bonds and Ca2+, CTLA4-based compounds, Fyn SH3, and aptamers (oligonucleic acid or peptide molecules that bind to a specific target molecules)

In case the immunoligand is not a protein or a peptide, e.g., if its an aptamer, it should preferably be provided with a peptide tag in order to provide a suitable substrate for the enzymatic conjugation disclosed further herein.

"Conjugation", as used herein, relates to the covalent association of a molecule to another molecule by formation of a covalent bond.

An "immunotoxin", as used herein, relates to an immunoligand conjugated to a protein or polypeptide representing a toxin, including, but not limited to bacterial toxins, e.g. diphteria-toxin A, *Pseudomonas* exotoxin, botulinum toxin, or e.g. proteinaceous venoms from invertebrates (e.g. but not limited spiders, scorpions, molluscs, jelly-fish), or vertebrates (e.g., but not limited to snakes), or functional fragments thereof.

The term "low molecular-weight payload" as used herein, represents a payload with a molecular weight not exceeding 2'500 Dalton.

The term "payload", as used herein, represents any naturally occurring or synthetically generated molecule, including small-molecular weight molecules or chemical entities that can chemically be synthesized, and larger molecules or biological entities that need to be produced by fermentation of host cells and that confer a novel functionality to an immunoligand specific for binding to targets or antigens.

The term "small molecular weight toxin", as used herein, means a cytotoxic compound of small molecular weight not exceeding a molecular weight of 2'500 Dalton that is cytotoxic to mammalian cells.

A "transpeptidase", as used herein, is an enzyme or a catalytic domain of an enzyme or a protein that is able to catalyze the breakage of peptide bonds and subsequently either directly, or by way of several reaction intermediates, the formation of novel peptide bonds, such that the energy of the first peptide bond is preserved during the reaction and transferred to a new peptide bond. Preferably, said transpeptidases preferably connect the C-terminus of one peptide or protein with the N-terminus of another peptide or protein. Due to the formation of a new peptide bond, these enzymes or functional domains are also referred to as "protein ligases", "peptide ligases", or nicknamed "protein or peptide staplers". Such protein ligases comprise, but are not limited to sortase enzymes, inteins and split-inteins.

As used herein, the term "sequence-specific transpepeptidase" is meant to define a transpeptidase which needs at least one substrate peptide or protein with a given peptide sequence as recognition sequence (N-terminally and/or C-terminally) to connect said substrate peptide or protein to another peptide or protein, or a small-molecular weight compound containing a peptide or protein component As used herein, the term "site-specific transpepeptidase" is meant to define a transpeptidase which has a specific site in at least one substrate peptide or protein which it uses to conjugate to another peptide or protein, or a small-molecular weight compound containing a peptide or protein component.

Background and General Description of the Invention

The invention discloses methods that utilize site-specific transpeptidases, e.g., sortase enzymes and split-inteins, to site-specifically and selectively conjugate payloads, preferably small molecular weight toxins to immunoligands, preferably antibodies, for the generation of immunoligand payloads, preferably antibody drug conjugates (ADCs). The preferred payloads are small molecular weight toxins modified with short, preferably less than 13 (thirteen) amino acid long synthetic amino acid sequence, which renders them as substrates for sortase enzymes or split intein mediated covalent conjugation either at the N- or C-terminus of the immunoligands (FIGS. 1 & 3). This conjugation is achieved in a site-specific manner and with defined stoichiometry, which is a distinguishing feature to conventional chemical conjugation of payloads to immunoligands, where the conjugation is a stochastic process, as disclosed further above.

Figure 6A:
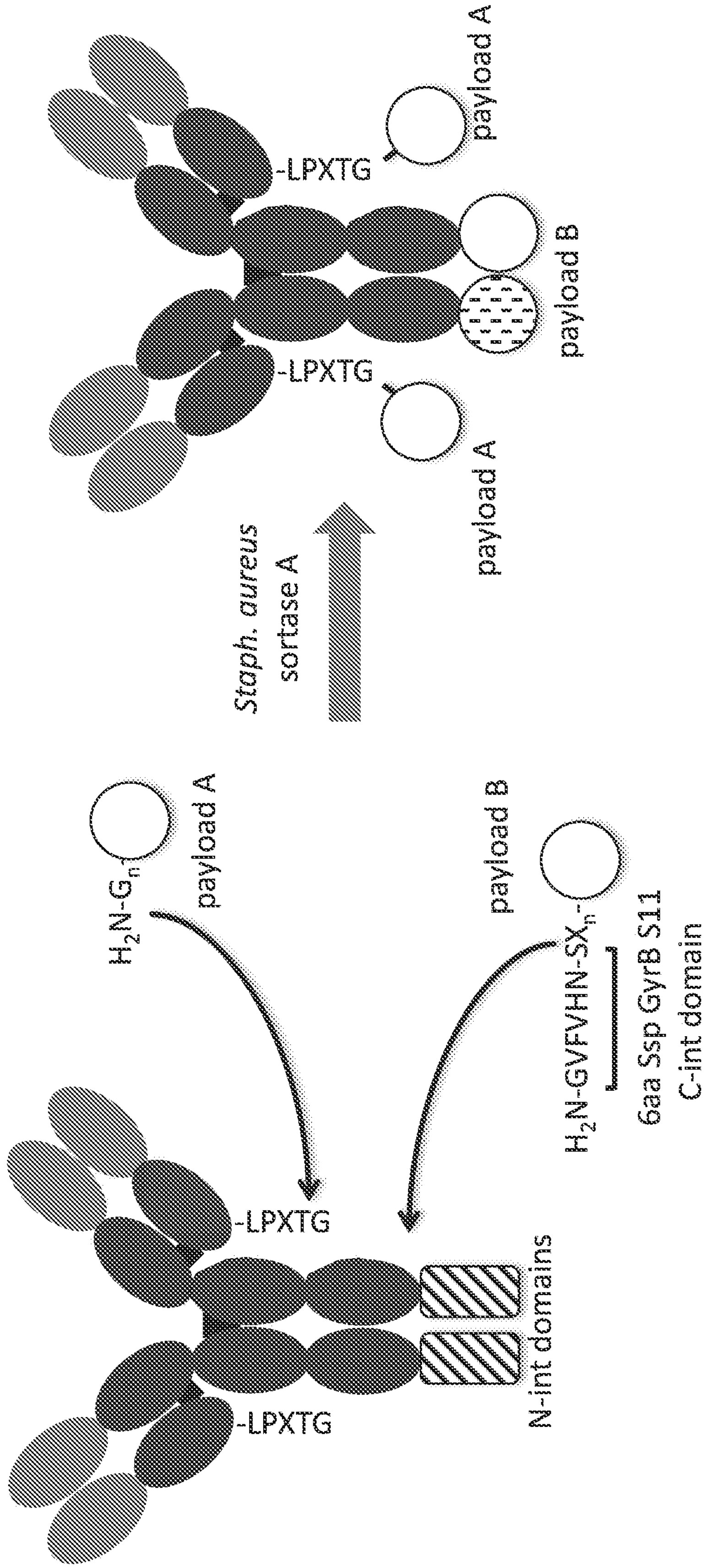
Figure 6B:
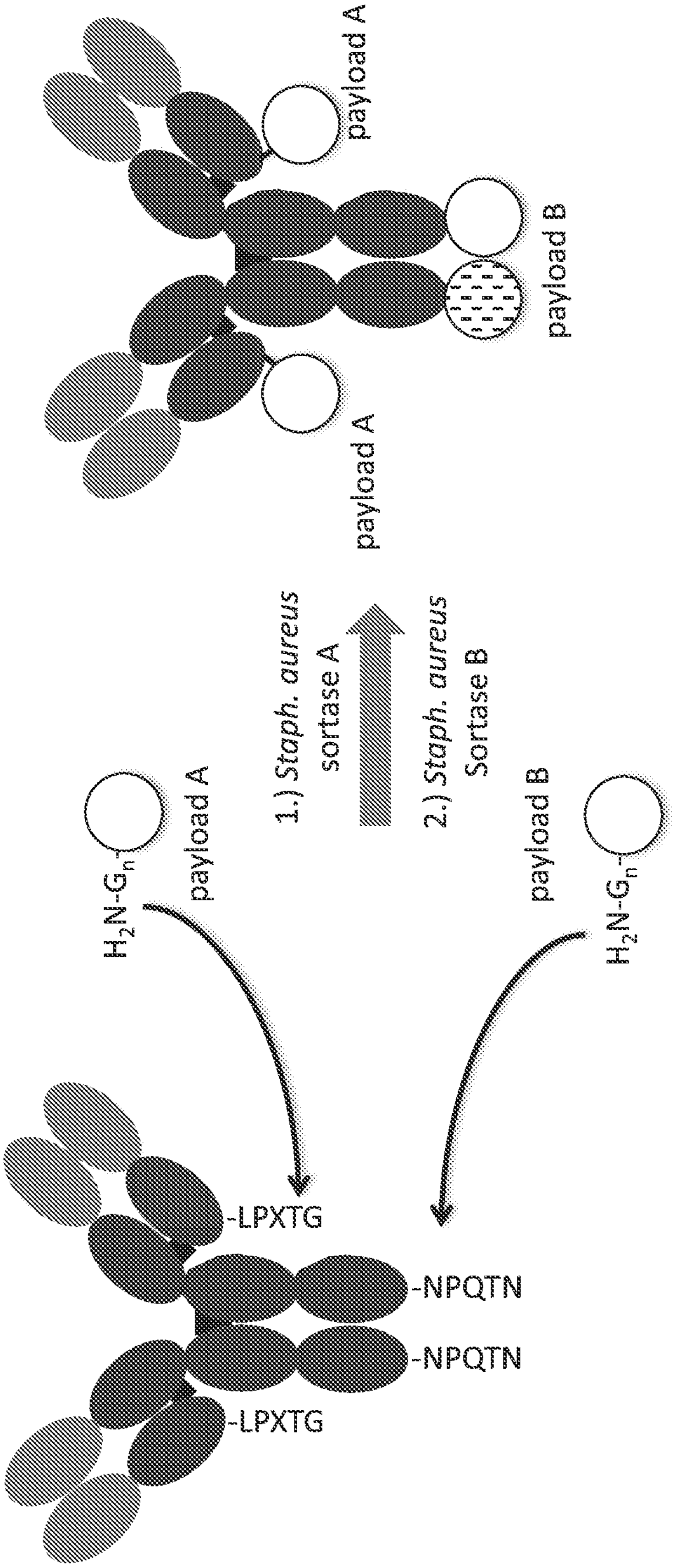

The invention further discloses site specific transpeptidase, e.g. sortase or split-intein mediated conjugation of multimeric immunoligands, preferably antibodies specifically with two different toxin molecules or other labels using different modifications of the subunits of the multimeric protein, e.g. antibody heavy and light chains, and different payloads modified with different, short amino acid stretches specific for different transpeptidases, in order to conjugate at least two different functional payloads to the multimeric immunoligand (FIGS. 6A-6B).

Figure 4A:
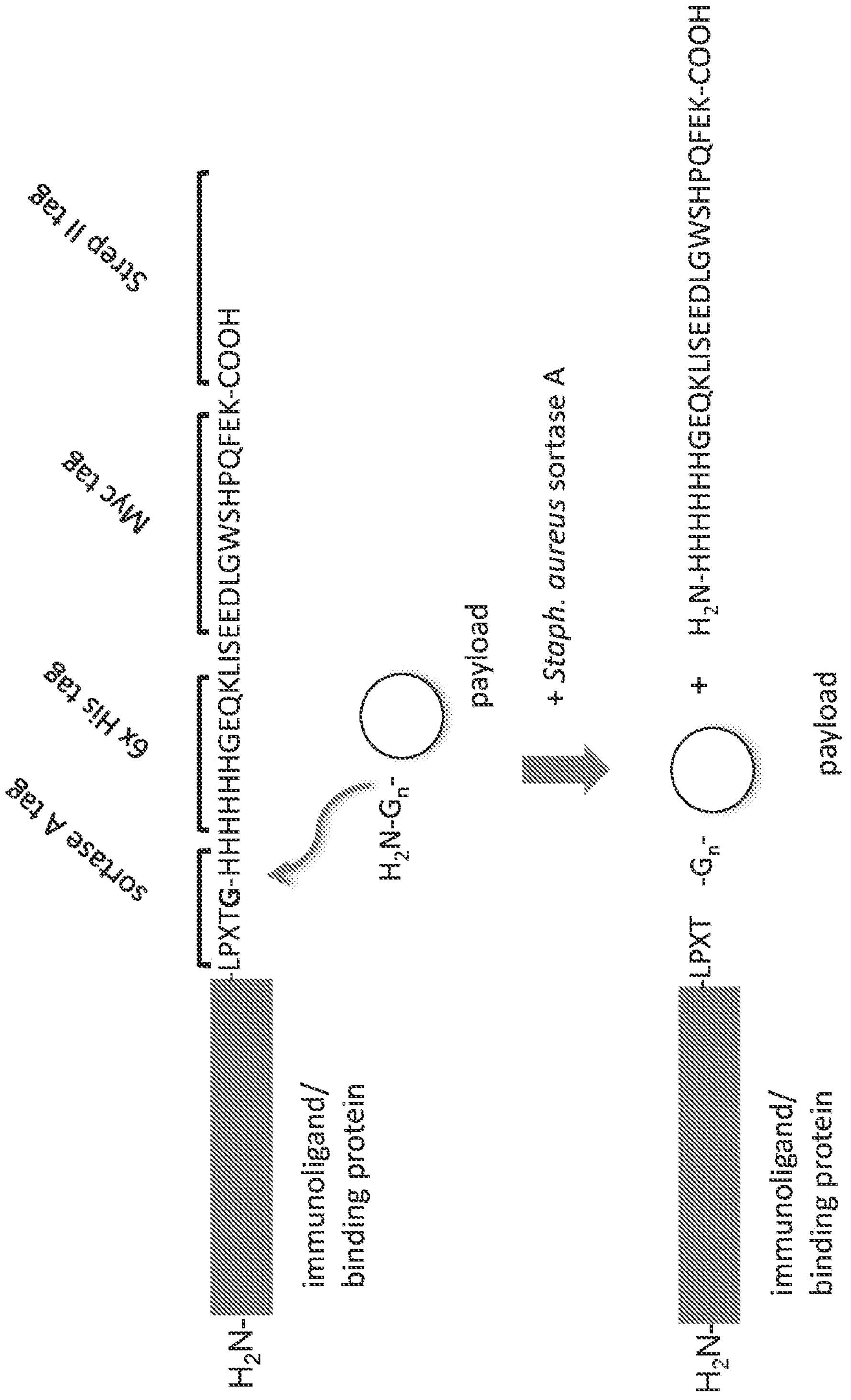
Figure 4B:
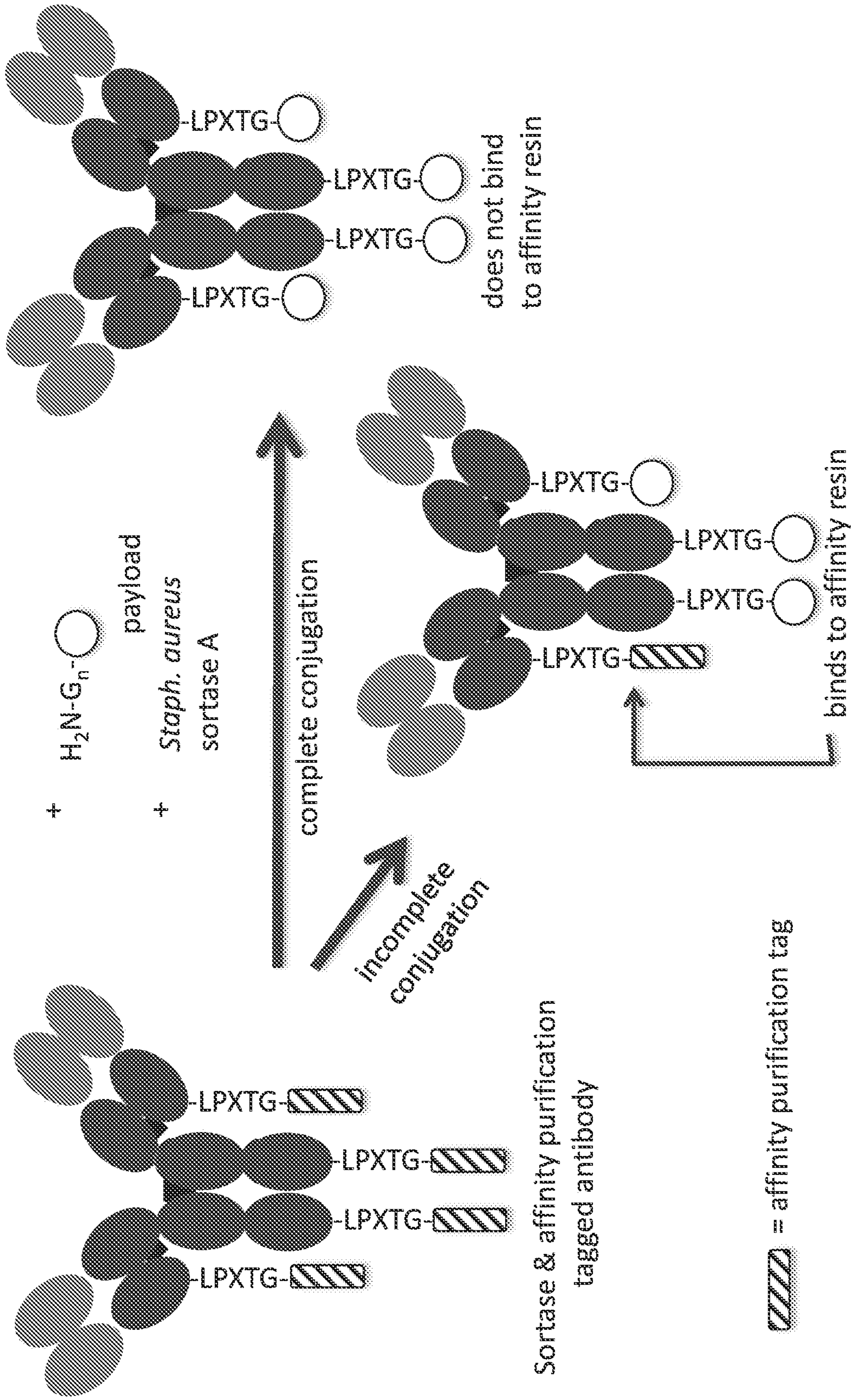

The invention further discloses methods to add affinity purification and/or detection tags to the N- or C-termini of the immunoligands, which undergo enzyme-mediated transpeptidation. such that the removal of the affinity purification and/or detection tag can be utilized to select for immunoligands with complete (100%) conjugation of the payload to the modified binding protein, by means of affinity resins that retain immunoligands that have not been completely conjugated, and therefore still retain the additional affinity purification and/or detection tag (FIGS. 4A-4B).

Figure 5:
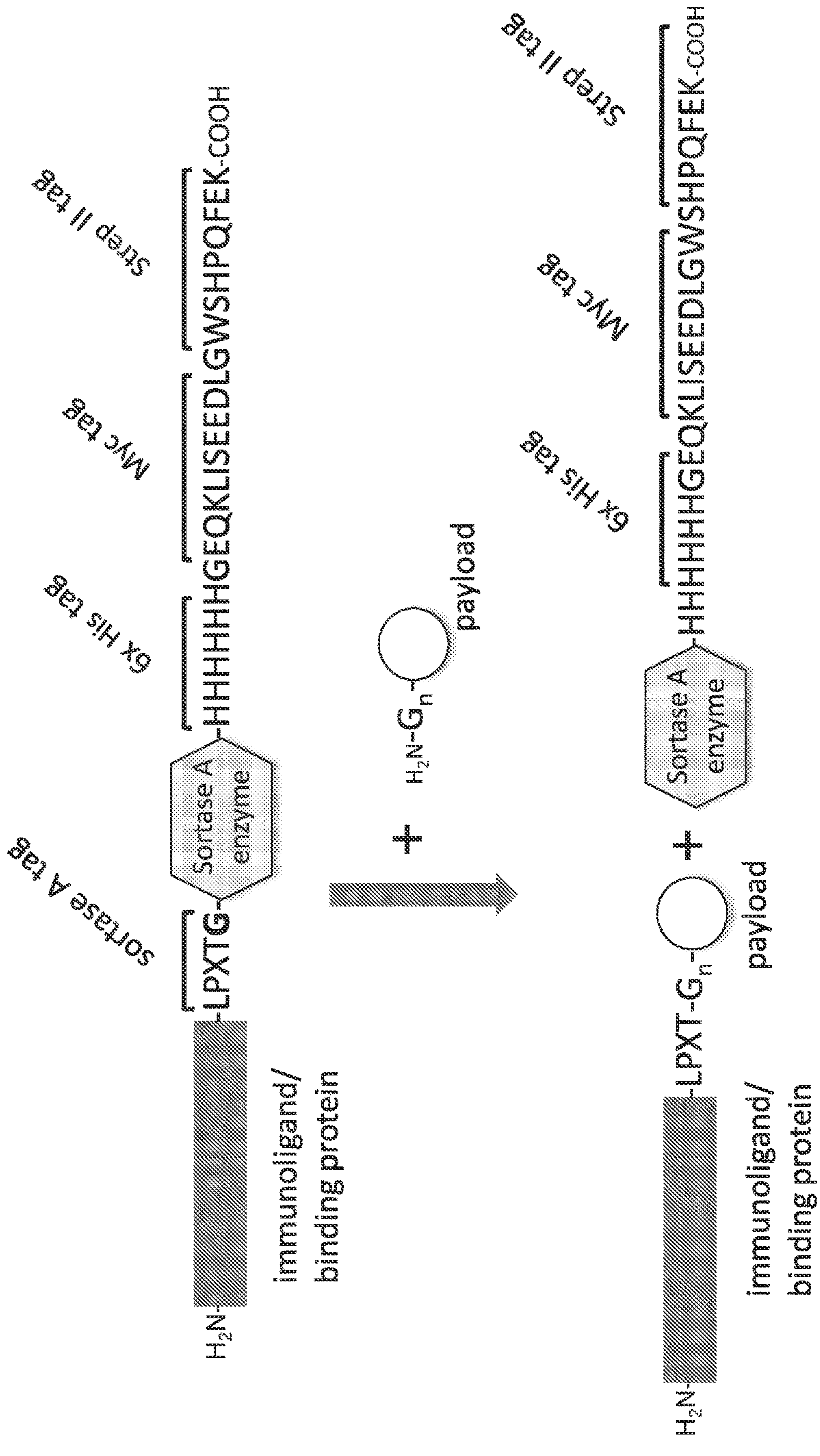

The invention further discloses immunoligands in which a catalytic transpeptidase domain is directly fused to the N- or C-terminus of the protein to be conjugated, such that the transpeptidation activity is integral part of immunoligand to be conjugated, and no additional soluble sortase enzyme needs to be provided in the course of the transpeptidase-mediated conjugation reaction (FIG. 5).

Figure 12A:
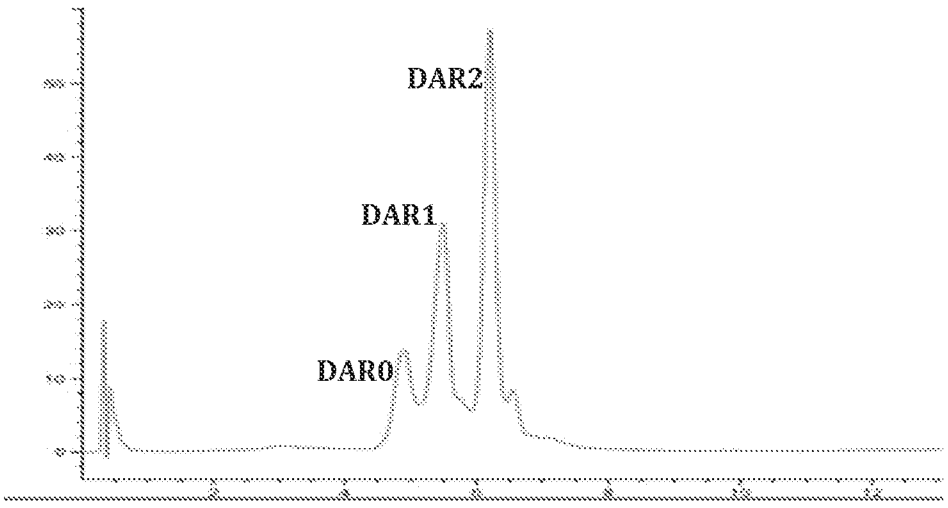
Figure 12B:
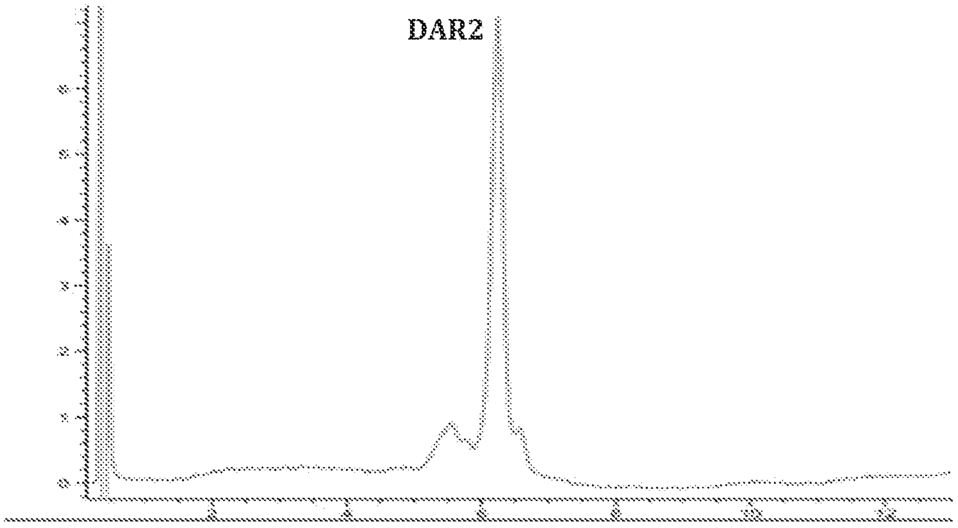

All of these embodiments mentioned above allow the site-specific and stoichiometrically controlled conjugation of any payload, including small molecule toxins (chemical entities), toxic proteins, or fluorescent labels, preferably small molecular weight toxins to immunoligands, including preferably antibodies, which is superior to standard chemical conjugation of payloads to proteins by chemical linker chemistry methods, which cannot be controlled for conjugation ratio and site. Therefore, for the generation of antibody drug conjugates (ADCs) conjugation of toxic payloads by transpeptidases, preferably sortase enzymes and split inteins to antibodies will lead to more homogeneous products with expected improved therapeutic properties for cancer therapy (FIGS. 12A-12B).

The enzymatic conjugation of payloads to immunoligands by sortase enzymes and split-intein allows site-specific and stoichiometric payload conjugation to proteins and immunoligands, lowering cost-of-goods and providing homogeneous immunoligand-payload conjugates, especially as the selectivity of the transpeptidases allows the conjugation of payloads to immunoligands in crude cell culture supernatant, and does not require purified components as in traditional linker-mediated chemical conjugation. Therefore, the use of sequence-specific transpeptidases for conjugation of payloads to immunoligands could significantly lower the cost of goods in immunoligand-payload, and particularly ADC manufacturing.

The first type of transpeptidase disclosed herein, the sortase enzymes, has been identified in a variety of gram-positive bacteria, like *Staphylococcus, Streptococcus* and Pneumococcus species, and catalyse the coupling of virulence factors to cell wall proteoglycans, in order to change the surface signature of the bacteria for evading an efficient immune response by the infected host (Mazmanian et al. (1999)). Sortase A enzyme of the gram-positive bacterium *Staphylococcus aureus* has been characterized first (Ton-That et al. (1999)) and has subsequently been characterized further as a tool for many protein modifications (Tsukiji (2009)). The attraction of sortase enzymes is that the two molecules to be conjugated only require to be modified or expressed on one hand with a short 5 amino-acid long peptide tag (sortase tag, LPXTG in case of *Staphylococcus aureus* sortase A, X being any of the 20 naturally occurring aminoacids), and a short, preferably 3 to 5 amino acid long glycine stretch (Antos et al. (2009a)) (FIGS. 1A-1B), which can easily be added to each of the molecules to achieve either N-terminal or C-terminal conjugation of proteins. This allows to utilize the system on one hand for the coupling or conjugation of two proteins, but also for the conjugation of smaller molecules to proteins.

Figure 2A:
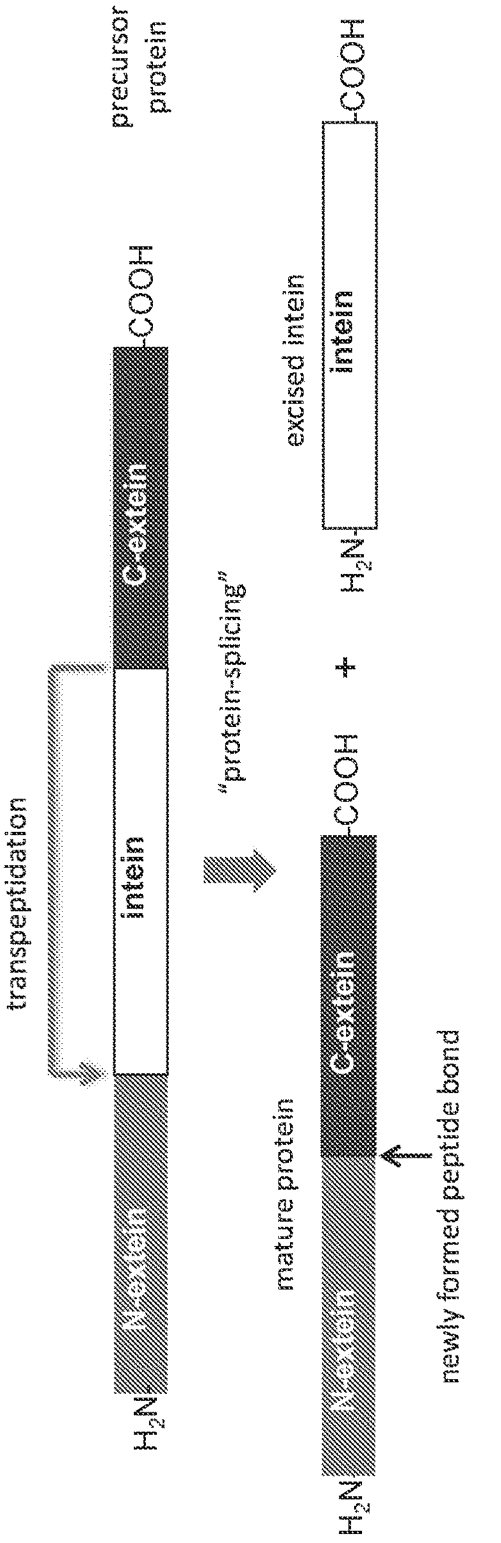
Figure 2B:
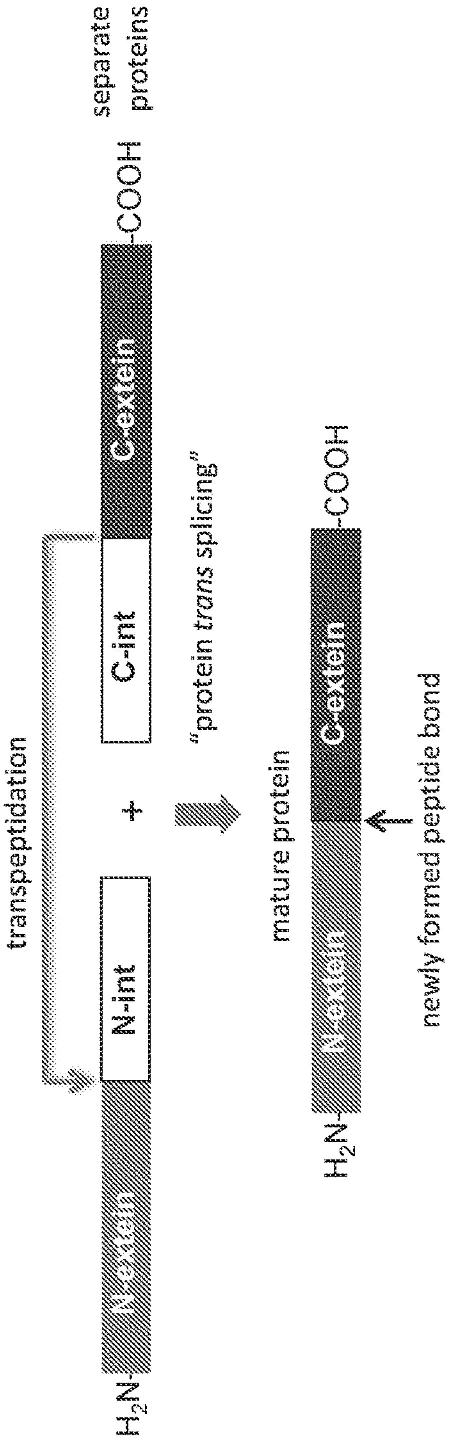
Figure 3A:
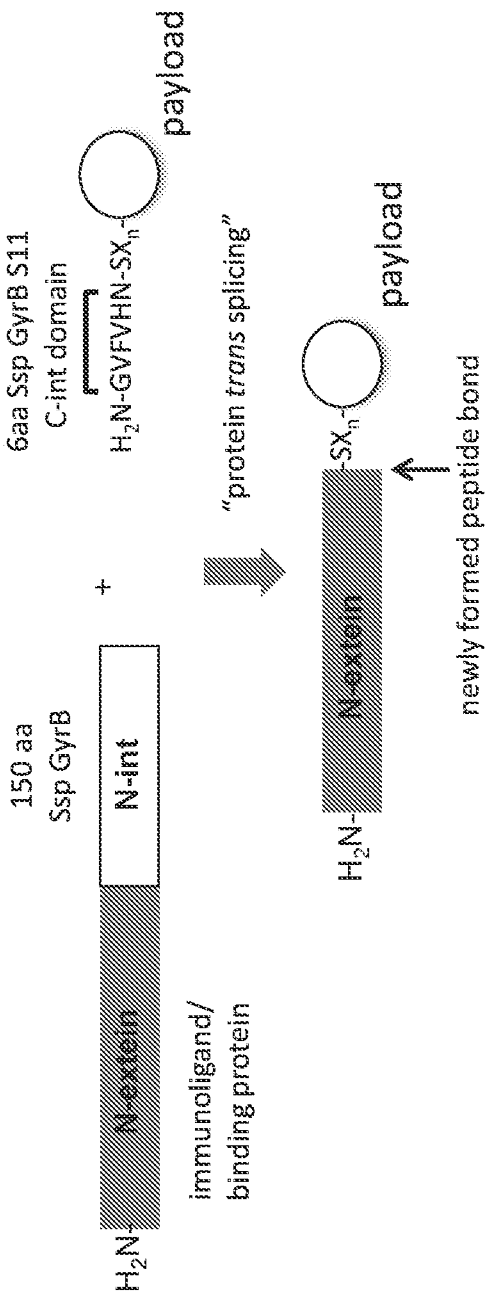
Figure 3B:
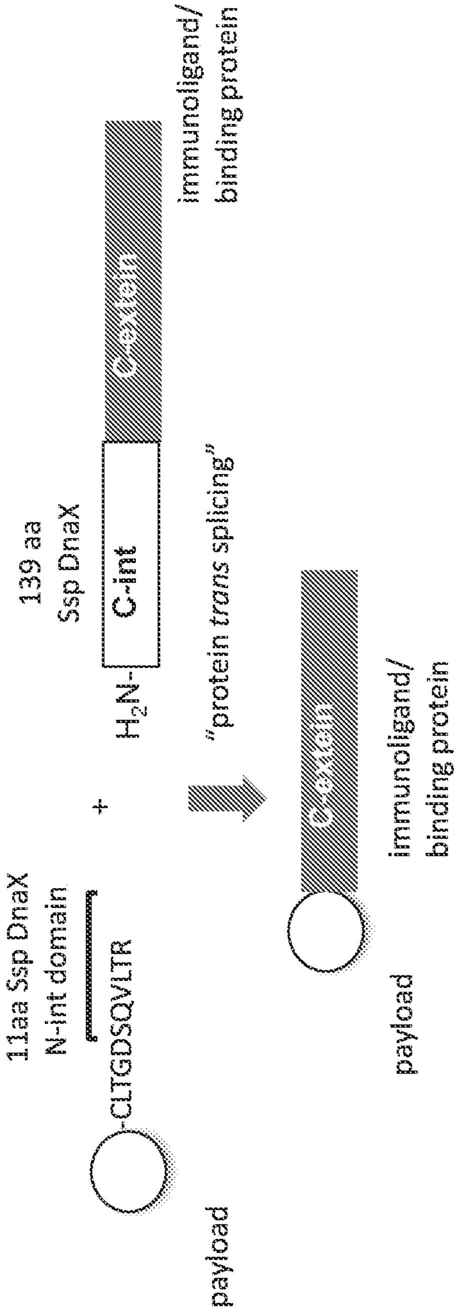

The second type of transpeptidase resulting in peptide-bond cleavage and formation, is represented by the so-called inteins, which have originally been discovered as protein introns, that can remove (splice) themselves out of precursor proteins by cleavage of peptide bonds and formation of new peptide-bonds (Xu et al. (1993)) (FIG. 2A). Inteins can also occur separated into N-intein and C-intein domains (so-called split-inteins) and attached to independent proteins that can subsequently catalyze the trans-splicing of the extein domains (FIG. 2B). Split-inteins have been utilized for the covalent coupling of N-extein and C-extein moieties, and also the purification and/or circularization of proteins (Elleuche (2010)). However, in order to utilize split-inteins also for the conjugation of small molecule payloads, it is necessary to utilize split inteins that function if either the N-intein or the C-intein domain can be reduced to few amino acids, that can easily be added to molecules of any size by chemical synthesis, similar to the short at preferably 3 glycine stretch required for sortase-mediated transpeptidation. With the development of the artificial Ssp GyrB S11 split-intein, in which the C-intein domain only comprises six amino acids (Sun et al. (2004)), this condition has been met and this split-intein has been utilized for the C-terminal labeling of proteins with biotin (Volkmann et al. (2009)) (FIG. 3A). Likewise, the development of a short 11 amino acid long N-intein from Ssp DnaX split-intein allows the N-terminal conjugation of proteins with any molecule, if such 11 amino acid long stretch is added by chemical synthesis to a payload of choice (FIG. 3B).

Therefore, one aspect of the invention is either to add a short, preferably 3 to 5 glycine amino-acid glycine stretch, or a short 12 amino-acid GVFVHNSXXXXX amino acid stretch (X any naturally occurring or artificial amino acids), containing a 6 amino acid C-int domain of Ssp GyrB or a 11 amino-acid N-int domain of Ssp DnaX to a payload-molecule, which is sufficient to allow the respective transpeptidase to conjugate the modified payload to proteins and immunoligands, preferably antibodies that, respectively, contain a sortase enzyme recognition motif, e.g. LPXTG in case of utilization of *Staphylococcus aureus* Sortase A, or a 150aa N-int domain in case of utilization of Ssp GyrB split intein, or a 139 aa C-int domain in case of utilization of Ssp DnaX split intein (see FIGS. 1 & 3).

The addition of short stretches of amino acids, like e.g. 3 or 5 glycine residues to a small molecular weight toxins as required for sortase mediated conjugation, or 12 amino acids as required for split-intein mediated conjugation, has been found to add to the water-solubility of certain hydrophobic toxin molecules (data not shown), such that the amino acid-toxin adduct can be dissolved in the physiologic buffer, ensuring optimal sortase or split-intein conjugation. This prevents stress on the structural integrity of large protein molecules, particularly antibodies that can easily be denatured by exposure to organic solvents and non-physiologic pH often associated with traditional linker chemistry and conjugation. In addition, conjugation of hydrophobic toxin molecules to large proteins, particular antibodies can induce certain levels of protein aggregation. Also this may be improved by using transpeptidases, particularly sortase enzymes, because further hydrophilic amino acids remain in the enzymatically generated conjugate, reducing the propensity for aggregation of large protein, or antibody drug conjugates.

Sortase enzymes have been widely described in the prior art for protein-protein or protein-peptide ligations (Mao et al. (2004), Parthasarathy et al. (2007) or WO2011/133704A2), even including circularization of proteins (Antos et al. (2009b)). The applications of sortase protein or peptide ligation also included protein or peptide ligation using antibody fragments, like Fab- and scFv-fragments with protein- or peptide labels (Mohlmann et al. (2011), Madej et al. (2012), or US2010/0055761A1 and WO2012/142659A1). Even two prior art documents were published, in which full-length antibodies have been sortase-ligated to proteins (Levary et al. (2011), e.g. EGFP, albumin, gelonin were conjugated to the light chain of an antibody), or in which full-length antibodies have been sortase-ligated to short peptides (Swee et al. (2013)). However, no prior art document could be identified demonstrating the sortase-mediated conjugation of small-molecular weight toxins, like e.g. auristatins or maytansins and the like, to full-length antibodies or antibody fragments. In particular no prior art documents could be identified, in which generation of ADCs with small molecular weight toxins has been been disclosed resulting in ADCs with small molecular weight toxins homogeneously conjugated to either IgH or IgL chains (drug-to-antibody ratio 2), or to IgH and IgL chains (drug to antibody ratio 4), as disclosed herein.

While the prior art also discloses the modification of non-protein substrates with glycine residues such that they could be used for sortase modification of simple, single-subunit proteins or peptides (Tsukiji (2009), or WO2007/108013A3, respectively), the more challenging homogeneous conjugation of non-protein substrates, preferably small molecular weight toxins, to multimeric proteins, preferrably antibodies, has not been described before, despite the fact that sortase enzyme mediated protein or peptide ligation has been in the prior art for many years.

Moreover, the conjugation of multimeric proteins, particularly full-length monoclonal antibodies with two different payloads, preferrably two different small molecular weight toxins as disclosed herein, has not been described in the prior art before, despite the fact that sortase enzyme mediated protein or peptide ligation has been in the prior art for many years (Panowski et al. (2014)).

It is known from the prior art that sortase enzymes may accept substrates that contain a minimum of 3 glycine amino acids (Parthasarathy et al. (2007), therefore the invention may include payloads that contain at least three (3) glycine amino acid residues added to the payload molecule of interest, although even one or two glycine residues may be sufficient, and should be comprised by the method disclosed herein. In case of small molecular weight payloads the addition of few glycine amino acid residues can be achieved by conventional synthetic peptide chemistry, as described herein. In case of proteins glycine residues can be added either by adding codons for a number of glycine residues, preferably at least three glycine residues, in-frame to the open reading frame of the protein, or by conventional synthetic peptide chemistry such that the recombinant protein contains at least three N-terminal glycine amino acid residues.

It is known from the literature that different Sortase enzymes, e.g. Sortase B from *Staphylococcus aureus*, or Sortases from other gram-positive bacteria recognize different pentapeptide motifs, which differ from the LPXTG sortase A recognition motif (X=any amino acid) from *Staphylococcus aureus* (Spirig et al. (2011)). Therefore, the invention shall also include the concept of adding other sortase recognition motifs to proteins and immunoligands, including preferably antibodies, that differ from the *Staphylococcus aureus* sortase A recognition motif LPXTG, in order to prepare them for sortase conjugation with different cognate sortase enzyme of different gram-positive bacterial species. Therefore, proteins and immunoligands, preferably antibodies, can also be expressed with a different sortase recognition motif, e.g. a NPQTN pentapeptide motif specific for sortase B from *Staphylococcus aureus* which can then be conjugated to glycine modified payloads.

In an another aspect of the invention, multimeric immunoligands, preferably but not limited to antibodies, which are composed of immunoglobulin heavy and light chains, allow the utilization of said different sortase recognition sequences added to the different polypeptides of such multimeric proteins (in case of antibodies adding different sortase recognition sequences to the antibody heavy and light chains), in order to allow conjugation of different payloads to said different polypeptides by performing sequential conjugations with $Gly_n$-tagged payloads (n>2) in the presence of the respective sortase enzyme (FIG. 6B). For this, an antibody needs to be expressed with different C-terminal modifications at heavy and light chains comprising different sortase recognition motifs for different sortase enzymes. Such an antibody can then sequentially be conjugated to two different payloads containing a glycine modification as described further above.

This format may have the advantage that ADCs specifically be loaded with two different toxins, preferably interfering with a different cellular pathway will be more potent in cancer cell killing, because it is more difficult for a targeted cancer cell to evade the attack of two toxins comprised in the ADCs.

It is clear to a person skilled in the art, that a sortase pentapeptide recognition motif, like the *Staphylococcus aureus* sortase A LPXTG motif, can be added selectively to individual polypeptides of multimeric immunoligands, in order to provide desired conjugation sites. For instance, in the case of antibodies, this allows the generation of modified antibodies, either only containing sortase recognition motifs added to the heavy chains (resulting in two payloads per antibody conjugation), or only containing sortase recognition motifs added to the light chains (resulting in two payloads per antibody conjugation), or containing sortase recognition motifs added to the heavy and the light chains (resulting in four payloads per antibody conjugation). These designed variations will allow specific conjugation of payloads to antibodies by sortase enzymes either to the heavy chains alone (generating ADCs with drug to antibody ratio of 2, i.e. DAR2), or to the light chains alone (generating ADCs with drug to antibody ratio of 2, i.e. DAR2), or simultaneously to the heavy and the light chains (generating ADCs with drug to antibody ratio of 4, i.e. DAR4). This way, the conjugation sites and stoichiometries for antibodies can be varied in a controlled fashion, either generating two payload conjugations per antibody heavy or light chain, or generating four payload conjugations per antibody by addition of the payload to the heavy and the light chains.

Similar to the above-described variations in conjugation sites and stoichiometries using different sortase recognition motifs and sortase enzymes in multimeric proteins or immunoligands, it is a further aspect of the invention to conjugate different payloads to different polypeptide chains of multimeric proteins combining sortase-mediated and split-intein mediated conjugation. This concept allows the simultaneous conjugation of different payloads to different polypeptide chains of multimeric proteins and immunoconjugates in one step, because different transpeptidases and substrates are being employed (FIG. 6A).

It is to be understood that the above-mentioned conjugation of two different payloads to a multimeric protein, preferably an antibody, which is composed of each two disulphide linked heavy and lights chains, can either be accomplished by combining sortase enzyme mediated conjugation with split intein mediated conjugation, as depicted, in FIG. 6A, but that it is also possible to conjugate two different payloads to a multimeric protein, preferably an antibody, by utilizing two different sortase enzymes, recognizing different sortase peptide motifs, for instance sortase A and sortase B from *Staphylococcus aureus*, as mentioned further above (FIG. 6B). However, this may also include sortase enzymes of other sortase classes (e.g. sortases C, D, E, F), or sortase enzymes from other bacterial species, differing in their sortase motif specificity.

Sortase-mediated conjugation of payloads to proteins and immunoligands can be achieved either by providing sortase recognition motif tagged proteins and at least tri-glycine tagged payloads and adding enzymatically active sortase enzyme or a functional fragment thereof as a soluble enzyme. In another aspect of the invention the enzymatically active domain of sortase enzyme can also be provided as a domain fused to either the N- or C-terminus of the protein. In this variation, is is advantageous, but not mandatory, to add the sortase enzymatic domain either N-terminal to an N-terminal sortase recognition motif, or C-terminal to a C-terminal sortase recognition motif Both possibilities ensure that the after the reaction with a glycine-tagged payload, that the enzymatic sortase domain is removed from the protein in the course of the reaction (FIG. 5).

This variation of applying sortase-mediated conjugation of payloads to proteins is similar in concept to split-intein mediated conjugation of payloads, where the enzymatically active N-intein domains of split inteins are tethered to the protein to be conjugated, in order to define the conjugation site in the protein.

Similar to the large number of different sortase transpeptidases with different substrate specificity that have been identified in the literature (Spirig et al. (2011)), there is also a large and growing number of split-inteins known from different species and proteins with different N-intein and C-intein sequences required for transpeptidation that can be retrieved from the so-called InBase database (Perler (2002). Therefore, while the examples of split-intein mediated conjugation of immunoligands with payloads disclose the preferred Ssp GyrB S11 split intein (Volkmann et al. (2009)), because the C-intein domain can be reduced to a short, linear 6-mer amino acid stretch, split-intein mediated conjugation of payloads to proteins and immunoligands can also be achieved with other split inteins from the InBase database, as long as the N-intein or C-intein domains are short enough (preferably shorter than 13 amino acids) to easily allow peptide synthesis and addition to any payload molecule of choice. However, it is clear to a person skilled in the art that in the case of protein payloads, C-intein domains of any size may be fused to the protein payload by genetic fusion to the ORF of the protein payload of interest, and there is no mechanistic advantage of using split-inteins with small (<13 amino acids) N-intein or C-intein domains.

However, if synthetic small-molecule payloads are to be conjugated to proteins and immunoligands, then a small N-int or C-int domain of less than 13 amino acids as disclosed herein are advantageous, as in the case of the preferred C-int of the Ssp GyrB S11 split intein, of the N-int of Ssp DnaX, because such a short peptide can synthetically be added to any synthetic small molecule weight payload by standard synthetic chemistry.

Figure 1B:
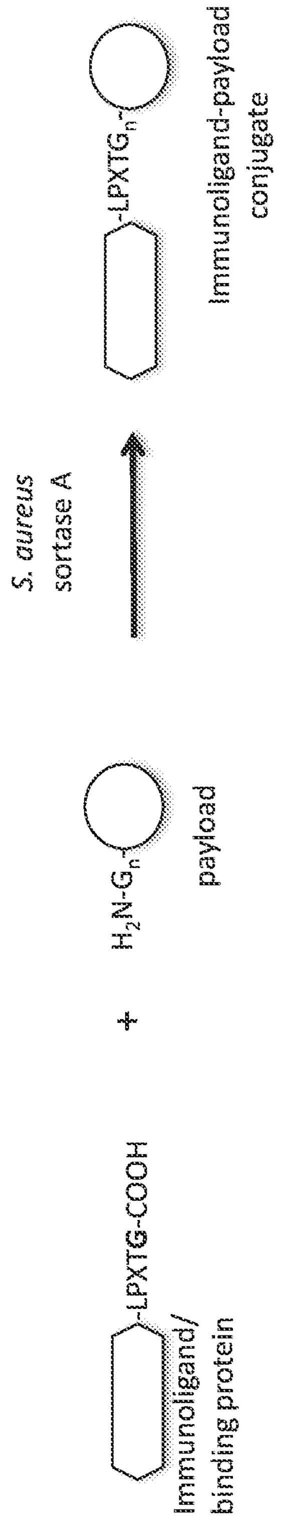

Sortase-mediated and split-intein mediated conjugation of payloads can be performed at either the N- or the C-termini of proteins and immunoligands. This is only dependent on how the sortase-motif/glycine stretch and N-intein/C-intein domains are positioned at protein and payload (FIGS. 1A-1B).

In the case of antibodies, which are the preferred immunoligands, it is preferred to conjugate the payloads to the C-termini of the antibodies, because this positions the payloads most distally to the antigen-binding sites of the antibody. However, this preference shall not be interpreted by way of limitation, and it may be advantageous to conjugate payloads to the N-terminus of other immunoligand molecules, like e.g. antibody mimetics, in which the functional binding domains are not located at the N-terminus of the molecule.

Another aspect of the invention is to improve the efficiency of sortase and split-intein conjugation of payloads to proteins and immunoligands by adding affinity purification or detection tags, like e.g., but not limited to small peptide tags (e.g. histidine tags, strep-tag, MYC-tag or HA-tag) or larger protein affinity purification tags (e.g. maltose-binding protein (MBP) tag, Glutathione-S-transferase (GST) tag, or Chitin-binding tag) distal to the sortase recognition motif or the split-intein domain fused to the protein or immunoligand of interest. With this aspect of the invention the affinity purification tag will be removed from the immunoligand to be conjugated as part of the transpeptidation reaction. This can be exploited to enrich fully payload conjugated immunoligands, as unreacted proteins and immunoligands, that still contain the affinity purification tag, can be removed by binding to a suitable affinity resin, while completely payload conjugated proteins and immunoligands will no longer contain the affinity purification tag, and can thus be specifically separated from the unreacted immunoligand substrates. This aspect of the invention is particularly powerful in the context of multimeric proteins and immunoligands, like the preferred antibodies, in which several payloads need to be conjugated. The use of affinity purification tags located distal to the sortase or intein transpeptidase conjugation site ensures that one can remove proteins and immunoligands in which the affinity purification tag is still present due to incomplete payload conjugation (FIG. 5).

In comparison to chemical conjugation, this provides a significant advantage in the process to obtain homogeneous immunoligand/payload conjugates, and preferably ADCs in which small molecular weight toxins are site specifically conjugated to the C-termini of antibody heavy and/or light chains.

Generally, the disclosed method provides a novel and efficient method to site-specifically and stoichiometrically conjugate payloads, preferably small molecular weight toxins to immunoligands, preferably antibodies, by which defined immunoligand/payload conjugates, preferably ADCs are generated, that are useful for the therapy of diseases, preferably of cancer. The method may also be utilized for the generation of immunoligand/payload conjugates useful for the diagnosis of diseases, preferably oncology diseases. The novel method allows generation covalent immunoligand/payload conjugates by utilization of peptide-bond breaking and forming enzymes (transpeptidases), including sortase enzymes and split-inteins, or catalytically active fragments thereof. Said enzymes can catalyze the covalent and site-specific conjugation of payloads containing short amino acid stretches (preferably shorter than 13 amino acids) either to the N- or C-termini of immunoligands which are suitably modified allowing sortase and split-inteins to break and to form peptide bonds in the course of the reaction. Immunoligands are preferably antibodies, for the site-specific conjugation of small molecular weight toxins, in order to generate antibody drug conjugates (ADCs) with defined antibody payload, or drug to antibody ratios.

EMBODIMENTS OF THE INVENTION

According to the invention, a method of producing an immunoligand/payload conjugate is disclosed, which method encompasses conjugating a payload to an immunoligand by means of a sequence-specific transpeptidase, or a catalytic domain thereof.

According to a preferred embodiment of the invention, the payload and/or the immunoligand either a) consists, entirely, of a protein or peptide
b) comprises at least one protein or peptide domain, or
c) comprises at least one peptide chain and, further, the protein or peptide or domain comprises, preferably, an amino acid sequence that can be detected by the sequence-specific transpeptidase, or a catalytic domain thereof.

This means, for example, that, in case the payload and/or the immunoligand is a protein, it means that said protein comprises, at its N- or C-terminus, an amino acid sequence which can be detected by the sequence-specific transpeptidase. If such amino acid sequence is lacking to the naïve protein, it can be fused to the N- or C-terminus of said protein by recombinant methods known in the art.

In case the payload and/or the immunoligand is not a protein, such amino acid sequence which can be detected by the sequence-specific transpeptidase, is to be conjugated to the former by conventional chemical crosslinking methods known in the art.

Additional functionalities may be incorporated between the recognition sequence for a specific transpeptidase and the payload. This can be realized by chemical structures either being categorized by being cleavable (e.g. containing hydrazone, or disulfide chemistry, or specific peptide sequences for intracellular proteases) or being non-cleavable (e.g. containing thioether chemistry) following internalization into cells.

Chemical structures containing hydrazone chemistry can selectively be cleaved within the intracellular compartment of lysosomes (lower pH compared to the systemic blood circulation).

Peptide linkers have the potential to be selectively cleaved by lysosomal proteases (e.g. cathepsin-B) and have demonstrated increased serum stability and improved anti-tumor effects compared to hydrazone linkers. Valine-citruline (Val-Cit) pairs are the most commonly used peptide linkers and are ideally suited to work with the auristatin family of drugs such as monomethyl auristatin E (MMAE).

Non-cleavable Linkers have long been overlooked as researchers were convinced the cleaving of the linker was the most reasonable way to free the drug. However, conjugates can, upon binding to a membrane receptor, get rapidly internalized and once internalized, the immunoligand can be degraded to the point where the payload, e.g., the drug is exposed. As one prominent example, thioether linkers, use the SMCC (N-succinimidyl-4-(N-maleimidomethyl)-cyclohexane-1-carboxylate) linker (FIG.

All of theses approaches have in common that there is no true site-specificity of the coupling reaction. Because linker-mediated, chemical conjugation is a stochastic process, linker-mediated chemical ligation of payloads leads to heterogeneous mixtures of conjugated proteins that may differ in their therapeutic efficacy and/or diagnostic potential. Obviously, mixtures of protein-payload conjugates also represent a significant challenge in the regulatory approval process for therapeutic conjugates, as batch-to-batch variation and/or variations in the active pharmaceutical ingredient (API) are negatively viewed by regulatory authorities due to potential safety concerns.

Non-cleavable Linkers have long been overlooked as researchers were convinced the cleaving of the linker was the most reasonable way to free the drug. However, conjugates can, upon binding to a membrane receptor, get rapidly internalized and once internalized, the immunoligand can be degraded to the point where the payload, e.g., the drug is exposed. One prominent example, thioether linkers, use the SMCC (N-succinimidyl-4-(N-maleimidomethyl)-cyclohexane-1-carboxylate) linker (See FIG. 14A, structure 2).

All of theses approaches have in common that there is no true site-specificity of the coupling reaction. Because linker-mediated, chemical conjugation is a stochastic process, linker-mediated chemical ligation of payloads leads to heterogeneous mixtures of conjugated proteins that may differ in their therapeutic efficacy and/or diagnostic potential. Obviously, mixtures of protein-payload conjugates also represent a significant challenge in the regulatory approval process for therapeutic conjugates, as batch-to-batch variation and/or variations in the active pharmaceutical ingredient (API) are negatively viewed by regulatory authorities due to potential safety concerns.

According to another preferred embodiment of the invention, the immunoligand comprised in the immunoligand/payload conjugate is at least one selected from the group consisting of an antibody, modified antibody format, antibody derivative or fragment, and/or an antibody mimetic Preferably, in this embodiment, a small molecular payload is rendered as substrate for the sequence-specific transpeptidase by coupling of a peptide of less than 13 amino acids to the small molecular payload, such that it can be conjugated by a transpeptidase to the C-termini of a monoclonal antibody containing C-terminal modifications recognized by said transpeptidases. Such C-terminal modifications may be contained on either both heavy chains, or both light chains, or of heavy and light chains of a full-length antibody, thereby allowing generation of a site-specifically conjugated ADC with either drug-to-antibody ratio of 2 or 4 (DAR2 or DAR4).

According to another preferred embodiment of the invention, the immunoligand binds at least one entity selected from the group consisting of a receptor an antigen, a growth factor a cytokine, and/or a hormone As used herein, the term "receptor" means a cell surface molecule, preferably a cell surface molecule that (i) binds specific, or groups of specific, signalling molecules (i.e. a receptor, like, e.g., the VEGF receptor), and/or (ii) has no known ligand (i.e. an orphan receptor, like, e.g. HER2/neu). The natural receptors are expressed on the surface of a population of cells, or they merely represent the extracellular domain of such a molecule (whether such a form exists naturally or not), or a soluble molecule performing natural binding function in the plasma, or within a cell or organ. Preferably, such receptor is a member of a signalling cascade that is involved in a particular pathogenic process (e.g., a receptor that belongs to a signalling cascade of a growth factor), or is expressed on the surface of a cell or particle that is involved in a pathological process, e.g., a cancer cell.

As used herein, the term "antigen" means a substance that has the ability to induce a specific immune response, and may include surface proteins or protein complexes (e.g. ion channels). Often times, antigens are associated to pathogenic entities, e.g., a cancer cell.

As used herein, the term "cytokine" refers to small cell-signaling protein molecules that are secreted by numerous cells and are a category of signaling molecules used extensively in intercellular communication. Cytokines can be classified as proteins, peptides, or glycoproteins; the term "cytokine" encompasses a large and diverse family of regulators produced throughout the body by cells of diverse embryological origin.

As used herein, the term "growth factor" relates to naturally occurring substances capable of stimulating cellular growth, proliferation and cellular differentiation. Usually a growth factor is a protein or a steroid hormone. Growth factors are important for regulating a variety of cellular processes.

As used herein, the term "hormone" relates to a chemical released by a cell, a gland, or an organ in one part of the body that sends out messages that affect cells in other parts of the organism. The term encompasses peptide hormones, lipid and phospholipid-derived hormones including steroid hormones, and monoamines.

In case the immunoligand binds a receptor or an antigen, the immunoligand-payload conjugate can for example be directed to a specific site, e.g., to a pathogenic entity, e.g., a cancer cell, where the payload, e.g. a toxin or a chemotherapeutic agent, is delivered. Thus, the systemic toxicity of the toxin or the chemotherapeutic agent is reduced, while the local concentration of the latter at the site of action is increased, thus providing a better efficacy while side effects are reduced. Furthermore, a respective signalling cascade can be inhibited by the binding of the immunoligand. In case the payload is a marker the latter can thus be used to mark a specific site, e.g., a cancer cell characterized by a given surface antigen detected by the immunoligand, for diagnosis.

In case the immunoligand binds a growth factor, a cytokine, and/or a hormone, the immunoligand/payload conjugate can for example be directed to the site the growth factor cytokine or hormone usually binds to, in order to deliver the payload in a site-specific manner.

Further, a respective signalling cascade can be inhibited by the binding of the immunoligand.

As used herein, the term "to bind" means the well-understood interaction or other nonrandom association between immunoligands, e.g., antibodies, or antibody fragments, and their targets. Preferably, such binding reaction is characterized by high specify and/or sensitivity to the target. Preferably, the binding reaction is characterized by a dissociation constant (Kd)$\leq 10^{-3}$ M, preferably $\leq 10^{-4}$ M, $\leq 10^{-5}$ M, $\leq 10^{-6}$ M, $\leq 10^{-7}$ M, $\leq 10^{-8}$ M, $\leq 10^{-9}$ M, and most preferred $\leq 10^{-10}$.

According to a preferred embodiment of the invention, it is provided that at least one catalytic domain of the sequence-specific transpeptidase is fused to the N-terminus or the C-terminus of either the immunoligand or the payload.

Such fusion may take place by recombinant engineering, or by chemical coupling. In this embodiment, the enzymatic activity leading to the site-specific conjugation of the immunoligand to the payload does not need to be added to the reaction as a separate recombinant enzyme, but is rather part of protein substrate to be conjugated.

Preferably, the sequence-specific transpeptidase is at least one selected from the group consisting of a sortase, or one or more fragments or derivatives thereof
a spilt-intein, or one or more fragments or derivatives thereof.

In a preferred embodiment, where the transpeptidase is a sortase, the payload, e.g., a toxin, is preferably rendered as substrate for sortase conjugation by addition of a small number of glycine amino acid residues, preferably 3 or 5 glycine residues.

In another preferred embodiment, where the transpeptidase is a split intein, e.g., a Ssp GyrB split intein, the payload, e.g., a toxin is rendered as substrate for split intein conjugation by addition of less than 13 amino acid residues of the sequence GVFVHN-SX$_n$, X being any amino acid and n being an integer between ≥0 and ≤5.

The use of transpeptidases, preferably sortase enzymes and split inteins for the generation of antibody drug conjugates, in which small molecular weight toxins are conjugated to full-length antibodies, has not yet been described in the prior art (Panowski et al. (2014)).

Sortase enzymes have been identified in a variety of gram-positive bacteria, like *Staphylococcus, Streptococcus* and Pneumococcus species, and catalyze, in vivo, the coupling of virulence factors to cell wall proteoglycans, in order to change the surface signature of the bacteria for evading an efficient immune response by the infected host (Mazmanian et al. (1999)).

The sortase A enzyme of the gram-positive bacterium *Staphylococcus aureus* has been characterized first (Ton-That et al. (1999)) and has subsequently been characterized further as a tool for many protein modifications (Tsukiji (2009)).

One beneficial feature of sortase enzymes is that the two molecules to be conjugated only require short peptide tags ("sortase tags"), which in case of *Staphylococcus aureus* sortase A is for example LPXTG at the C-terminus of one molecule (e.g., the payload), and a short 3 to 5 amino acid glycine stretch at the N-terminus of the other molecule (e.g., the immunoligand, see FIGS. 1A-1B). These peptide tags can either be fused to the molecules, or conjugated thereto by means of conventional crosslinking chemistry. This allows to utilize the system on one hand for the ligation of two proteins, but also for the conjugation of small molecular weight compounds, preferably small molecular weight toxins to proteins. In case of *Staphylococcus aureus* sortase B, the respective sortase motif is NPQTN.

Inteins, which have originally been discovered as protein introns that can remove (splice) themselves out of precursor proteins by cleavage of peptide bonds and new peptide-bond formation (Xu et al. (1993)) (FIG. 2A).

Naturally occurring and artificial split-inteins involve that the intein coding region has been split into N-intein and C-intein domains, which can be attached to different proteins or peptides in such way that, subsequently the trans-splicing of the extein domains (FIG. 2B) leads to the conjugation of the two proteins Split-inteins have thus been utilized for the covalent coupling of N-extein and C-extein moieties, and also for the purification and/or circularization of proteins (Elleuche (2010)). One embodiment disclosed herein is to utilize split-inteins for the conjugation of small molecular weight compounds, preferably small molecular weight toxins and other small molecule labels, in which a short C-extein peptide sequence of smaller than 13 amino acids is coupled to molecules of any size, similar to the short glycine amino acid stretch required for sortase-mediated transpeptidation.

In case of sortase enzymes addition of a short glycine stretch (>2 glycine residues) to a molecule of choice is sufficient to allow the molecule to be conjugated to immunoligands containing a penta-peptide sortase recognition motif, like e.g. LPXTG in case of sortase A of *S. aureus*. In case of split-inteins, minimally a short 12 amino-acid GVFVHNSAGSGK amino acid stretch containing a short, 6 amino acid C-intein (GVFVHN) from Ssp GyrB and a short C-extein (here: SAGSGK) are sufficient to modify any payload molecule, preferably a small molecular weight toxin, for split-intein mediated conjugation to immunoligands containing the N-intein domain of the Ssp GyrB split intein (Volkmann et al. (2009)). Other split inteins, in which functional intein domains can be reduced to small <13 amino acid long peptide stretches may be utilized as well.

Even if, in the literature, split-enzymes are not always referred to as enzymes, they qualify as such, because the reaction they catalyze results in the breakage of a peptide bond and the formation of a new peptide bond and this can be viewed as transpeptidases, because the energy of an existing peptide bond is transferred to a new peptide bond.

Other than chemical conjugation, the transpeptidase-mediated conjugation occurs under physiologic aqueous buffer conditions and physiologic temperatures, thereby minimally affecting the protein or antibody integrity in the conjugation reaction. This feature ensures optimal functionality of the resulting conjugate According to another preferred embodiment of the invention, it is provided that the payload comprised in the immunoligand/payload conjugate is at least one selected from the group consisting of a marker
a processing tag, and/or
a drug.

The term "marker" (also called "detection tag"), as used herein, may refer to any molecule or moiety that comprises one or more appropriate chemical substances or enzymes, which directly or indirectly generate a detectable compound or signal in a chemical, physical or enzymatic reaction.

The term "processing tag" as used herein, may encompass affinity tags, solubilization tags, chromatography tags and epitope tags. Affinity tags (also used as purification tags) are appended to proteins so that they allow purification of the tagged molecule from their crude biological source using an affinity technique. These include chitin-binding protein (CBP), maltose binding protein (MBP), and glutathione-S-transferase (GST). The poly(His) tag, preferably a 6×His tag, is a widely-used processing tag; it binds to metal matrices. Solubilization tags are used, especially for recombinant proteins expressed in chaperone-deficient species such as *E. coli*, to assist in the proper folding in proteins and keep them from precipitating. These include thioredoxin (TRX) and poly(NANP). Some affinity tags have a dual role as a solubilization agent, such as MBP, and GST.

Chromatography tags are used to alter chromatographic properties of the protein to afford different resolution across a particular separation technique. Often, these consist of polyanionic amino acids, such as FLAG-tag.

Epitope tags are short peptide sequences which are chosen because high-affinity antibodies can be reliably produced in many different species. Epitope tags are usually derived from viral genes, which explain their high immunoreactivity. Epitope tags include e.g. the V5-tag, MYC-tag, and HA-tag. These tags are particularly useful for western blotting, immunofluorescence and immunoprecipitation experiments, although they also find use in protein purification.

Processing tags find many other usages, such as specific enzymatic modification (such as biotin ligase tags) and chemical modification (FlAsH) tag. Often tags are combined to produce multifunctional modifications of the protein.

Preferably, said marker is at least one selected from the group consisting of a radiolabel, preferably a radioactively labelled peptide or protein a fluorescent label, preferably a fluorescent peptide or protein, and/or an enzyme label, preferably a peroxidase.

This enumeration of potential marker payloads is by no means restrictive. According to another preferred embodiment, said drug is at least one selected from the group consisting of a cytokine a radioactive agent an anti-inflammatory drug a toxin, and/or a chemotherapeutic agent This enumeration of potential drug payloads is by no means restrictive. As used herein, the term "cytokine" refers to small cell-signaling protein molecules that are secreted by numerous cells and are a category of signaling molecules used extensively in intercellular communication. Cytokines can be classified as proteins, peptides, or glycoproteins; the term "cytokine" encompasses a large and diverse family of regulators produced throughout the body by cells of diverse embryological origin. In the present context, cytokines are for example meant to impair, or even kill, pathogenic entity, e.g., a cancer cell.

As used herein, the term "radioactive agent" relates to an entity which has at least one atom with an unstable nucleus, and which is thus prone to undergo radioactive decay, resulting in the emission of gamma rays and/or subatomic particles such as alpha or beta particles, which have a cell killing effect. In the present context, radioactive agents are meant to impair, or even kill, pathogenic entity, e.g., a cancer cell.

As used herein, the term "anti-inflammatory drug" relates to compounds that reduce inflammation. This can be, e.g., steroids, just like specific glucocorticoids (often referred to as corticosteroids), which reduce inflammation or swelling by binding to glucocorticoid receptors. The term further encompasses non-steroidal anti-inflammatory drugs (NSAIDs), which counteract the cyclooxygenase (COX) enzyme. On its own, COX enzyme synthesizes prostaglandins, creating inflammation. In whole, the NSAIDs prevent the prostaglandins from ever being synthesized, reducing or eliminating the pain. The term further encompasses Immune Selective Anti-Inflammatory Derivatives (ImSAIDs), which are a class of peptides that alter the activation and migration of inflammatory cells, which are immune cells responsible for amplifying the inflammatory response.

As used herein, the term "toxin" relates to a molecule which is toxic to a living cell or organism. Toxins may be peptides, or proteins or preferably small molecular weight compounds, that are meant to impair, or even kill, pathogenic entity, e.g., a cancer cell. Toxins, as meant herein, encompass, in particular, cellular toxins. Preferably, said toxin is a small molecular toxin, i.e., having a molecular weight of ≤2500 Da.

As used herein, the term "chemotherapeutic agent" relates to molecules that have the functional property of inhibiting a development or progression of a neoplasm, particularly a malignant (cancerous) lesion, such as a carcinoma, sarcoma, lymphoma, or leukemia. Inhibition of metastasis or angiogenesis is frequently a property of anti-cancer or chemotherapeutic agents. A chemotherapeutic agent may be a cytotoxic or chemotherapeutic agent. Preferably, said chemotherapeutic agent is a small molecular weight cytostatic agent, which inhibits or suppresses growth and/or multiplication of cancer cells.

Conjugating cytokines, radioactive agents, toxins or chemotherapeutic agents to an immunologand can help to reduce side effects and risks related to their administration, because a) the immunoligand directs the conjugate to a specific site, e.g., to a pathogenic entity, e.g., a cancer cell where the payload effects its toxic function. Thus, the systemic toxicity of the payload is reduced, while the local concentration of the latter at the site of action is increased, thus providing a better efficacy while side effects are reduced.

b) it can be provided that the conjugate is internalized by the pathogenic entity, in such way that after internalization, the payload is released and only then develops its desired cytotoxic function, i.e., without affecting the surrounding cells or tissue.

The following table is a non restrictive list of potential targets/antigens (1$^{st}$ column) and examples for existing immunoligands targeting the former (2$^{nd}$ column). The 3$^{rd}$ columns shows a non restrictive list of potential toxins, cytokines or chemotherapeutic agents. Note that the examples from the 1$^{st}$ and the 3$^{rd}$ column can be combined with one another ad libitum, while hundreds of further targets and payloads exist. Respective target/payload combinations not explicitly mentioned in the table are encompassed by the scope of the present invention.

| target/antigen | example of an existing immunoligand | payload |
|---|---|---|
| Endothelial Growth factor receptor (EGFR) | Cetuximab | Maytansinoides, e.g. Mertansine, Ansamitocin Ravtansin, DM4, DM1 |
| CD20 | Rituximab, Ibritumomab, Tositumomab (mAb) | Calicheamicins, e.g. Ozogamicin |
| CD44 | | Doxorubicin |
| MUC1 | Cantuzumab (mAb) | bacterial *Pseudomonas* exotoxin PE38 |
| CD30 | Brentuximab (mAb) | Monomethyl Auristatin F (MMAF); Monomethyl Auristatin E (MMAE) |
| CD22 | inotuzumab (mAb) | Pyrrolobenzodiazepine (PBD) |
| transmembrane glycoprotein NMB (GPNMB) | Glembatumumab (mAb) | Interleukin-10 (IL10) (anti-inflammatory) |

-continued

| target/antigen | example of an existing immunoligand | payload |
|---|---|---|
| CD56 | Lorvotuzumab (mAb) | Diphtheria toxin |
| CanAg | huC242 (mAb) | Tumor necroris factor (TNF) |
| luteinizing hormone releasing hormone (LHRH) receptor | [D-Lys(6)] LHRH | RNase |
| Prostate-specific membrane antigen (PSMA) | | $Yttrium^{90}$ |
| CD74 | Milatuzumab (mAb) | $Iodine^{131}$ |
| CD70 | | $Lutetium^{177}$ |
| AGS-16 | | Cyclosporine |
| Integrin | | Methotrexate |
| CD19 | | Taxanes, e.g., Paclitaxel or Docetaxel |
| Nectin-4 | | |
| Interleukin 2 receptor | Interleukin-2 (Proleukin) | |
| CD3 | UCHT1 (mAb) | |
| extra domain B of fibronectin | L19-SIP (scFv fused in with the constant domain CH4 | |
| SLAMF7 (CD319) | Elotuzumab (mAb) | |
| SDC1 | Indatuximab (mAb) | |
| Her-2/neu | Trastuzumab (mAb) | |
| CD33 | Gemtuzumab (mAb) | |

According to yet another embodiment of the present invention, the immunoligand comprises at least two subunits each being conjugated to a payload.

Preferably, at least two different payloads can be conjugated to the at least two subunits. This option provides a versatile toolbox with which a large variety of different immunoligand-payload constructs can be created. For example, a bispecific dual-domain immunoligand can be conjugated with two different payloads, for example one marker and one toxin.

Preferably the at least two different payloads are toxic payloads interfering with one or more cellular pathways.

Such embodiment can be accomplished, e.g., by conjugating the two different payloads to each the 2 light chains of a full-length antibody, and to the 2 heavy chains of a full length antibody, respectively, by utilizing two different sortase enzymes, recognizing different sortase recognition motifs, plus an antibody that contains different C-terminal modifications at heavy and light chains comprising the respective recognition motifs for said different sortase enzymes.

In such way, an Antibody Drug Conjugate can be created which is composed of each two full-length Ig light chains and Ig heavy chains, containing different payloads covalently attached to said heavy and light chains.

Such embodiment results, preferably, in the synchronous conjugation of the at least two subunits for the generation of immunoligand payloads with equal payload conjugation to each of said subunits.

According to another preferred embodiment, said immunoligand with at least two subunits is being conjugated with at least 80% efficiency per conjugation site.

According to yet another preferred embodiment, said immunoligand with at least two subunits contains a peptide spacer sequence of at least two amino acids, preferably 2-5 amino acids, appended to the C-termini of at least one of the two subunits This approach results, advantageously, in synchronous conjugation of the at least two subunits for the generation of immunoligand payloads with equal payload conjugation to each of said subunits. According to another embodiment of the present invention, the method allows a stoichiometrically defined relationship between immunoligand and payload.

According to this embodiment, a strict quantitative relationship between immunoligand and payload can be provided, thus improving the reproducibility and the overall performance of the respective immunoligand/payload conjugate particularly for clinical and/or therapeutic applications. This is accounted for by the sequence- and/or site specificity of the transpeptidase used.

According to a particularly preferred embodiment said stoichiometrically defined relationship between immunoligand and payload is achieved by removal of partially reacted C-terminally modified immunoligand substrate. Such removal can, for example, be carried out via affinity purification. Said approach results, preferably, in a homogeneous drug to immunoligand ratio.

Preferably, said removal is carried out by affinity purification using an affinity tag positioned C-terminal to the transpeptidase recognition motif or domain. Standard methods known to the skilled person can be used for this purpose, e.g., HIS tag, CBP tag, CYD (covalent yet dissociable NorpD peptide) tag, Strep II tag, FLAG tag, HPC (heavy chain of protein C) tag, and the GST and MBP protein fusion tags.

According to another embodiment of the present invention, the method allows a site-specific conjugation of a payload to the immunoligand. According to this embodiment, it is ensured that the conjugation process does not interfere with the activity of the immunoligand, or the payload, itself, thus improving the reproducibility and the overall performance of the respective immunoligand/payload conjugate particularly for clinical and/or therapeutic applications. This is accounted for by the sequence- and/or site specificity of the transpeptidase used. Other than with conventional binding chemistry, which is not site specific in most cases, or has limited site specificity (e.g., when the payload is conjugated to a free amino group, like in Arg, Lys, Asn or Gln), the binding site can thus be exactly determined, so that the characterizing features of the immunoligand (e.g., target specificity) or the payload (e.g., toxicity) are not affected.

The invention further provides an immunoligand/payload conjugate obtained with a method according to the above-mentioned embodiments.

Preferably, said immunoligand/payload conjugate is selected from the group consisting of an antibody/drug conjugate, and/or an antibody/marker conjugate.

The invention further provides the use of an immunoligand/payload conjugate according to the above mentioned embodiments for in vitro or in vivo diagnosis of a given pathologic condition in vitro or in vivo prediction or prognosis with respect to a given pathologic condition the treatment of a human or animal subject suffering from or being at risk of developing a given pathologic condition, and/or research and/or development purposes Preferably, said pathologic condition is at least one selected from the group consisting of Neoplastic disease Autoimmune disease Neurodegenerative disease, and/or Infectious disease In all these cases, the immunoligand/payload conjugate according to the invention can have beneficial effects, e.g., by directing the latter to a specific site, e.g., a cancer cell, a site of neuropathology, or a site of an autoimmune reaction.

The payload, e.g., a toxin, a chemotherapeutic agent, a cytokine or a drug is delivered at said site, e.g., to deplete a cancer cell, to act anti-proliferatively on a cancer cell, to dissolve a plaque, to inhibit autoantibodies, and the like.

In all these cases, the immunoligand/payload conjugate according to the invention can have beneficial effects, e.g., by directing the latter to a specific site, e.g., a cancer cell, where the payload, e.g. a toxin or a chemotherapeutic agent, is delivered, e.g., to deplete a cancer cell, to act anti-proliferatively on a cancer cell.

Thus, the systemic toxicity of the toxin or the chemotherapeutic agent is reduced, while the local of the latter at the site of action is increased, thus providing a better efficacy while side effects are reduced. Further, a respective signalling cascade can be inhibited by the binding of the immunoligand. In case the payload is a marker the latter can thus be used to mark a specific site, e.g., a cancer cell characterized by a given surface antigen detected by the immunoligand, for diagnosis.

The site-specify of the conjugating process ensures a high reproducibility and overall performance of the respective immunoligand/payload conjugate particularly for clinical and/or therapeutic applications.

The term "neoplastic disease", as used herein, refers to an abnormal state or condition of cells or tissue characterized by rapidly proliferating cell growth or neoplasm. In a more specific meaning, the term relates to cancerous processes, e.g., tumors and/or leukemias.

The term "neuropathological diseases" encompasses, among others, neurodegenerative diseases, neuroinflammatory diseases or seizure disorders.

Neurodegenerative diseases are characterized by progressive loss of structure or function of neurons, including death of neurons. Many neurodegenerative diseases including Parkinson's, Alzheimer's, Huntington's, Amyotrophic lateral sclerosis and Multiple Sclerosis occur as a result of neurodegenerative processes. There are many parallels between different neurodegenerative disorders including atypical protein assemblies as well as induced cell death. Neurodegeneration can further be found in many different levels of neuronal circuitry ranging from molecular to systemic.

The terms "Neurodegenerative diseases" and "Neuroinflammatory diseases" have a partially overlapping scope. Inflammatory responses are a hallmark of neurodegenerative disease and participate, or contribute, through different mechanisms in the neuronal cell death. The tryptophan catabolism along the Kynurenine pathway (KP) represents one of these mechanisms.

Seizure disorders are brain disorders which are characterized by abnormal signaling between brain cells. Seizure disorders can affect part of the brain (Partial seizures) or the entire brain (Generalized seizures). The most prominent Seizure disorder is epilepsy.

The term "Autoimmune disease", as used herein, encompasses organ-specific autoimmune diseases, in which an autoimmune response is directed against a single tissue, such as Crohn's disease and ulcerative colitis, Type I diabetes mellitus, myasthenia gravis, vitiligo, Graves' disease, Hashimoto's disease, Addison's disease and autoimmune gastritis and autoimmune hepatitis. The term also encompasses non-organ specific autoimmune diseases, in which an autoimmune response is directed against a component present in several or many organs throughout the body.

Such autoimmune diseases include, for example, rheumatoid arthritis, disease, systemic lupus erythematosus, progressive systemic sclerosis and variants, polymyositis and dermatomyositis.

Additional autoimmune diseases include pernicious anemia including some of autoimmune gastritis, primary biliary cirrhosis, autoimmune thrombocytopenia, Sjögren's syndrome, multiple sclerosis and psoriasis. One skilled in the art understands that the methods of the invention can be applied to these or other autoimmune diseases, as desired.

The term "infectious disease" as used herein, includes, but is not limited to any disease that is caused by an infectious organism. Infectious organisms may comprise viruses, (e.g., single stranded RNA viruses, single stranded DNA viruses, human immunodeficiency virus (HIV), hepatitis A, B, and C virus, herpes simplex virus (HSV), cytomegalovirus (CMV) Epstein-Barr virus (EBV), human papilloma virus (HPV)), parasites (e.g., protozoan and metazoan pathogens such as Plasmodia species, *Leishmania* species, *Schistosoma* species, *Trypanosoma* species), bacteria (e.g., Mycobacteria, in particular, *M. tuberculosis, Salmonella*, Streptococci, *E. coli*, Staphylococci), fungi (e.g., *Candida* species, *Aspergillus* species), *Pneumocystis carinii*, and prions.

The invention further provides a low molecular-weight payload modified with a $Gly_n$-modification, wherein, n>1, preferably n=3 or n=5.

As used herein, the term "$Gly_n$-modification" means that an oligo- or polypeptide consisting of n Glycin residues has been added to said payload. As used herein, the term "low molecular-weight payload compound" shall encompass payloads that have a molecular weight of 2500 Da or less.

Said payload is, preferably, at least one selected from the group consisting of a marker, a processing tag, and/or a drug.

Said marker is at least one selected from the group consisting of a radiolabel, preferably a radioactively labelled peptide or protein a fluorescent label, preferably a fluorescent peptide or protein, and/or an enzyme label, preferably a peroxidase.

Said drug is at least one selected from the group consisting of a cytokine a radioactive agent a toxin, and/or a chemotherapeutic agent As discussed above already, said toxin is preferably a small molecular toxin, i.e., having a molecular weight of ≤2500 Da. Preferably, said toxin is at least one selected from the group consisting of Maytansine Monomethyl auristatin, and/or Alpha-amanitin or derivatives of the former. Examples for such $Gly_n$-modified toxions are shown in structures 1 to 9 of FIG. 14A-14C The invention further provides the use of a glycine-modified low molecular-weight payload for conjugation thereof to an immunoligand.

Preferably, and as mentioned above, the conjugation is a transpeptidase-mediated conjugation, preferably with a sortase and/or a split intein. Likewise preferably, the immunologand is an antibody.

Preferably, said immunoligand is an antibody. In such way, an antibody drug conjugate (ADC) can be provided.

Preferably, the immunologand-payload conjugation reaction is performed in crude cell culture supernatant. This means that, preferably, the conjugation reaction may take place with unpurified or only partially purified components.

Experiments and Figures

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

All amino acid sequences disclosed herein are shown from N-terminus to C-terminus; all nucleic acid sequences disclosed herein are shown 5'→3'.

Example 1: Cloning of Expression Vectors and Expression of a CD19 Monoclonal Antibody with C-Terminal LPETG Sortase Tag and Additional 6×-his and StrepII Affinity Purification Tags In order to perform the C-terminal conjugation of a payload to an antibody, first a recombinant antibody needs to be expressed that contains C-terminal modifications, including a recognition motif, e.g. for sortase A of *Staphylococcus aureus*.

For this, first ORFs for heavy and light chains of an anti-human CD19 specific antibody can be gene synthesized, e.g. at contract research organizations (CROs) offering such gene synthesis services, like e.g. Genscript (www.genscript.com, Piscataway, NJ, USA). As an example, the heavy and light chain sequences of a humanized anti-human CD19 antibody hBU12 can be found in U.S. Pat. No. 8,242,252 B2 under Seq 53 (variant HF) and Seq 58 (variant LG). The $V_H$ and $V_L$ regions of this anti-human CD19 antibody are as follows:

($V_H$ coding region of humanized anti-human CD19 antibody hBU12):

SEQ ID NO 1

```
ATGGGATGGAGCTGGATCTTTCTTTTCCTCCTGTCAGGAACTGCAGGTGTCCATTGTCAGGTTCAGCTGCAAGA

GTCTGGCCCTGGGTTGGTTAAGCCCTCCCAGACCCTCAGTCTGACTTGTACTGTGTCTGGGGGTTCAATCAGCA

CTTCTGGTATGGGTGTAGGCTGGATTAGGCAGCACCCAGGGAAGGGTCTGGAGTGGATTGGACACATTTGGTGG

GATGATGACAAGAGATATAACCCAGCCCTGAAGAGCAGAGTGACAATCTCTGTGGATACCTCCAAGAACCAGTT

TAGCCTCAAGCTGTCCAGTGTGACAGCTGCAGATACTGCTGTCTACTACTGTGCTAGAATGGAACTTTGGTCCT

ACTATTTTGACTACTGGGGCCAAGGCACCCTTGTCACAGTCTCCTCA
```

This translates to the following amino acid sequence (SEQ ID NO 2):

```
MGWSWIFLFLLSGTAGVHCQVQLQESGPGLVKPSQTLSLTCTVSGGSISTSGMGVGWIRQHPGKGLEWIGHIWW

DDDKRYNPALKSRVTISVDTSKNQFSLKLSSVTAADTAVYYCARMELWSYYFDYWGQGTLVTVSS
```

($V_L$ coding region of humanized anti-human CD19 antibody hBU12)

SEQ ID NO 3

```
ATGAAGTTGCCTGTTAGGCTGTTGGTGCTGATGTTCTGGATTCCTGCTTCCAGCAGTGAAATTGTTCTCACCCA

GTCTCCAGCAACCCTGTCTCTCTCTCCAGGGGAAAGGGCTACCCTGAGCTGCAGTGCCAGCTCAAGTGTAAGTT

ACATGCACTGGTACCAGCAGAAGCCAGGGCAGGCTCCCAGACTCCTGATTTATGACACATCCAAACTGGCTTCT

GGTATTCCAGCAAGGTTCAGTGGCAGTGGGTCTGGAACAGATTTTACACTCACAATCAGCAGCCTGGAGCCAGA

GGATGTTGCTGTCTATTACTGTTTTCAGGGGAGTGTATACCCATTCACTTTTGGCCAAGGGACAAAGTTGGAAA

TCAAA
```

This translates to the following amino acid sequence (SEQ ID NO 4):

```
MKLPVRLLVLMFWIPASSSEIVLTQSPATLSLSPGERATLSCSASSSVSYMHWYQQKPGQAPRLLIYDTSKLAS

GIPARFSGSGSGTDFTLTISSLEPEDVAVYYCFQGSVYPFTFGQGTKLEIK
```

These sequences can be fused to human $IgG_1$ constant heavy and constant light chain regions containing additional C-terminal tags, in order to realize the method disclosed herein.

In order to realize the invention, the human constant IgG1 heavy chain region can be synthesized with additional 3'-codons, encoding an LPETG *Staphylococcus aureus* sortase A recognition tag, followed by a 6×His tag (HHHHHH), a MYC-tag (EQKLISEEDL) and a strep II tag (WSHPQFEK) resulting in a sequence, which is as follows:

(human IgG1 heavy chain constant coding region with in-frame 3' extension encoding an LPETG sortase tag, an 6xHis tag and a strepII tag):

SEQ ID NO 5

AGCACCAAGGGCCCATCTGTCTTCCCCCTGGCACCCTCCTCCAAGAGCACCTCTGGGGGCACAGCTGCCCTGGG

CTGCCTGGTCAAGGACTACTTCCCTGAACCTGTGACAGTGTCCTGGAACTCAGGCGCCCTGACCAGCGGCGTGC

ACACCTTCCCGGCTGTCCTACAGTCCTCAGGACTCTACTCCCTCAGCAGCGTGGTGACCGTGCCCTCCAGCAGC

TTGGGCACCCAGACCTACATCTGCAACGTGAATCACAAGCCCAGCAACACCAAGGTGGACAAGAAAGTTGAGCC

CAAATCTTGTGACAAAACTCACACATGCCCACCGTGCCCAGCACCTGAACTCCTGGGGGGACCGTCAGTCTTCC

TCTTCCCCCCAAAACCCAAGGACACCCTCATGATCTCCCGGACCCCTGAGGTCACATGCGTGGTGGTGGACGTG

AGCCACGAAGACCCTGAGGTCAAGTTCAACTGGTACGTGGACGGCGTGGAGGTGCATAATGCCAAGACAAAGCC

GCGGGAGGAGCAGTACAACAGCACGTACCGTGTGGTCAGCGTCCTCACCGTCCTGCACCAGGACTGGCTGAATG

GCAAGGAGTACAAGTGCAAGGTCTCCAACAAAGCCCTCCCAGCCCCCATCGAGAAAACCATCTCCAAAGCCAAA

GGGCAGCCCCGAGAACCACAGGTGTACACCCTGCCCCCATCCCGGGATGAGCTGACCAAGAACCAGGTCAGCCT

GACCTGCCTGGTCAAAGGCTTCTATCCCAGCGACATCGCCGTGGAGTGGGAGAGCAATGGGCAGCCGGAGAACA

ACTACAAGACCACGCCTCCCGTGCTGGACTCCGACGGCTCCTTCTTCCTCTACAGCAAGCTCACCGTGGACAAG

AGCAGGTGGCAGCAGGGGAACGTCTTCTCATGCTCCGTGATGCATGAGGCTCTGCACAACCACTACACACAGAA

GAGCCTCTCCCTGTCTCCGGGTAAACTGCCCGAGACCGGCCACCACCACCACCACCACGGCGAGCAGAAGCTGA

TCAGCGAGGAGGACCTGGGCTGGAGCCACCCCCAGTTCGAGAAGTAG

This translates to the following amino acid sequence (SEQ ID NO 6, amino acids of the tags are underlined):

STKGPSVFPLAPSSKSTSGGTAALGCLVKDYFPEPVTVSWNSGALTSGVHTEPAVLQSSGLYSLSSVVTVPSSS

LGTQTYICNVNHKPSNTKVDKKVEPKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKEYKCKVSNKALPAPIEKTISKAK

GQPREPQVYTLPPSRDELTKNQVSLTCLVKGFYPSDIAVEWESNGQPENNYKTTPPVLDSDGSFFLYSKLTVDK

SRWQQGNVFSCSVMHEALHNHYTQKSLSLSPGKLPETGHHHHHHGEQKLISEEDLGWSHPQFEK•

Furthermore, the human constant IgG1 kappa light chain region can be synthesized with additional 3'-codons, encoding an LPETG *Staphylococcus aureus* sortase A recognition tag, followed by a 6×His tag and a strep II tag (WSHPQFEK) resulting in a sequence, which is as follows:

(human IgG1 kappa light chain constant coding region with in-frame 3' extension encoding an LPETG sortase tag, an 6xHis tag, a Myc tag, and a strepII tag):

SEQ ID NO 7

ACGGTGGCTGCACCATCTGTCTTCATCTTCCCGCCATCTGATGAGCAGTTGAAATCTGGAACTGCCTCTGTTGT

GTGCCTGCTGAATAACTTCTATCCCAGAGAGGCCAAAGTACAGTGGAAGGTGGATAACGCCCTCCAATCGGGTA

ACTCCCAGGAGAGTGTCACAGAGCAGGACAGCAAGGACAGCACCTACAGCCTCAGCAGCACCCTGACGCTGAGC

AAAGCAGACTACGAGAAACACAAAGTCTACGCCTGCGAAGTCACCCATCAGGGCCTGAGCTCGCCCGTCACAAA

GAGCTTCAACAGGGGAGAGTGTCTGCCCGAGACCGGCCACCACCACCACCACCACGGCGAGCAGAAGCTGATCA

GCGAGGAGGACCTGGGCTGGAGCCACCCCCAGTTCGAGAAGTAG

-continued

This translates to the following amino acid sequence (SEQ ID NO 8, amino acids of the tags are underlined):
TVAAPSVFIFPPSDEQLKSGTASVVCLLNNFYPREAKVQWKVDNALQSGNSQESVTEQDSKDSTYSLSSTLTLS

KADYEKHKVYACEVTHQGLSSPVTKSFNRGECLPETGHHHHHHGEQKLISEEDLGWSHPQFEK•

The complete coding regions for LPETG sortase tag, 6×His and strepII tagged heavy and light chains of the humanized anti-human CD19 antibody hBU12 are then as follows:

(Complete human IgG1 $V_H$-$C_H$ heavy chain coding region for hBU12 with C-terminal LPETG sortase tag, 6xHis tag, Myc tag, and a strepII tag):

SEQ ID NO 9

ATGGGATGGAGCTGGATCTTTCTTTTCCTCCTGTCAGGAACTGCAGGTGTCCATTGTCAGGTTCAGCTGCAAGA

GTCTGGCCCTGGGTTGGTTAAGCCCTCCCAGACCCTCAGTCTGACTTGTACTGTGTCTGGGGGTTCAATCAGCA

CTTCTGGTATGGGTGTAGGCTGGATTAGGCAGCACCCAGGGAAGGGTCTGGAGTGGATTGGACACATTTGGTGG

GATGATGACAAGAGATATAACCCAGCCCTGAAGAGCAGAGTGACAATCTCTGTGGATACCTCCAAGAACCAGTT

TAGCCTCAAGCTGTCCAGTGTGACAGCTGCAGATACTGCTGTCTACTACTGTGCTAGAATGGAACTTTGGTCCT

ACTATTTTGACTACTGGGGCCAAGGCACCCTTGTCACAGTCTCCTCAGCTAGCACCAAGGGCCCATCTGTCTTC

CCCCTGGCACCCTCCTCCAAGAGCACCTCTGGGGGCACAGCTGCCCTGGGCTGCCTGGTCAAGGACTACTTCCC

TGAACCTGTGACAGTGTCCTGGAACTCAGGCGCCCTGACCAGCGGCGTGCACACCTTCCCGGCTGTCCTACAGT

CCTCAGGACTCTACTCCCTCAGCAGCGTGGTGACCGTGCCCTCCAGCAGCTTGGGCACCCAGACCTACATCTGC

AACGTGAATCACAAGCCCAGCAACACCAAGGTGGACAAGAAAGTTGAGCCCAAATCTTGTGACAAAACTCACAC

ATGCCCACCGTGCCCAGCACCTGAACTCCTGGGGGGACCGTCAGTCTTCCTCTTCCCCCCAAAACCCAAGGACA

CCCTCATGATCTCCCGGACCCCTGAGGTCACATGCGTGGTGGTGGACGTGAGCCACGAAGACCCTGAGGTCAAG

TTCAACTGGTACGTGGACGGCGTGGAGGTGCATAATGCCAAGACAAAGCCGCGGGAGGAGCAGTACAACAGCAC

GTACCGTGTGGTCAGCGTCCTCACCGTCCTGCACCAGGACTGGCTGAATGGCAAGGAGTACAAGTGCAAGGTCT

CCAACAAAGCCCTCCCAGCCCCCATCGAGAAAACCATCTCCAAAGCCAAAGGGCAGCCCCGAGAACCACAGGTG

TACACCCTGCCCCCATCCCGGGATGAGCTGACCAAGAACCAGGTCAGCCTGACCTGCCTGGTCAAAGGCTTCTA

TCCCAGCGACATCGCCGTGGAGTGGGAGAGCAATGGGCAGCCGGAGAACAACTACAAGACCACGCCTCCCGTGC

TGGACTCCGACGGCTCCTTCTTCCTCTACAGCAAGCTCACCGTGGACAAGAGCAGGTGGCAGCAGGGGAACGTC

TTCTCATGCTCCGTGATGCATGAGGCTCTGCACAACCACTACACACAGAAGAGCCTCTCCCTGTCTCCGGGTAA

ACTGCCCGAGACCGGCCACCACCACCACCACCACGGCGAGCAGAAGCTGATCAGCGAGGAGGACCTGGGCTGGA

GCCACCCCCAGTTCGAGAAGTAG

This translates to the following amino acid sequence (SEQ ID NO 10, amino acids of the tags are underlined):
MGWSWIFLFLLSGTAGVHCQVQLQESGPGLVKPSQTLSLTCTVSGGSISTSGMGVGWIRQHPGKGLEWIGHIWW

DDDKRYNPALKSRVTISVDTSKNQFSLKLSSVTAADTAVYYCARMELWSYYFDYWGQGTLVTVSSASTKGPSVF

PLAPSSKSTSGGTAALGCLVKDYFPEPVTVSWNSGALTSGVHTFPAVLQSSGLYSLSSVVTVPSSSLGTQTYIC

NVNHKPSNTKVDKKVEPKSCDKTHTCPPCPAPELLGGPSVFLFPPKPKDTLMISRTPEVTCVVVDVSHEDPEVK

FNWYVDGVEVHNAKTKPREEQYNSTYRWSVLTVLHQDWLNGKEYKCKVSNKALPAPIEKTISKAKGQPREPQV

YTLPPSRDELTKNQVSLTCLVKGFYPSDIAVEWESNGQPENNYKTTPPVLDSDGSFFLYSKLTVDKSRWQQGNV

FSCSVMHEALHNHYTQKSLSLSPGKLPETGHHHHHHGEQKLISEEDLGWSHPQFEK•

-continued (Complete human IgG1 $V_L$-$C_L$ kappa chain coding region for hBU12 with C-terminal LPETG sortase tag, 6xHis tag, Myc tag, and a strepII tag):

SEQ ID NO 11

ATGAAGTTGCCTGTTAGGCTGTTGGTGCTGATGTTCTGGATTCCTGCTTCCAGCAGTGAAATTGTTCTCACCCA

GTCTCCAGCAACCCTGTCTCTCTCTCCAGGGGAAAGGGCTACCCTGAGCTGCAGTGCCAGCTCAAGTGTAAGTT

ACATGCACTGGTACCAGCAGAAGCCAGGGCAGGCTCCCAGACTCCTGATTTATGACACATCCAAACTGGCTTCT

GGTATTCCAGCAAGGTTCAGTGGCAGTGGGTCTGGAACAGATTTTACACTCACAATCAGCAGCCTGGAGCCAGA

GGATGTTGCTGTCTATTACTGTTTTCAGGGGAGTGTATACCCATTCACTTTTGGCCAAGGGACAAAGTTGGAAA

TCAAAAGAACTGTGGCTGCACCATCTGTCTTCATCTTCCCGCCATCTGATGAGCAGTTGAAATCTGGAACTGCC

TCTGTTGTGTGCCTGCTGAATAACTTCTATCCCAGAGAGGCCAAAGTACAGTGGAAGGTGGATAACGCCCTCCA

ATCGGGTAACTCCCAGGAGAGTGTCACAGAGCAGGACAGCAAGGACAGCACCTACAGCCTCAGCAGCACCCTGA

CGCTGAGCAAAGCAGACTACGAGAAACACAAAGTCTACGCCTGCGAAGTCACCCATCAGGGCCTGAGCTCGCCC

GTCACAAAGAGCTTCAACAGGGGAGAGTGTCTGCCCGAGACCGGCCACCACCACCACCACCACGGCGAGCAGAA

GCTGATCAGCGAGGAGGACCTGGGCTGGAGCCACCCCCAGTTCGAGAAGTAG

This translates to the following amino acid sequence (SEQ ID NO 12, amino acids of the tags are underlined):

MKLPVRLLVLMFWIPASSSEIVLTQSPATLSLSPGERATLSCSASSSVSYMHWYQQKPGQAPRLLIYDTSKLAS

GIPARFSGSGSGTDFTLTISSLEPEDVAVYYCFQGSVYPFTFGQGTKLEIKRTVAAPSVFIFPPSDEQLKSGTA

SWCLLNNFYPREAKVQWKVDNALQSGNSQESVTEQDSKDSTYSLSSTLTLSKADYEKHKVYACEVTHQGLSSP

VTKSFNRGECLPETGHHHHHHGEQKLISEEDLGWSHPQFEK•

The coding regions for the heavy and light chains of the anti-human CD19 specific antibody as disclosed in SEQ ID NOs 9 and 11, respectively, can then be synthesized with flanking restriction enzyme sites (e.g. HindIII and NotI) such that they can be cloned into a standard mammalian expression vector, such as pCDNA3.1-hygro (+) (Invitrogen), by standard molecular biology methods known in the art.

The complete DNA sequence of pCDNA3.1-hygro (+)-IgH chain expression vector for the tagged hBU12 anti-human CD19 antibody will be as follows:

(coding region of human IgG1 $V_H$-$C_H$ heavy chain for hBU12 with C-terminal LPETG sortase tag, 6xHis tag and a strepII tag underlined, and HindIII and NotI cloning sites shaded):

SEQ ID NO 13

GACGGATCGGGAGATCTCCCGATCCCCTATGGTCGACTCTCAGTACAATCTGCTCTGATGCCGCATAGTTAAGC

CAGTATCTGCTCCCTGCTTGTGTGTTGGAGGTCGCTGAGTAGTGCGCGAGCAAAATTTAAGCTACAACAAGGCA

AGGCTTGACCGACAATTGCATGAAGAATCTGCTTAGGGTTAGGCGTTTTGCGCTGCTTCGCGATGTACGGGCCA

GATATACGCGTTGACATTGATTATTGACTAGTTATTAATAGTAATCAATTACGGGGTCATTAGTTCATAGCCCA

TATATGGAGTTCCGCGTTACATAACTTACGGTAAATGGCCCGCCTGGCTGACCGCCCAACGACCCCCGCCCATT

GACGTCAATAATGACGTATGTTCCCATAGTAACGCCAATAGGGACTTTCCATTGACGTCAATGGGTGGACTATT

TACGGTAAACTGCCCACTTGGCAGTACATCAAGTGTATCATATGCCAAGTACGCCCCCTATTGACGTCAATGAC

GGTAAATGGCCCGCCTGGCATTATGCCCAGTACATGACCTTATGGGACTTTCCTACTTGGCAGTACATCTACGT

ATTAGTCATCGCTATTACCATGGTGATGCGGTTTTGGCAGTACATCAATGGGCGTGGATAGCGGTTTGACTCAC

GGGGATTTCCAAGTCTCCACCCCATTGACGTCAATGGGAGTTTGTTTTGGCACCAAAATCAACGGGACTTTCCA

AAATGTCGTAACAACTCCGCCCCATTGACGCAAATGGGCGGTAGGCGTGTACGGTGGGAGGTCTATATAAGCAG

AGCTCTCTGGCTAACTAGAGAACCCACTGCTTACTGGCTTATCGAAATTAATACGACTCACTATAGGGAGACCC

AAGCTGGCTAGCGTTTAAACTTAAGCTTCCATGGGATGGAGCTGGATCTTTCTTTTCCTCCTGTCAGGAACTGC

-continued

AGGTGTCCATTGTCAGGTTCAGCTGCAAGAGTCTGGCCCTGGGTTGGTTAAGCCCTCCCAGACCCTCAGTCTGA

CTTGTACTGTGTCTGGGGGTTCAATCAGCACTTCTGGTATGGGTGTAGGCTGGATTAGGCAGCACCCAGGGAAG

GGTCTGGAGTGGATTGGACACATTTGGTGGGATGATGACAAGAGATATAACCCAGCCCTGAAGAGCAGAGTGAC

AATCTCTGTGGATACCTCCAAGAACCAGTTTAGCCTCAAGCTGTCCAGTGTGACAGCTGCAGATACTGCTGTCT

ACTACTGTGCTAGAATGGAACTTTGGTCCTACTATTTTGACTACTGGGGCCAAGGCACCCTTGTCACAGTCTCC

TCAGCTAGCACCAAGGGCCCATCTGTCTTCCCCCTGGCACCCTCCTCCAAGAGCACCTCTGGGGGCACAGCTGC

CCTGGGCTGCCTGGTCAAGGACTACTTCCCTGAACCTGTGACAGTGTCCTGGAACTCAGGCGCCCTGACCAGCG

GCGTGCACACCTTCCCGGCTGTCCTACAGTCCTCAGGACTCTACTCCCTCAGCAGCGTGGTGACCGTGCCCTCC

AGCAGCTTGGGCACCCAGACCTACATCTGCAACGTGAATCACAAGCCCAGCAACACCAAGGTGGACAAGAAAGT

TGAGCCCAAATCTTGTGACAAAACTCACACATGCCCACCGTGCCCAGCACCTGAACTCCTGGGGGGACCGTCAG

TCTTCCTCTTCCCCCCAAAACCCAAGGACACCCTCATGATCTCCCGGACCCCTGAGGTCACATGCGTGGTGGTG

GACGTGAGCCACGAAGACCCTGAGGTCAAGTTCAACTGGTACGTGGACGGCGTGGAGGTGCATAATGCCAAGAC

AAAGCCGCGGGAGGAGCAGTACAACAGCACGTACCGTGTGGTCAGCGTCCTCACCGTCCTGCACCAGGACTGGC

TGAATGGCAAGGAGTACAAGTGCAAGGTCTCCAACAAAGCCCTCCCAGCCCCCATCGAGAAAACCATCTCCAAA

GCCAAAGGGCAGCCCCGAGAACCACAGGTGTACACCCTGCCCCCATCCCGGGATGAGCTGACCAAGAACCAGGT

CAGCCTGACCTGCCTGGTCAAAGGCTTCTATCCCAGCGACATCGCCGTGGAGTGGGAGAGCAATGGGCAGCCGG

AGAACAACTACAAGACCACGCCTCCCGTGCTGGACTCCGACGGCTCCTTCTTCCTCTACAGCAAGCTCACCGTG

GACAAGAGCAGGTGGCAGCAGGGGAACGTCTTCTCATGCTCCGTGATGCATGAGGCTCTGCACAACCACTACAC

ACAGAAGAGCCTCTCCCTGTCTCCGGGTAAACTGCCCGAGACCGGCCACCACCACCACCACCACGGCGAGCAGA

AGCTGATCAGCGAGGAGGACCTGGGCTGGAGCCACCCCCAGTTCGAGAAGTAGGCGGCCGCTCGAGTCTAGAGG

GCCCGTTTAAACCCGCTGATCAGCCTCGACTGTGCCTTCTAGTTGCCAGCCATCTGTTGTTTGCCCCTCCCCCG

TGCCTTCCTTGACCCTGGAAGGTGCCACTCCCACTGTCCTTTCCTAATAAAATGAGGAAATTGCATCGCATTGT

CTGAGTAGGTGTCATTCTATTCTGGGGGGTGGGGTGGGGCAGGACAGCAAGGGGGAGGATTGGGAAGACAATAG

CAGGCATGCTGGGGATGCGGTGGGCTCTATGGCTTCTGAGGCGGAAAGAACCAGCTGGGGCTCTAGGGGGTATC

CCCACGCGCCCTGTAGCGGCGCATTAAGCGCGGCGGGTGTGGTGGTTACGCGCAGCGTGACCGCTACACTTGCC

AGCGCCCTAGCGCCCGCTCCTTTCGCTTTCTTCCCTTCCTTTCTCGCCACGTTCGCCGGCTTTCCCCGTCAAGC

TCTAAATCGGGGCATCCCTTTAGGGTTCCGATTTAGTGCTTTACGGCACCTCGACCCCAAAAAACTTGATTAGG

GTGATGGTTCACGTAGTGGGCCATCGCCCTGATAGACGGTTTTTCGCCCTTTGACGTTGGAGTCCACGTTCTTT

AATAGTGGACTCTTGTTCCAAACTGGAACAACACTCAACCCTATCTCGGTCTATTCTTTTGATTTATAAGGGAT

TTTGGGGATTTCGGCCTATTGGTTAAAAAATGAGCTGATTTAACAAAAATTTAACGCGAATTAATTCTGTGGAA

TGTGTGTCAGTTAGGGTGTGGAAAGTCCCCAGGCTCCCCAGGCAGGCAGAAGTATGCAAAGCATGCATCTCAAT

TAGTCAGCAACCAGGTGTGGAAAGTCCCCAGGCTCCCCAGCAGGCAGAAGTATGCAAAGCATGCATCTCAATTA

GTCAGCAACCATAGTCCCGCCCCTAACTCCGCCCATCCCGCCCCTAACTCCGCCCAGTTCCGCCCATTCTCCGC

CCCATGGCTGACTAATTTTTTTTATTTATGCAGAGGCCGAGGCCGCCTCTGCCTCTGAGCTATTCCAGAAGTAG

TGAGGAGGCTTTTTTGGAGGCCTAGGCTTTTGCAAAAAGCTCCCGGGAGCTTGTATATCCATTTTCGGATCTGA

TCAGCACGTGATGAAAAAGCCTGAACTCACCGCGACGTCTGTCGAGAAGTTTCTGATCGAAAAGTTCGACAGCG

TCTCCGACCTGATGCAGCTCTCGGAGGGCGAAGAATCTCGTGCTTTCAGCTTCGATGTAGGAGGGCGTGGATAT

GTCCTGCGGGTAAATAGCTGCGCCGATGGTTTCTACAAAGATCGTTATGTTTATCGGCACTTTGCATCGGCCGC

GCTCCCGATTCCGGAAGTGCTTGACATTGGGGAATTCAGCGAGAGCCTGACCTATTGCATCTCCCGCCGTGCAC

AGGGTGTCACGTTGCAAGACCTGCCTGAAACCGAACTGCCCGCTGTTCTGCAGCCGGTCGCGGAGGCCATGGAT

-continued

GCGATCGCTGCGGCCGATCTTAGCCAGACGAGCGGGTTCGGCCCATTCGGACCGCAAGGAATCGGTCAATACAC

TACATGGCGTGATTTCATATGCGCGATTGCTGATCCCCATGTGTATCACTGGCAAACTGTGATGGACGACACCG

TCAGTGCGTCCGTCGCGCAGGCTCTCGATGAGCTGATGCTTTGGGCCGAGGACTGCCCCGAAGTCCGGCACCTC

GTGCACGCGGATTTCGGCTCCAACAATGTCCTGACGGACAATGGCCGCATAACAGCGGTCATTGACTGGAGCGA

GGCGATGTTCGGGGATTCCCAATACGAGGTCGCCAACATCTTCTTCTGGAGGCCGTGGTTGGCTTGTATGGAGC

AGCAGACGCGCTACTTCGAGCGGAGGCATCCGGAGCTTGCAGGATCGCCGCGGCTCCGGGCGTATATGCTCCGC

ATTGGTCTTGACCAACTCTATCAGAGCTTGGTTGACGGCAATTTCGATGATGCAGCTTGGGCGCAGGGTCGATG

CGACGCAATCGTCCGATCCGGAGCCGGGACTGTCGGGCGTACACAAATCGCCCGCAGAAGCGCGGCCGTCTGGA

CCGATGGCTGTGTAGAAGTACTCGCCGATAGTGGAAACCGACGCCCCAGCACTCGTCCGAGGGCAAAGGAATAG

CACGTGCTACGAGATTTCGATTCCACCGCCGCCTTCTATGAAAGGTTGGGCTTCGGAATCGTTTTCCGGGACGC

CGGCTGGATGATCCTCCAGCGCGGGGATCTCATGCTGGAGTTCTTCGCCCACCCCAACTTGTTTATTGCAGCTT

ATAATGGTTACAAATAAAGCAATAGCATCACAAATTTCACAAATAAAGCATTTTTTTCACTGCATTCTAGTTGT

GGTTTGTCCAAACTCATCAATGTATCTTATCATGTCTGTATACCGTCGACCTCTAGCTAGAGCTTGGCGTAATC

ATGGTCATAGCTGTTTCCTGTGTGAAATTGTTATCCGCTCACAATTCCACACAACATACGAGCCGGAAGCATAA

AGTGTAAAGCCTGGGGTGCCTAATGAGTGAGCTAACTCACATTAATTGCGTTGCGCTCACTGCCCGCTTTCCAG

TCGGGAAACCTGTCGTGCCAGCTGCATTAATGAATCGGCCAACGCGCGGGGAGAGGCGGTTTGCGTATTGGGCG

CTCTTCCGCTTCCTCGCTCACTGACTCGCTGCGCTCGGTCGTTCGGCTGCGGCGAGCGGTATCAGCTCACTCAA

AGGCGGTAATACGGTTATCCACAGAATCAGGGGATAACGCAGGAAAGAACATGTGAGCAAAAGGCCAGCAAAAG

GCCAGGAACCGTAAAAAGGCCGCGTTGCTGGCGTTTTTCCATAGGCTCCGCCCCCCTGACGAGCATCACAAAAA

TCGACGCTCAAGTCAGAGGTGGCGAAACCCGACAGGACTATAAAGATACCAGGCGTTTCCCCCTGGAAGCTCCC

TCGTGCGCTCTCCTGTTCCGACCCTGCCGCTTACCGGATACCTGTCCGCCTTTCTCCCTTCGGGAAGCGTGGCG

CTTTCTCAATGCTCACGCTGTAGGTATCTCAGTTCGGTGTAGGTCGTTCGCTCCAAGCTGGGCTGTGTGCACGA

ACCCCCCGTTCAGCCCGACCGCTGCGCCTTATCCGGTAACTATCGTCTTGAGTCCAACCCGGTAAGACACGACT

TATCGCCACTGGCAGCAGCCACTGGTAACAGGATTAGCAGAGCGAGGTATGTAGGCGGTGCTACAGAGTTCTTG

AAGTGGTGGCCTAACTACGGCTACACTAGAAGGACAGTATTTGGTATCTGCGCTCTGCTGAAGCCAGTTACCTT

CGGAAAAAGAGTTGGTAGCTCTTGATCCGGCAAACAAACCACCGCTGGTAGCGGTGGTTTTTTTGTTTGCAAGC

AGCAGATTACGCGCAGAAAAAAAGGATCTCAAGAAGATCCTTTGATCTTTTCTACGGGGTCTGACGCTCAGTGG

AACGAAAACTCACGTTAAGGGATTTTGGTCATGAGATTATCAAAAAGGATCTTCACCTAGATCCTTTTAAATTA

AAAATGAAGTTTTAAATCAATCTAAAGTATATATGAGTAAACTTGGTCTGACAGTTACCAATGCTTAATCAGTG

AGGCACCTATCTCAGCGATCTGTCTATTTCGTTCATCCATAGTTGCCTGACTCCCCGTCGTGTAGATAACTACG

ATACGGGAGGGCTTACCATCTGGCCCCAGTGCTGCAATGATACCGCGAGACCCACGCTCACCGGCTCCAGATTT

ATCAGCAATAAACCAGCCAGCCGGAAGGGCCGAGCGCAGAAGTGGTCCTGCAACTTTATCCGCCTCCATCCAGT

CTATTAATTGTTGCCGGGAAGCTAGAGTAAGTAGTTCGCCAGTTAATAGTTTGCGCAACGTTGTTGCCATTGCT

ACAGGCATCGTGGTGTCACGCTCGTCGTTTGGTATGGCTTCATTCAGCTCCGGTTCCCAACGATCAAGGCGAGT

TACATGATCCCCCATGTTGTGCAAAAAAGCGGTTAGCTCCTTCGGTCCTCCGATCGTTGTCAGAAGTAAGTTGG

CCGCAGTGTTATCACTCATGGTTATGGCAGCACTGCATAATTCTCTTACTGTCATGCCATCCGTAAGATGCTTT

TCTGTGACTGGTGAGTACTCAACCAAGTCATTCTGAGAATAGTGTATGCGGCGACCGAGTTGCTCTTGCCCGGC

GTCAATACGGGATAATACCGCGCCACATAGCAGAACTTTAAAAGTGCTCATCATTGGAAAACGTTCTTCGGGGC

GAAAACTCTCAAGGATCTTACCGCTGTTGAGATCCAGTTCGATGTAACCCACTCGTGCACCCAACTGATCTTCA

GCATCTTTTACTTTCACCAGCGTTTCTGGGTGAGCAAAAACAGGAAGGCAAAATGCCGCAAAAAAGGGAATAAG

-continued

GGCGACACGGAAATGTTGAATACTCATACTCTTCCTTTTTCAATATTATTGAAGCATTTATCAGGGTTATTGTC

TCATGAGCGGATACATATTTGAATGTATTTAGAAAAATAAACAAATAGGGGTTCCGCGCACATTTCCCCGAAAA

GTGCCACCTGACGTC

The complete DNA sequence of pCDNA3.1-hygro (+)-IgL chain expression vector for the tagged hBU12 anti-human CD19 antibody will be as follows:

(coding region of human IgG1 $V_L$-$C_L$ kappa light chain for hBU12 with C-terminal LPETG sortase tag, 6xHis tag, Myc tag, and a strepII tag underlined, and HindIII and NotI cloning sites shaded):

SEQ ID NO 14

GACGGATCGGGAGATCTCCCGATCCCCTATGGTCGACTCTCAGTACAATCTGCTCTGATGCCGCATAGTTAAGC

CAGTATCTGCTCCCTGCTTGTGTGTTGGAGGTCGCTGAGTAGTGCGCGAGCAAAATTTAAGCTACAACAAGGCA

AGGCTTGACCGACAATTGCATGAAGAATCTGCTTAGGGTTAGGCGTTTTGCGCTGCTTCGCGATGTACGGGCCA

GATATACGCGTTGACATTGATTATTGACTAGTTATTAATAGTAATCAATTACGGGGTCATTAGTTCATAGCCCA

TATATGGAGTTCCGCGTTACATAACTTACGGTAAATGGCCCGCCTGGCTGACCGCCCAACGACCCCCGCCCATT

GACGTCAATAATGACGTATGTTCCCATAGTAACGCCAATAGGGACTTTCCATTGACGTCAATGGGTGGACTATT

TACGGTAAACTGCCCACTTGGCAGTACATCAAGTGTATCATATGCCAAGTACGCCCCCTATTGACGTCAATGAC

GGTAAATGGCCCGCCTGGCATTATGCCCAGTACATGACCTTATGGGACTTTCCTACTTGGCAGTACATCTACGT

ATTAGTCATCGCTATTACCATGGTGATGCGGTTTTGGCAGTACATCAATGGGCGTGGATAGCGGTTTGACTCAC

GGGGATTTCCAAGTCTCCACCCCATTGACGTCAATGGGAGTTTGTTTTGGCACCAAAATCAACGGGACTTTCCA

AAATGTCGTAACAACTCCGCCCCATTGACGCAAATGGGCGGTAGGCGTGTACGGTGGGAGGTCTATATAAGCAG

AGCTCTCTGGCTAACTAGAGAACCCACTGCTTACTGGCTTATCGAAATTAATACGACTCACTATAGGGAGACCC

AAGCTGGCTAGCGTTTAAACTTAAGCTTCCATGAAGTTGCCTGTTAGGCTGTTGGTGCTGATGTTCTGGATTCC

TGCTTCCAGCAGTGAAATTGTTCTCACCCAGTCTCCAGCAACCCTGTCTCTCTCTCCAGGGGAAAGGGCTACCC

TGAGCTGCAGTGCCAGCTCAAGTGTAAGTTACATGCACTGGTACCAGCAGAAGCCAGGGCAGGCTCCCAGACTC

CTGATTTATGACACATCCAAACTGGCTTCTGGTATTCCAGCAAGGTTCAGTGGCAGTGGGTCTGGAACAGATTT

TACACTCACAATCAGCAGCCTGGAGCCAGAGGATGTTGCTGTCTATTACTGTTTTCAGGGGAGTGTATACCCAT

TCACTTTTGGCCAAGGGACAAAGTTGGAAATCAAAAGAACTGTGGCTGCACCATCTGTCTTCATCTTCCCGCCA

TCTGATGAGCAGTTGAAATCTGGAACTGCCTCTGTTGTGTGCCTGCTGAATAACTTCTATCCCAGAGAGGCCAA

AGTACAGTGGAAGGTGGATAACGCCCTCCAATCGGGTAACTCCCAGGAGAGTGTCACAGAGCAGGACAGCAAGG

ACAGCACCTACAGCCTCAGCAGCACCCTGACGCTGAGCAAAGCAGACTACGAGAAACACAAAGTCTACGCCTGC

GAAGTCACCCATCAGGGCCTGAGCTCGCCCGTCACAAAGAGCTTCAACAGGGGAGAGTGTCTGCCCGAGACCGG

CCACCACCACCACCACCACGGCGAGCAGAAGCTGATCAGCGAGGAGGACCTGGGCTGGAGCCACCCCCAGTTCG

AGAAGTAGGCGGCCGCTCGAGTCTAGAGGGCCCGTTTAAACCCGCTGATCAGCCTCGACTGTGCCTTCTAGTTG

CCAGCCATCTGTTGTTTGCCCCTCCCCCGTGCCTTCCTTGACCCTGGAAGGTGCCACTCCCACTGTCCTTTCCT

AATAAAATGAGGAAATTGCATCGCATTGTCTGAGTAGGTGTCATTCTATTCTGGGGGGTGGGGTGGGGCAGGAC

AGCAAGGGGGAGGATTGGGAAGACAATAGCAGGCATGCTGGGGATGCGGTGGGCTCTATGGCTTCTGAGGCGGA

AAGAACCAGCTGGGGCTCTAGGGGGTATCCCCACGCGCCCTGTAGCGGCGCATTAAGCGCGGCGGGTGTGGTGG

TTACGCGCAGCGTGACCGCTACACTTGCCAGCGCCCTAGCGCCCGCTCCTTTCGCTTTCTTCCCTTCCTTTCTC

GCCACGTTCGCCGGCTTTCCCCGTCAAGCTCTAAATCGGGGCATCCCTTTAGGGTTCCGATTTAGTGCTTTACG

GCACCTCGACCCCAAAAAACTTGATTAGGGTGATGGTTCACGTAGTGGGCCATCGCCCTGATAGACGGTTTTTC

-continued

GCCCTTTGACGTTGGAGTCCACGTTCTTTAATAGTGGACTCTTGTTCCAAACTGGAACAACACTCAACCCTATC

TCGGTCTATTCTTTTGATTTATAAGGGATTTTGGGGATTTCGGCCTATTGGTTAAAAAATGAGCTGATTTAACA

AAAATTTAACGCGAATTAATTCTGTGGAATGTGTGTCAGTTAGGGTGTGGAAAGTCCCCAGGCTCCCCAGGCAG

GCAGAAGTATGCAAAGCATGCATCTCAATTAGTCAGCAACCAGGTGTGGAAAGTCCCCAGGCTCCCCAGCAGGC

AGAAGTATGCAAAGCATGCATCTCAATTAGTCAGCAACCATAGTCCCGCCCCTAACTCCGCCCATCCCGCCCCT

AACTCCGCCCAGTTCCGCCCATTCTCCGCCCCATGGCTGACTAATTTTTTTTATTTATGCAGAGGCCGAGGCCG

CCTCTGCCTCTGAGCTATTCCAGAAGTAGTGAGGAGGCTTTTTTGGAGGCCTAGGCTTTTGCAAAAAGCTCCCG

GGAGCTTGTATATCCATTTTCGGATCTGATCAGCACGTGATGAAAAAGCCTGAACTCACCGCGACGTCTGTCGA

GAAGTTTCTGATCGAAAAGTTCGACAGCGTCTCCGACCTGATGCAGCTCTCGGAGGGCGAAGAATCTCGTGCTT

TCAGCTTCGATGTAGGAGGGCGTGGATATGTCCTGCGGGTAAATAGCTGCGCCGATGGTTTCTACAAAGATCGT

TATGTTTATCGGCACTTTGCATCGGCCGCGCTCCCGATTCCGGAAGTGCTTGACATTGGGGAATTCAGCGAGAG

CCTGACCTATTGCATCTCCCGCCGTGCACAGGGTGTCACGTTGCAAGACCTGCCTGAAACCGAACTGCCCGCTG

TTCTGCAGCCGGTCGCGGAGGCCATGGATGCGATCGCTGCGGCCGATCTTAGCCAGACGAGCGGGTTCGGCCCA

TTCGGACCGCAAGGAATCGGTCAATACACTACATGGCGTGATTTCATATGCGCGATTGCTGATCCCCATGTGTA

TCACTGGCAAACTGTGATGGACGACACCGTCAGTGCGTCCGTCGCGCAGGCTCTCGATGAGCTGATGCTTTGGG

CCGAGGACTGCCCCGAAGTCCGGCACCTCGTGCACGCGGATTTCGGCTCCAACAATGTCCTGACGGACAATGGC

CGCATAACAGCGGTCATTGACTGGAGCGAGGCGATGTTCGGGGATTCCCAATACGAGGTCGCCAACATCTTCTT

CTGGAGGCCGTGGTTGGCTTGTATGGAGCAGCAGACGCGCTACTTCGAGCGGAGGCATCCGGAGCTTGCAGGAT

CGCCGCGGCTCCGGGCGTATATGCTCCGCATTGGTCTTGACCAACTCTATCAGAGCTTGGTTGACGGCAATTTC

GATGATGCAGCTTGGGCGCAGGGTCGATGCGACGCAATCGTCCGATCCGGAGCCGGGACTGTCGGGCGTACACA

AATCGCCCGCAGAAGCGCGGCCGTCTGGACCGATGGCTGTGTAGAAGTACTCGCCGATAGTGGAAACCGACGCC

CCAGCACTCGTCCGAGGGCAAAGGAATAGCACGTGCTACGAGATTTCGATTCCACCGCCGCCTTCTATGAAAGG

TTGGGCTTCGGAATCGTTTTCCGGGACGCCGGCTGGATGATCCTCCAGCGCGGGGATCTCATGCTGGAGTTCTT

CGCCCACCCCAACTTGTTTATTGCAGCTTATAATGGTTACAAATAAAGCAATAGCATCACAAATTTCACAAATA

AAGCATTTTTTTCACTGCATTCTAGTTGTGGTTTGTCCAAACTCATCAATGTATCTTATCATGTCTGTATACCG

TCGACCTCTAGCTAGAGCTTGGCGTAATCATGGTCATAGCTGTTTCCTGTGTGAAATTGTTATCCGCTCACAAT

TCCACACAACATACGAGCCGGAAGCATAAAGTGTAAAGCCTGGGGTGCCTAATGAGTGAGCTAACTCACATTAA

TTGCGTTGCGCTCACTGCCCGCTTTCCAGTCGGGAAACCTGTCGTGCCAGCTGCATTAATGAATCGGCCAACGC

GCGGGGAGAGGCGGTTTGCGTATTGGGCGCTCTTCCGCTTCCTCGCTCACTGACTCGCTGCGCTCGGTCGTTCG

GCTGCGGCGAGCGGTATCAGCTCACTCAAAGGCGGTAATACGGTTATCCACAGAATCAGGGGATAACGCAGGAA

AGAACATGTGAGCAAAAGGCCAGCAAAAGGCCAGGAACCGTAAAAAGGCCGCGTTGCTGGCGTTTTTCCATAGG

CTCCGCCCCCCTGACGAGCATCACAAAAATCGACGCTCAAGTCAGAGGTGGCGAAACCCGACAGGACTATAAAG

ATACCAGGCGTTTCCCCCTGGAAGCTCCCTCGTGCGCTCTCCTGTTCCGACCCTGCCGCTTACCGGATACCTGT

CCGCCTTTCTCCCTTCGGGAAGCGTGGCGCTTTCTCAATGCTCACGCTGTAGGTATCTCAGTTCGGTGTAGGTC

GTTCGCTCCAAGCTGGGCTGTGTGCACGAACCCCCCGTTCAGCCCGACCGCTGCGCCTTATCCGGTAACTATCG

TCTTGAGTCCAACCCGGTAAGACACGACTTATCGCCACTGGCAGCAGCCACTGGTAACAGGATTAGCAGAGCGA

GGTATGTAGGCGGTGCTACAGAGTTCTTGAAGTGGTGGCCTAACTACGGCTACACTAGAAGGACAGTATTTGGT

ATCTGCGCTCTGCTGAAGCCAGTTACCTTCGGAAAAAGAGTTGGTAGCTCTTGATCCGGCAAACAAACCACCGC

TGGTAGCGGTGGTTTTTTTGTTTGCAAGCAGCAGATTACGCGCAGAAAAAAAGGATCTCAAGAAGATCCTTTGA

TCTTTTCTACGGGGTCTGACGCTCAGTGGAACGAAAACTCACGTTAAGGGATTTTGGTCATGAGATTATCAAAA

AGGATCTTCACCTAGATCCTTTTAAATTAAAAATGAAGTTTTAAATCAATCTAAAGTATATATGAGTAAACTTG

-continued

GTCTGACAGTTACCAATGCTTAATCAGTGAGGCACCTATCTCAGCGATCTGTCTATTTCGTTCATCCATAGTTG

CCTGACTCCCCGTCGTGTAGATAACTACGATACGGGAGGGCTTACCATCTGGCCCCAGTGCTGCAATGATACCG

CGAGACCCACGCTCACCGGCTCCAGATTTATCAGCAATAAACCAGCCAGCCGGAAGGGCCGAGCGCAGAAGTGG

TCCTGCAACTTTATCCGCCTCCATCCAGTCTATTAATTGTTGCCGGGAAGCTAGAGTAAGTAGTTCGCCAGTTA

ATAGTTTGCGCAACGTTGTTGCCATTGCTACAGGCATCGTGGTGTCACGCTCGTCGTTTGGTATGGCTTCATTC

AGCTCCGGTTCCCAACGATCAAGGCGAGTTACATGATCCCCCATGTTGTGCAAAAAAGCGGTTAGCTCCTTCGG

TCCTCCGATCGTTGTCAGAAGTAAGTTGGCCGCAGTGTTATCACTCATGGTTATGGCAGCACTGCATAATTCTC

TTACTGTCATGCCATCCGTAAGATGCTTTTCTGTGACTGGTGAGTACTCAACCAAGTCATTCTGAGAATAGTGT

ATGCGGCGACCGAGTTGCTCTTGCCCGGCGTCAATACGGGATAATACCGCGCCACATAGCAGAACTTTAAAAGT

GCTCATCATTGGAAAACGTTCTTCGGGGCGAAAACTCTCAAGGATCTTACCGCTGTTGAGATCCAGTTCGATGT

AACCCACTCGTGCACCCAACTGATCTTCAGCATCTTTTACTTTCACCAGCGTTTCTGGGTGAGCAAAAACAGGA

AGGCAAAATGCCGCAAAAAAGGGAATAAGGGCGACACGGAAATGTTGAATACTCATACTCTTCCTTTTTCAATA

TTATTGAAGCATTTATCAGGGTTATTGTCTCATGAGCGGATACATATTTGAATGTATTTAGAAAAATAAACAAA

TAGGGGTTCCGCGCACATTTCCCCGAAAAGTGCCACCTGACGTC

These constructs allow upon transfection into mammalian cells, like e.g.—but not limited to —CHO cells, that are typically used for recombinant antibody expression, the expression of the anti-human CD19 specific humanized antibody hBU12 with C-terminal additions of a sortase A tag, a 6×His tag, a Myc tag, and a strepII tag at both the IgH and IgL chains.

Example 2: Cloning of Expression Vectors for Monoclonal Antibody with C-Terminal N-Intein Domain of Ssp GyrB 11 Split-Intein with Additional C-Terminal 6xhis and StrepII Affinity Purification Tags Similar to the design of expression cassettes and vectors of *Staphylococcus aureus* sortase A tagged IgG1 heavy and light chains, the coding regions for a C-terminal fusion of N-intein domain of Ssp GyrB 11 split-intein to either the IgH and IgL chain can be designed as follows, in order to gene synthesize the genes by a qualified CRO (e.g. Genscript (www.genscript.com, Piscataway, NJ, USA), with the same elements for the anti-human CD19 antibody as disclosed further above.

The 150 amino acid sequence of the N-intein domain of Ssp GyrB 11 split-intein can be found in a publication by Appleby et al. (2009), and is as follows:

(N-intein domain of Ssp GyrB 11 split-intein)
SEQ ID NO 15
CFSGDTLVALTDGRSVSFEQLVEEEKQGKQNFCYTIRHDGSIGVEKIIN

ARKTKTNAKVIKVTLDNGESIICTPDHKFMLRDGSYKCAMDLTLDDSLM

-continued

PLHRKISTTEDSGHMEAVLNYNHRIVNIEAVSETIDVYDIEVPHTHNFA

LAS

Reverse translation of that amino acid sequence with mammalian codon usage will result in the coding sequence for the N-intein domain of Ssp GyrB 11 split-intein as follows:

SEQ ID NO 16 (endocing sequence for N-intein domain of Ssp GyrB 11 split-intein):
TGCTTCAGCGGCGACACCCTGGTGGCCCTGACCGACGGCAGAAGCGTGA

GCTTCGAGCAGCTGGTGGAGGAGGAGAAGCAGGGCAAGCAGAACTTCTG

CTACACCATCAGACACGACGGCAGCATCGGCGTGGAGAAGATCATCAAC

GCCAGAAAGACCAAGACCAACGCCAAGGTGATCAAGGTGACCCTGGACA

ACGGCGAGAGCATCATCTGCACCCCCGACCACAAGTTCATGCTGAGAGA

CGGCAGCTACAAGTGCGCCATGGACCTGACCCTGGACGACAGCCTGATG

CCCCTGCACAGAAAGATCAGCACCACCGAGGACAGCGGCCACATGGAGG

CCGTGCTGAACTACAACCACAGAATCGTGAACATCGAGGCCGTGAGCGA

GACCATCGACGTGTACGACATCGAGGTGCCCCACACCCACAACTTCGCC

CTGGCCAGC

With this sequence information at hand, the complete IgG1 heavy chain coding region for anti-human CD19 antibody hBU12 with C-terminal extension, comprising the N-intein domain of Ssp GyrB 11 split-intein, followed by a 6×His-tag and a strepII tag can be designed as disclosed in SEQ ID NO 17 below:

ATGAATTTTGGACTGAGGCTGATTTTCCTGGTGCTGACCCTGAAAGGCGTCCAGTGTCAGGTTCAGCTGCAAGA

GTCTGGCCCTGGGTTGGTTAAGCCCTCCCAGACCCTCAGTCTGACTTGTACTGTGTCTGGGGGTTCAATCAGCA

CTTCTGGTATGGGTGTAGGCTGGATTAGGCAGCACCCAGGGAAGGGTCTGGAGTGGATTGGACACATTTGGTGG

GATGATGACAAGAGATATAACCCAGCCCTGAAGAGCAGAGTGACAATCTCTGTGGATACCTCCAAGAACCAGTT

-continued

TAGCCTCAAGCTGTCCAGTGTGACAGCTGCAGATACTGCTGTCTACTACTGTGCTAGAATGGAACTTTGGTCCT

ACTATTTTGACTACTGGGGCCAAGGCACCCTTGTCACAGTCTCCTCAGCTAGCACCAAGGGCCCATCTGTCTTC

CCCCTGGCACCCTCCTCCAAGAGCACCTCTGGGGGCACAGCTGCCCTGGGCTGCCTGGTCAAGGACTACTTCCC

TGAACCTGTGACAGTGTCCTGGAACTCAGGCGCCCTGACCAGCGGCGTGCACACCTTCCCGGCTGTCCTACAGT

CCTCAGGACTCTACTCCCTCAGCAGCGTGGTGACCGTGCCCTCCAGCAGCTTGGGCACCCAGACCTACATCTGC

AACGTGAATCACAAGCCCAGCAACACCAAGGTGGACAAGAAAGTTGAGCCCAAATCTTGTGACAAAACTCACAC

ATGCCCACCGTGCCCAGCACCTGAACTCCTGGGGGGACCGTCAGTCTTCCTCTTCCCCCCAAAACCCAAGGACA

CCCTCATGATCTCCCGGACCCCTGAGGTCACATGCGTGGTGGTGGACGTGAGCCACGAAGACCCTGAGGTCAAG

TTCAACTGGTACGTGGACGGCGTGGAGGTGCATAATGCCAAGACAAAGCCGCGGGAGGAGCAGTACAACAGCAC

GTACCGTGTGGTCAGCGTCCTCACCGTCCTGCACCAGGACTGGCTGAATGGCAAGGAGTACAAGTGCAAGGTCT

CCAACAAAGCCCTCCCAGCCCCCATCGAGAAAACCATCTCCAAAGCCAAAGGGCAGCCCCGAGAACCACAGGTG

TACACCCTGCCCCCATCCCGGGATGAGCTGACCAAGAACCAGGTCAGCCTGACCTGCCTGGTCAAAGGCTTCTA

TCCCAGCGACATCGCCGTGGAGTGGGAGAGCAATGGGCAGCCGGAGAACAACTACAAGACCACGCCTCCCGTGC

TGGACTCCGACGGCTCCTTCTTCCTCTACAGCAAGCTCACCGTGGACAAGAGCAGGTGGCAGCAGGGGAACGTC

TTCTCATGCTCCGTGATGCATGAGGCTCTGCACAACCACTACACACAGAAGAGCCTCTCCCTGTCTCCGGGTAA

ATGCTTCAGCGGCGACACCCTGGTGGCCCTGACCGACGGCAGAAGCGTGAGCTTCGAGCAGCTGGTGGAGGAGG

AGAAGCAGGGCAAGCAGAACTTCTGCTACACCATCAGACACGACGGCAGCATCGGCGTGGAGAAGATCATCAAC

GCCAGAAAGACCAAGACCAACGCCAAGGTGATCAAGGTGACCCTGGACAACGGCGAGAGCATCATCTGCACCCC

CGACCACAAGTTCATGCTGAGAGACGGCAGCTACAAGTGCGCCATGGACCTGACCCTGGACGACAGCCTGATGC

CCCTGCACAGAAAGATCAGCACCACCGAGGACAGCGGCCACATGGAGGCCGTGCTGAACTACAACCACAGAATC

GTGAACATCGAGGCCGTGAGCGAGACCATCGACGTGTACGACATCGAGGTGCCCCACACCCACAACTTCGCCCT

GGCCAGCCACCATCACCATCACCATGGCTGGAGCCACCCCCAGTTCGAGAAGTAG

This translates to amino acid sequence SEQ ID NO 18 (amino acids of the N-intein domain are underlined, 6xHis tag and strepII tag are shaded):

MNFGLRLIFLVLTLKGVQCQVQLQESGPGLVKPSQTLSLTCTVSGGSISTSGMGVGWIRQHPGKGLEWIGHIWW

DDDKRYNPALKSRVTISVDTSKNQFSLKLSSVTAADTAVYYCARMELWSYYFDYWGQGTLVTVSSASTKGPSVF

PLAPSSKSTSGGTAALGCLVKDYFPEPVTVSWNSGALTSGVHTFPAVLQSSGLYSLSSVVTVPSSSLGTQTYIC

NVNHKPSNTKVDKKVEPKSCDKTHTCPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVLDSDGSFFLYSKLTVDKSRWQQGNV

FSCSVMHEALHNHYTQKSLSLSPGKCFSGDTLVALTDGRSVSFEQLVEEEKQGKQNFCYTIRHDGSIGVEKIIN

ARKTKTNAKVIKVTLDNGESIICTPDHKFMLRDGSYKCAMDLTLDDSLMPLHRKISTTEDSGHMEAVLNYNHRI

VNIEAVSETIDVYDIEVPHTHNFALASHHHHHHGWSHPQFEK·

Likewise, a complete IgG1 kappa light chain coding region for anti-human CD19 antibody hBU12 with C-terminal extension, comprising the N-intein domain of Ssp GyrB 11 split-intein, followed by a 6×His-tag and a strepII tag can be designed as disclosed in SEQ ID NO 19 below:

ATGAATTTTGGACTGAGGCTGATTTTCCTGGTGCTGACCCTGAAAGGCGTCCAGTGTGACATTGTGCTGACCCA

ATCTCCAGCTTCTTTGGCTGTGTCTCTAGGGCAGAGGGCCACCATCTCCTGCAAGGCCAGCCAAAGTGTTGATT

TTGATGGTGATAGTTATATGAACTGGTACCAACAGAAACCAGGACAGCCACCCAAAGTCCTCATCTATGCTGCA

-continued

TCCAATCTAGAATCTGGGATCCCAGCCAGGTTTAGTGGCAGTGGGTCTGGGACAGACTTCACCCTCAACATCCA

TCCTGTGGAGGAGGAGGATGCTGCAACCTATTACTGTCAGCAAAGTAATGAGGATCCGTGGACGTTCGGTGGAG

GCACCAAGCTGGAAATCAAACGTACGGTGGCTGCACCATCTGTCTTCATCTTCCCGCCATCTGATGAGCAGTTG

AAATCTGGAACTGCCTCTGTTGTGTGCCTGCTGAATAACTTCTATCCCAGAGAGGCCAAAGTACAGTGGAAGGT

GGATAACGCCCTCCAATCGGGTAACTCCCAGGAGAGTGTCACAGAGCAGGACAGCAAGGACAGCACCTACAGCC

TCAGCAGCACCCTGACGCTGAGCAAAGCAGACTACGAGAAACACAAAGTCTACGCCTGCGAAGTCACCCATCAG

GGCCTGAGCTCGCCCGTCACAAAGAGCTTCAACAGGGGAGAGTGCTTCAGCGGCGACACCCTGGTGGCCCTGAC

CGACGGCAGAAGCGTGAGCTTCGAGCAGCTGGTGGAGGAGGAGAAGCAGGGCAAGCAGAACTTCTGCTACACCA

TCAGACACGACGGCAGCATCGGCGTGGAGAAGATCATCAACGCCAGAAAGACCAAGACCAACGCCAAGGTGATC

AAGGTGACCCTGGACAACGGCGAGAGCATCATCTGCACCCCCGACCACAAGTTCATGCTGAGAGACGGCAGCTA

CAAGTGCGCCATGGACCTGACCCTGGACGACAGCCTGATGCCCCTGCACAGAAAGATCAGCACCACCGAGGACA

GCGGCCACATGGAGGCCGTGCTGAACTACAACCACAGAATCGTGAACATCGAGGCCGTGAGCGAGACCATCGAC

GTGTACGACATCGAGGTGCCCCACACCCACAACTTCGCCCTGGCCAGCCACCATCACCATCACCATGGCTGGAG

CCACCCCCAGTTCGAGAAGTAG

This translates to amino acid sequence SEQ ID NO 20 (amino acids of the N-intein domain are underlined, 6xHis tag and strepII tag are shaded):

MNFGLRLIFLVLTLKGVQCDIVLTQSPASLAVSLGQRATISCKASQSVDFDGDSYMNWYQQKPGQPPKVLIYAA

SNLESGIPARFSGSGSGTDFTLNIHPVEEEDAATYYCQQSNEDPWTFGGGTKLEIKRTVAAPSVFIFPPSDEQL

KSGTASVVCLLNNFYPREAKVQWKVDNALQSGNSQESVTEQDSKDSTYSLSSTLTLSKADYEKHKVYACEVTHQ

GLSSPVTKSFNRGECFSGDTLVALTDGRSVSFEQLVEEEKQGKQNFCYTIRHDGSIGVEKIINARKTKTNAKVI

KVTLDNGESIICTPDHKFMLRDGSYKCAMDLTLDDSLMPLHRKISTTEDSGHMEAVLNYNHRIVNIEAVSETID

VYDIEVPHTHNFALASHHHHHHGWSHPQFEK

The coding regions for the N-intein modified heavy and light chains of the anti-human CD19 specific antibody as disclosed in SEQ ID NOs 17 and 19, respectively, can then be synthesized with flanking restriction enzyme sites (e.g. HindIII and NotI) such that they can be cloned into a standard mammalian expression vector, such as pCDNA3.1-hygro (+) (Invitrogen), by standard molecular biology methods known in the art.

The complete DNA sequence of pCDNA3.1-hygro (+)-IgH chain expression vector for the N-intein tagged hBU12 anti-human CD19 antibody is then as follows:

(coding region of human IgG1 $V_H$-$C_H$ heavy chain for hBU12 with C-terminal N-intein domain of Ssp GyrB S11 split intein, followed by 6xHis tag strepII tag (underlined), and HindIII and NotI cloning sites (shaded)):

SEQ ID NO 21

GACGGATCGGGAGATCTCCCGATCCCCTATGGTCGACTCTCAGTACAATCTGCTCTGATGCCGCATAGTTAAGC

CAGTATCTGCTCCCTGCTTGTGTGTTGGAGGTCGCTGAGTAGTGCGCGAGCAAAATTTAAGCTACAACAAGGCA

AGGCTTGACCGACAATTGCATGAAGAATCTGCTTAGGGTTAGGCGTTTTGCGCTGCTTCGCGATGTACGGGCCA

GATATACGCGTTGACATTGATTATTGACTAGTTATTAATAGTAATCAATTACGGGGTCATTAGTTCATAGCCCA

TATATGGAGTTCCGCGTTACATAACTTACGGTAAATGGCCCGCCTGGCTGACCGCCCAACGACCCCCGCCCATT

GACGTCAATAATGACGTATGTTCCCATAGTAACGCCAATAGGGACTTTCCATTGACGTCAATGGGTGGACTATT

TACGGTAAACTGCCCACTTGGCAGTACATCAAGTGTATCATATGCCAAGTACGCCCCCTATTGACGTCAATGAC

GGTAAATGGCCCGCCTGGCATTATGCCCAGTACATGACCTTATGGGACTTTCCTACTTGGCAGTACATCTACGT

ATTAGTCATCGCTATTACCATGGTGATGCGGTTTTGGCAGTACATCAATGGGCGTGGATAGCGGTTTGACTCAC

GGGGATTTCCAAGTCTCCACCCCATTGACGTCAATGGGAGTTTGTTTTGGCACCAAAATCAACGGGACTTTCCA

AAATGTCGTAACAACTCCGCCCCATTGACGCAAATGGGCGGTAGGCGTGTACGGTGGGAGGTCTATATAAGCAG

-continued

AGCTCTCTGGCTAACTAGAGAACCCACTGCTTACTGGCTTATCGAAATTAATACGACTCACTATAGGGAGACCC

AAGCTGGCTAGCGTTTAAACTTAAGCTTCCATGAATTTTGGACTGAGGCTGATTTTCCTGGTGCTGACCCTGAA

AGGCGTCCAGTGTCAGGTTCAGCTGCAAGAGTCTGGCCCTGGGTTGGTTAAGCCCTCCCAGACCCTCAGTCTGA

CTTGTACTGTGTCTGGGGGTTCAATCAGCACTTCTGGTATGGGTGTAGGCTGGATTAGGCAGCACCCAGGGAAG

GGTCTGGAGTGGATTGGACACATTTGGTGGGATGATGACAAGAGATATAACCCAGCCCTGAAGAGCAGAGTGAC

AATCTCTGTGGATACCTCCAAGAACCAGTTTAGCCTCAAGCTGTCCAGTGTGACAGCTGCAGATACTGCTGTCT

ACTACTGTGCTAGAATGGAACTTTGGTCCTACTATTTTGACTACTGGGGCCAAGGCACCCTTGTCACAGTCTCC

TCAGCTAGCACCAAGGGCCCATCTGTCTTCCCCCTGGCACCCTCCTCCAAGAGCACCTCTGGGGGCACAGCTGC

CCTGGGCTGCCTGGTCAAGGACTACTTCCCTGAACCTGTGACAGTGTCCTGGAACTCAGGCGCCCTGACCAGCG

GCGTGCACACCTTCCCGGCTGTCCTACAGTCCTCAGGACTCTACTCCCTCAGCAGCGTGGTGACCGTGCCCTCC

AGCAGCTTGGGCACCCAGACCTACATCTGCAACGTGAATCACAAGCCCAGCAACACCAAGGTGGACAAGAAAGT

TGAGCCCAAATCTTGTGACAAAACTCACACATGCCCACCGTGCCCAGCACCTGAACTCCTGGGGGGACCGTCAG

TCTTCCTCTTCCCCCCAAAACCCAAGGACACCCTCATGATCTCCCGGACCCCTGAGGTCACATGCGTGGTGGTG

GACGTGAGCCACGAAGACCCTGAGGTCAAGTTCAACTGGTACGTGGACGGCGTGGAGGTGCATAATGCCAAGAC

AAAGCCGCGGGAGGAGCAGTACAACAGCACGTACCGTGTGGTCAGCGTCCTCACCGTCCTGCACCAGGACTGGC

TGAATGGCAAGGAGTACAAGTGCAAGGTCTCCAACAAAGCCCTCCCAGCCCCCATCGAGAAAACCATCTCCAAA

GCCAAAGGGCAGCCCCGAGAACCACAGGTGTACACCCTGCCCCCATCCCGGGATGAGCTGACCAAGAACCAGGT

CAGCCTGACCTGCCTGGTCAAAGGCTTCTATCCCAGCGACATCGCCGTGGAGTGGGAGAGCAATGGGCAGCCGG

AGAACAACTACAAGACCACGCCTCCCGTGCTGGACTCCGACGGCTCCTTCTTCCTCTACAGCAAGCTCACCGTG

GACAAGAGCAGGTGGCAGCAGGGGAACGTCTTCTCATGCTCCGTGATGCATGAGGCTCTGCACAACCACTACAC

ACAGAAGAGCCTCTCCCTGTCTCCGGGTAAATGCTTCAGCGGCGACACCCTGGTGGCCCTGACCGACGGCAGAA

GCGTGAGCTTCGAGCAGCTGGTGGAGGAGGAGAAGCAGGGCAAGCAGAACTTCTGCTACACCATCAGACACGAC

GGCAGCATCGGCGTGGAGAAGATCATCAACGCCAGAAAGACCAAGACCAACGCCAAGGTGATCAAGGTGACCCT

GGACAACGGCGAGAGCATCATCTGCACCCCCGACCACAAGTTCATGCTGAGAGACGGCAGCTACAAGTGCGCCA

TGGACCTGACCCTGGACGACAGCCTGATGCCCCTGCACAGAAAGATCAGCACCACCGAGGACAGCGGCCACATG

GAGGCCGTGCTGAACTACAACCACAGAATCGTGAACATCGAGGCCGTGAGCGAGACCATCGACGTGTACGACAT

CGAGGTGCCCCACACCCACAACTTCGCCCTGGCCAGCCACCATCACCATCACCATGGCTGGAGCCACCCCCAGT

TCGAGAAGTAGGCGGCCGCTCGAGTCTAGAGGGCCCGTTTAAACCCGCTGATCAGCCTCGACTGTGCCTTCTAG

TTGCCAGCCATCTGTTGTTTGCCCCTCCCCCGTGCCTTCCTTGACCCTGGAAGGTGCCACTCCCACTGTCCTTT

CCTAATAAAATGAGGAAATTGCATCGCATTGTCTGAGTAGGTGTCATTCTATTCTGGGGGGTGGGGTGGGGCAG

GACAGCAAGGGGGAGGATTGGGAAGACAATAGCAGGCATGCTGGGGATGCGGTGGGCTCTATGGCTTCTGAGGC

GGAAAGAACCAGCTGGGGCTCTAGGGGGTATCCCCACGCGCCCTGTAGCGGCGCATTAAGCGCGGCGGGTGTGG

TGGTTACGCGCAGCGTGACCGCTACACTTGCCAGCGCCCTAGCGCCCGCTCCTTTCGCTTTCTTCCCTTCCTTT

CTCGCCACGTTCGCCGGCTTTCCCCGTCAAGCTCTAAATCGGGGCATCCCTTTAGGGTTCCGATTTAGTGCTTT

ACGGCACCTCGACCCCAAAAAACTTGATTAGGGTGATGGTTCACGTAGTGGGCCATCGCCCTGATAGACGGTTT

TTCGCCCTTTGACGTTGGAGTCCACGTTCTTTAATAGTGGACTCTTGTTCCAAACTGGAACAACACTCAACCCT

ATCTCGGTCTATTCTTTTGATTTATAAGGGATTTTGGGGATTTCGGCCTATTGGTTAAAAAATGAGCTGATTTA

ACAAAAATTTAACGCGAATTAATTCTGTGGAATGTGTGTCAGTTAGGGTGTGGAAAGTCCCCAGGCTCCCCAGG

CAGGCAGAAGTATGCAAAGCATGCATCTCAATTAGTCAGCAACCAGGTGTGGAAAGTCCCCAGGCTCCCCAGCA

-continued

GGCAGAAGTATGCAAAGCATGCATCTCAATTAGTCAGCAACCATAGTCCCGCCCCTAACTCCGCCCATCCCGCC

CCTAACTCCGCCCAGTTCCGCCCATTCTCCGCCCCATGGCTGACTAATTTTTTTTATTTATGCAGAGGCCGAGG

CCGCCTCTGCCTCTGAGCTATTCCAGAAGTAGTGAGGAGGCTTTTTTGGAGGCCTAGGCTTTTGCAAAAAGCTC

CCGGGAGCTTGTATATCCATTTTCGGATCTGATCAGCACGTGATGAAAAAGCCTGAACTCACCGCGACGTCTGT

CGAGAAGTTTCTGATCGAAAAGTTCGACAGCGTCTCCGACCTGATGCAGCTCTCGGAGGGCGAAGAATCTCGTG

CTTTCAGCTTCGATGTAGGAGGGCGTGGATATGTCCTGCGGGTAAATAGCTGCGCCGATGGTTTCTACAAAGAT

CGTTATGTTTATCGGCACTTTGCATCGGCCGCGCTCCCGATTCCGGAAGTGCTTGACATTGGGGAATTCAGCGA

GAGCCTGACCTATTGCATCTCCCGCCGTGCACAGGGTGTCACGTTGCAAGACCTGCCTGAAACCGAACTGCCCG

CTGTTCTGCAGCCGGTCGCGGAGGCCATGGATGCGATCGCTGCGGCCGATCTTAGCCAGACGAGCGGGTTCGGC

CCATTCGGACCGCAAGGAATCGGTCAATACACTACATGGCGTGATTTCATATGCGCGATTGCTGATCCCCATGT

GTATCACTGGCAAACTGTGATGGACGACACCGTCAGTGCGTCCGTCGCGCAGGCTCTCGATGAGCTGATGCTTT

GGGCCGAGGACTGCCCCGAAGTCCGGCACCTCGTGCACGCGGATTTCGGCTCCAACAATGTCCTGACGGACAAT

GGCCGCATAACAGCGGTCATTGACTGGAGCGAGGCGATGTTCGGGGATTCCCAATACGAGGTCGCCAACATCTT

CTTCTGGAGGCCGTGGTTGGCTTGTATGGAGCAGCAGACGCGCTACTTCGAGCGGAGGCATCCGGAGCTTGCAG

GATCGCCGCGGCTCCGGGCGTATATGCTCCGCATTGGTCTTGACCAACTCTATCAGAGCTTGGTTGACGGCAAT

TTCGATGATGCAGCTTGGGCGCAGGGTCGATGCGACGCAATCGTCCGATCCGGAGCCGGGACTGTCGGGCGTAC

ACAAATCGCCCGCAGAAGCGCGGCCGTCTGGACCGATGGCTGTGTAGAAGTACTCGCCGATAGTGGAAACCGAC

GCCCCAGCACTCGTCCGAGGGCAAAGGAATAGCACGTGCTACGAGATTTCGATTCCACCGCCGCCTTCTATGAA

AGGTTGGGCTTCGGAATCGTTTTCCGGGACGCCGGCTGGATGATCCTCCAGCGCGGGGATCTCATGCTGGAGTT

CTTCGCCCACCCCAACTTGTTTATTGCAGCTTATAATGGTTACAAATAAAGCAATAGCATCACAAATTTCACAA

ATAAAGCATTTTTTTCACTGCATTCTAGTTGTGGTTTGTCCAAACTCATCAATGTATCTTATCATGTCTGTATA

CCGTCGACCTCTAGCTAGAGCTTGGCGTAATCATGGTCATAGCTGTTTCCTGTGTGAAATTGTTATCCGCTCAC

AATTCCACACAACATACGAGCCGGAAGCATAAAGTGTAAAGCCTGGGGTGCCTAATGAGTGAGCTAACTCACAT

TAATTGCGTTGCGCTCACTGCCCGCTTTCCAGTCGGGAAACCTGTCGTGCCAGCTGCATTAATGAATCGGCCAA

CGCGCGGGGAGAGGCGGTTTGCGTATTGGGCGCTCTTCCGCTTCCTCGCTCACTGACTCGCTGCGCTCGGTCGT

TCGGCTGCGGCGAGCGGTATCAGCTCACTCAAAGGCGGTAATACGGTTATCCACAGAATCAGGGGATAACGCAG

GAAAGAACATGTGAGCAAAAGGCCAGCAAAAGGCCAGGAACCGTAAAAAGGCCGCGTTGCTGGCGTTTTTCCAT

AGGCTCCGCCCCCCTGACGAGCATCACAAAAATCGACGCTCAAGTCAGAGGTGGCGAAACCCGACAGGACTATA

AAGATACCAGGCGTTTCCCCCTGGAAGCTCCCTCGTGCGCTCTCCTGTTCCGACCCTGCCGCTTACCGGATACC

TGTCCGCCTTTCTCCCTTCGGGAAGCGTGGCGCTTTCTCAATGCTCACGCTGTAGGTATCTCAGTTCGGTGTAG

GTCGTTCGCTCCAAGCTGGGCTGTGTGCACGAACCCCCCGTTCAGCCCGACCGCTGCGCCTTATCCGGTAACTA

TCGTCTTGAGTCCAACCCGGTAAGACACGACTTATCGCCACTGGCAGCAGCCACTGGTAACAGGATTAGCAGAG

CGAGGTATGTAGGCGGTGCTACAGAGTTCTTGAAGTGGTGGCCTAACTACGGCTACACTAGAAGGACAGTATTT

GGTATCTGCGCTCTGCTGAAGCCAGTTACCTTCGGAAAAAGAGTTGGTAGCTCTTGATCCGGCAAACAAACCAC

CGCTGGTAGCGGTGGTTTTTTTGTTTGCAAGCAGCAGATTACGCGCAGAAAAAAAGGATCTCAAGAAGATCCTT

TGATCTTTTCTACGGGGTCTGACGCTCAGTGGAACGAAAACTCACGTTAAGGGATTTTGGTCATGAGATTATCA

AAAAGGATCTTCACCTAGATCCTTTTAAATTAAAAATGAAGTTTTAAATCAATCTAAAGTATATATGAGTAAAC

TTGGTCTGACAGTTACCAATGCTTAATCAGTGAGGCACCTATCTCAGCGATCTGTCTATTTCGTTCATCCATAG

TTGCCTGACTCCCCGTCGTGTAGATAACTACGATACGGGAGGGCTTACCATCTGGCCCCAGTGCTGCAATGATA

CCGCGAGACCCACGCTCACCGGCTCCAGATTTATCAGCAATAAACCAGCCAGCCGGAAGGGCCGAGCGCAGAAG

TGGTCCTGCAACTTTATCCGCCTCCATCCAGTCTATTAATTGTTGCCGGGAAGCTAGAGTAAGTAGTTCGCCAG

-continued

TTAATAGTTTGCGCAACGTTGTTGCCATTGCTACAGGCATCGTGGTGTCACGCTCGTCGTTTGGTATGGCTTCA

TTCAGCTCCGGTTCCCAACGATCAAGGCGAGTTACATGATCCCCCATGTTGTGCAAAAAAGCGGTTAGCTCCTT

CGGTCCTCCGATCGTTGTCAGAAGTAAGTTGGCCGCAGTGTTATCACTCATGGTTATGGCAGCACTGCATAATT

CTCTTACTGTCATGCCATCCGTAAGATGCTTTTCTGTGACTGGTGAGTACTCAACCAAGTCATTCTGAGAATAG

TGTATGCGGCGACCGAGTTGCTCTTGCCCGGCGTCAATACGGGATAATACCGCGCCACATAGCAGAACTTTAAA

AGTGCTCATCATTGGAAAACGTTCTTCGGGGCGAAAACTCTCAAGGATCTTACCGCTGTTGAGATCCAGTTCGA

TGTAACCCACTCGTGCACCCAACTGATCTTCAGCATCTTTTACTTTCACCAGCGTTTCTGGGTGAGCAAAAACA

GGAAGGCAAAATGCCGCAAAAAAGGGAATAAGGGCGACACGGAAATGTTGAATACTCATACTCTTCCTTTTTCA

ATATTATTGAAGCATTTATCAGGGTTATTGTCTCATGAGCGGATACATATTTGAATGTATTTAGAAAAATAAAC

AAATAGGGGTTCCGCGCACATTTCCCCGAAAAGTGCCACCTGACGTC

The complete DNA sequence of pCDNA3.1-hygro (+)-IgL chain expression vector for the Ssp GyrB S11 N-intein domain tagged hBU12 anti-human CD19 antibody will be as follows:

(coding region of human IgG1 $V_L$-$C_L$ kappa light chain for hBU12 with C-terminal Ssp GyrB S11 N-intein domain, 6xHis tag and a strepII tag underlined, and HindIII and NotI cloning sites shaded):

SEQ ID NO 22

GACGGATCGGGAGATCTCCCGATCCCCTATGGTCGACTCTCAGTACAATCTGCTCTGATGCCGCATAGTTAAGC

CAGTATCTGCTCCCTGCTTGTGTGTTGGAGGTCGCTGAGTAGTGCGCGAGCAAAATTTAAGCTACAACAAGGCA

AGGCTTGACCGACAATTGCATGAAGAATCTGCTTAGGGTTAGGCGTTTTGCGCTGCTTCGCGATGTACGGGCCA

GATATACGCGTTGACATTGATTATTGACTAGTTATTAATAGTAATCAATTACGGGGTCATTAGTTCATAGCCCA

TATATGGAGTTCCGCGTTACATAACTTACGGTAAATGGCCCGCCTGGCTGACCGCCCAACGACCCCCGCCCATT

GACGTCAATAATGACGTATGTTCCCATAGTAACGCCAATAGGGACTTTCCATTGACGTCAATGGGTGGACTATT

TACGGTAAACTGCCCACTTGGCAGTACATCAAGTGTATCATATGCCAAGTACGCCCCCTATTGACGTCAATGAC

GGTAAATGGCCCGCCTGGCATTATGCCCAGTACATGACCTTATGGGACTTTCCTACTTGGCAGTACATCTACGT

ATTAGTCATCGCTATTACCATGGTGATGCGGTTTTGGCAGTACATCAATGGGCGTGGATAGCGGTTTGACTCAC

GGGGATTTCCAAGTCTCCACCCCATTGACGTCAATGGGAGTTTGTTTTGGCACCAAAATCAACGGGACTTTCCA

AAATGTCGTAACAACTCCGCCCCATTGACGCAAATGGGCGGTAGGCGTGTACGGTGGGAGGTCTATATAAGCAG

AGCTCTCTGGCTAACTAGAGAACCCACTGCTTACTGGCTTATCGAAATTAATACGACTCACTATAGGGAGACCC

AAGCTGGCTAGCGTTTAAACTTAAGCTTCCATGAATTTTGGACTGAGGCTGATTTTCCTGGTGCTGACCCTGAA

AGGCGTCCAGTGTGACATTGTGCTGACCCAATCTCCAGCTTCTTTGGCTGTGTCTCTAGGGCAGAGGGCCACCA

TCTCCTGCAAGGCCAGCCAAAGTGTTGATTTTGATGGTGATAGTTATATGAACTGGTACCAACAGAAACCAGGA

CAGCCACCCAAAGTCCTCATCTATGCTGCATCCAATCTAGAATCTGGGATCCCAGCCAGGTTTAGTGGCAGTGG

GTCTGGGACAGACTTCACCCTCAACATCCATCCTGTGGAGGAGGAGGATGCTGCAACCTATTACTGTCAGCAAA

GTAATGAGGATCCGTGGACGTTCGGTGGAGGCACCAAGCTGGAAATCAAACGTACGGTGGCTGCACCATCTGTC

TTCATCTTCCCGCCATCTGATGAGCAGTTGAAATCTGGAACTGCCTCTGTTGTGTGCCTGCTGAATAACTTCTA

TCCCAGAGAGGCCAAAGTACAGTGGAAGGTGGATAACGCCCTCCAATCGGGTAACTCCCAGGAGAGTGTCACAG

AGCAGGACAGCAAGGACAGCACCTACAGCCTCAGCAGCACCCTGACGCTGAGCAAAGCAGACTACGAGAAACAC

AAAGTCTACGCCTGCGAAGTCACCCATCAGGGCCTGAGCTCGCCCGTCACAAAGAGCTTCAACAGGGGAGAGTG

CTTCAGCGGCGACACCCTGGTGGCCCTGACCGACGGCAGAAGCGTGAGCTTCGAGCAGCTGGTGGAGGAGGAGA

AGCAGGGCAAGCAGAACTTCTGCTACACCATCAGACACGACGGCAGCATCGGCGTGGAGAAGATCATCAACGCC

-continued

AGAAAGACCAAGACCAACGCCAAGGTGATCAAGGTGACCCTGGACAACGGCGAGAGCATCATCTGCACCCCCGA

CCACAAGTTCATGCTGAGAGACGGCAGCTACAAGTGCGCCATGGACCTGACCCTGGACGACAGCCTGATGCCCC

TGCACAGAAAGATCAGCACCACCGAGGACAGCGGCCACATGGAGGCCGTGCTGAACTACAACCACAGAATCGTG

AACATCGAGGCCGTGAGCGAGACCATCGACGTGTACGACATCGAGGTGCCCCACACCCACAACTTCGCCCTGGC

CAGCCACCATCACCATCACCATGGGCTGGAGCCACCCCCAGTTCGAGAAGTAGGCGGCCGCTCGAGTCTAGAGG

CCCGTTTAAACCCGCTGATCAGCCTCGACTGTGCCTTCTAGTTGCCAGCCATCTGTTGTTTGCCCCTCCCCCGT

GCCTTCCTTGACCCTGGAAGGTGCCACTCCCACTGTCCTTTCCTAATAAAATGAGGAAATTGCATCGCATTGTC

TGAGTAGGTGTCATTCTATTCTGGGGGGTGGGGTGGGGCAGGACAGCAAGGGGGAGGATTGGGAAGACAATAGC

AGGCATGCTGGGGATGCGGTGGGCTCTATGGCTTCTGAGGCGGAAAGAACCAGCTGGGGCTCTAGGGGGTATCC

CCACGCGCCCTGTAGCGGCGCATTAAGCGCGGCGGGTGTGGTGGTTACGCGCAGCGTGACCGCTACACTTGCCA

GCGCCCTAGCGCCCGCTCCTTTCGCTTTCTTCCCTTCCTTTCTCGCCACGTTCGCCGGCTTTCCCCGTCAAGCT

CTAAATCGGGGCATCCCTTTAGGGTTCCGATTTAGTGCTTTACGGCACCTCGACCCCAAAAAACTTGATTAGGG

TGATGGTTCACGTAGTGGGCCATCGCCCTGATAGACGGTTTTTCGCCCTTTGACGTTGGAGTCCACGTTCTTTA

ATAGTGGACTCTTGTTCCAAACTGGAACAACACTCAACCCTATCTCGGTCTATTCTTTTGATTTATAAGGGATT

TTGGGGATTTCGGCCTATTGGTTAAAAAATGAGCTGATTTAACAAAAATTTAACGCGAATTAATTCTGTGGAAT

GTGTGTCAGTTAGGGTGTGGAAAGTCCCCAGGCTCCCCAGGCAGGCAGAAGTATGCAAAGCATGCATCTCAATT

AGTCAGCAACCAGGTGTGGAAAGTCCCCAGGCTCCCCAGCAGGCAGAAGTATGCAAAGCATGCATCTCAATTAG

TCAGCAACCATAGTCCCGCCCCTAACTCCGCCCATCCCGCCCCTAACTCCGCCCAGTTCCGCCCATTCTCCGCC

CCATGGCTGACTAATTTTTTTTATTTATGCAGAGGCCGAGGCCGCCTCTGCCTCTGAGCTATTCCAGAAGTAGT

GAGGAGGCTTTTTTGGAGGCCTAGGCTTTTGCAAAAAGCTCCCGGGAGCTTGTATATCCATTTTCGGATCTGAT

CAGCACGTGATGAAAAAGCCTGAACTCACCGCGACGTCTGTCGAGAAGTTTCTGATCGAAAAGTTCGACAGCGT

CTCCGACCTGATGCAGCTCTCGGAGGGCGAAGAATCTCGTGCTTTCAGCTTCGATGTAGGAGGGCGTGGATATG

TCCTGCGGGTAAATAGCTGCGCCGATGGTTTCTACAAAGATCGTTATGTTTATCGGCACTTTGCATCGGCCGCG

CTCCCGATTCCGGAAGTGCTTGACATTGGGGAATTCAGCGAGAGCCTGACCTATTGCATCTCCCGCCGTGCACA

GGGTGTCACGTTGCAAGACCTGCCTGAAACCGAACTGCCCGCTGTTCTGCAGCCGGTCGCGGAGGCCATGGATG

CGATCGCTGCGGCCGATCTTAGCCAGACGAGCGGGTTCGGCCCATTCGGACCGCAAGGAATCGGTCAATACACT

ACATGGCGTGATTTCATATGCGCGATTGCTGATCCCCATGTGTATCACTGGCAAACTGTGATGGACGACACCGT

CAGTGCGTCCGTCGCGCAGGCTCTCGATGAGCTGATGCTTTGGGCCGAGGACTGCCCCGAAGTCCGGCACCTCG

TGCACGCGGATTTCGGCTCCAACAATGTCCTGACGGACAATGGCCGCATAACAGCGGTCATTGACTGGAGCGAG

GCGATGTTCGGGGATTCCCAATACGAGGTCGCCAACATCTTCTTCTGGAGGCCGTGGTTGGCTTGTATGGAGCA

GCAGACGCGCTACTTCGAGCGGAGGCATCCGGAGCTTGCAGGATCGCCGCGGCTCCGGGCGTATATGCTCCGCA

TTGGTCTTGACCAACTCTATCAGAGCTTGGTTGACGGCAATTTCGATGATGCAGCTTGGGCGCAGGGTCGATGC

GACGCAATCGTCCGATCCGGAGCCGGGACTGTCGGGCGTACACAAATCGCCCGCAGAAGCGCGGCCGTCTGGAC

CGATGGCTGTGTAGAAGTACTCGCCGATAGTGGAAACCGACGCCCCAGCACTCGTCCGAGGGCAAAGGAATAGC

ACGTGCTACGAGATTTCGATTCCACCGCCGCCTTCTATGAAAGGTTGGGCTTCGGAATCGTTTTCCGGGACGCC

GGCTGGATGATCCTCCAGCGCGGGGATCTCATGCTGGAGTTCTTCGCCCACCCCAACTTGTTTATTGCAGCTTA

TAATGGTTACAAATAAAGCAATAGCATCACAAATTTCACAAATAAAGCATTTTTTTCACTGCATTCTAGTTGTG

GTTTGTCCAAACTCATCAATGTATCTTATCATGTCTGTATACCGTCGACCTCTAGCTAGAGCTTGGCGTAATCA

TGGTCATAGCTGTTTCCTGTGTGAAATTGTTATCCGCTCACAATTCCACACAACATACGAGCCGGAAGCATAAA

GTGTAAAGCCTGGGGTGCCTAATGAGTGAGCTAACTCACATTAATTGCGTTGCGCTCACTGCCCGCTTTCCAGT

-continued

CGGGAAACCTGTCGTGCCAGCTGCATTAATGAATCGGCCAACGCGCGGGGAGAGGCGGTTTGCGTATTGGGCGC

TCTTCCGCTTCCTCGCTCACTGACTCGCTGCGCTCGGTCGTTCGGCTGCGGCGAGCGGTATCAGCTCACTCAAA

GGCGGTAATACGGTTATCCACAGAATCAGGGGATAACGCAGGAAAGAACATGTGAGCAAAAGGCCAGCAAAAGG

CCAGGAACCGTAAAAAGGCCGCGTTGCTGGCGTTTTTCCATAGGCTCCGCCCCCCTGACGAGCATCACAAAAAT

CGACGCTCAAGTCAGAGGTGGCGAAACCCGACAGGACTATAAAGATACCAGGCGTTTCCCCCTGGAAGCTCCCT

CGTGCGCTCTCCTGTTCCGACCCTGCCGCTTACCGGATACCTGTCCGCCTTTCTCCCTTCGGGAAGCGTGGCGC

TTTCTCAATGCTCACGCTGTAGGTATCTCAGTTCGGTGTAGGTCGTTCGCTCCAAGCTGGGCTGTGTGCACGAA

CCCCCCGTTCAGCCCGACCGCTGCGCCTTATCCGGTAACTATCGTCTTGAGTCCAACCCGGTAAGACACGACTT

ATCGCCACTGGCAGCAGCCACTGGTAACAGGATTAGCAGAGCGAGGTATGTAGGCGGTGCTACAGAGTTCTTGA

AGTGGTGGCCTAACTACGGCTACACTAGAAGGACAGTATTTGGTATCTGCGCTCTGCTGAAGCCAGTTACCTTC

GGAAAAAGAGTTGGTAGCTCTTGATCCGGCAAACAAACCACCGCTGGTAGCGGTGGTTTTTTTGTTTGCAAGCA

GCAGATTACGCGCAGAAAAAAAGGATCTCAAGAAGATCCTTTGATCTTTTCTACGGGGTCTGACGCTCAGTGGA

ACGAAAACTCACGTTAAGGGATTTTGGTCATGAGATTATCAAAAAGGATCTTCACCTAGATCCTTTTAAATTAA

AAATGAAGTTTTAAATCAATCTAAAGTATATATGAGTAAACTTGGTCTGACAGTTACCAATGCTTAATCAGTGA

GGCACCTATCTCAGCGATCTGTCTATTTCGTTCATCCATAGTTGCCTGACTCCCCGTCGTGTAGATAACTACGA

TACGGGAGGGCTTACCATCTGGCCCCAGTGCTGCAATGATACCGCGAGACCCACGCTCACCGGCTCCAGATTTA

TCAGCAATAAACCAGCCAGCCGGAAGGGCCGAGCGCAGAAGTGGTCCTGCAACTTTATCCGCCTCCATCCAGTC

TATTAATTGTTGCCGGGAAGCTAGAGTAAGTAGTTCGCCAGTTAATAGTTTGCGCAACGTTGTTGCCATTGCTA

CAGGCATCGTGGTGTCACGCTCGTCGTTTGGTATGGCTTCATTCAGCTCCGGTTCCCAACGATCAAGGCGAGTT

ACATGATCCCCCATGTTGTGCAAAAAAGCGGTTAGCTCCTTCGGTCCTCCGATCGTTGTCAGAAGTAAGTTGGC

CGCAGTGTTATCACTCATGGTTATGGCAGCACTGCATAATTCTCTTACTGTCATGCCATCCGTAAGATGCTTTT

CTGTGACTGGTGAGTACTCAACCAAGTCATTCTGAGAATAGTGTATGCGGCGACCGAGTTGCTCTTGCCCGGCG

TCAATACGGGATAATACCGCGCCACATAGCAGAACTTTAAAAGTGCTCATCATTGGAAAACGTTCTTCGGGGCG

AAAACTCTCAAGGATCTTACCGCTGTTGAGATCCAGTTCGATGTAACCCACTCGTGCACCCAACTGATCTTCAG

CATCTTTTACTTTCACCAGCGTTTCTGGGTGAGCAAAAACAGGAAGGCAAAATGCCGCAAAAAAGGGAATAAGG

GCGACACGGAAATGTTGAATACTCATACTCTTCCTTTTTCAATATTATTGAAGCATTTATCAGGGTTATTGTCT

CATGAGCGGATACATATTTGAATGTATTTAGAAAAATAAACAAATAGGGGTTCCGCGCACATTTCCCCGAAAAG

TGCCACCTGACGTC

These pcDNA3.1-hygro(+) based expression vectors disclosed in SEQ ID NOs 21 and 22 allow upon transfection into mammalian cells, like e.g. but not limited to CHO cells, that are typically used for recombinant antibody expression, the expression of the anti-human CD19 specific humanized antibody hBU12 with C-terminal N-intein domain fused, followed by a 6×His tag and a strepII tag at both the IgH and IgL chains.

Example 3: Cloning and Expression of Recombinant Sortase A Enzyme from *Staphylococcus Aureus*

The ORF of Sortase A from *Staphylococcus aureus* is published in Genbank and can be found under entry: AF162687.1. The aa-sequence in that record reads is shown as SEQ ID NO 23 (amino acid sequence of sortase A from *Staphylococcus aureus*):

MKKWTNRLMTIAGVVLILVAAYLFAKPHIDNYLHDKDKDEKIEQYDKNV

KEQASKDKKQQAKPQIPKDKSKVAGYIEIPDADIKEPVYPGPATPEQLN

RGVSFAEENESLDDQNISIAGHTFIDRPNYQFTNLKAAKKGSMVYFKVG

NETRKYKMTSIRDVKPTDVGVLDEQKGKDKQLTLITCDDYNEKTGVWEK

RKIFVATEVK

The corresponding nucleotide sequence in this Genbank entry is provided as SEQ ID NO 24:

ATGAAAAAATGGACAAATCGATTAATGACAATCGCTGGTGTGGTACTTA

TCCTAGTGGCAGCATATTTGTTTGCTAAACCACATATCGATAATTATCT

TCACGATAAAGATAAAGATGAAAAGATTGAACAATATGATAAAAATGTA

AAAGAACAGGCGAGTAAAGATAAAAAGCAGCAAGCTAAACCTCAAATTC

CGAAAGATAAATCGAAAGTGGCAGGCTATATTGAAATTCCAGATGCTGA

-continued

```
TATTAAAGAACCAGTATATCCAGGACCAGCAACACCTGAACAATTAAAT

AGAGGTGTAAGCTTTGCAGAAGAAAATGAATCACTAGATGATCAAAATA

TTTCAATTGCAGGACACACTTTCATTGACCGTCCGAACTATCAATTTAC

AAATCTTAAAGCAGCCAAAAAAGGTAGTATGGTGTACTTTAAAGTTGGT

AATGAAACACGTAAGTATAAAATGACAAGTATAAGAGATGTTAAGCCTA

CAGATGTAGGAGTTCTAGATGAACAAAAAGGTAAAGATAAACAATTAAC

ATTAATTACTTGTGATGATTACAATGAAAAGACAGGCGTTTGGGAAAAA

CGTAAAATCTTTGTAGCTACAGAAGTCAAATAA
```

Technical information with respect to the expression of an enzymatically active fragment of recombinant sortase A in *E. coli*, comprising amino acids 60-205 with 6×His tag are disclosed in reference WO2007/108013A2. The coding region for a 6×His tagged version of *Staphylococcus aureus* sortase A (aa60-205) is provided below as SEQ ID NO 25:

```
ATGCAAGCTAAACCTCAAATTCCGAAAGATAAATCGAAAGTGGCAGGCT

ATATTGAAATTCCAGATGCTGATATTAAAGAACCAGTATATCCAGGACC

AGCAACACCTGAACAATTAAATAGAGGTGTAAGCTTTGCAGAAGAAAAT

GAATCACTAGATGATCAAAATATTTCAATTGCAGGACACACTTTCATTG

ACCGTCCGAACTATCAATTTACAAATCTTAAAGCAGCCAAAAAAGGTAG

TATGGTGTACTTTAAAGTTGGTAATGAAACACGTAAGTATAAAATGACA

AGTATAAGAGATGTTAAGCCTACAGATGTAGGAGTTCTAGATGAACAAA

AAGGTAAAGATAAACAATTAACATTAATTACTTGTGATGATTACAATGA

AAAGACAGGCGTTTGGGAAAAACGTAAAATCTTTGTAGCTACAGAAGTC

AAACACCATCACCATCACCATTAA
```

```
This translates to amino acid sequence SEQ ID
NO 26:
MQAKPQIPKDKSKVAGYIEIPDADIKEPVYPGPATPEQLNRGVSFAEEN

ESLDDQNISIAGHTFIDRPNYQFTNLKAAKKGSMVYFKVGNETRKYKMT

SIRDVKPTDVGVLDEQKGKDKQLTLITCDDYNEKTGVWEKRKIFVATEV

KHHHHHH*
```

The coding region for the 6×His tagged sortase A fragment of *Staphylococcus aureus*, as provided in SEQ ID NO 25, can be cloned into a standard bacterial expression vector, like e.g. pET29 (Novagen), in order to transform *E. coli* strain BL21(DE3) (Novagen) and to generate an *E. coli* clone that can be used for the bacterial production of recombinant sortase A according to standard methods known in the art. In short, *E. coli* BL21(DE3) transformed with pET29 expression plasmids for sortase A can be cultured at 37° C. in LB medium with 50 µg/mL kanamycin until until an $OD_{600}$=0.5-0.8 is reached. IPTG can then be added to a final concentration of 0.4 mM and protein expression can be induced for three hours at 30° C. The cells can then be harvested by centrifugation and resuspended in lysis buffer (50 mM Tris pH 8.0, 300 mM NaCl supplemented with 1 mM MgCl2, 2 units/mL DNAseI (NEB), 260 nM aprotinin, 1.2 µM leupeptin, and 1 mM PMSF). Cells can then be lysed by sonication and clarified supernatant can then be purified on Ni-NTA agarose following the manufacturer's instructions.

Fractions that are of >90% purity, as judged by SDS-PAGE, can then be consolidated and dialyzed against Tris-buffered saline (25 mM Tris pH 7.5, 150 mM NaCl), and the enzyme concentration can be calculated from the measured $A_{280}$ using the published extinction coefficient of 17,420 $M^{-1}$ $cm^{-1}$. The above-mentioned protocol has been followed and ca. 20 mg of >90% pure recombinant enzymatically active fragment (of ca. 17 kD) sortase A of *Staphylococcus aureus* has been produced and the analysis of the recombinant protein by SDS-PAGE and Western blotting is disclosed in FIGS. 7A-7B.

Example 4: Expression and Purification of Sortase Tagged or N-Intein Tagged Recombinant Antibodies in Cho Cells a.) CHO cell expression: Expression of recombinant IgG1 antibodies from the expression constructs disclosed under Examples 2 and 3 can be achieved by transient transfection using e.g. commercially available CHO expression systems, like the FreeStyle CHO system from Invitrogen following the instructions of the FreeStyle CHO manual.

In brief, about 1 day prior to transfection, CHO cells shall be seeded at 5-6×$10^6$ cells/ml in FreeStyle CHO medium in shaker-flasks in order to expand them at 120 rpm on an orbital shaker at 37° C. in a humidified incubator at 7.5% $CO_2$ atmosphere. The following day the cells can be transfected, when they reach a density of 1.2-1.5×$10^6$/ml. Cells then need to be diluted to 1×$10^6$ cells/ml. 30 ml of such a cell suspension then needs to be added to a 125 ml shake flask and 40 µg of 1:1 mixed IgH and IgL expression plasmid DNA is added to 600 µl OptiPro SF-medium (Invitrogen). At the same time, 40 µl of FreeStyle MAX transfection reagent needs to be added to 600 µl OptiPro SF-medium, and both samples need to be gently mixed, and incubated for 10 min at room temperature to allow DNA-transfection reagent complexes to form. Then the DNA-transfection reagent mix can be added slowly to the 125 ml CHO cell culture from above and the transfected cells are then grown for up to 6 days at 120 rpm on an orbital shaker at 37° C. in a humidified incubator at 7.5% $CO_2$ atmosphere. Thereafter, cell culture supernatant can be collected and analyzed for antibody expression titer by appropriate methods known in the art (ELISA, Luminex, etc.).

b.) Protein A purification: Protein A purification of recombinant antibodies from the CHO cell supernatant can be performed with commercially available protein A sepharose columns (Thermo Fisher, Pierce) according to instructions from the manufacturer.

In brief, cleared cell culture supernatant is run over a protein A column of appropriate size and capacity equilibrated with PBS. Residual medium is washed with PBS and eventually bound IgG can be eluted with low pH buffer, like 0.1 M citric acid-NaOH, pH 3.0. Eluted IgG should be neutralized immediately with 1/10th volume of 1M Tris/Cl, pH7.4. Combined fractions containing IgG can then be dialized against PBS over night at 4° C.

The protocols provided in Example 4 provide the skilled person in the art with the instruction to produce sufficient quantities of purified, recombinant antibodies from the constructs disclosed in Examples 1 and 2.

Example 5: Generation of Site-Specifically C-Terminally MMAE Toxic Payload Conjugated Monoclonal Antibodies by Sortase and Split-Intein Mediated Transpeptidation Monomethyl Auristatin A toxin coupled to a 5 amino acid glycine stretch and a 6 amino acid SSp GyrB S11 C-int split intein peptide according to the formulas provided below, can be custom ordered from qualified chemistry CROs.

Formula 1

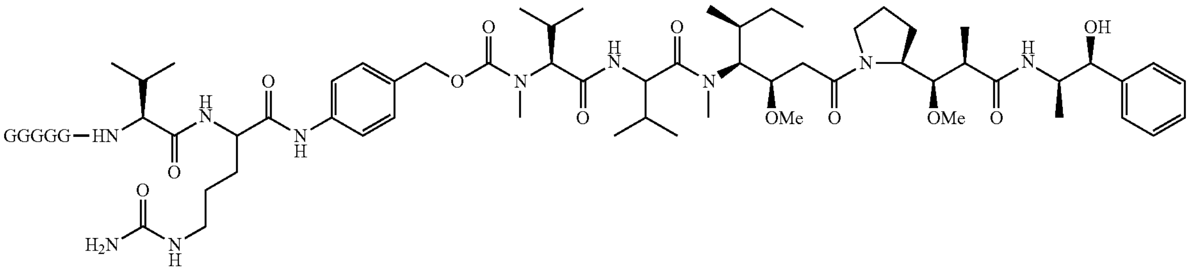

5-glycine modified MMAE with vcPAB linker
Me = methyl ( —— $CH_3$) group
G = glycine amino acid and residue Formula 2

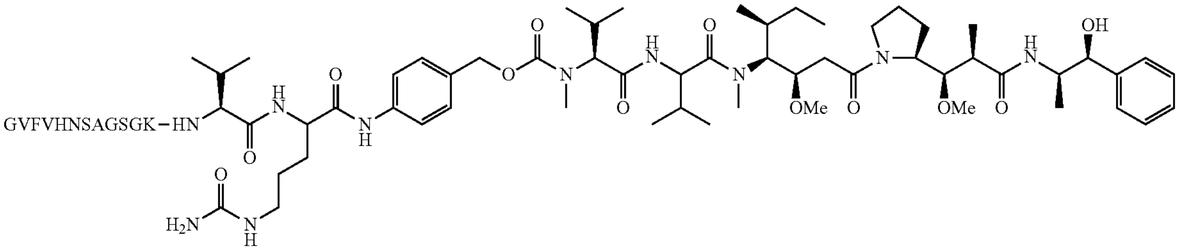

MMAE with vcPAB linker, modified with 6 amino acid C-intein domain GVFVHN and 6 amino acid SAGSGK C-extein peptide
Me = methyl ( —— $CH_3$) group
GVFHNSAGSGK = Gly-Val-Phe-Val-His-Asn-Ser-Ala-Gly-Ser-Gly-Lys stretch a.) Toxic MMAE payload conjugation of LPETG sortaseA motif tagged recombinant IgG antibodies Conjugation of 5 glycine amino acid modified MMAE toxic payload to LPETG sortase A tagged IgG1 antibody (that can be produced by following Examples 1 and 4) can be achieved by mixing appropriate ratios of LPETG tagged IgG1 antibody with the glycine-modified MMAE toxin disclosed in Formula 1 (e.g. at 1:1 ratio and 50 μM concentration) and with recombinant sortase A (production described in Example 3) (e.g. at 5 μM concentration), and using physiologic incubation buffer, like e.g.; 5 mM Tris/Cl, 15 mM NaCl, 6 mM $CaCl_2$), pH 8.0, and incubating at 37° C. to 40° C. for a minimum of 2 hours.

Efficiency of the conjugation can be monitored by analyzing the absence of the 6xHis tag and/or the strepII tag after stopping the reaction, e.g. by western-blot analysis or ELISA with anti-His-tag and/or anti strepII tag antibodies.

Completely conjugated product can be enriched by Nickel-NTA columns, or streptactin column binding, which bind to the 6xHis tag or strepII tag, respectively, which can only be present in incompletely reacted IgG1 substrate. Final IgG-payload conjugate can eventually be purified using protein A purification as described above.

b.) Toxic MMAE payload conjugation of SSp GyrB S11 N-intein tagged recombinant IgG antibodies Conjugation of Ssp GyrB S11 C-intein amino acid modified MMAE toxic payload to N-intein tagged IgG1 antibody (that can be produced by following Examples 2 and 4) can be achieved by mixing appropriate ratios of N-intein tagged IgG1 antibody with the C-intein amino acid-modified MMAE toxin disclosed in Formula 2 (e.g. at 1:10 or 1:25 ratio at 5 μM concentration of the IgG antibody) using physiologic incubation buffer, like e.g.; 20 mM Tris/Cl, 250 mM NaCl, 1 mM EDTA, pH 8.5, and incubating at room temperature or at 37° C. a minimum of 4 hours.

Efficiency of the conjugation can be monitored by analyzing the absence of the 6xHis tag and/or the strepII tag after stopping the reaction, e.g. by western-blot analysis or ELISA with anti-His-tag and/or anti strepII tag antibodies.

Completely conjugated product can be enriched by Nickel-NTA columns, or streptactin column binding, which bind to the 6xHis tag or strepII tag, respectively, which can only be present in incompletely reacted IgG1 substrate. Final IgG-payload conjugate can eventually be purified using protein A purification as described above.

In summary, the Examples 1-5 disclosed above allow a person skilled in the art to practice the invention of enzymatically conjugating a toxic payload site-specifically to the C-terminus either using sortase A mediated or split-intein mediated transpeptidation.

Example 6: Production of Trastuzumab with C-Terminal GS (Glycine-Serine) Linker, LPETG Sortase Motif and Additional 6x-his and Strep II Affinity Purification Tags on Either Heavy or Light Chain Antibody expression constructs encoding monoclonal antibody Trastuzumab (Tras) heavy and light chains, either untagged (SEQ ID NOs: 31-34) or C-terminally tagged with GS (glycine-serine) linker, LPETG Sortase tag, 6xHis tag, and Strep II tag (SEQ ID NOs: 35-38) were generated essentially as described in Example 1. Using these expression constructs, Tras-HC-GS-LHS and Tras-LC-GS-LHS (HC=heavy chain, LC=light chain, GS=glycine-serine, LHS=LPETG-tag+6xHis-tag+strepII-tag) were produced in CHO cells by co-transfection of the corresponding expression constructs. Tras-HC-GS-LHS is a Trastuzumab variant with an unmodified light chain (SEQ ID NOs: 35-36), and a heavy chain C-terminally tagged with GS (glycine-serine) linker, LPETG Sortase motif, 6×His-tag, and strepII-tag (SEQ ID NOs: 33-34). Tras-LC-GS-LHS is a Trastuzumab variant with an unmodified heavy chain (SEQ ID NOs: 31-32), and a light chain C-terminally tagged with GS linker, LPETG Sortase motif, 6×His-tag, and strepII-tag (SEQ ID NOs: 37-38). CHO cell transfection and affinity purification of antibodies by proteinA-sepharose chromatography was done essentially as described in Example 4.

Example 7: Sortase A-Mediated Conjugation of Heavy or Light Chain of Trastuzumab with Gly5-Modified DM1 Toxin Conjugation reactions containing Gly5-modified DM1 toxin (ordered from Concortis, San Diego, CA, U.S., structure see FIG. 14A) and a 17 kD recombinant sortase A fragment from *Staphylococcus aureus* (see Example 3) were carried out with 10.5 mg of each monoclonal antibody (mAb) (see Example 6) in 1× Sortase buffer (25 mM Tris-HCl, pH8.2; 150 mM NaCl; 7.5 mM $CaCl_2$)), as shown in Table II, below. The Tras-HC-GS-LHS conjugation reaction was incubated at 25° C. for 2 h; the Tras-LC-GS-LHS conjugation reaction was incubated at 25° C. for 18 h. Each reaction mixture was then passed over a Strep-Tactin® Sepharose columns (IBA Life-Sciences, Göttingen, Germany). For this, 1 ml of Strep-Tactin® Agarose was packed under gravity into a fritted column and equilibrated with 2 column volumes of equilibration buffer (100 mM Tris-HCl, pH 8.0; 150 mM NaCl; 1 mM EDTA). Each conjugation mixture was passed twice down the same column using gravity flow (to increase residence time on the resin). The resin was washed with an additional column volume of equilibration buffer to maximize conjugate yield and the pool then applied immediately to a protein A column. For this, a 1 ml Protein A HiTrap column was equilibrated with 10 column volumes of buffer (25 mM sodium phosphate pH 7.5). Each conjugation reaction was then applied to an equilibrated column and the column washed with a further 5 column volumes of buffer. Bound conjugate was eluted with 5 column volumes of elution buffer (0.1M succinic acid, pH 2.8) with 1 column volume fractions collected (into tubes containing 25% v/v 1M Tris Base to neutralise the acid) and analysed for protein content. Protein containing fractions were pooled and formulated by G25 column chromatography. For this, NAP 25 columns of an appropriate size for each scale of manufacture were used to formulate the conjugates for long term storage. The columns were equilibrated, loaded and eluted with 10 mM Sodium Succinate pH 5.0, 100 mg/mL Trehalose, 0.1% % w/v Polysorbate 20 (Formulation Buffer for Kadcyla® (T-DM1), marketed by Roche/Genentech) according to the manufacturer's instructions.

The Tras-HC-GS-LHS and Tras-LC-GS-LHS DM1-conjugate yields were, respectively, 8.0 mg (76.2%) and 5.9 mg (56.2%). The major process losses occurred during Protein A and G25 purification, most probably as a result of peak cutting to ensure maximal concentration of the product for each subsequent step or storage.

TABLE 2

Conjugation conditions for Tras-HC-GS-LHS and Tras-LC-GS-LHS:

| Reaction component | HC | LC | Final concentration |
|---|---|---|---|
| Tras-HC-GS-LHS (5.3 mg/ml) | 1981 μl | — | 5 μM |
| Tras-LC-GS-LHS (5.5 mg/ml) | — | 1911 μl | 5 μM |
| $H_2O$ | 7775.25 μl | 7714 μl | |
| $Gly_5$-DM1 (1 mM) | 1400 μl | 1400 μl | 100 μM |
| Sortase A (0.85 mg/ml = ca. 50 μM) | 43.75 μl | 175 μl | 0.156/0.625 μM |
| 5× Sortase buffer* | 2800 μl | 2800 μl | 1× |

The drug loading was assessed by Hydrophobic Interaction Chromatography (HIC), and was performed on a TOSOH Butyl-NPR 4.6 mm×3.5 cm, 2.5 μm column run at 0.8 mL/min with a 12 minute linear gradient between A—1.5M $(NH_4)_2SO_4$, 25 mM NaPi, pH=6.95±0.05 and B—75% 25 mM NaPi, pH=6.95±0.05, 25% IPA. The HIC profiles revealed that for both, Tras-HC-GS-LHS and Tras-LC-GS-LHS, there was no detectable unconjugated mAb left, and a major fraction of each mAb was loaded with 2 drugs (see FIG. 8).

Example 8: In Vitro Toxicity Assay with Sortase A—Mediated Trastuzumab-DM1 Conjugates Cytotoxicity of DM1-sortaseA-conjugated Tras-HC-GS-LHS and DM1-sortaseA-conjugated Tras-LC-GS-LHS was investigated and compared to Kadcyla© (Roche/Genentech) using SKBR3 cells, a human breast cancer cell line over-expressing the cognate antigen of trastuzumab (Tras) HER-2/neu, and T47D-5R cells, a breast cancer cell line naturally expressing low levels of HER-2/neu, engineered to be devoid of cell surface HER-2/neu (Graus-Porta et al. (1995)). Cells were plated on 96 well plates in 100 μl complete DMEM (10'000 cells per well). After one day incubation, 50 μl medium was carefully removed from each well and replaced by 50 μl of 3.5-fold serial dilutions of each ADC in complete DMEM, resulting in ADC concentrations ranging from 20 μg/ml to 0.25 ng/ml. Each dilution was done in duplicates or triplicates. After 3 additional days incubation at 37° C. in a humidified incubator at 5% $CO_2$ atmosphere, plates were removed from the incubator and equilibrated to room temperature. After approximately 30 minutes, 100 μl CellTiter-Glo® Luminescent Solution (Promega, Cat. No G7570) was added to each well and, after shaking the plates at 450 rpm for 5 min followed by a 10 min incubation without shaking, luminescence was measured on a Tecan Infinity F200 with an integration time of 1 second per well. All three ADCs were highly cytotoxic for the HER-2/neu overexpressing SKBR3 breast cancer cell line, but not for the HER-2/neu-negative T47D-5R breast cancer cell line (see FIGS. 9A-9B). The $EC_{50}$ values for Her-2/neu positive breast cancer cell line SKBR3 were: Kadcyla®, 32.4 ng/ml; DM1-conjugated Tras-HC-GS-LHS, 45.6 ng/ml; Tras-LC-GS-LHS, 51.4 ng/ml, and thus are within similar range of potency in the in vitro tumor cell killing experiment. Conversely, no specific cellular toxicity was detectable with the Her-2/neu negative breast cancer cell line T47D-5R, demonstrating the functional equivalence of sortaseA, enzymatically conjugated ADC versus traditional, chemically conjugated ADC, when the comparison entails the same targeting antibody and the same toxin (DM1) (FIGS. 9A-9B).

Figure 8A:
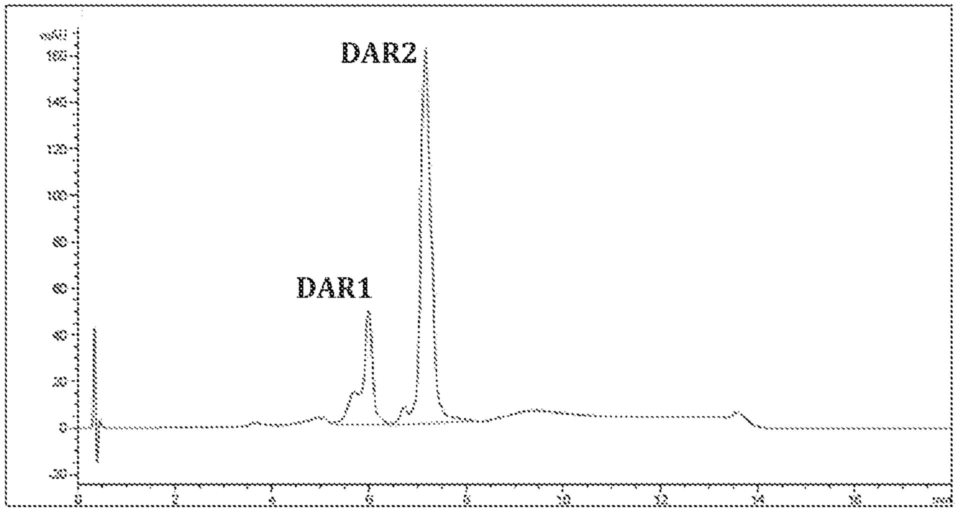
Figure 8B:
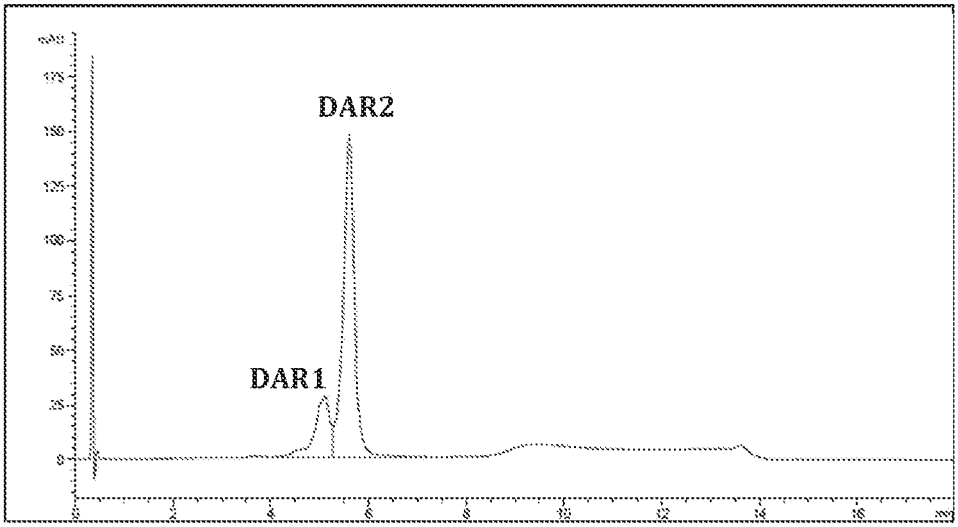
Figure 9A:
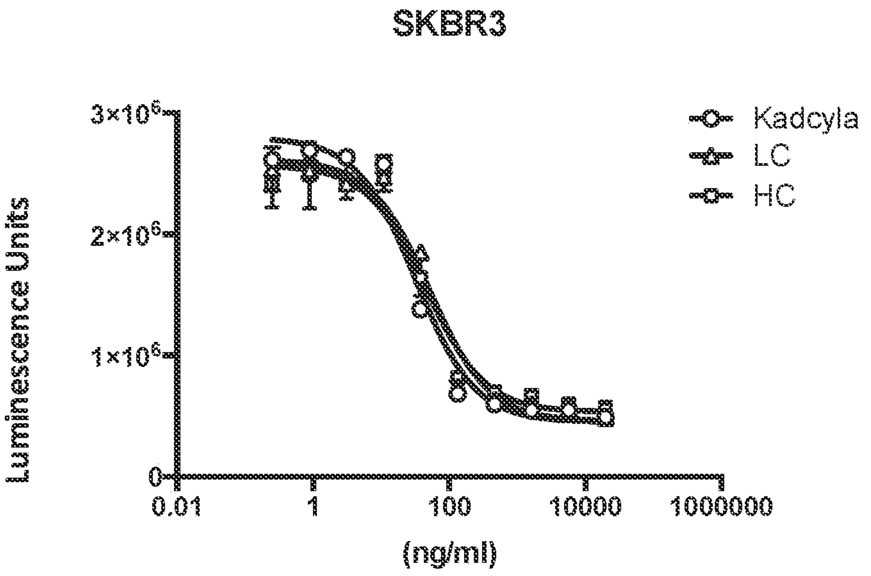
Figure 9B:
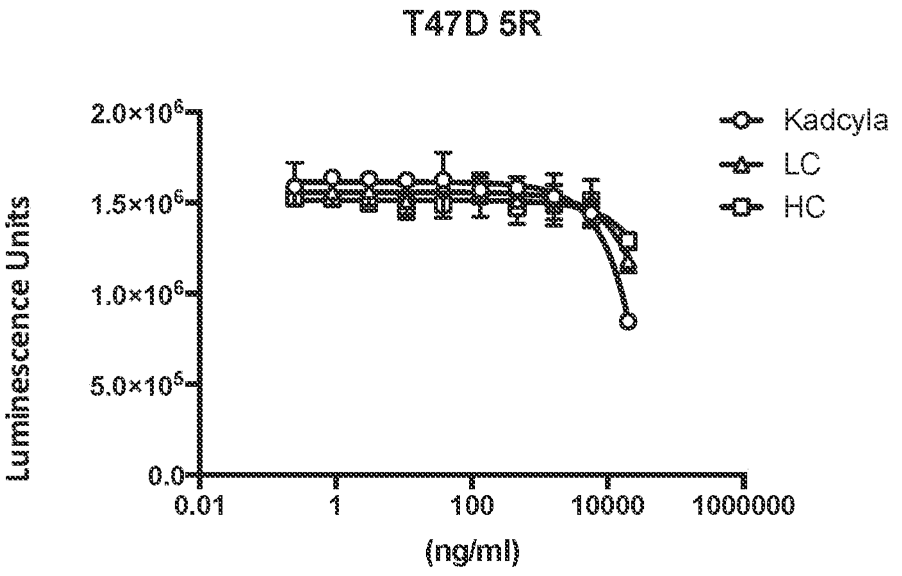

However, it appears that the lower drug-to antibody ratio of ca. 1.80 (deducted from intergration of the DAR1 and DAR2 peaks in FIGS. 8A-8B) for the Tras-HC-GS-LHS and Tras-LC-GS-LHS sortase A-conjugated ADCs, as compared to the DAR of ca. 3-4, reported for Kadcyla® does not translate into a proportionally different cellular cytotoxicity in the in vitro tumor cell killing assays (FIGS. 9A-9B). This unexpected finding may be the result of a more defined and site-specific toxin-antibody conjugation mediated by sortase A in comparison to the less defined, stochastically, chemically conjugated Kadcyla®.

Example 9: Optimization of Synchronization of SortaseA Mediated Antibody Heavy Chain and Light Chain Payload Conjugation by Variation of Peptide-Spacer Length Inserted Between C-Terminal End of Antibody Heavy Chain and Light Chain and the SortaseA Recognition Motif The influence of peptide-spacer length positioned between the C-terminus of antibody heavy or light chain and LPETG sortase A recognition motif was investigated. For this, antibody heavy chain and light chain expression constructs encoding chimeric CD30-specific mAb Ac10 heavy and light chains (HC sequence derived from US 2008213289A1, Seq1, LC sequence derived from US 2008213289A1, Seq9), C-terminally modified with sequences comprising or not comprising a 2 amino acid GS (glycine-serine) spacer, and comprising a LPETG sortaseA recognition motif, and a strep-II purification tag (SEQ ID NOs: 39-46), have been cloned essentially according to instructions disclosed in Example 1. Using these expression constructs, mAbs Ac10-HC-GS-LHS/LC-GS-LHS and Ac10-HC-LS/LC-LS were produced in CHO cells by co-transfection of the corresponding plasmids. Ac10-HC-GS-LHS/LC-GS-LHS is an Ac10 variant with heavy and light chains modified at the C-termini of each HC and LC with a GS peptide spacer, a LPETG sortaseA motif, a 6×His tag, and a strep-II tag (SEQ ID NOs:39-42; Table 3). Ac10-HC-LS/LC-LS is an Ac10 variant with heavy and light chains modified at the C-termini with LPETG Sortase motif and strep-II tag without the 2-peptide GS linker (SEQ ID NOs: 43-46; Table 3). CHO cell transfection and affinity purification of antibodies by protein A-sepharose chromatography was done essentially as described in Example 4.

To investigate efficiency of conjugation, serial dilutions of Sortase A were used to conjugate penta-glycine-modified FITC ($Gly_5$-FITC, see Formula 3 below).

Formula 3

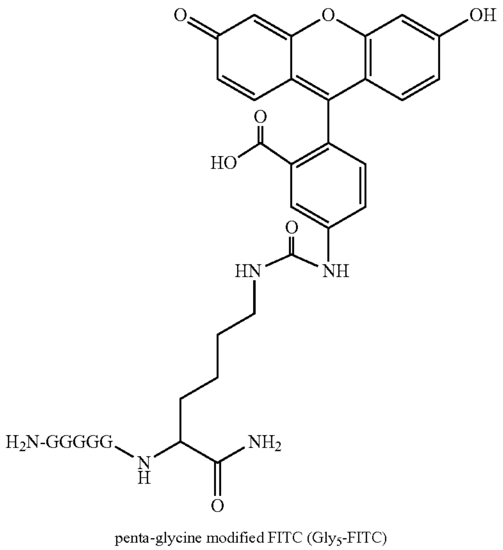

penta-glycine modified FITC ($Gly_5$-FITC)
G = glycine residue

Figure 10A:
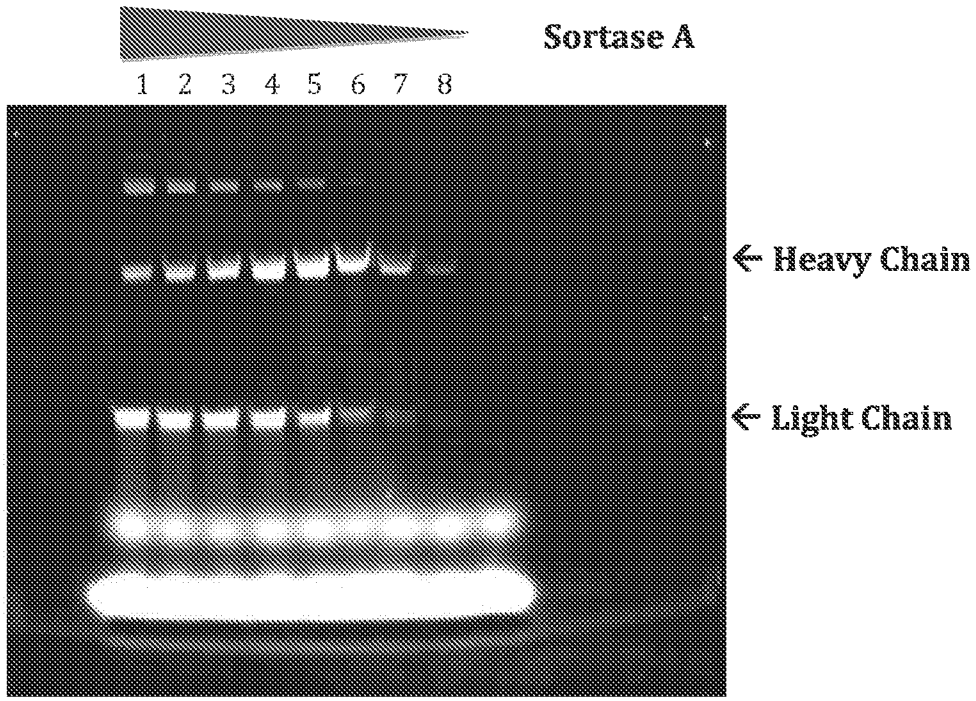
Figure 10B:
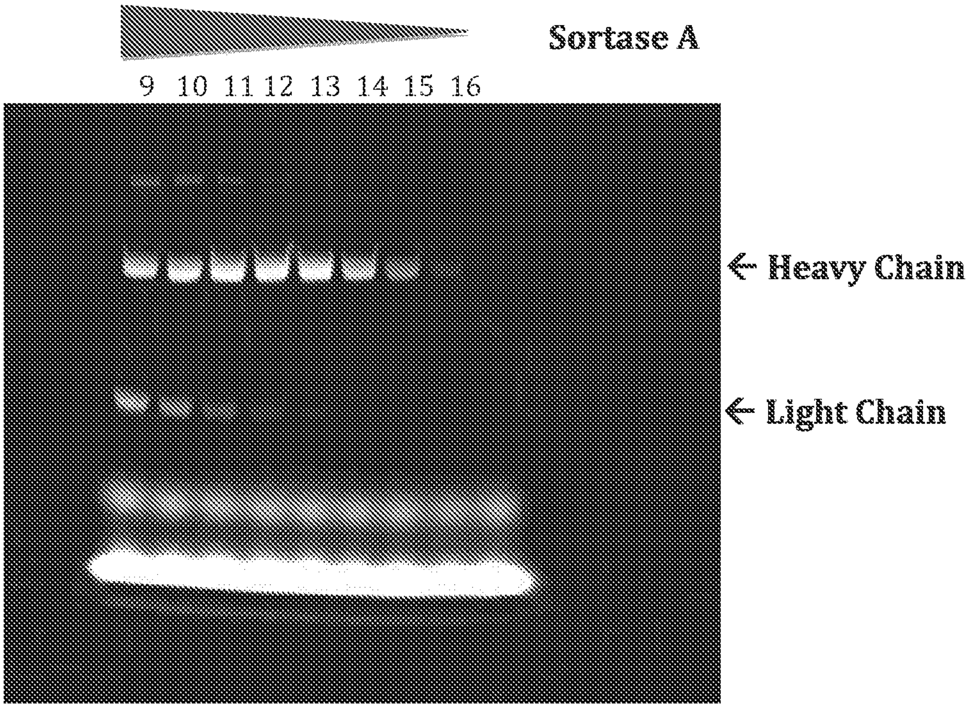

For this, Gly5-FITC was sortaseA conjugated to two Ac10 variants in 1× Sortase buffer (25 mM Tris-HCl, pH8.2; 150 mM NaCl; 7.5 mM $CaCl_2$)), as shown in Table 4. After 4 h at 42° C., reaction products were analyzed by denaturing, reducing SDS-PAGE gel electrophoresis, and FITC was visualized by placing the gels on a UV box (FIGS. 10A-10B). Conjugation to the heavy chain was found to be highly efficient irrespective of the presence absence of the GS-linker between heavy chain C-terminus and LPETG Sortase recognition motif Unexpectedly, sortaseA mediated conjugation to the light chain was significantly less efficient in comparison to sortaseA mediated heavy chain conjugation. Furthermore, it was surprisingly found that coupling efficiency was dramatically affected by the presence or absence of the 2 peptide GS (glycine-serine) spacer positioned between the C-terminus of the antibody light chains and the LPETG sortaseA recognition motif Whereas in the presence of the GS-linker, conjugation to the light chain took place with about 5-10× lower efficiency than to the heavy chain, it was about 50-100× less efficient in the absence of a linker. Therefore, it was concluded that increasing the peptide spacer length between the light chain and the LPETG Sortase recognition motif might further improve conjugation efficiency.

Therefore, the influence of increasing the length of the peptide spacer between light chain and LPETG Sortase A recognition motif on conjugation efficacy was investigated next. Expression constructs encoding mAb Ac10 light chains, C-terminally tagged with LPETG Sortase recognition motif and strep-II purification tag, with a 2 to 5 amino acid linker (SEQ ID NOs: 47-54), were generated essentially as described in Example 1. Using these expression constructs, mAbs Ac10-HC-LS/LC-GS-LS, Ac10-HC-LS/LC-GGS-LS, Ac0-HC-LS/LC-GGGS-LS and Ac10-HC-LS/LC-GGGGS-LS were produced in CHO cells by co-transfection of the corresponding expression constructs. In each of these antibodies, the heavy chain is C-terminally modified with an LPETG Sortase recognition motif and a strep-II purification tag (SEQ ID NOs: 43-44; Table 3). The light chain is C-terminally modified with an LPETG Sortase tag and strep-II tag containing either a GS, GGS, GGGS, or a GGGGS peptide spacer (SEQ ID NOs: 47-54; Table 3) in front of the LPETG motif. CHO cell transfection and affinity purification of antibodies by protein A-sepharose chromatography was done essentially as described in Example 4.

To investigate conjugation efficiency, serial dilutions of Sortase A were used to conjugate penta-glycine-modified FITC (Gly5-FITC, see Formula 3, above) to the four different Ac10 mAb variants in 1× Sortase buffer (25 mM Tris-HCl, pH8.2; 150 mM NaCl; 7.5 mM $CaCl_2$)), as shown in Table 5. After 4 h at 42° C., reaction products were analyzed by denaturing, reducing SDS-PAGE gel electrophoresis, and FITC was visualized by placing the gels on a UV box (FIG. 11). As expected, conjugation to the heavy chain was equally efficient in all four antibody variants. In contrast, conjugation to the light chain was improved significantly by increasing peptide-spacer length. Significantly, with the longest peptide-spacer analyzed (GGGGS), light chain conjugation efficiency was equally efficient in comparison to conjugation of the heavy chain, thereby allowing synchronous conjugation of heavy and light chains of an antibody C-terminally modified at both heavy and light chain. It is concluded that this antibody format will facilitate Sortase A-mediated production of homogeneous ADCs loaded with 4 drugs per antibody (DAR4).

TABLE 3

C-terminally modified monoclonal antibody Ac10 variants produced

| Antibody | Heavy Chain modification | SEQ ID NOs | Light Chain modification | SEQ ID NOs |
|---|---|---|---|---|
| Ac10-HC-GS-LHS/LC-GS-LHS | GS-LPETG-G-HHHHHH-G-WSHPQFEK | 39, 40 | GS-LPETG-G-HHHHHH-G-WSHPQFEK | 41, 42 |
| Ac10-HC-LS/LC-LS | LPETG-G-WSHPQFEK | 43, 44 | LPETG-G-WSHPQFEK | 45, 46 |
| Ac10-HC-LS/LC-GS-LS | LPETG-G-WSHPQFEK | 43, 44 | GS-LPETG-G-WSHPQFEK | 47, 48 |
| Ac10-HC-LS/LC-GGS-LS | LPETG-G-WSHPQFEK | 43, 44 | GGS-LPETG-G-WSHPQFEK | 49, 50 |
| Ac10-HC-LS/LC-GGGS-LS | LPETG-G-WSHPQFEK | 43, 44 | GGGS-LPETG-G-WSHPQFEK | 51, 52 |
| Ac10-HC-LS/LC-GGGGS-LS | LPETG-G-WSHPQFEK | 43, 44 | GGGGS-LPETG-G-WSHPQFEK | 53, 54 |

TABLE 4

Conjugation conditions for mAbs Ac10-HC-GS-LHS/LC-GS-LHS and Ac10-HC-LS/LC-LS

| Reaction component | 1-8 | 9-16 | Final concentration |
|---|---|---|---|
| Ac10-HC-GS-LHS/LC-GS-LHS (3.75 mg/ml = 25 μM) | 10 | — | 5 μM |
| Ac10-HC-LS/LC-LS (3.75 mg/ml = 25 μM) | — | 10 | 5 μM |
| $H_2O$ | 20 | 20 | — |
| $Gly_5$-FITC (1 mM) | 5 | 5 | 100 μM |
| Sortase A (2× serial dil. of ca. 50 μM) | 5 | 5 | 5 → 0.039 μM |
| 5× Sortase buffer | 10 | 10 | 1× |

TABLE 5

Conjugation conditions for mAbs Ac10-HC-LS/LC-GS-LS, Ac10-HC-LS/LC-GGS-LS, Ac10-HC-LS/LC-GGGS-LS and Ac10-HC-LS/LC-GGGGS-LS.

| Reaction component | 1-7 | 8-14 | 15-21 | 22-28 | Final conc. |
|---|---|---|---|---|---|
| Ac10-HC-LS/LC-GS-LS (3.75 mg/ml = 25 μM) | 10 | — | — | — | 5 μM |
| Ac10-HC-LS/LC-GGS-LS (3.75 mg/ml = 25 μM) | — | 10 | — | — | 5 μM |

TABLE 5-continued

Conjugation conditions for mAbs Ac10-HC-LS/LC-GS-LS, Ac10-HC-LS/LC-GGS-LS, Ac10-HC-LS/LC-GGGS-LS and Ac10-HC-LS/LC-GGGGS-LS.

| Reaction component | 1-7 | 8-14 | 15-21 | 22-28 | Final conc. |
|---|---|---|---|---|---|
| Ac10-HC-LS/LC-GGGS-LS (3.75 mg/ml = 25 μM) | — | — | 10 | — | 5 μM |
| Ac10-HC-LS/LC-GGGGS-LS (3.75 mg/ml = 25 μM) | — | — | | 10 | 5 μM |
| $H_20$ | 20 | 20 | 20 | 20 | — |
| $Gly_5$-FITC (ImM) | 5 | 5 | 5 | 5 | 100 μM |
| Sortase A (2× serial dil. of ca. 25 μM) | 5 | 5 | 5 | 5 | 2.5 → 0.039 μM |
| 5× Sortase buffer | 10 | 10 | 10 | 10 | 1× |

Example 10: Generation of Homogeneous ADC by StrepII-Tag Affinity Purification Sortase A mediated conjugation with Gly5-labeled vc-PAB-MMA (see Formula 1, Example 5) was performed with anti-CD3W antibody ASH modified at the C-termini of either the heavy chains, or the light chains with sequences comprising an LPETG sortase A motif and a strepII-affinity purification tag as provided in Table 6 below:

TABLE 6

C-terminally modified antibody Ac10 with either HC or LC modification

| Antibody | Heavy Chain modification | SEQ ID NOs | Light Chain modification | SEQ ID NOs |
|---|---|---|---|---|
| Ac10-HC-LS Ac-10-LC | LPETG-G-WSHPQFEK | 43, 44 | none | 29, 30 |
| Ac10-HC Ac10-LC-GS-LHS | none | 27, 28 | GS-LPETG-G-HHHHHH-G-WSHPQFEK | 41,42 |

The expression vectors encoding the Ac10 heavy or light chain sequences of Table 4 have been constructed essentially as disclosed in Example 1. CHO cell transfection and affinity purification of antibodies by protein A-sepharose chromatography was done essentially as described in Example 4.

Sortase A mediated conjugation of heavy or light chaing sortase motif tagged anti-CD30 antibodies with Gly5-labeled vc-PAB-MMAE (see Formula 1, Example 5) was performed essentially according to the protocol provided in Example 7.

As described further above in the detailed description of the invention, unreacted antibody will retain the C-terminal strep-II affinity purification tag, which can be exploited to enrich fully reacted ADC with DAR2. Analysis of the heavy chain sortase A conjugation with vc-PAB-MMAE toxin via hydrophobicity interaction chromatography (HIC) (FIG. 12A), shows that the majority of the sortase-motif modified heavy chains have been conjugated, but a certain percentage of unreacted substrate (DAR0=drug to antibody ratio=zero), or partially reacted substrate (DAR1=drug to antibody ratio=1) was still detectable by HIC (FIG. 12A).

Therefore, the protein A purified vc-PAB-MMAE conjugate was passed 4 times times over a StrepTactin® affinity column (IBA Sciences, Göttingen, Germany), essentially as described in Example 7, in order to remove unreacted or partially reacted sortase A-modified antibody. FIG. 12B shows that upon several passages of the heterogeneous vc-PAB-MMAE antibody drug conjugate, completely reacted DAR2 ADCs (DAR2=drug to antibody ratio=2) could be highly enriched. This experiment demonstrates the feasibility to utilize additional affinity purification tags added C-terminally to the sortase A LPETG recognition motif to generate homogeneous ADC with a defined drugs per antibody ratio (here DAR2).

Example 11: Synthesis of 5×Glycine-Modified Maytansine and Alpha-Amanitin Toxins In order to allow conjugation of two different payloads, preferably toxic payloads to a single antibody, modified with different sortase motifs at heavy and light chain C-termini, it is required to modify two different toxins with glycine residues, preferably toxins with different mode of actions, such that a cancer cell targeted with a dual payload conjugated ADC, is attacked with via two different, potentially synergistic routes. The synthesis of two different glycine-modified toxic payloads (here maytansine and alpha-amanitin) satisfying this requirement has been performed and is described herein.

11.1 Synthesis of Glycine-Modified Alpha-Amanitin:

30 mg alpha-amanitin (Structure 1) (Sigma-Aldrich, order #A2263) was dissolved in 1 ml anhydrous DMSO. To this solution 19 mg NH-Boc-amino-hexylbromide were added, followed by potassium tert-butoxide (1M solution in THF, 35 μl). The reaction mixture was stirred at room temperature for 6 h and more potassium tert-butoxide (1M solution in THF, 20 μl) was added. The reaction was kept at room temperature for 16 h. Acetic acid (10 μl) was added and the crude mixture was purified by RP-HPLC directly (Sunfire C18 5μ 3 cm×10 cm column, 50 mL/min, 5-50% acetonitrile/water 15 min gradient). The desired fraction was collected and lyophilized to give Structure 2 as a white powder (15 mg), which was treated with TFA/DCM solution (1/1, v/v, 1 ml) for 30 minutes at room temperature. The volatiles were removed under reduced pressure to give Structure 3 as a slightly yellowish gum, which was used in the next step without further purification.

Fmoc-Gly5-OH (8 mg) was dissolved in anhydrous DMF (0.5 ml). HATU (Sigma-Aldrich, order #445460) (6 mg) was added, followed by DIEA (10 ml) (Sigma-Aldrich, order #496219). The mixture was agitated gently at room temperature for 30 s and then transferred to a solution of compound 3 in DMF (0.5 ml). After 30 mins, LC/MS analysis showed that all of compound 3 was consumed. Piperidine (30 μl) was added and the progress of the reaction was monitored by LC/MS. Acetic acid was added to neutralize the reaction after 1 h and the mixture was purified by RP-HPLC (Sunfire C18 5μ 3 cm×25 cm column, 50 mL/min, 2-40% acetonitrile/water 30 min gradient). The fractions were pooled and lyophilized to give structure 5 as a white powder (12 mg). Analytical data for compound 5 is provided in FIG. 13A).

Scheme 1 Synthesis of glycine-modified alpha-amanitin

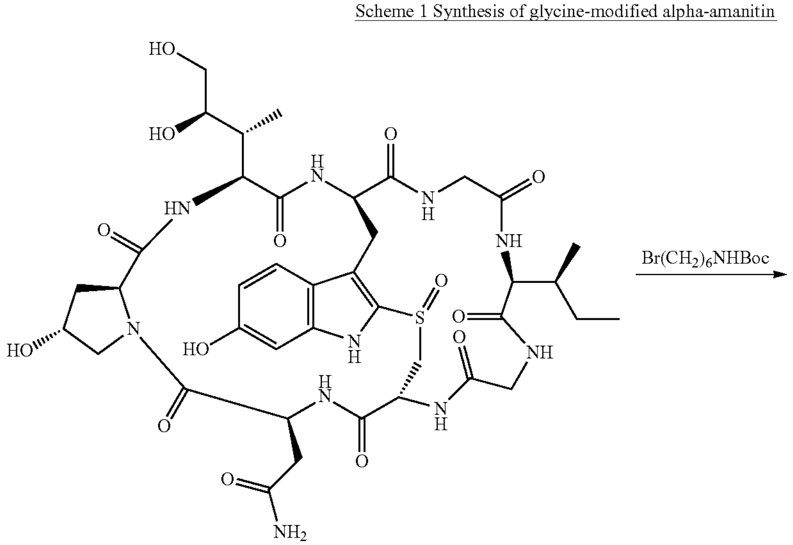

1

-continued

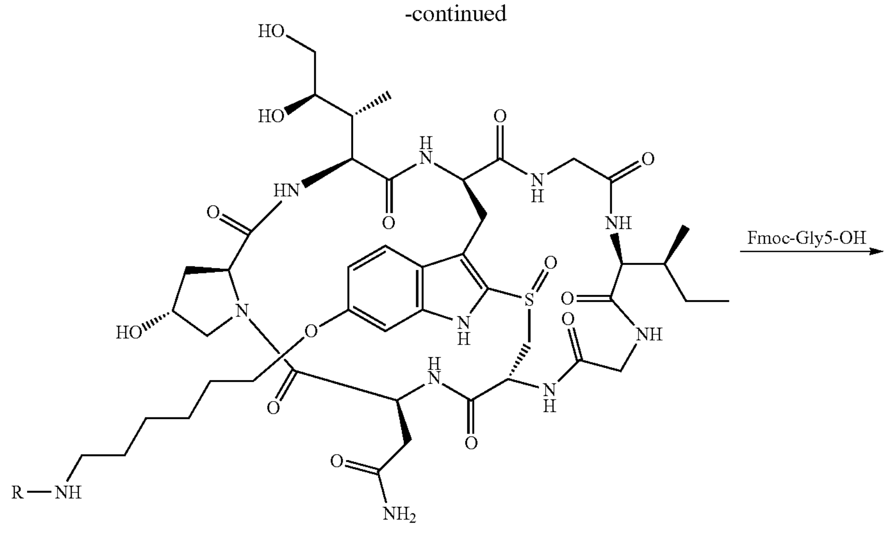

2 R = Boc
3 R =H

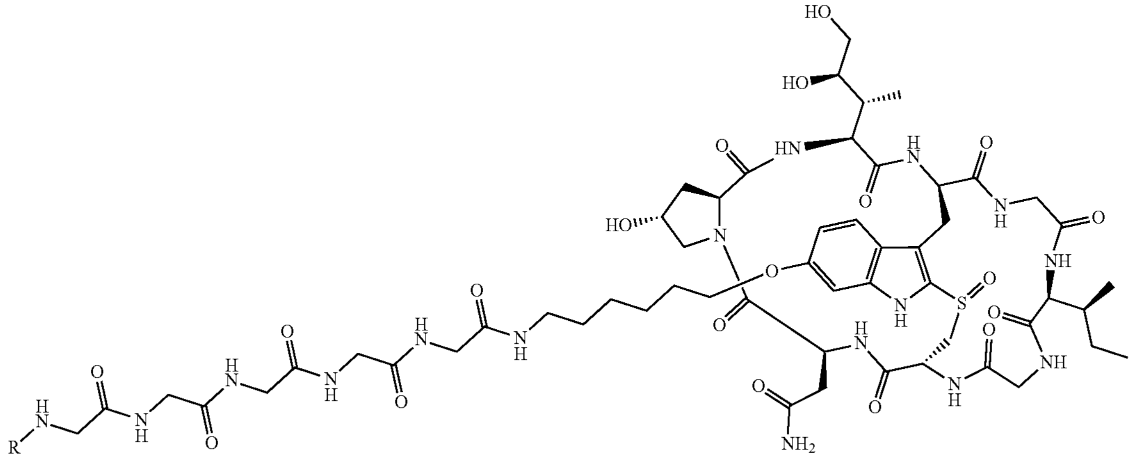

4 R = Fmoc
3 R = h 11.2. Synthesis of Glycine-Modified Maytansine:

Maytansinol (0.6 g, 1.1 mmol) (Clearsynth Labs, Mumbai, India) was dissolved in anhydrous THF (6 ml) and anhydrous DMF (3 ml) after which 1.2 ml DIEA (Sigma-Aldrich, order #496219) was added. The solution was placed under argon atmosphere. Zinc triflate (1.2 g) and NMeAla NCA (0.7 g) were added in one portion. The mixture was sonicated until the solid was dissolved. The reaction mixture was stirred at room temperature for 2 days and then diluted with ethyl acetate (100 ml). It was washed with saturated $NaHCO_3$ (aq. solution, 2×50 ml) and brine (50 ml). The organic layer was dried (over $MgSO_4$) and concentrated to give the crude maytansinol 3-(S)-alpha-N-methylaminopropionate (8) which was used directly in the next step without further purification.

Fmoc-Gly5-OH (26 mg) was dissolved in anhydrous DMF (1 ml). HATU (Sigma-Aldrich, order #445460) (19 mg) was added, followed by DIEA (18 μL). The mixture was agitated gently at room temperature for 30 s and then transferred to a solution of compound 8 in THF (1 ml). After 30 mins, LC/MS analysis showed that all compound 8 was consumed. Piperidine (40 μl) was added and the progress of the reaction was monitored by LC/MS. Ether (40 ml) was added to the reaction after 2 h and the precipitated solid was collected and washed with ether. The crude compound was purified by RP-HPLC (Sunfire C18 5μ 3 cm×10 cm column, 50 ml/min, 10-60% acetonitrile/water 20 min gradient). The fractions were pooled and lyophilized to give compound 10 as a white powder (33 mg). Analytical data for compound 10 is provided in FIG. 13B.

Scheme2 Synthesis of glycine-modified maytansine

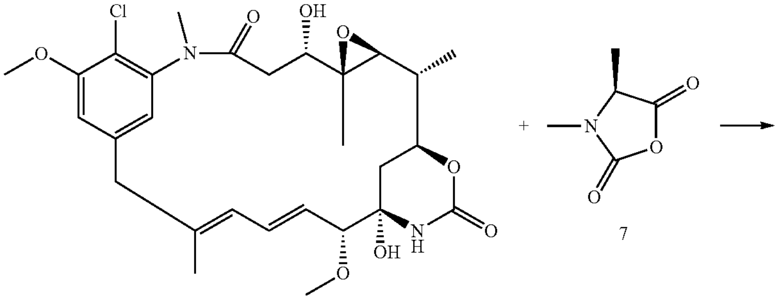

6

7

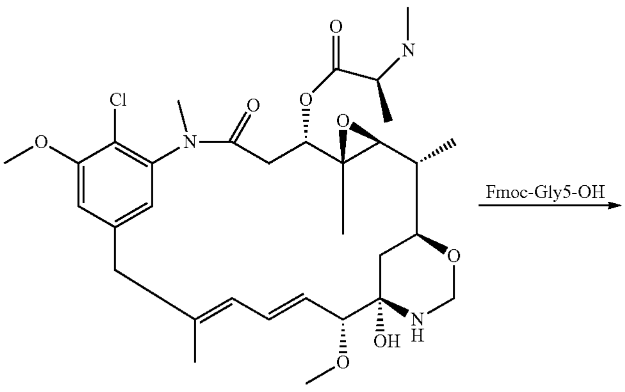

8

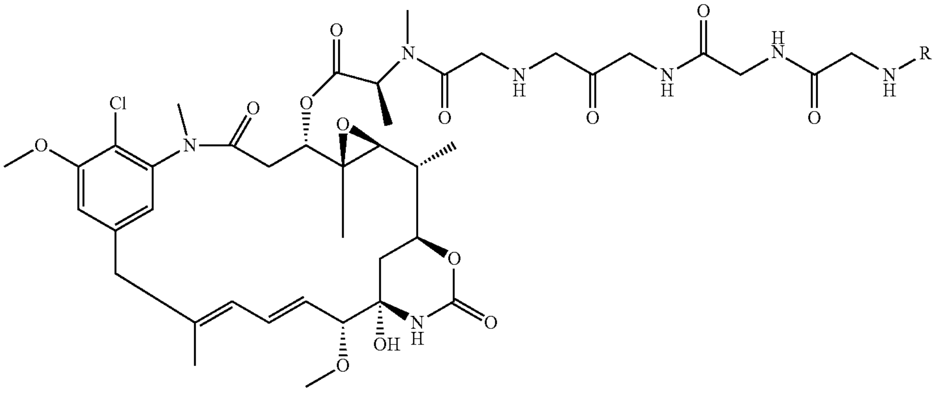

9 R = Fmoc
10 R = h

Figure 14A:
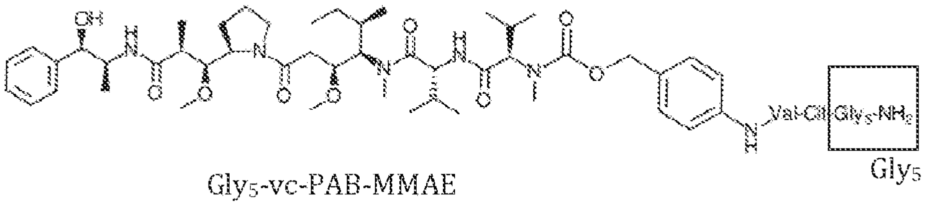
Figure 14A:
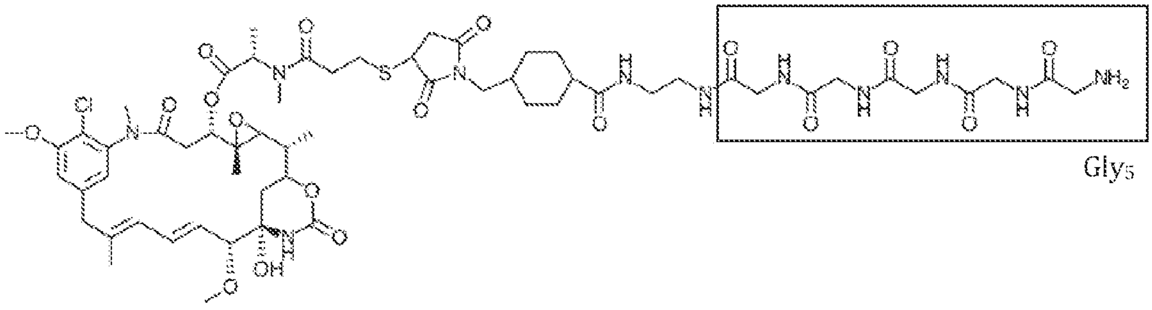
Figure 14A:
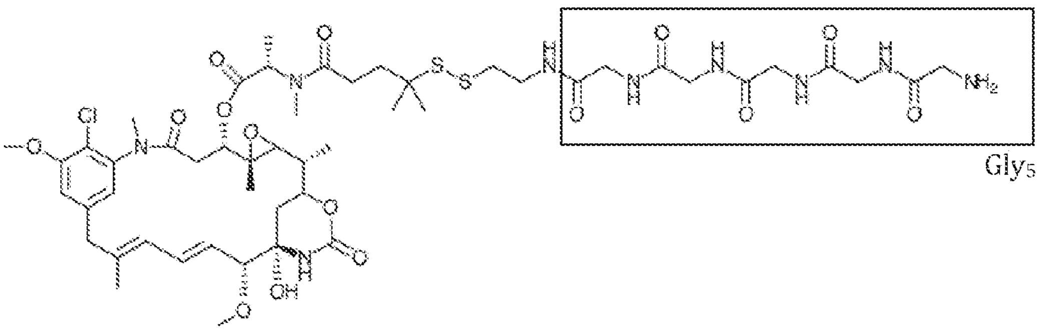
Figure 14B:
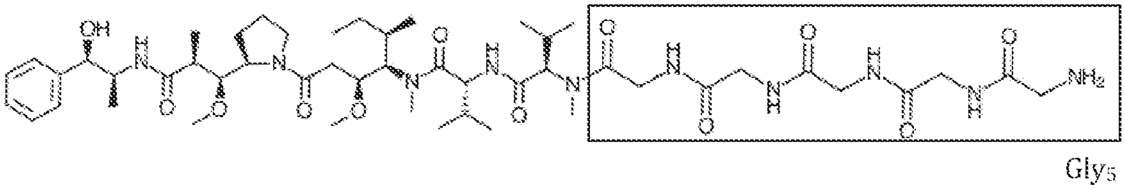
Figure 14B:
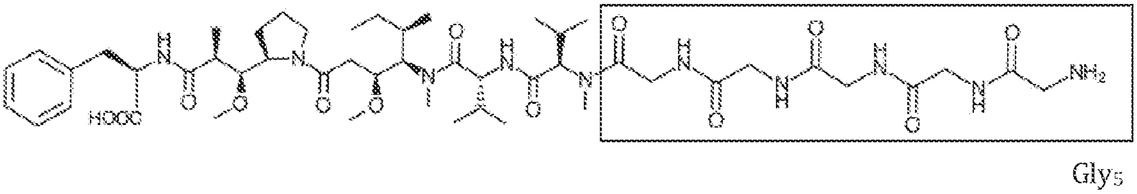
Figure 14B:
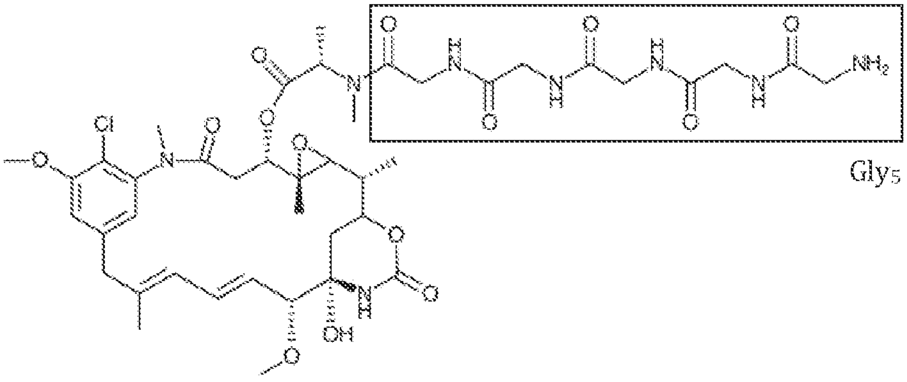
Figure 14C:
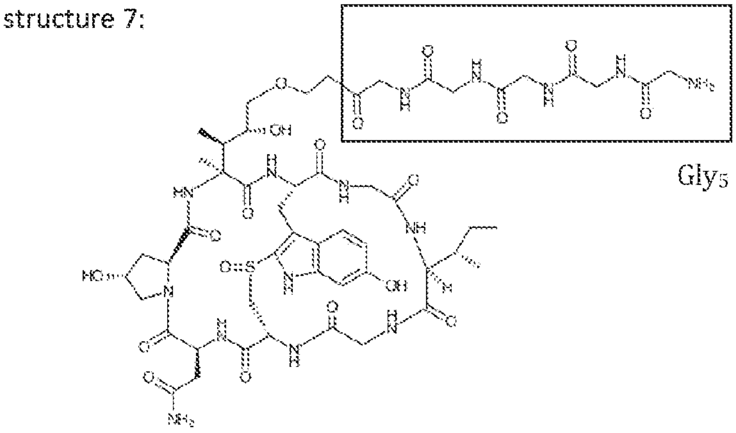
Figure 14C:
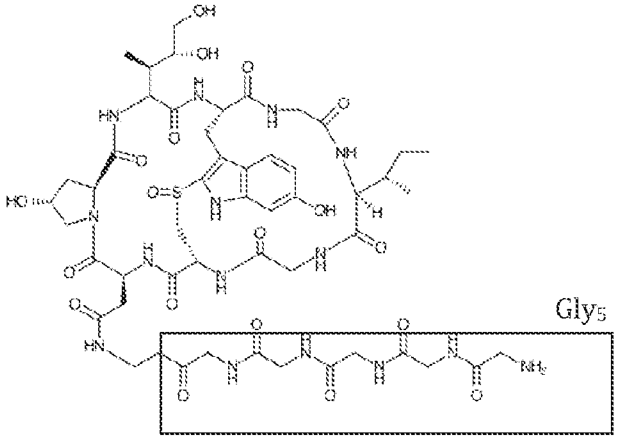
Figure 14C:
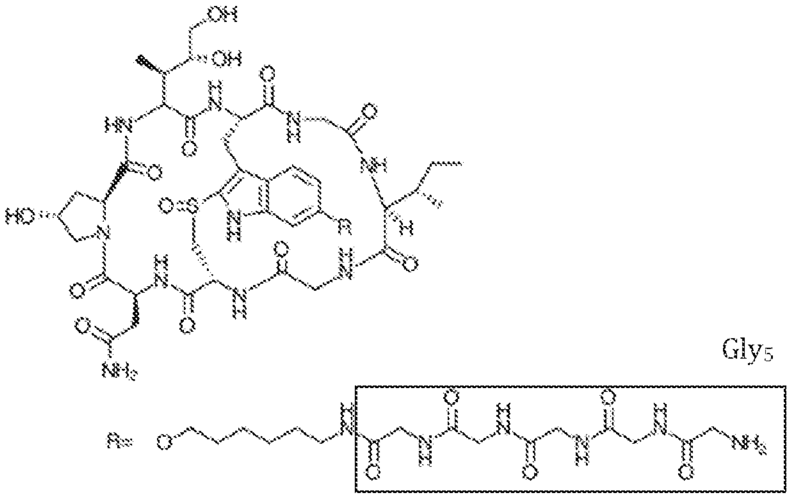

Importantly, it is to be noted that in principle, any toxin can be functionalized for sortase mediated enzymatic conjugation, if either 5 glycines (as shown here), or any number of glycine residues greater or equal than one glycine, are attached to the toxins (see FIGS. 14A-14C).

Figure 15:
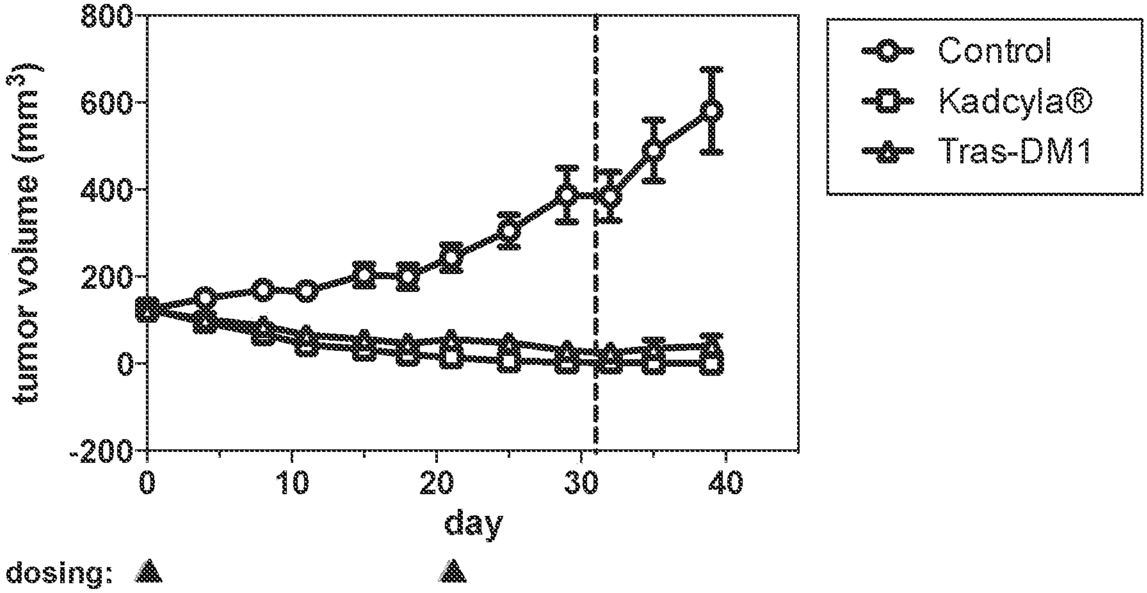

Example 12: In Vivo Tumor Inhibition of Sortase A-Conjugated Trastuzumab-DM1 in SKOV3 Ovarial Carcinoma Xenograft Models $5\times10^6$ SKOV3 tumor cells in 200 μl PBS/Matrigel (1:1 ratio) were implanted subcutaneously into the left flanks of 5-6 weeks old female NMRI nude mice. Primary tumor volumes were monitored by calipering. After a mean tumor volume of 100-200 $mm^3$ was reached, tumor-bearing animals were randomized into 3 Groups according to tumor sizes (10 animals per group). On the day of randomization (day 0) and on day 21, animals of Groups 1, 2 and 3 were injected intravenously with, respectively, 5 ml/kg PBS, 15 mg/kg Kadcyla©, or 15 mg/kg sortase A-conjugated Trastuzumab-DM1. Tumor volumes were measured bi-weekly by calipering (FIG. 15). The study was terminated after 39 days and animals were euthanized according to accepted animal experimentation guidelines.

In the course of the study, tumors in control animals mock-injected with PBS grew steadily to a volume of approximately 600 $mm^3$. In contrast, tumors in Kadcyla®-treated animals shrank and were essentially undetectable on day 39. Anti-tumor activity of Sortase A-conjugated Trastuzumab-DM1 did not differ significantly from that of commercially available Kadcyla©, despite the fact that the sortase-conjugated T-DM1 exhibited a lower drug to antibody ratio of approximately 2, in comparison of a reported DAR of 3.5 of Kadcyla©. In combination with the data from Example 8, the results demonstrate that sortase conjugated ADCs, using identical antibody and toxin moiety, have comparable tumor killing activity in comparison to commercially available chemically conjugated Kadcyla® in vitro and in vivo, albeit at lower drug to antibody ratio.

Example 13: Sortase A-Mediated Conjugation in Crude CHO Cell Supernatant

Figure 16A:
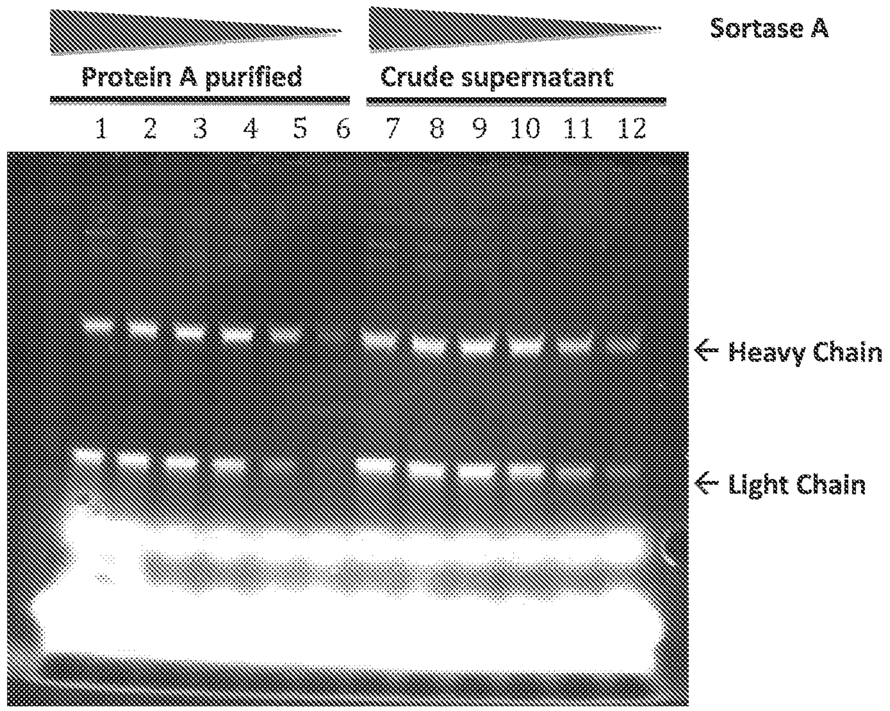
Figure 16B:
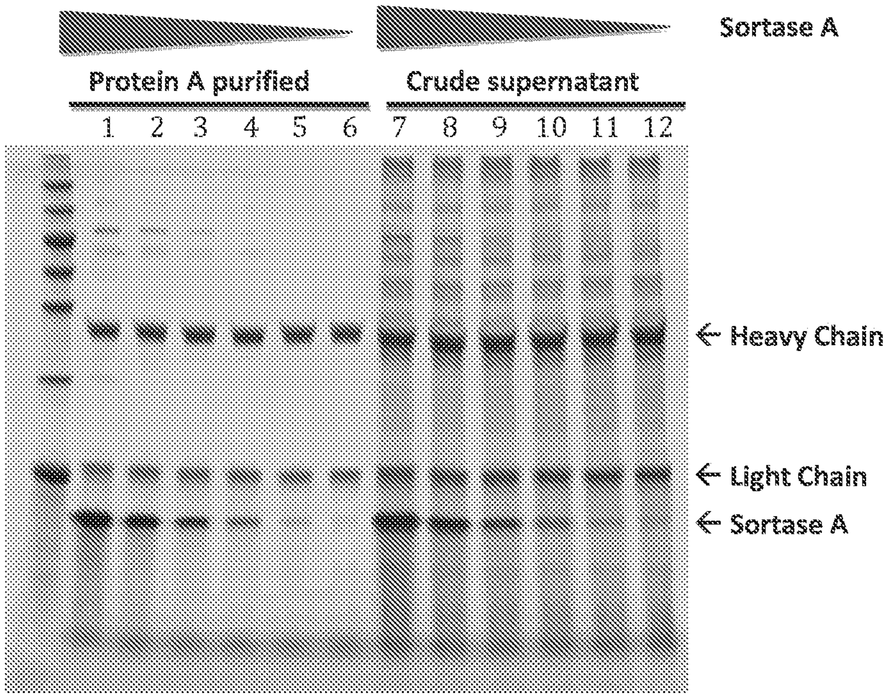

The Trastuzumab variant Tras-HC-LS/LC-GGGGS-LS, consisting of heavy chains C-terminally tagged with LPETG Sortase motif and Strep II purification tag (SEQ ID NOs: 055-056), and light chains C-terminally tagged with a 5 amino acid Gly4-Ser spacer (GGGGS), LPETG Sortase motif and Strep II tag (SEQ ID NOs: 057-058), was produced in CHO cells essentially as described in Example 4. The resulting serum-free crude cell supernatant contained approximately 157 mg/L Tras-HC-LS/LC-GGGGS-LS and was directly used for conjugation essentially as described in Example 9, by adding Sortase buffer, Gly5-FITC, and serial dilutions of Sortase A directly to the supernatant. In parallel, Tras-HC-LS/LC-GGGGS-LS purified by protein A affinity chromatography was also conjugated under otherwise identical conditions. After 4 hours at 42° C., the reactions were analyzed by denaturing, reducing SDS-PAGE gel electrophoresis. After visualizing FITC by placing the gel on a UV box, protein was stained using Coomassie Brilliant Blue (FIGS. 16A-16B). The data shows the unexpected finding that Sortase A-mediated conjugation of antibodies in crude cell culture supernatant was as efficient as that of purified antibody. Further, the conjugation reaction was highly specific and none of the protein contaminants present in crude CHO cell supernatant were non-specifically conjugated. Together, these data suggest that the robustness of the Sortase reaction may help facilitate ADC manufacturing by allowing to perform drug conjugation directly after production in CHO cells prior to purification and downstream processing.

FIGURE LEGENDS

FIGS. 1A-1B: These figures illustrate the principle of the sortase A mediated site-specific payload conjugation to an immunoligand (or binding protein), which can be performed at the N-terminus of a protein (FIG. 1A), or at the C-terminus of the protein (FIG. 1B). In order to achieve N-terminal conjugation, the payload needs to contain a sortase pentapeptide recognition motif (here LPXTG, the recognition motif of sortase A from *Staphylococcus aureus* (X representing any of the 20 natural amino acids), whereas the N-terminus of the immunologand/binding protein to be labeled needs to be expressed with an N-terminal extension of minimally 3 glycine residues, here indicated as $G_n$, (with n>2), that has a free N-terminal amino group (here indicated by the smaller $H_2N$— symbol). Typically 3-5 glycines are used in order to modify a substrate for sortase-mediated conjugation. Addition of recombinant sortas A enzyme from *Staphylococcus aureus*, as indicated here, then catalyzes the breakage of the peptide bond between the T and the C-terminal G residue in the LPXTG penta-peptide motif and forms a new peptide bond between the N-terminal glycine of the $G_n$ stretch (n>2) and the T residue. The C-terminal G residue of the LPXTG motif (here highlighted in boldface print) is removed in the transpeptidation reaction. (FIG. 1B) Conversely, in order to achieve C-terminal conjugation of a payload to a protein, which is the preferred method for conjugation of payloads, particularly toxins, to antibodies (see FIGS. 6A-6B), the LPXTG sortase recognition pentapeptide motif needs to be added to the C-terminal end of the immunoligand/binding protein (e.g. by recombinant protein expression technology, as described in the Examples), and the payload needs to be modified with a short glycine stretch ($G_n$, with n>2, typically 3-5 glycines). As described under FIG. 1A, addition of sortase A from *Staphylococcus aureus* will then catalyze the transpeptidation of the $G_n$-stretch to the LPXTG motif, whereby the terminal G residue of the LPXTG motif (in boldface) will be removed.

FIGS. 2A-2B: These figures illustrate the principle of intein (FIG. 2A) and split-intein (FIG. 2B) mediated transpeptidation. (FIG. 2A) Inteins can occur as so-called "protein-introns" in precursor proteins, where they separate N-terminal and C-terminal parts of a mature protein, which are generally called N-extein and C-extein. The intein "protein-intron" can catalyze the breakage of the peptide bond between the intein and the C-extein and the formation of a new peptide bond between the N-extein and C-extein by transferring the N-terminal amino acid of the C-extein to the C-terminal amino acid of the N-extein in a transpeptidation reaction. The result of the reaction is the removal of the intein "protein-intron" from the precursor protein and the generation of a mature protein with a newly created peptide bond between the N-extein and C-intein domains. (FIG. 2B) The intein activity has also been described to be separable into distinct domains, that can be attached to different proteins, for which this intein variation has been termed split-intein. The N-int and C-int domains of the split intein form a non-covalent structural complex, that can perform the same transpeptidation reaction as a contiguous intein, on the attached N-extein and C-extein domains that are then in spatial proximity and part of the complex. The result of the transpeptidation of N-int and C-int split-intein reaction is then a "protein trans-splicing", or essentially a protein ligation between the N-extein and C-extein domains, by formation of a novel peptide bond.

FIGS. 3A-3B: These figures illustrate how particular split inteins that are characterized by either an extremely short C-int domain or an extremely short N-int domain can be used to conjugate any payload to an immunoligand (or binding protein), including small molecular entities, because short amino acid stretches can be synthesize chemically and can easily be attached to small molecular entities by conventional chemical coupling. (FIG. 3A) This part of the illustration shows the use of the Ssp GyrB S11 split intein (described in Appleby et al. (2009)) for the C-terminal conjugation of a payload to an immunoligand/binding protein. Here the C-int domain is only 6 amino acids long and comprises the amino acid sequence GVFVHN, as indicated. However, as there need to be some peptides that are the equivalent of an C-extein domain, additional amino acids need to be added, of which the first one needs to be a serine or cysteine amino acid residue, whereas the remaining amino acids can be chosen. This is indicated by the $SX_n$ symbol, which means that a short amino acid stretch lead at the N-terminal side by serine and followed by n amino acids (n>2, preferably 5), which can be any of the 20 naturally occurring amino acids (therefore indicated as X). Thus, as described in the Example, a short 12 amino acid stretch comprising a 6 amino acid mini C-int domain and 6 amino acid C-ext amino acid stretch are sufficient to allow the N-int/C-int complex to catalyze the transpeptidation from the asparagine-serine peptide bond in the GVFVHN-$SX_n$(X any amino acid, n>2, preferably 5) to the peptide bond between the N-extein and N-int transition. This will result in a C-terminally conjugated immunologand/binding protein with the payload attached via the short C-extein amino acid stretch. (FIG. 3B) This part of the illustration shows the use of the Ssp DnaX split intein (described in Song et al. (2012)), which can be separate into a very short, 11 amino acid N-int domain and a 139 aa C-int domain for N-terminal conjugation of a payload to an immunologand/binding protein. As indicated here, this only requires the synthesis and coupling of a short 11 amino acid N-int domain to any payload (or the addition by recombinant protein technology), which then allows the specific conjugation of the payload to the N-terminus of any immunoligand or protein, that has a 139 amino acid long Ssp DnaX C-int domain fused to the N-terminus. The result of this reaction is then a N-terminally conjugated immunoligand/binding protein. Therefore, like in the case of sortase transpeptidation, where the N- or C-terminal conjugation only depends on the arrangement of the LPXTG and $G_n$ peptide motifs with regard to protein and payload, split inteins can also mediate site-specific N- and C-terminal conjugation of proteins with short peptide modified payloads, and by exploit short mini C-int, or mini N-int peptide domains, like those of Ssp GyrB and Ssp DnaX split inteins, respectively.

FIGS. 4A-4B: These figures illustrate the utility of adding additional affinity purification and/or detection tags in addition to a sortase tag in the conjugation of payloads to immunoligands. (FIG. 4A) this part of the Figure shows how an additionally added amino acids representing a 6×His purification tag (HHHHHH), a Myc-detection tag (EQKLISEEDL) and a strepII affinity purification tag (WSHPQFEK), as described in the Examples are removed in the course of the C-terminal payload conjugation via *Staphylococcus aureus* sortase A transpeptidase. This allows to select for the conjugated product, if Ni-NTA affinity resins (for the 6×His-tag) or streptactin affinity resins (for the strep II-tag) are employed to separate non-conjugated substrate from conjugated product. This combination of tags is only provided by way of Example.

(FIG. 4B) This Figure illustrates that the use of affinity purification tags is particularly useful to select/purify completely conjugated product in the case of multimeric proteins, like antibodies as illustrated here. As also provided in the examples, antibodies can be modified with specific conjugations sites at heavy and light chains, and if the modification is targeted to the C-termini of IgH and IgL chains, then up to four payloads may be conjugated to the antibody. The addition of (a) further affinity purification tag(s), e.g. as described in FIG. 4A allows to bind incompletely conjugated product, that may only have one, two, or three (as illustrated here) payloads conjugated to the antibody, still bind to the respective affinity purification resin, and can thus easily be separated from the fully payload-conjugated product. This paradigm is of course also applicable to intein-modified immunologands, and not only to sortase-motif-modified immunologands, as depicted here.

FIG. 5: This figure illustrates a variation of the sortase-mediated conjugation that can also be applied, in which the sortase-enzyme is not added as a separate recombinant protein to the sortase tagged immunologand and glycine-stretch modified payload, but where the enzymatic sortase domain is expressed as a fusion protein C-terminal to the LPXTG sortase tag. The sortase enzyme domain will be inactive as long as it is not incubated with glycine-stretch modified payload (or substrate). As soon as glycine-stretch modified substrate (or here payload) is added to such a construct, the fused sortase domain will catalyze the transpeptidation of glycine-payload substrate to the LPXTG sortase tag, by cleaving the protein between the threonine-4 and glycine-5 position of the LPXTG tag, and thereby removing the sortase enzyme domain with additional affinity purification tags, that can be added optionally, as depicted here. This procedure has the advantage that, similar to the addition of catalytically active split-intein domains, the sortase enzyme domain can be expressed by recombinant protein technology as an integral component of the immunoligand to be conjugated.

FIGS. 6A-6B: (FIG. 6A) This figure illustrates the use of different transpeptidases (here sortase and split-intein), in order to simultaneously conjugate different payloads to different subunits of a multimeric protein, like e.g., as depicted here, the heavy and the light chains of an antibody. In this selected example, the C-termini of the heavy chains are modified with the N-int domain of Ssp GyrB (as provided in Example 2), while the light chains are modified with the sortase A penta-peptide motif LPXTG (as provided in Example 1, the additional tags are omitted for simplicity). Incubation with a glycine-stretch modified payload A and with a C-int-domain modified payload B and sortase enzyme will allow the simultaneous and selective conjugation of payload B to the heavy chains and payload A to the light chains. If payloads A and B are toxins addressing different cellular pathways, this strategy could generate more potent anti-cancer drugs, as conventional ADCs, only containing a single toxin moiety. (FIG. 6B) This figure illustrates the use of different sortase enzymes (here sortase A and sortase B from *Staphylococcus aureus*), in order to simultaneously conjugate different payloads to different subunits of a multimeric protein, like e.g., as depicted here, the heavy and the light chains of an antibody. In this selected example, the C-termini of the heavy chains are modified with the penta-peptide recognition motif for sortase B, NPQTN, while the light chains are modified with the sortase A penta-peptide motif LPXTG. Sequential conjugation of glycine-stretch modified payloads A and B with sortase A and sortase B will allow the simultaneous and selective conjugation of payload B to the heavy chains and payload A to the light chains (remaining peptide sequences from LPXTG and NPQTN are omitted in the conjugated structure for simplicity). If payloads A and B are toxins addressing different cellular pathways, this strategy could generate more potent anti-cancer drugs, as conventional ADCs, only containing a single toxin moiety.

Figure 7A:
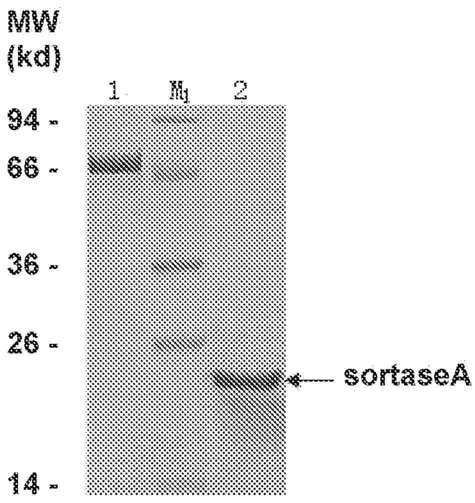
Figure 7B:
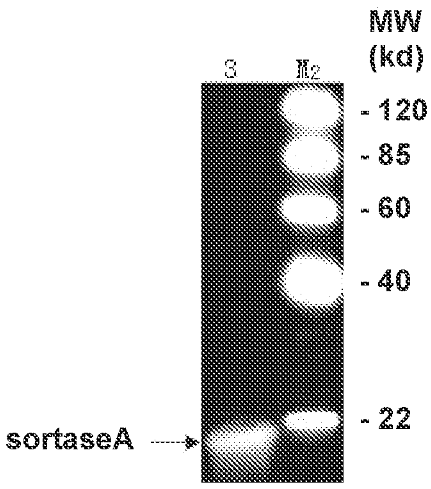

FIGS. 7A-7B: SDS-PAGE (FIG. 7A) and Western-blot (FIG. 7B) analysis of recombinant enzymatically active sortase A fragment of *Staphylococcus aureus*. (FIG. 7A) Lane 1 in the SDS-PAGE contains BSA (ca. 66.4 kD), Lane $M_1$ contains protein molecular weight standard of Genscript (Cat.-Nr.: MO0505), Lane 2 contains His-tag purified recombinant sortase A fragment of *Staphylococcus aureus*. The proteins in the SDS-PAGE are stained with Commassie blue. (FIG. 7B) The Western-blot was developed with an anti-His antibody (Genscript Cat.-Nr.: AO0186). Lane 3 contains His-tag purified recombinant sortase A fragment of *Staphylococcus aureus*. Lane $M_2$ contains molecular weight standard of Genscript (Cat.-Nr.: MM0908).

FIGS. 8A-8B: Hydrophobic Interaction Chromatography (HIC) analysis of DM1-toxin conjugated Tras-HC-GS-LHS (FIG. 8A) and Tras-LC-GS-LHS (FIG. 8B). DAR1 indicates drug to antibody ratio of 1; DAR2 indicates a drug to antibody ratio of 2.

FIGS. 9A-9B: Dose response of cytotoxic effects of the indicated ADCs on HER2-overexpressing SKBR3 (FIG. 9A) and HER2-negative T47D-5R cells (FIG. 9B). Cells were incubated with serial dilutions of ADCs for 3 days, after which cell viability was detected by CellTiter-Glo® Luminescent Solution (Promega). LC: DM1-sortaseA-conjugated Tras-LC-GS-LHS; HC: DM1-sortaseA-conjugated Tras-HC-GS-LHS.

FIGS. 10A-10B: Sortase A-mediated conjugation of Gly5-FITC to mAb Ac10 variants with or without GS peptide spacer. Serial dilutions of Sortase A were used to conjugate Gly5-FITC to mAb Ac10-HC-GS-LHS/LC-GS-LHS (FIG. 10A) and mAb Ac10-HC-LS/LC-LS (FIG. 10B) under otherwise identical conditions. Reaction products were separated by size on denaturing, reducing SDS-PAGE gels. FITC was visualized by placing the gels on a UV box. Sortase A concentrations used were: lanes 1, 9: 50 μM; lanes 2, 10: 25 μM; lanes 3, 11: 12.5 μM; lanes 4, 12: 6.25 μM; lanes 5, 13: 3.13 μM; lanes 6, 14: 1.56 μM; lanes 7, 15: 0.78 μM; lanes 8, 16: 0.39 μM.

Figure 11A:
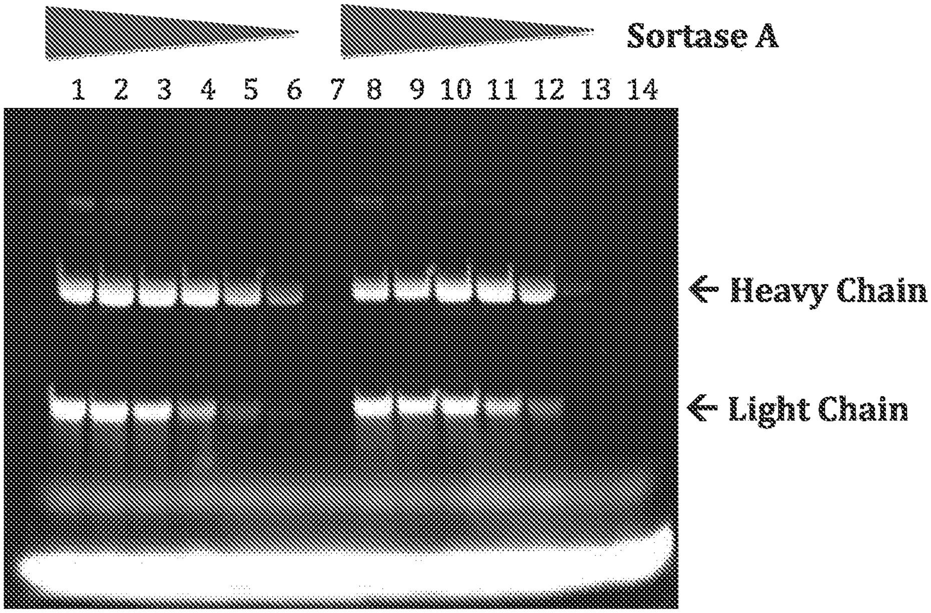
Figure 11B:
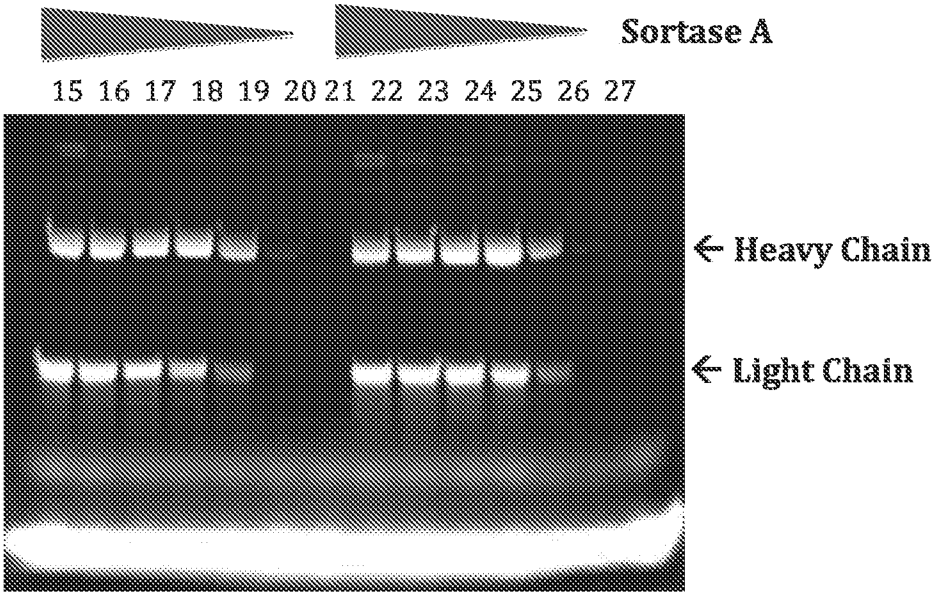

FIGS. 11A-11B: Influence of peptide spacer length on light chain conjugation efficiency. Serial dilutions of Sortase A were used to conjugate Gly5-FITC to mAbs Ac10-HC-LS/LC-GS-LS (FIG. 11A, left), Ac10-HC-LS/LC-GGS-LS (FIG. 11A, right), Ac10-HC-LS/LC-GGGS-LS (FIG. 111B, left) and Ac10-HC-LS/LC-GGGGS-LS (FIG. 111B, right) under otherwise identical conditions. Reaction products were separated by size on denaturing, reducing SDS-PAGE gels. FITC was visualized by placing the gels on a UV box. Sortase A concentrations used were: lanes 1, 8, 15, 22: 25 μM; lanes 2, 9, 16, 23: 12.5 μM; lanes 3, 10, 17, 24: 6.25 μM; lanes 4, 11, 18, 25: 3.13 μM; lanes 5, 12, 19, 26: 1.56 μM; lanes 6, 13, 20, 27: 0.78 μM; lanes 7, 14, 21, 28: 0.39 μM FIGS. 12A-12B: Analysis of sortaseA vc-PAB-MMAE toxin heavy-chain-conjugated ADC of mAb Ac10 by hydrophobicity interaction chromatography (HIC), which is able to differentiate unreacted substrate (DAR0=0 drug to antibody ratio), substrate in which one of the two heavy chains has been conjugated (DAR1=1 drug to antibody ratio), and substrate in which both modified heavy chains have been conjugated (DAR2=2 drugs to antibody ratio), as indicated. Panel A shows the HIC profile after a standard sortase A mediated conjugation of HC modified Ac10 mAb, in which still DAR0 and DAR1 species are detectable, next to the desired DAR2 product. Panel B shows the HIC profile after 4 passes of the ADC preparation analyzed in Panel A over a StrepTactin© affinity purification column.

Figure 13A:
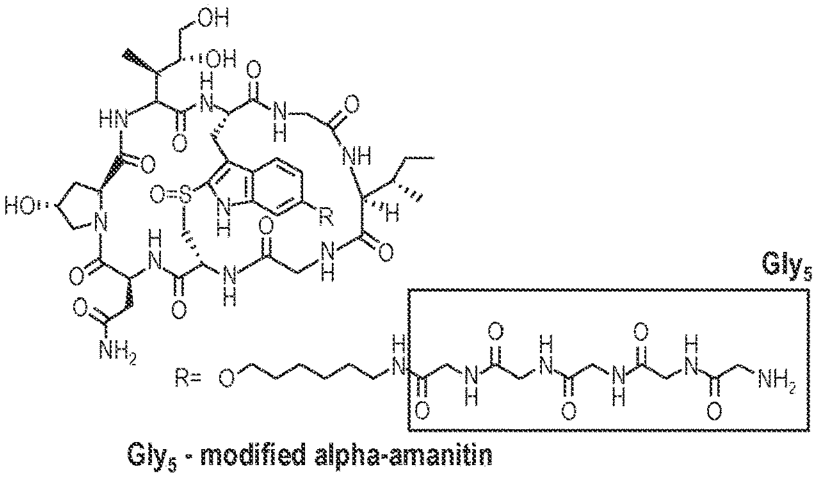
Figure 13A:
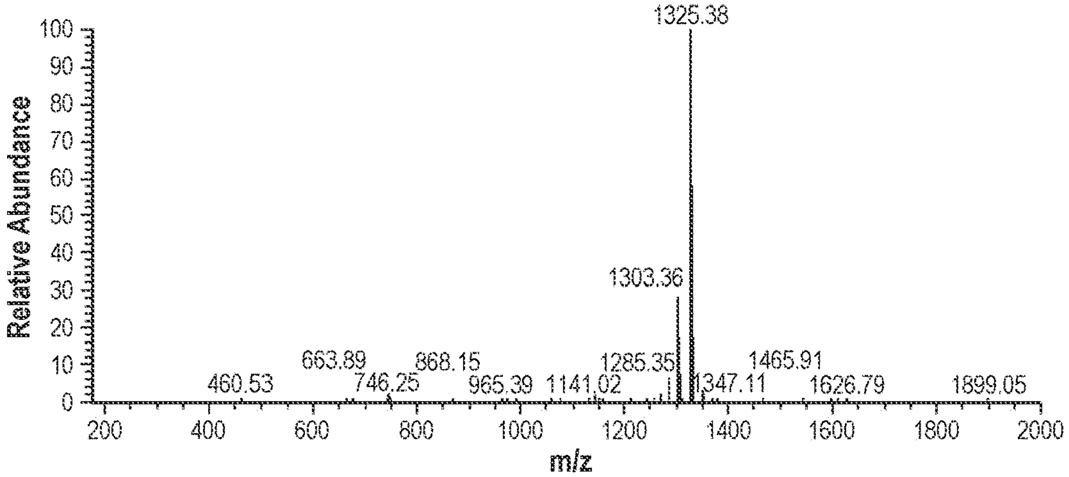
Figure 13A:
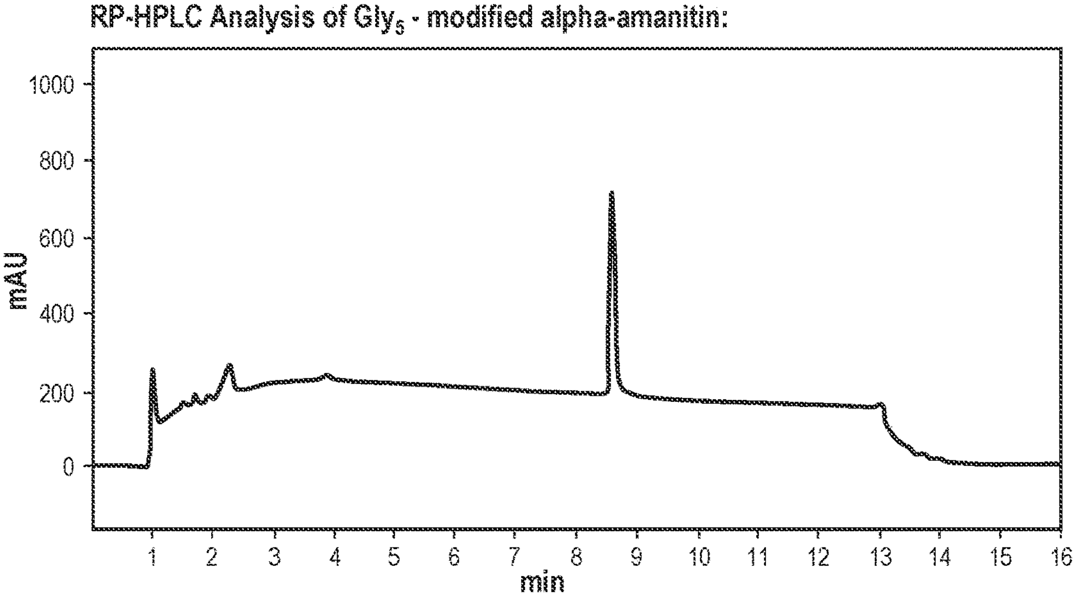
Figure 13B:
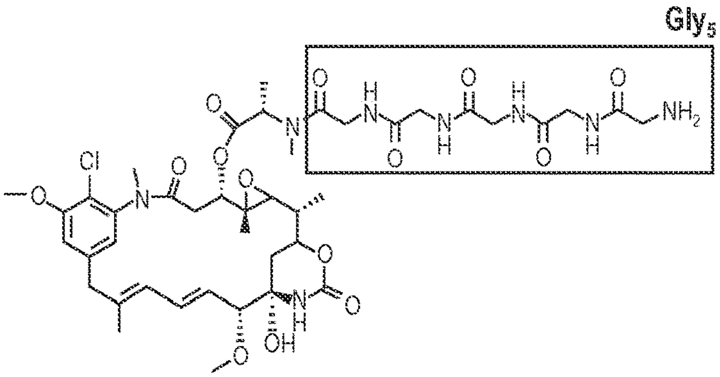
Figure 13B:
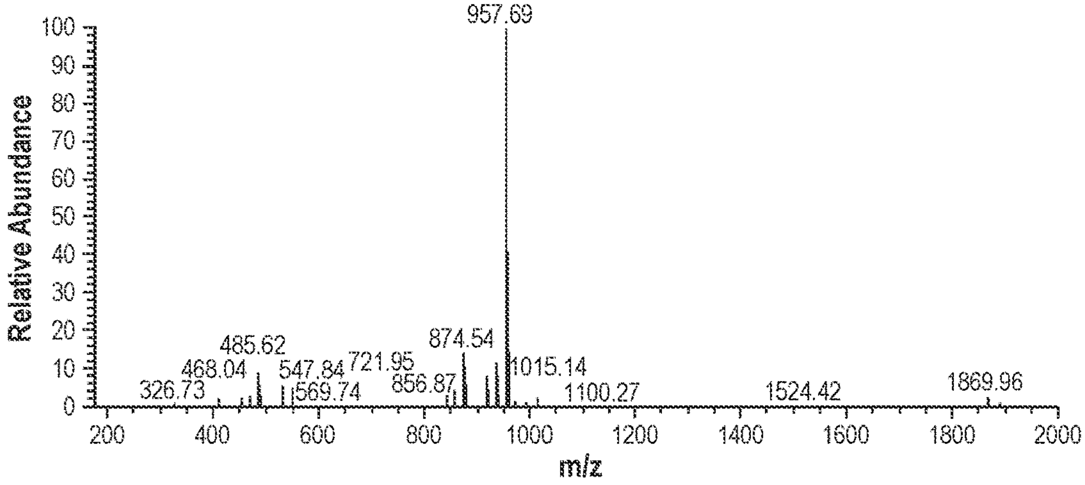
Figure 13B:
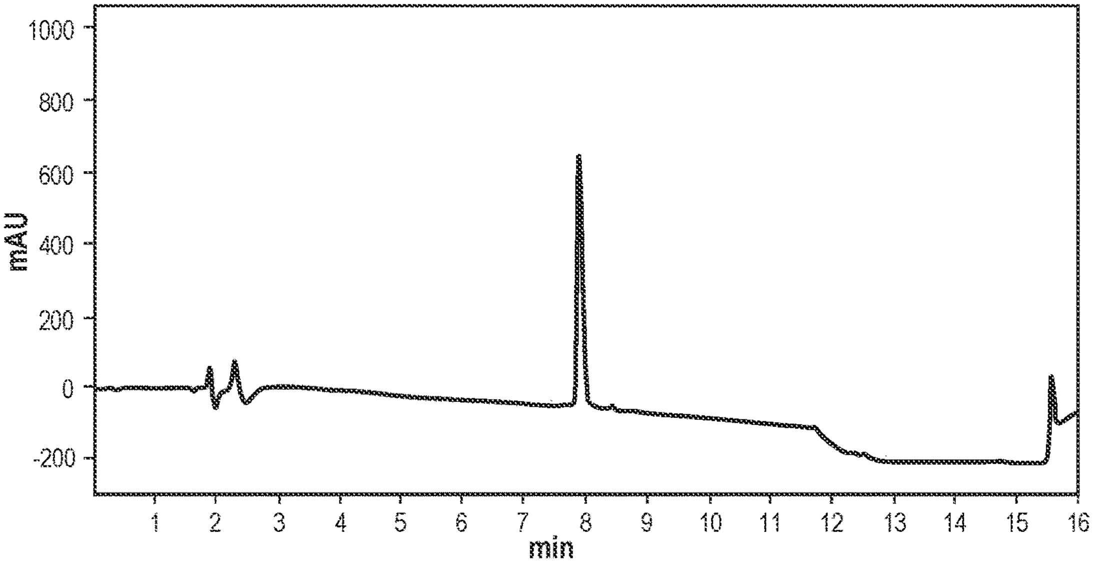

FIGS. 13A-13B: Analysis of synthesized Gly5-modified alpha-amanitin toxin (FIG. 13A) and Gly5-modified maytansin toxin (FIG. 13B). In each of the panels FIG. 13A and FIG. 13B the synthesized structure is provided on top, with the five glycines highlighted by a box. The analysis of each compound by mass spectrometry and reverse-phase HPLC is provided below. a.) The expected mass of the Gly5-modified alpha-amanitin toxin is 1302.07 D, the observed mass is 1325.38 D, corresponding to $Ms+Na^+$. The RP-HPLC profile indicates a purity of >95%. b.) The expected mass of the Gly5-modified maytansine toxin is 991.41 D, the observed mass is 957.69 D, corresponding to $Ms+Na^+$. The RP-HPLC profile indicates a purity of >95%.

FIGS. 14A-14C: Structures of 5×Glycine ($Gly_5$) modified toxins that either have been synthesized by Concortis, San Diego, CA, U.S. (structures 1-6, and 9), or that can be synthesized (structures 7 & 8), demonstrating that any toxin can be functionalized for sortase mediated enzymatic conjugation, if either 5 glycines are attached to the toxins (as shown here), or any number of glycine residues greater or equal than one glycine. Glycine-modified toxins can either be synthesized containing additional validated linker/spacer structures as provided in structures 1-3 in FIG. 14A), potentially adding certain additional functionality (e.g. cleavability in certain subcellular compartments) or without additional linkers, as depicted in structures 4-6 in FIG. 14B). If several reactive groups are available at a given toxin, like e.g. in the case of alpha-amanitin toxin, glycine residues can be added to these different groups as exemplified in structures 7-9 in FIG. 14C).

FIG. 15: Tumor volumes as determined in Example 12. The results demonstrate that sortase conjugated ADCs, using identical antibody and toxin moiety, have comparable tumor killing activity in comparison to commercially available chemically conjugated Kadcyla®.

FIGS. 16A-16B: Gels stained with Coomassie blue as described in example 13 The data shows the unexpected finding that Sortase A-mediated conjugation of antibodies in crude cell culture supernatant was as efficient as that of purified antibody.

REFERENCES

Antos et al. (2009a) J. Am. Chem. Soc. 131, pp. 10800-10801

Antos et al. (2009b) J. Biol. Chem. 284, 16028-16036

Appleby et al. (2009) JBC 284, 6194-99

Axup et al. (2012) Proc. Natl. Acad. Sci USA 109, 16102-16106

Elleuche (2010) Appl. Microbiol. Biotechnol. 87, 479-489

Graus-Porta et al. (1995) Mol. Cell. Biol. 15, p 1182ff

Hofer et al. (2009) Biochemistry 48, 12047-57

Junutula et al. (2008) Nat. Biotechol., 26, 925-932

Lambert (2012) British J Clin Pharmacol 76, 248-262,

Lemke (2011) Methods Mol. Biol. 751, 3-15

Levary et al. (2011) PLoS One 6, e18342

Madej et al. (2012) Biotechnol. Bioeng. 109, 1461-1470

Mao et al. (2004) J. Am. Chem. Soc. 126, 2670-2671,

Mazmanian et al. (1999) Science 285, 760-763

McDonagh et al. (2006) Prot. Engin. Design Selection 19, 299-307

Mohlmann et al. (2011) Chembiochem. 12, 1774-1780,

Mullard (2013) Nature Rev. Drug Discov. 12, 329-332).

Parthasarathy et al. (2007) Bioconjugate Chem. 18, 469-476

Perler (2002) Nucl. Acids Res. 30, 383-384

Song et al. (2012) PLoS One 7, e45355

Spirig et al. (2011) Molecular Microbiol. 82, 1044-1059

Sun et al. (2004) J. Biol. Chem. 279, 35281-35286

Swee et al. (2013) Proc. Natl. Acad. Sci USA 110, 1428-1433

Ton-That et al. (1999) Proc. Natl. Acad. Sci USA 96, 12424-12429

Tsukiji (2009) Chembiochem. 10, 787-798)

Volkmann et al. (2009) PLoS One 4, e8381

Xu et al. (1993) Cell 75, 1371-1377

What is claimed is:

1. An immunoligand/payload conjugate comprising a) an immunoligand selected from the group consisting of one or more of:

i) an antibody, ii) an antibody-based binding protein being a protein containing at least one antibody-derived $V_H$, $V_L$, or $C_H$ immunoglobulin domain, iii) an antibody fragment binding to a receptor, antigen, growth factor, cytokine, or hormone, or iv) an antibody mimetic selected from the group consisting of DARPins, C-type lectins, A-domain proteins of *S. aureus*, transferrins, lipocalins, $10^{th}$ type III domains of fibronectin, Kunitz domain protease inhibitors, affilins, gamma crystallin derived binders, cysteine knots or knottins, thioredoxin A scaffold based binders, nucleic acid aptamers, artificial antibodies produced by molecular imprinting of polymers, and stradobodies, b) at least one payload having a molecular weight not exceeding 2,500 Dalton, and c) a linker conjugating the immunoligand of (a) or a subunit thereof to the payload, said linker comprising a sortase recognition motif having its C-terminal amino acid replaced with a $Gly_n$, wherein n>1.

2. The immunoligand/payload conjugate of claim 1, wherein the sortase recognition motif comprises LPXTG (SEQ ID NO: 27) or NPQTN (SEQ ID NO: 28), or wherein the sortase recognition motif is LPXTG (SEQ ID NO: 27) or NPQTN (SEQ ID NO: 28).

3. The immunoligand/payload conjugate of claim 2, wherein the linker of (c) comprises, from its N-terminus to its C-terminus, $LPXTG_n$, wherein n>1.

4. The immunoligand/payload conjugate of claim 1, wherein the immunoligand of (a) comprises two or more subunits, and wherein the linker of (c) conjugates one of the two or more subunits to one payload.

5. The immunoligand/payload conjugate of claim 1, wherein the immunoligand of (a) comprises two or more subunits, wherein a first linker of (c) conjugates a first subunit to a first payload, and wherein a second linker of (c) conjugates a second subunit to a second payload.

6. The immunoligand/payload conjugate of claim 5, wherein the first payload is different from the second payload, or wherein the first payload is the same as the second payload.

7. The immunoligand/payload conjugate of claim 5, wherein the first linker is the same as the second linker, or wherein the first linker is different from the second linker.

8. The immunoligand/payload conjugate of claim 5, wherein the immunoligand comprises two light chains and two heavy chains, and wherein one linker of (c) conjugates each of the two light chains to one payload.

9. The immunoligand/payload conjugate of claim 5, wherein the immunoligand comprises two light chains and two heavy chains, and wherein one linker of (c) conjugates each of the two light chains and the two heavy chains to one payload.

10. The immunoligand/payload conjugate of claim 9, wherein the linker conjugating either of the two heavy chains to one payload is different from the linker conjugating either of the two light chains to one payload.

11. The immunoligand/payload conjugate of claim 9, wherein the linker conjugating one heavy chain is the same as the linker conjugating the other heavy chain.

12. The immunoligand/payload conjugate of claim 9, wherein the linker conjugating one light chain is the same as the linker conjugating the other light chain.

13. The immunoligand/payload conjugate of claim 9, wherein the linker conjugating one heavy chain is the same as the linker conjugating the other heavy chain, wherein the linker conjugating one light chain is the same as the linker conjugating the other light chain, wherein the linker conjugating the heavy chain is different from the linker conjugating the light chain, and wherein the payload conjugated to the heavy chain is different or the same from the payload conjugated to the light chain.

14. The immunoligand/payload conjugate of claim 1, wherein the immunoligand of (a) comprises two or more subunits, and wherein one linker of (c) conjugates each of the two or more subunits to one payload.

15. The immunoligand/payload conjugate of claim 1 comprising, starting from its N-terminus in the following order: the immunoligand (a) or a subunit thereof, the linker of (c), and the payload of (c).

16. The immunoligand/payload conjugate of claim 1 comprising, starting from its C-terminus in the following order: the immunoligand (a) or a subunit thereof, the linker of (c), and the payload of (c).

17. The immunoligand/payload conjugate of claim 1, wherein the immunoligand of (a) or a subunit thereof further comprises a spacer of at least two amino acids at its C terminus.

18. The immunoligand/payload conjugate of claim 17, wherein the spacer comprises 2-5 amino acids.

19. The immunoligand/payload conjugate of claim 1, wherein the ratio of the immunoligand to the payload is stoichiometrically defined.

20. The immunoligand/payload conjugate of claim 1, wherein the conjugation of the payload to the immunoligand or a subunit thereof is site-specific.

21. The immunoligand/payload conjugate of claim 1, wherein the payload is a drug or a marker.

22. The immunoligand/payload conjugate of claim 21, wherein the drug is a cytokine, a radioactive agent, a toxin, or a chemotherapeutic agent.

23. The immunoligand/payload conjugate of claim 21, wherein the marker is a radiolabel, a fluorescent label, or an enzyme label.

* * * * *